(12) United States Patent
Cai et al.

(10) Patent No.: US 8,927,484 B2
(45) Date of Patent: Jan. 6, 2015

(54) ANTIVIRAL COMPOUNDS

(75) Inventors: Zhenhong R. Cai, Palo Alto, CA (US);
Michael O'Neil Hanrahan Clarke, Redwood City, CA (US); Edward Doerffler, Union City, CA (US); Mingzhe Ji, Union City, CA (US); Choung U. Kim, San Carlos, CA (US); Hyung-jung Pyun, Fremont, CA (US); Xiaoning C. Sheng, Foster City, CA (US); Qiaoyin Wu, Foster City, CA (US)

(73) Assignee: Gilead Sciences, Inc., Foster City, CA (US)

(*) Notice: Subject to any disclaimer, the term of this patent is extended or adjusted under 35 U.S.C. 154(b) by 893 days.

(21) Appl. No.: 12/958,112

(22) Filed: Dec. 1, 2010

(65) Prior Publication Data
US 2011/0135599 A1    Jun. 9, 2011

Related U.S. Application Data

(60) Provisional application No. 61/266,381, filed on Dec. 3, 2009.

(51) Int. Cl.
*A61K 38/00* (2006.01)
*C07D 498/04* (2006.01)
*C07D 487/04* (2006.01)
*C07D 471/04* (2006.01)

(52) U.S. Cl.
CPC ............ *C07D 471/04* (2013.01); *C07D 498/04* (2013.01); *C07D 487/04* (2013.01); *A61K 38/00* (2013.01)
USPC ............................ 514/1.1; 514/221; 424/85.4

(58) Field of Classification Search
None
See application file for complete search history.

(56) References Cited

U.S. PATENT DOCUMENTS

| 7,037,911 | B2* | 5/2006 | Zhang ........................... 514/249 |
| 7,273,851 | B2 | 9/2007 | Miao et al. |
| 7,491,794 | B2 | 2/2009 | Blatt et al. |
| 7,642,339 | B2 | 1/2010 | Chaudhary et al. |

FOREIGN PATENT DOCUMENTS

WO    WO-2009/70689 A1    6/2009

* cited by examiner

*Primary Examiner* — James H Alstrum Acevedo
*Assistant Examiner* — Roy Teller
(74) *Attorney, Agent, or Firm* — Sheppard Mullin Richter & Hampton, LLP

(57) ABSTRACT

The present application includes novel inhibitors of HCV, compositions containing such compounds, therapeutic methods that include the administration of such compounds.

20 Claims, 1 Drawing Sheet

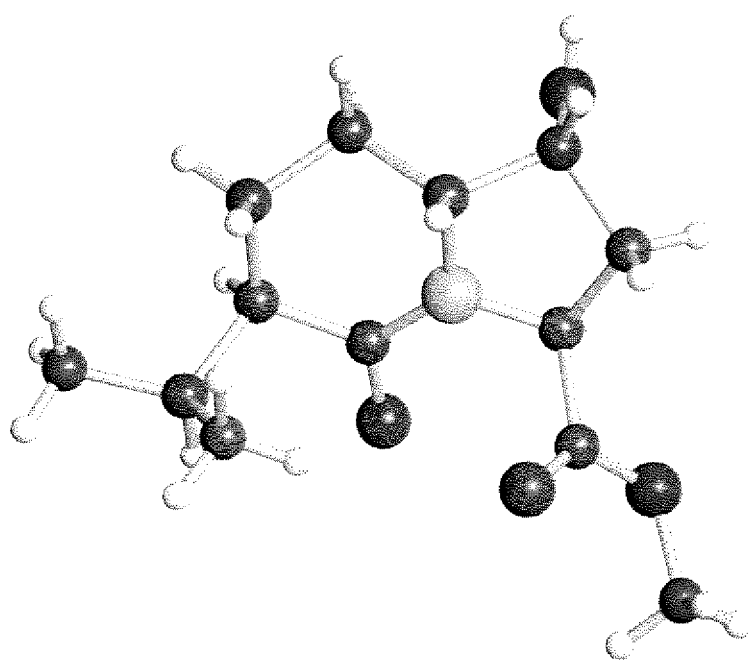
Compound 51

ANTIVIRAL COMPOUNDS

CROSS-REFERENCE TO RELATED APPLICATIONS

This application claims priority to U.S. Provisional Application Ser. No. 61/266,381, filed Dec. 3, 2009. The content of this provisional application is herein incorporated by reference in its entirety for all purposes.

FIELD OF THE INVENTION

The invention relates generally to compounds with HCV inhibitory activity, compositions containing such compounds, therapeutic methods that include the administration of such compounds.

BACKGROUND OF THE INVENTION

Hepatitis is a disease occurring throughout the world. Hepatitis is generally of viral nature, although there are other known causes. Viral hepatitis is by far the most common form of hepatitis. In the U.S. nearly 750,000 are affected by hepatitis each year, and out of those, more than 150,000 are infected with the hepatitis C virus ("HCV"). HCV is a positive-stranded RNA virus belonging to the Flaviviridae family and has closest relationship to the pestiviruses that include hog cholera virus and bovine viral diarrhea virus (BVDV).

HCV is believed to replicate through the production of a complementary negative-strand RNA template. The HCV genome is a single-stranded, positive-sense RNA of about 9,600 bp coding for a polyprotein of 3009-3030 amino-acids, which is cleaved co- and post-translationally by cellular and two viral proteinases into mature viral proteins (core, E1, E2, p7, NS2, NS3, NS4A, NS4B, NS5A, NS5B). The structural proteins, E1 and E2, are believed to be embedded into a viral lipid envelope and form stable heterodimers. The structural core protein is believed to interact with the viral RNA genome to form the nucleocapsid. The nonstructural proteins designated NS2 to NS5 include proteins with enzymatic functions involved in virus replication and protein processing including a polymerase, protease, and helicase.

The main source of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

One available treatment for HCV infection is interferon-α (IFN-a). According to different clinical studies, however, only 70% of treated patients normalize alanine aminotransferase (ALT) levels in the serum and after discontinuation of IFN, 35% to 45% of these responders relapse. In general, only 20% to 25% of patients have long-term responses to IFN. Clinical studies have shown that combination treatment with IFN and ribavirin (RIBA) results in a superior clinical response than IFN alone. Different genotypes of HCV respond differently to IFN therapy; genotype 1 is more resistant to IFN therapy than types 2 and 3.

There is therefore a great need for the development of anti-viral agents.

SUMMARY OF THE INVENTION

One aspect of the present invention includes a compound of Formula I:

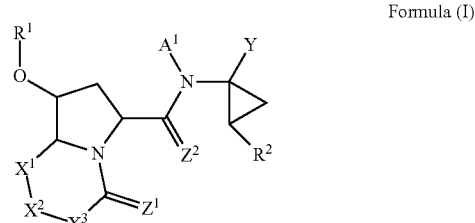

Formula (I)

or a pharmaceutically acceptable salt thereof, wherein $R^1$ is

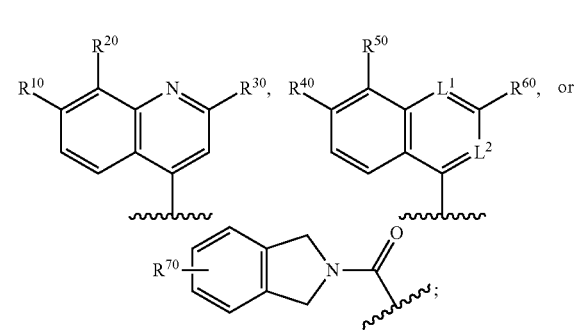

$R^{10}$ is hydrogen or $C_{1-6}$alkoxy optionally substituted with one or more $C_{1-6}$alkoxy or heterocyclyl;
$R^{20}$ is hydrogen, halogen, $C_{1-6}$alkyl, or $C_{1-6}$haloalkyl; or $R^{10}$ and $R^{20}$ combine with the atoms to which they are attached to form a 5 to 7 membered heterocycle;
$R^{30}$ is
  $C_{1-6}$alkoxy,
  aryl, optionally substituted with one or more $C_{1-6}$alkyl,
    heteroaryl, optionally substituted with one or more $C_{1-6}$alkyl, or $C_{1-6}$alkyl substituted with $NA^1A^2$;
$R^{40}$ is hydrogen or $C_{1-6}$alkoxy optionally substituted with one or more $C_{1-6}$alkoxy or heterocyclyl;
$R^{50}$ is hydrogen, halogen, $C_{1-6}$alkyl, or $C_{1-6}$haloalkyl;
$R^{60}$ is hydrogen, halogen, —ON, —C(O)$NA^1A^2$, $C_{1-6}$alkoxy, or $C_{6-10}$aryl, where said $C_{6-10}$aryl is optionally substituted with one or more halogen, $C_{1-6}$alkyl, or $C_{1-6}$alkoxy;
$L^1$ is CH or N;
$L^2$ is CH or N;
$R^{70}$ is halogen or $C_{1-6}$alkoxy substituted with $NA^1A^2$;
$X^1$ is —$CH_2$— or —$CH_2$—$CH_2$—;
$X^2$ is, —$CH_2$—, or —O—;
$X^3$ is —$NA^1$- or —$CR^{80}R^{90}$—;
$R^{80}$ is hydrogen;
$R^{90}$ is hydrogen, $C_{1-6}$alkyl, $C_{1-6}$alkyl substituted with $C_{1-6}$alkoxy or $C_{6-14}$aryl, $C_{2-6}$alkenyl, 3 to 8 membered heterocyclyl, or —$NA^1A^2$;
$Z^1$ is O, S, $NA^1$, $N(OA^1)$, or $N(N(A^1)(A^2))$;
$Z^2$ is O, S, or $NA^1$;
each $A^1$ independently is hydrogen, $C_{1-6}$alkyl, —C(O)O$C_{1-6}$alkyl, $C_{3-8}$cycloalkyl, —C(O)O$C_{3-8}$cycloalkyl, —C(O)NH$C_{1-6}$alkyl, —C(O)$C_{1-6}$alkyl, or —S(O)$_2C_{1-6}$alkyl;
each $A^2$ independently is hydrogen or $C_{1-6}$alkyl;
$R^2$ is $C_{1-8}$alkyl, $C_{1-8}$alkyl substituted with halogen, $C_{2-8}$alkenyl, or $C_{2-8}$alkynyl; or $R^2$ may combine with $X^3$ and the atoms to which they are attached to form a 14 to 16 membered heterocycle;

Y is —C(O)OH, —C(O)NHS(O)$_2$OR$^{100}$, —C(O)NHS(O)$_2$R$^{100}$, —C(O)NHS(O)$_2$NA$^1$A$^2$, or —P(O)(OH)R$^{110}$;

$R^{100}$ is $C_{1-6}$alkyl, $C_{1-6}$alkyl substituted with $C_{3-8}$cycloalkyl, or $C_{3-8}$ cycloalkyl; and $R^{110}$ is hydrogen, —OH, —C(O)OH, —CN, $C_{1-6}$alkyl, $C_{2-6}$alkenyl, $C_{2-6}$alkynyl, —NA$^1$A$^2$, —C(O)NA$^1$A$^2$, —NA$^1$C(O)A$^2$, —C(O)NA$^1$C(O)A$^2$, —C(=NA$^1$)A$^2$, halogen, $C_{1-6}$haloalkyl, $C_{3-8}$ cycloalkyl, —NO$_2$, $C_{6-14}$aryl, $C_{7-20}$aralkyl, $C_{1-6}$alkoxy, $C_{6-14}$aryloxy, 3 to 8 membered heterocyclyl, or 3 to 8 membered heteroaryl.

In one embodiment, at least one of $X^2$ or $X^3$ is —NA$^1$-. Further, $X^2$ is —NA$^1$-. Still further, $X^3$ is —CR$^{80}$R$^{90}$—; R$^{80}$ is hydrogen; and R$^{90}$ is hydrogen, $C_{1-6}$alkyl, $C_{1-6}$-alkyl substituted with $C_{1-6}$alkoxy or $C_{6-14}$aryl, $C_{2-6}$alkenyl, or 3 to 8 membered heterocyclyl. More particularly, R$^{90}$ is $C_{1-6}$alkyl, $C_{1-6}$alkyl substituted with $C_{1-6}$alkoxy or $C_{6-14}$aryl, $C_{2-6}$alkenyl, or 3 to 8 membered heterocyclyl. Further, R$^{90}$ is ethyl, isopropyl, t-butyl, sec-butyl, benzyl, 1-propenyl, —C(CH$_3$)$_2$OCH$_3$, —CH(CH$_3$)OCH$_3$, or oxane. Still further, R$^{90}$ is $C_{1-6}$alkyl. In one embodiment, R$^{90}$ is t-butyl.

While not wishing to be bound by any particular theory, the particular aspects and embodiments concerning $X^2$, $X^3$ and $R^{90}$ are believed to provide potential benefits to such compounds not heretofore recognized. Applicants believe the reduction of hydrogen bond donor/acceptor pairs could provide beneficial pharmacokinetic properties.

In another embodiment, which may be distinct or combined with other aspects and embodiments, R$^1$ is

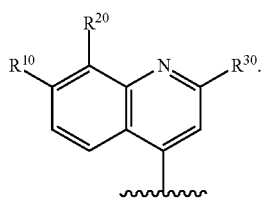

Further, R$^{10}$ is $C_{1-6}$alkoxy optionally substituted with one or more $C_{1-6}$alkoxy or heterocyclyl; R$^{20}$ is halogen or $C_{1-6}$alkyl; and R$^{30}$ is heteroaryl, optionally substituted with one or more $C_{1-6}$alkyl.

In another embodiment, which may be distinct or combined with other aspects and embodiments, $Z^1$ is —O— and $Z^2$ is —O—.

In another embodiment, which may be distinct or combined with other aspects and embodiments, A$^1$ is hydrogen.

In another embodiment, which may be distinct or combined with other aspects and embodiments, R$^2$ is $C_{1-6}$alkyl or $C_{2-6}$alkenyl. In particular, R$^2$ is ethyl or vinyl. In one embodiment, which may be distinct or combined with other embodiments, R$^2$ is $C_{1-6}$alkyl substituted with halogen, preferably mono-, di-, or tri-substituted with fluorine.

In another embodiment, which may be distinct or combined with other aspects and embodiments, Y is —C(O)NHS(O)$_2$OR$^{100}$. Further, R$^{100}$ is $C_{3-8}$ cycloalkyl. In particular, R$^{100}$ is cyclopropyl. Alternatively, R$^{100}$ is $C_{1-6}$alkyl substituted with $C_{3-8}$cycloalkyl. In particular, R$^{100}$ is ethyl substituted with cyclopropyl, preferably ethyl spiro-substituted with cyclopropyl, namely —C(—CH$_2$—CH$_2$—)—CH$_3$, or otherwise referenced as 1-methyl-cyclopropyl.

As will be appreciated by those skilled in the art, a variety of additional substituent patterns may be employed for Y. As examples, substituent patterns such as those listed in WO 06/020276, WO 08/005,565, WO 09/070,689, WO 09/005,676, or WO 09/005677 may be employed.

Another embodiment, which may be distinct or combined with other aspects and embodiments, provides the compound of Formula I:

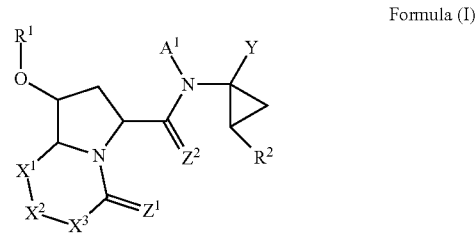

Formula (I)

or a pharmaceutically acceptable salt thereof, wherein R$^1$ is

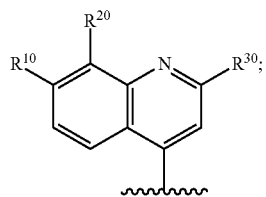

R$^{10}$ is hydrogen or $C_{1-6}$alkoxy optionally substituted with one or more $C_{1-6}$alkoxy or heterocyclyl;

R$^{20}$ is hydrogen, halogen, $C_{1-6}$alkyl, or $C_{1-6}$haloalkyl;

R$^{30}$ is heteroaryl, optionally substituted with one or more $C_{1-6}$alkyl;

$X^1$ is —CH$_2$— or —CH$_2$—CH$_2$—;

$X^2$ is —NA$^1$-, —O—, or —CH$_2$—;

$X^3$ is —NA$^1$- or —CR$^{80}$R$^{90}$—;

R$^{80}$ is hydrogen;

R$^{90}$ is hydrogen, $C_{1-6}$alkyl, $C_{1-6}$alkyl substituted with $C_{1-6}$alkoxy or $C_{6-14}$aryl, $C_{2-6}$alkenyl, or 3 to 8 membered heterocyclyl;

$Z^1$ is O or S;

$Z^2$ is O or S;

each A$^1$ independently is hydrogen, $C_{1-6}$alkyl, —C(O)OC$_{1-6}$alkyl, —C(O)OC$_{3-8}$cycloalkyl, —C(O)NHC$_{1-6}$alkyl, —C(O)C$_{1-6}$alkyl, or —S(O)$_2$C$_{1-6}$alkyl;

R$^2$ is $C_{1-8}$alkyl, $C_{2-8}$alkenyl, or $C_{2-8}$alkynyl;

Y is —C(O)NHS(O)$_2$OR$^{100}$; and

R$^{100}$ is $C_{1-6}$alkyl, $C_{1-6}$alkyl substituted with $C_{3-8}$cycloalkyl, or $C_{3-8}$ cycloalkyl.

In another embodiment, which may be distinct or combined with other aspects and embodiments, R$^2$ may combine with $X^3$ and the atoms to which they are attached to form a 14 to 16 membered heterocycle. Further, the heterocycle is 15 membered and contains a double bond from R$^2$. Still further, R$^1$ is

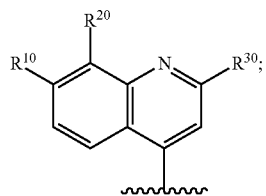

$R^{10}$ is hydrogen or $C_{1-6}$alkoxy optionally substituted with one or more $C_{1-6}$alkoxy or heterocyclyl; $R^{20}$ is hydrogen, halogen, $C_{1-6}$alkyl, or $C_{1-6}$haloalkyl; $R^{30}$ is heteroaryl, optionally substituted with one or more $C_{1-6}$alkyl; $X^1$ is —$CH_2$— or —$CH_2$—$CH_2$—; $X^2$ is —$NA^1$- or —$CH_2$—; $X^3$ is —$NA^1$- or —$CR^{80}R^{90}$—; $R^{80}$ is hydrogen; $R^{90}$ is hydrogen, $C_{1-6}$alkyl, $C_{1-6}$alkyl substituted with $C_{1-3}$alkoxy or $C_{6-14}$aryl, $C_{2-6}$alkenyl, or 3 to 8 membered heterocyclyl; $Z^1$ is O or S; $Z^2$ is O or S; each $A^1$ independently is hydrogen, $C_{1-6}$alkyl, —C(O)OC$_{1-6}$alkyl, —C(O)OC$_{3-8}$cycloalkyl, —C(O)NHC$_{1-6}$alkyl, —C(O)C$_{1-6}$alkyl, or —S(O)$_2$C$_{1-6}$alkyl; $R^2$ is $C_{1-8}$alkyl, $C_{2-8}$alkenyl, or $C_{2-8}$alkynyl; Y is —C(O)NHS(O)$_2$OR$^{100}$; and $R^{100}$ is $C_{1-6}$alkyl, $C_{1-6}$alkyl substituted with $C_{3-8}$cycloalkyl, or $C_{3-8}$ cycloalkyl.

In one embodiment, the compound of Formula I has a stereochemical configuration of:

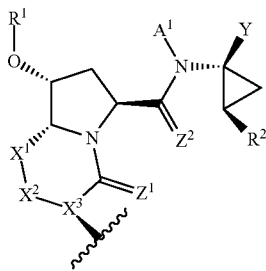

Another aspect of the present invention, which may be distinct or combined with other aspects and embodiments, includes a compound of Formula (Ia):

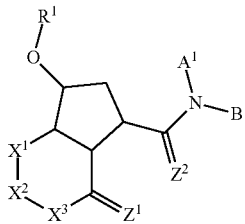

Formula (Ia)

or a pharmaceutically acceptable salt thereof, wherein
B is i) —(CHA$^2$)-C(O)—C(O)—NHA$^1$; or ii)

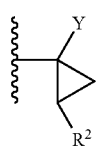

$R^1$ is

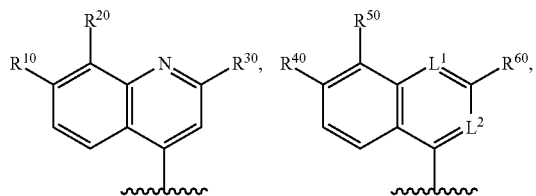

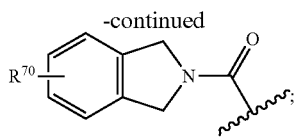

$R^{10}$ is hydrogen or $C_{1-6}$alkoxy optionally substituted with one or more $C_{1-6}$alkoxy or heterocyclyl;
$R^{20}$ is hydrogen, halogen, $C_{1-6}$alkyl, or $C_{1-6}$haloalkyl; or
$R^{10}$ and $R^{20}$ combine with the atoms to which they are attached to form a 5 to 7 membered heterocycle;
$R^{30}$ is
  $C_{1-6}$alkoxy,
  aryl, optionally substituted with one or more $C_{1-6}$alkyl,
  heteroaryl, optionally substituted with one or more $C_{1-6}$alkyl, or $C_{1-6}$alkyl substituted with NA$^1$A$^2$;
$R^{40}$ is hydrogen or $C_{1-6}$alkoxy optionally substituted with one or more $C_{1-6}$alkoxy or heterocyclyl;
$R^{50}$ is hydrogen, halogen, $C_{1-6}$alkyl, or $C_{1-6}$haloalkyl;
$R^{60}$ is hydrogen, halogen, —CN, —C(O)NA$^1$A$^2$, $C_{1-6}$alkoxy, or $C_{6-10}$aryl, where said $C_{6-10}$aryl is optionally substituted with one or more halogen, $C_{1-6}$alkyl, or $C_{1-6}$alkoxy;
$L^1$ is CH or N;
$L^2$ is CH or N;
$R^{70}$ is halogen or $C_{1-6}$alkoxy substituted with NA$^1$A$^2$;
$X^1$ is —$CH_2$— or —$CH_2$—$CH_2$—;
$X^2$ is —NA$^1$-, —$CH_2$—, or —O—;
$X^3$ is —NA$^1$- or —CR$^{90}$R$^{90}$—;
$R^{80}$ is hydrogen;
$R^{90}$ is hydrogen, $C_{1-6}$alkyl, $C_{1-6}$alkyl substituted with $C_{1-6}$alkoxy or $C_{6-14}$aryl, $C_{2-6}$alkenyl, 3 to 8 membered heterocyclyl, or —NA$^1$A$^2$;
$Z^1$ is O, S, NA$^1$, N(OA$^1$), or N(N(A$^1$)(A$^2$));
$Z^2$ is O, S, or NA$^1$;
each $A^1$ independently is hydrogen, $C_{1-6}$alkyl, —C(O)OC$_{1-6}$alkyl, —$C_{3-8}$cycloalkyl, —C(O)OC$_{3-8}$cycloalkyl, —C(O)NHC$_{1-6}$alkyl, —C(O)C$_{1-6}$alkyl, or —S(O)$_2$C$_{1-6}$alkyl;
each $A^2$ independently is hydrogen or $C_{1-6}$alkyl;
$R^2$ is $C_{1-8}$alkyl, $C_{1-8}$alkyl substituted with halogen, $C_{2-8}$alkenyl, or $C_{2-8}$alkynyl; or
$R^2$ may combine with $X^3$ and the atoms to which they are attached to form a 14 to 16 membered heterocycle;
Y is —C(O)OH, —C(O)NHS(O)$_2$OR$^{100}$, —C(O)NHS(O)$_2$R$^{100}$, —C(O)NHS(O)$_2$NA$^1$A$^2$, or —P(O)(OH)R$^{110}$;
$R^{100}$ is $C_{1-6}$alkyl, $C_{1-6}$alkyl substituted with $C_{3-8}$cycloalkyl, or $C_{3-8}$ cycloalkyl; and
$R^{110}$ is hydrogen, —OH, —C(O)OH, —CN, $C_{1-6}$alkyl, $C_{2-6}$alkenyl, $C_{2-6}$alkynyl, —NA$^1$A$^2$, —C(O)NA$^1$A$^2$, —NA$^1$C(O)A$^2$, —C(O)NA$^1$C(O)A$^2$, —C(=NA$^1$)A$^2$, halogen, $C_{1-6}$haloalkyl, $C_{3-8}$ cycloalkyl, —NO$_2$, $C_{6-14}$aryl, $C_{7-20}$aralkyl, $C_{1-6}$alkoxy, $C_{6-14}$aryloxy, 3 to 8 membered heterocyclyl, or 3 to 8 membered heteroaryl.

Another aspect of the present invention includes a pharmaceutical composition comprising a compound according to the present invention and one or more pharmaceutically acceptable carrier or excipient. In a further embodiment, one or more additional therapeutic agent is also provided in the composition.

Another aspect of the present invention includes a method for treating a viral infection comprising administering a compound of the present invention. In one embodiment, the treatment results in one or more of a reduction in viral load or clearance of RNA.

Another aspect of the present invention includes use of a compound of the present invention for the manufacture of a medicament for the treatment of a viral infection. Another aspect includes a compound for use in treating a viral infection. In one embodiment of each aspect of use and compound, the treatment results in one or more of a reduction in viral load or clearance of RNA.

Another aspect of the present invention includes a method for treating or preventing HCV comprising administering a compound of the present invention. Another aspect includes the use of a compound of the present invention for the manufacture of a medicament for the treatment or prevention of HCV.

The present invention also provides a pharmaceutical composition comprising a compound of the invention and at least one pharmaceutically acceptable carrier.

The present invention also provides a pharmaceutical composition for use in treating disorders associated with HCV.

The present invention also provides a pharmaceutical composition further comprising a nucleoside analog.

The present invention also provides for a pharmaceutical composition further comprising an interferon or pegylated interferon.

The present invention also provides for a pharmaceutical composition wherein said nucleoside analogue is selected from ribavirin, viramidine levovirin, a L-nucleoside, and isatoribine and said interferon is a-interferon or pegylated interferon.

The present invention also provides for a method of treating disorders associated with hepatitis C, said method comprising administering to an individual a pharmaceutical composition which comprises a therapeutically effective amount of a compound of the invention.

The present invention also provides a method of inhibiting HCV, comprising administering to a mammal afflicted with a condition associated with HCV activity, an amount of a compound of the invention, effective to inhibit HCV.

The present invention also provides a compound of the invention for use in medical therapy (preferably for use in inhibiting HCV or treating a condition associated with HCV activity), as well as the use of a compound of the invention for the manufacture of a medicament useful for inhibiting HCV or the treatment of a condition associated with HCV activity in a mammal.

The present invention also provides synthetic processes and novel intermediates disclosed herein which are useful for preparing compounds of the invention. Some of the compounds of the invention are useful to prepare other compounds of the invention.

In another aspect the invention provides a method of inhibiting HCV activity in a sample comprising treating the sample with a compound of the invention.

In one embodiment the invention provides a compound having improved inhibitory or pharmacokinetic properties, including enhanced activity against development of viral resistance, improved oral bioavailability, greater potency or extended effective half-life in vivo. Certain compounds of the invention may have fewer side effects, less complicated dosing schedules, or be orally active.

Another aspect of the present invention includes pharmaceutical composition comprising a compound of the present invention and one or more pharmaceutically acceptable carrier or excipient. The pharmaceutical composition of the present invention may further comprise one or more additional therapeutic agent. The one or more additional therapeutic agent may be, without limitation, selected from: interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophilin inhibitors, HCV IRES inhibitors, pharmacokinetic enhancers, and other drugs for treating HCV, or mixtures thereof.

Another aspect of the present invention includes a method for treating a viral infection comprising administering a compound of the present invention. The compound is administered to a human subject in need thereof, such as a human being who is infected with a virus of the Flaviviridae family, such as hepatitis C virus. In one embodiment, the viral infection is acute or chronic HCV infection. In one embodiment, the treatment results in one or more of a reduction in viral load or clearance of RNA.

Another aspect of the present invention includes the use of a compound according to the present invention for the manufacture of a medicament for the treatment of a viral infection. Another aspect of the present invention includes a compound according to the present invention for the use in treating a viral infection. In one embodiment, the viral infection is acute or chronic HCV infection. In one embodiment, the treatment results in one or more of a reduction in viral load or clearance of RNA.

The present invention includes combinations of aspects and embodiments, as well as preferences, as herein described throughout the present specification.

BRIEF DESCRIPTION OF THE FIGURES

FIG. 1 illustrates compound 51, a single diastereomer as determined by X-ray crystallography.

DETAILED DESCRIPTION OF THE INVENTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

All documents referenced herein are each incorporated by reference in their entirety for all purposes.

Definitions

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and octyl (—(CH$_2$)$_7$CH$_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—CH$_3$ or —OMe), ethoxy (—OCH$_2$CH$_3$ or —OEt), t-butoxy (—O—C(CH$_3$)$_3$ or —OtBu), and the like.

"Alkenyl" is a hydrocarbon containing normal, secondary, tertiary, or cyclic carbon atoms with at least one site of unsaturation, i.e. a carbon-carbon, sp2 double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne,), or 2 to 6 carbon atoms (i.e., $C_2$-$C_6$ alkynyl). Examples of suitable alkynyl groups include, but are not limited to, acetylenic (—C≡CH), propargylic (—CH$_2$C≡CH), and the like.

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylalkyl" or "aralkyl" refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

Similarly, "aryloxy" refers to an acyclic alkoxy radical in which one of the hydrogen atoms bonded to a carbon atom, typically a terminal or sp3 carbon atom, is replaced with an aryl radical. The arylalkoxy group can comprise 6 to 20 carbon atoms, e.g., the alkoxy moiety is 1 to 6 carbon atoms and the aryl moiety is 6 to 14 carbon atoms.

"Cycloalkyl" refers to a saturated or partially unsaturated ring having 3 to 7 carbon atoms as a monocycle, 7 to 12 carbon atoms as a bicycle, and up to about 20 carbon atoms as a polycycle. Monocyclic cycloalkyl groups have 3 to 6 ring atoms, still more typically 5 or 6 ring atoms. Bicyclic cycloalkyl groups have 7 to 12 ring atoms, e.g., arranged as a bicyclo (4,5), (5,5), (5,6) or (6,6) system, or 9 or 10 ring atoms arranged as a bicyclo (5,6) or (6,6) system. Cycloalkyl groups include hydrocarbon mono-, bi-, and poly-cyclic rings, whether fused, bridged, or spiro. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

"Halogen" refers to F, Cl, Br, or I.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —CF$_3$.

As used herein, the term "haloalkoxy" refers to a group —OR$^a$, where R$^a$ is a haloalkyl group as herein defined. As non-limiting examples, haloalkoxy groups include —O(CH$_2$)F, —O(CH)F$_2$, and —OCF$_3$.

"Heterocycle" or "heterocyclyl" refers to a saturated or partially saturated cyclic group having from 1 to 14 carbon atoms and from 1 to 6 heteroatoms selected from N, S, P, or O, and includes single ring and multiple ring systems including, fused, bridged, and spiro ring systems. "Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and J. Am. Chem. Soc. (1960) 82:5566. In one embodiment, the carbon, nitrogen, phosphorus, or sulfur atom(s) of the heterocyclic group may be oxidized to provide for C(=O), N-oxide, phosphinane oxide, sulfinyl, or sulfonyl moieties.

As one example, substituted heterocyclyls include, for example, heterocyclic rings substituted with any of the substituents disclosed herein, including oxo groups. A non-limiting example of a carbonyl substituted heterocyclyl is:

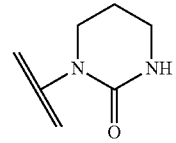

Examples of heterocycles include by way of example and not limitation dihydroypyridyl, tetrahydropyridyl (piperidyl), tetrahydrothiophenyl, sulfur oxidized tetrahydrothiophenyl, piperidinyl, 4-piperidonyl, pyrrolidinyl, azetidinyl, 2-pyrrolidonyl, tetrahydrofuranyl, decahydroquinolinyl, octahy droisoquinolinyl, pyranyl, morpholinyl, and bis-tetrahydrofuranyl:

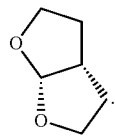

"Heteroaryl" refers to a monovalent aromatic heterocyclyl having at least one heteroatom in the ring. Thus, "heteroaryl" refers to an aromatic group of from 1 to 14 carbon atoms and 1 to 6 heteroatoms selected from oxygen, nitrogen, sulfur, or phosphorus. For multiple ring systems, including fused, bridged, and spiro ring systems having aromatic and non-aromatic rings. In one embodiment, the carbon, nitrogen, or sulfur ring atom(s) of the heteroaryl group may be oxidized to provide for C(=O), N-oxide, sulfinyl, or sulfonyl moieties.

Non-limiting examples of heteroaryl rings include by way of example and not limitation pyridyl, thiazolyl, pyrimidinyl, furanyl, thienyl, pyrrolyl, pyrazolyl, imidazolyl, tetrazolyl, benzofuranyl, thianaphthalenyl, indolyl, quinolinyl, isoquinolinyl, benzimidazolyl, tetrahydroquinolinyl, tetrahydroisoquinolinyl, 6H-1,2,5-thiadiazinyl, 2H,6H-1,5,2-dithiazinyl, thienyl, thianthrenyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl, and the like.

When there is a sulfur atom present, the sulfur atom can be at different oxidation levels, namely, S, SO, $SO_2$, or $SO_3$. All such oxidation levels are within the scope of the present invention.

The term "optionally substituted" in reference to a particular moiety of the compound of the Formulae of the invention, for example an "optionally substituted aryl group", refers to a moiety having none, one, or more substituents.

The term "substituted" in reference to a particular moiety of the compound of the Formulae of the invention, for example, "substituted aryl", refers to a moiety in which one or more hydrogen atoms are each independently replaced with a non-hydrogen substituent. Divalent groups may also be similarly substituted.

Those skilled in the art will recognize that when moieties such as "alkyl", "aryl", "heterocyclyl", etc. are substituted with one or more substituents, they could alternatively be referred to as "alkylene", "arylene", "heterocyclylene", etc. moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc. are understood to be interchangeable with "alkylene", "arylene", "heterocyclylene", etc.

As will be appreciated by those skilled in the art, the compounds of the present invention may exist in solvated or hydrated form. The scope of the present invention includes such forms. Again, as will be appreciated by those skilled in the art, the compounds may be capable of esterification. The scope of the present invention includes esters and other physiologically functional derivatives. The scope of the present invention includes prodrug forms of the compound herein described.

"Ester" means any ester of a compound in which any of the —COOH functions of the molecule is replaced by a —C(O) OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Example of prodrugs include ester moieties, quaternary ammonium moieties, glycol moieties, and the like.

One skilled in the art will recognize that substituents and other moieties of the compounds of Formula I should be selected in order to provide a compound which is sufficiently stable to provide a pharmaceutically useful compound which can be formulated into an acceptably stable pharmaceutical composition. Compounds of Formula I which have such stability are contemplated as falling within the scope of the present invention.

As will be appreciated by those skilled in the art, the compounds of the present invention may contain one or more chiral centers. The scope of the present invention includes such forms. Again, as will be appreciated by those skilled in the art, the compound is capable of esterification. The scope of the present invention includes esters and other physiologically functional derivatives. In addition, the scope of the present invention includes prodrug forms of the compound herein described.

In one embodiment, the compounds of the present invention have a preferential stereochemical configuration:

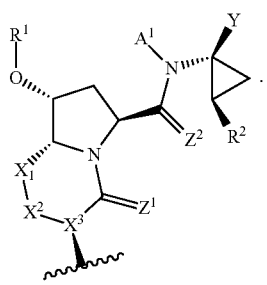

The compounds of the present invention may crystallize in more than one form, a characteristic known as polymorphism, and such polymorphic forms ("polymorphs") are within the scope of the present invention. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or 1 meaning that the compound is levorotatory. A compound prefixed with (+) or d is dextrorotatory.

A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, N.Y., 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

The definitions and substituents for various genus and sub-genus of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-dial, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.001 to about 100 mg/kg body weight per day, typically from about 0.1 to about 50 mg/kg body weight per day, more typically from about 1.0 to about 10 mg/kg body weight per day.

In yet another embodiment, the present application discloses pharmaceutical compositions comprising a compound of Formula I or a pharmaceutically acceptable salt thereof, and a pharmaceutically acceptable carrier or excipient.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy, Including HCV Combination Therapy

In another embodiment, the compounds of the present invention may be combined with one or more active agent. Non-limiting examples of suitable combinations include combinations of one or more compounds of the present invention with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

More specifically, one or more compounds of the present invention may be combined with one or more compounds selected from the group consisting of:

1) interferons, e.g., pegylated rIFN-alpha 2b (PEG-Intron), pegylated rIFN-alpha 2a (Pegasys), rIFN-alpha 2b (IntronA), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Weliferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (ION-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), AZD-7295 (A-689), and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib).

In yet another embodiment, the present application discloses pharmaceutical compositions comprising a compound of the present invention, or a pharmaceutically acceptable salt thereof, in combination with at least one additional active agent, and a pharmaceutically acceptable carrier or excipient. In yet another embodiment, the present application provides a combination pharmaceutical agent with two or more therapeutic agents in a unitary dosage form. Thus, it is also possible to combine any compound of the invention with one or more other active agents in a unitary dosage form.

The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Methods of Treatment

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" or a "partial antagonist" is a substance that provides a level of stimulation or inhibition, respectively, to its binding partner that is not fully or completely agonistic or antagonistic, respectively. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. Where such contextually specific evaluations are relevant, and how they might be relevant in the context of the present invention, will be apparent to one of ordinary skill in the art.

As used herein, modulation of a receptor includes agonism, partial agonism, antagonism, partial antagonism, or inverse agonism of a receptor.

As will be appreciated by those skilled in the art, when treating a viral infection such as HCV, such treatment may be characterized in a variety of ways and measured by a variety of endpoints. The scope of the present invention is intended to encompass all such characterizations.

SYNTHETIC EXAMPLES

Preparation of the HCl salt of 1-methyl-cyclopropanesulfonic acid ((1R,2S)-1-amino-2-vinyl-cyclopropanecarbonyl)-amide and the HCl salt of cyclopropanesulfonic acid ((1R,2S)-1-amino-2-vinyl-cyclopropanecarbonyl)-amide The HCl salt of 1-methyl-cyclopropanesulfonic acid ((1R,2S)-1-amino-2-vinyl-cyclopropanecarbonyl)-amide and the HCl salt of cyclopropanesulfonic acid ((1R,2S)-1-amino-2-vinyl-cyclopropanecarbonyl)-amide were prepared as described in U.S. Pat. No. 7,592,336B2 and WO2005051410A1

Preparation of the HCl salt of cyclopropanesulfonic acid ((1R,2S)-1-amino-2-ethyl-cyclopropanecarbonyl)-amide The HCl salt of cyclopropanesulfonic acid ((1R,2S)-1-amino-2-ethyl-cyclopropanecarbonyl)-amide could be prepared by a diimide reduction of Boc protected ((1R,2S)-1-amino-2-vinyl-cyclopropanecarbonyl)-amide, followed by removal of the Cob protecting group with 4N HCl in dioxane.

Preparation of 4,8-dichloro-2-(2-isopropyl-thiazol-4-yl)-7-(2-morpholin-4-yl-ethoxy)-quinoline

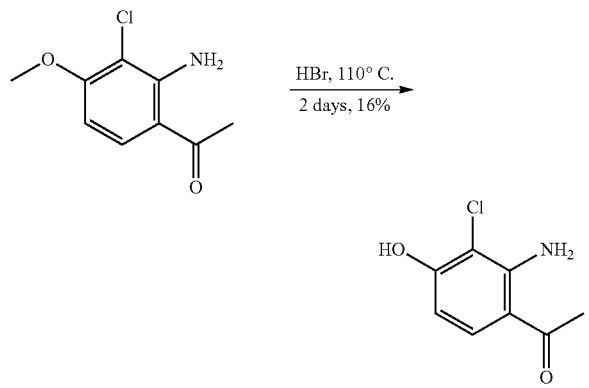

1-(2-Amino-4-methoxy-3-chloro-phenyl)ethanone (71.55 g, 358 mmol) was dissolved in HBr (500 mL, 48% in H₂O). The reaction was heated to 110° C. for 2 days. The reaction was cooled to rt then the solids were filtered. The solids were partitioned between EtOAc and ½ sat Na₂CO₃(aq). Organics were dried over Na₂SO₄, filtered and solvent removed under reduced pressure. 1-(2-Amino-3-chloro-4-hydroxy-phenyl)-ethanone (15.5 g, 16%) was isolated by silica gel chromatography as an off-white solid.
LC/MS=186 (M⁺+1)

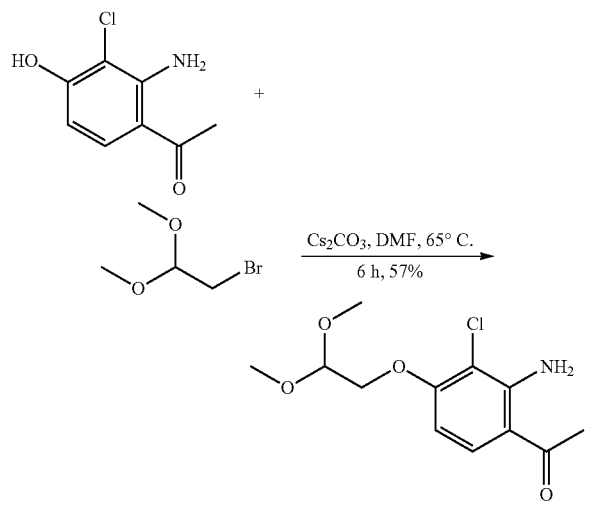

1-(2-Amino-3-chloro-4-hydroxy-phenyl)-ethanone (15.5 g, 83.8 mmol), Cs₂CO₃ (54.6 g, 167 mmol) and 2-bromo-1,1-dimethoxy-ethane (14.78 mL, 126 mmol) was dissolved in DMF (125 mL) under an atmosphere of nitrogen. The reaction was heated to 65° C. for 6 hours. The reaction was determined to be complete by LC/MS. The reaction was taken up in EtOAc (500 mL) and washed with 5% LiCl(aq) (3×250 mL). Organics were dried over Na₂SO₄, filtered and solvent removed under reduced pressure. 1-[2-Amino-3-chloro-4-(2, 2-dimethoxy-ethoxy)-phenyl]-ethanone (12.99 g, 57%) was isolated by silica gel chromatography as a white solid.
LC/MS=274 (M⁺+1)

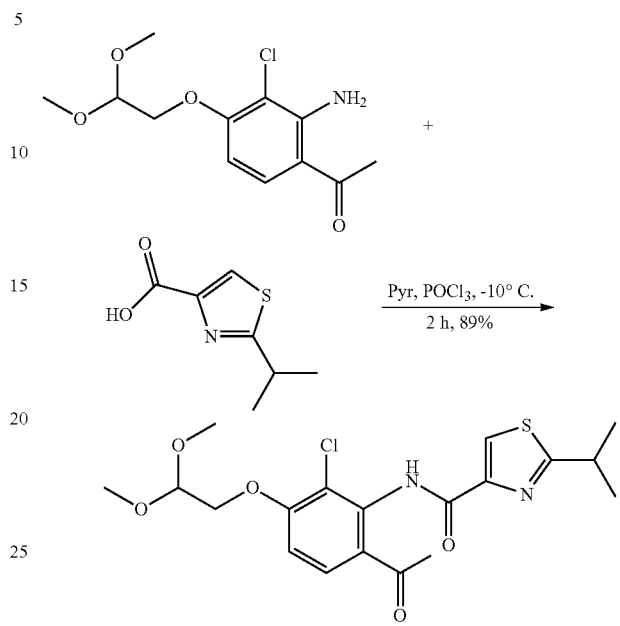

1-[2-amino-3-chloro-4-(2,2-dimethoxy-ethoxy)phenyl]-ethanone (3.98 g, 14.6 mmol) and 2-isopropyl-thiazole-4-carboxylic acid (2.5 g, 14.6 mmol) was dissolved in pyridine (40 mL) and was cooled to −10° C. POCl₃ (1.74 mL, 19.0 mmol) was added dropwise. The reaction was stirred at −10° C. for 2 hours. The reaction was quenched with CH₃OH (5 mL). After 15 minutes, the reaction was taken up in EtOAc and extracted with 2N HCl(aq). The organic layer was dried with Na₂SO₄, filtered and was concentrated. 2-Isopropyl-thiazole-4-carboxylic acid [6-acetyl-2-chloro-3-(2,2-dimethoxy-ethoxy)-phenyl]-amide (5.58 g, 89%) was isolated by silica gel chromatography as a white solid.
LC/MS=427 (M⁺)

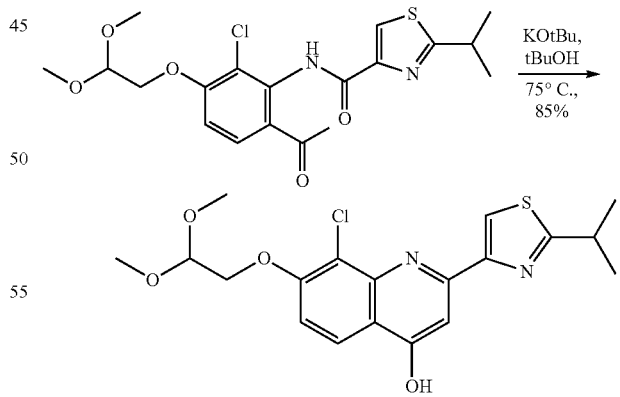

2-Isopropyl-thiazole-4-carboxylic acid [6-acetyl-2-chloro-3-(2,2-dimethoxy-ethoxy)-phenyl]-amide (5.5 g, 12.91 mmol) and KOtBu (3.04 g, 27.11 mmol) were dissolved in tBuOH (100 mL) under an atmosphere of nitrogen. The reaction was heated to 75° C. for 4 hours. The reaction was cooled to rt and the pH was adjusted to 4 with 2N HCl(aq). The reaction mixture was concentrated and taken up in EtOAc (100 mL). The mixture was washed with ½ sat. brine. The organic layer was dried with Na₂SO₄, filtered and was concentrated. 8-Chloro-7-(2,2-dimethoxy-ethoxy)-2-(2-isopropyl-thiazol-4-yl)-quinolin-4-ol (4.49 g, 85%) was isolated by silica gel chromatography as a yellow solid.

LC/MS=409 (M⁺+1)

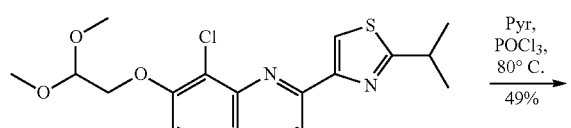

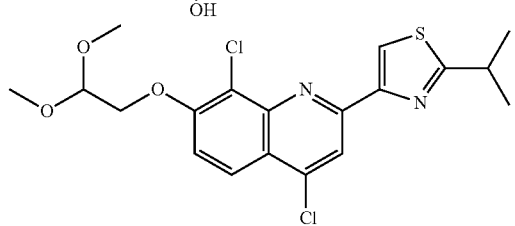

8-Chloro-7-(2,2-dimethoxy-ethoxy)-2-(2-isopropyl-thiazol-4-yl)-quinolin-4-ol (502 mg, 1.20 mmol) was dissolved in pyridine (10 mL). POCl₃ (2.29 mL, 25.0 mmol) was added slowly. The reaction was heated at 80° C. for 4 hours. The reaction was cooled to 0° C. and methanol (5 mL) was added. The reaction was neutralized with a sat NaHCO₃₍aq₎ solution. The product was extracted with EtOAc (3×20 mL). The combined organics were dried with Na₂SO₄, filtered and was concentrated. 4,8-Dichloro-7-(2,2-dimethoxy-ethoxy)-2-(2-isopropyl-thiazol-4-yl)-quinoline (256 mg, 49%) was isolated by silica gel chromatography as a yellow solid.

LC/MS=427 (M⁺+1)

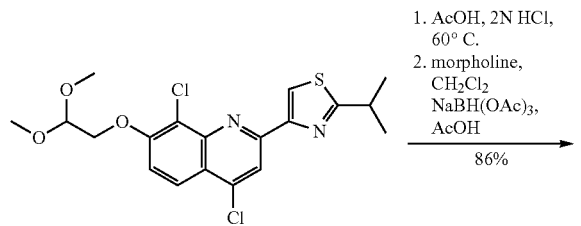

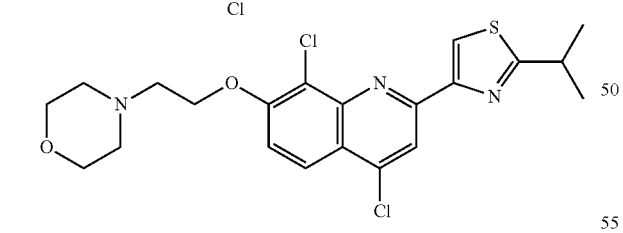

4,8-Dichloro-7-(2,2-dimethoxy-ethoxy)-2-(2-isopropyl-thiazol-4-yl)-quinoline (250 mg, 0.565 mmol) was dissolved in AcOH (5.0 mL) and 2N HCl₍aq₎. The reaction mixture was placed in a 60° C. oil bath and stirred for 1 h. Remove solvent under reduced pressure. The crude material was taken up in EtOAc and washed with ½ sat NaHCO₃₍aq₎. Organics were dried over Na₂SO₄, filtered and was concentrated. The crude material was then taken up in CH₂Cl₂. Morpholine (77 µL, 0.88 mmol) was added to the reaction mixture and stirred for 15 min. NaBH(OAc)₃ (161 mg, 0.761 mmol) and AcOH (1 drop) were added and the reaction was monitored by LC/MS.

After 5 min the reaction was determined to be complete. The mixture was diluted with DCM and washed with ½ sat brine, dried with Na₂SO₄, filtered and was concentrated. 4,8-dichloro-2-(2-isopropyl-thiazol-4-yl)-7-(2-morpholin-4-yl-ethoxy)-quinoline (218 mg, 86%) was isolated by silica gel chromatography as a yellow solid.

LC/MS=452 (M⁺+1)

Preparation of 4-chloro-2-(4-isopropyl-thiazol-2-yl)-7-methoxy-8-methyl-quinoline

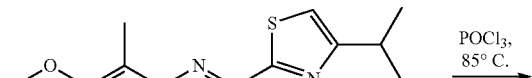

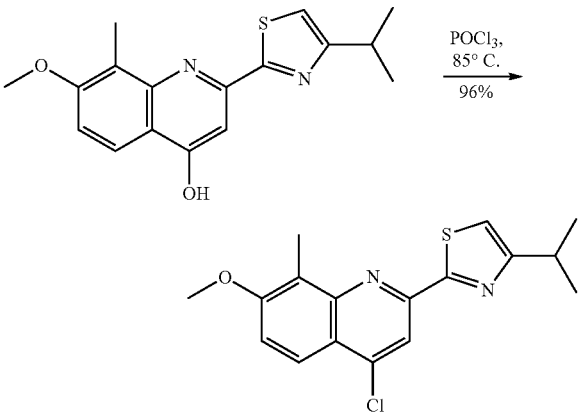

2-(4-Isopropyl-thiazol-2-yl)-7-methoxy-8-methyl-quinolin-4-ol (526 mg, 1.67 mmol) was taken up in POCl₃ (4.0 mL) and placed in a 85° C. oil bath. The reaction was monitored by LC/MS and determined to be complete after 40 min. The reaction was cooled to rt, and poured into ice water. Adjust pH=10 with 10N NaOH. The mixture was extracted with CH₂Cl₂, dried with Na₂SO₄, filtered and was concentrated to afford analytically clean 4-chloro-2-(4-isopropyl-thiazol-2-yl)-7-methoxy-8-methyl-quinoline (532 mg, 96%) as a yellow solid.

LC/MS=333 (M⁺+1)

Preparation of 4,8-dichloro-7-(2,2-dimethoxy-ethoxy)-2-(4-isopropyl-thiazol-2-yl)-quinoline

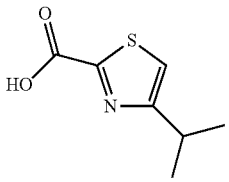

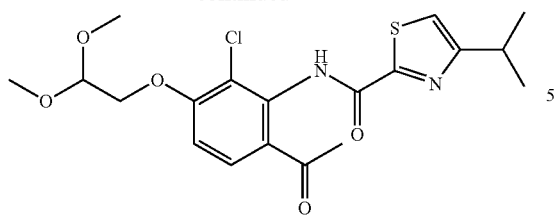

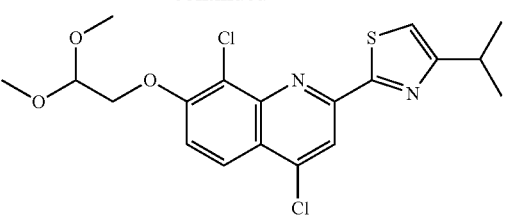

1-[2-amino-3-chloro-4-(2,2-dimethoxy-ethoxy)-phenyl]-ethanone (1.89 g, 6.92 mmol) and 4-isopropyl-thiazole-2-carboxylic acid (1.77 g, 10.38 mmol) was dissolved in pyridine (20 mL) and was cooled to −10° C. POCl$_3$ (0.823 mL, 8.99 mmol) was added dropwise. The reaction was stirred at −10° C. for 2 hours. The reaction was quenched with CH$_3$OH (5 mL). After 15 minutes, the reaction was taken up in EtOAc and extracted with 2N HCl$_{(aq)}$. The organic layer was dried with Na$_2$SO$_4$, filtered and was concentrated. 4-Isopropyl-thiazole-2-carboxylic acid [6-acetyl-2-chloro-3-(2,2-dimethoxy-ethoxy)-phenyl]-amide (2.84 g, 96%) was isolated by silica gel chromatography as a white solid.

LC/MS=427 (M$^+$)

8-Chloro-7-(2,2-dimethoxy-ethoxy)-2-(4-isopropyl-thiazol-2-yl)-quinolin-4-ol (512 mg, 1.25 mmol) was dissolved in pyridine (10 mL). POCl$_3$ (2.30 mL, 25.0 mmol) was added slowly. The reaction was heated at 80° C. for 4 hours. The reaction was cooled to 0° C. and methanol (5 mL) was added. The reaction was neutralized with a sat NaHCO$_{3(aq)}$ solution. The product was extracted with EtOAc (3×20 mL). The combined organics were dried with Na$_2$SO$_4$, filtered and was concentrated. 4,8-dichloro-7-(2,2-dimethoxy-ethoxy)-2-(4-isopropyl-thiazol-2-yl)-quinoline (0.275 mg, 52%) was isolated by silica gel chromatography as a yellow solid.

LC/MS=427 (M$^+$+1)

Preparation of 4,8-Dichloro-2-(4-isopropyl-thiazol-2-yl)-7-(2-morpholin-4-yl-ethoxy)-quinoline

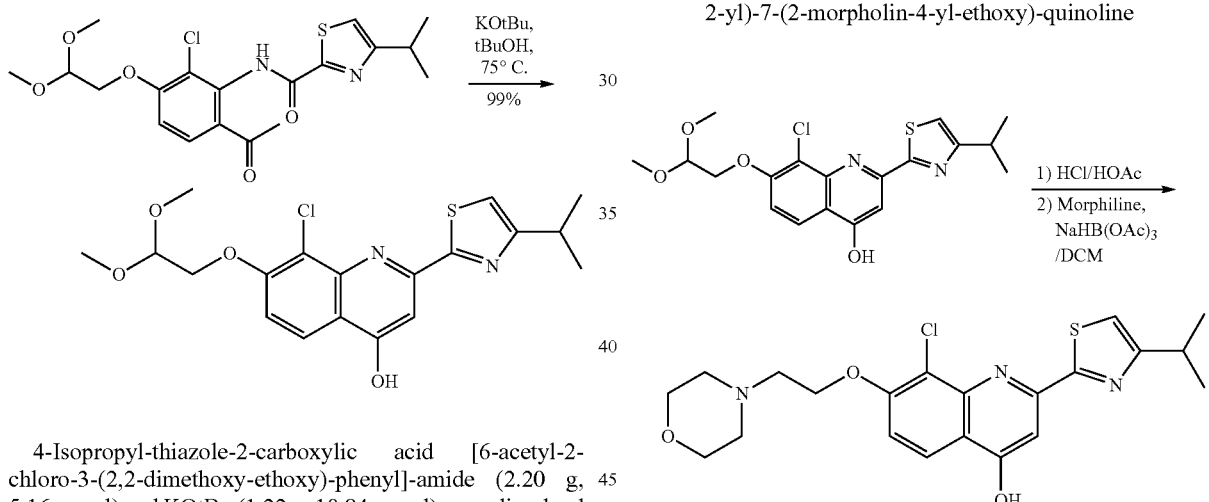

4-Isopropyl-thiazole-2-carboxylic acid [6-acetyl-2-chloro-3-(2,2-dimethoxy-ethoxy)-phenyl]-amide (2.20 g, 5.16 mmol) and KOtBu (1.22 g, 10.84 mmol) were dissolved in tBuOH (50 mL) under an atmosphere of nitrogen. The reaction was heated to 75° C. for 4 hours. The reaction was cooled to rt and the pH was adjusted to 4 with 2N HCl$_{(aq)}$. The reaction mixture was concentrated and taken up in EtOAc (100 mL). The mixture was washed with ½ sat. brine. The organic layer was dried with Na$_2$SO$_4$, filtered and was concentrated. 8-Chloro-7-(2,2-dimethoxy-ethoxy)-2-(4-isopropyl-thiazol-2-yl)-quinolin-4-ol (2.11 g, 99%) was isolated by silica gel chromatography as a yellow solid.

LC/MS=409 (M$^+$+1)

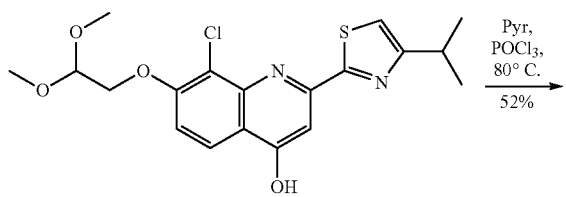

8-Chloro-7-(2,2-dimethoxy-ethoxy)-2-(4-isopropyl-thiazol-2-yl)-quinolin-4-ol (5.0 g, 12.3 mmol) was dissolved in HOAc (100 mL) and 1.4 N HCl/H$_2$O (50 mL). The reaction mixture was heated to 60° C. with stirring for 2 hrs. After cooled back to room temperature and concentrated, the residue was co-evaporated with toluene (2×50 mL). Then the crude was dissolved in DCM (100 mL) and cooled to 0° C. with stirring. Morphiline (1.6 g, 18.4 mmol) and NaHB(OAc)$_3$ (3.9 g, 18.4 mmol) were added to the reaction mixture. After stirring at room temperature for 1 h, the reaction mixture was washed with sat. NaHCO$_3$, brine and dried by Na$_2$SO$_4$. After concentration, the crude was purified by silica gel chromatography to afford 5.0 g of 8-chloro-2-(4-isopropyl-thiazol-2-yl)-7-(2-morpholin-4-yl-ethoxy)-quinolin-4-ol as a white solid.

LC/MS=434 (M$^+$+1)

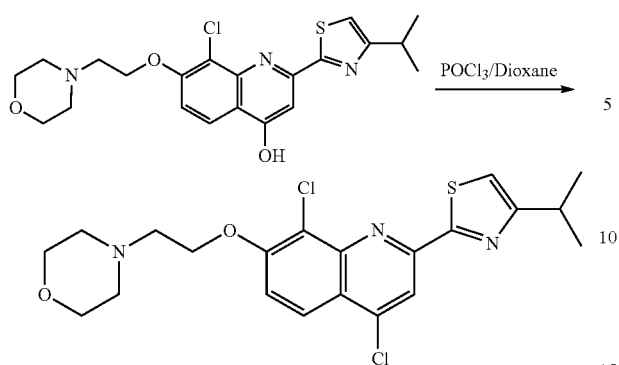

Preparation of 4,8-Dichloro-2-(6-isopropyl-pyridin-2-yl)-7-(2-methoxy-ethoxy)-quinoline

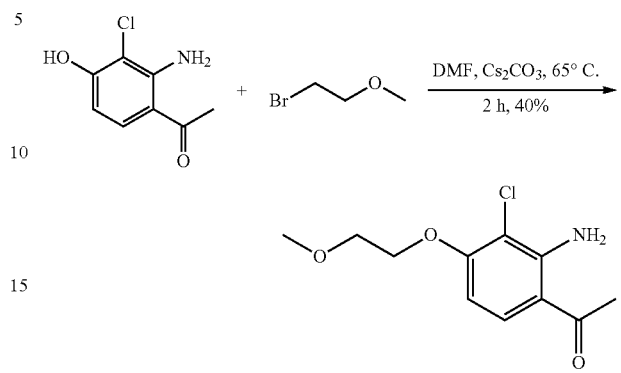

8-Chloro-2-(4-isopropyl-thiazol-2-yl)-7-(2-morpholin-4-yl-ethoxy)-quinolin-4-ol (5.0 g, 11.5 mmol) in dioxane (50 mL) were stirred at room temperature. POCl$_3$ (5.4 g, 34.6 mmol) was added slowly to the reaction mixture. The reaction was heated to 85° C. with stirring for 10 mins. The reaction was cooled to room temperature and was quenched with ice water. The solution was extracted with ethyl acetate (3×100 mL). The combined organics were dried with sodium sulfate, filtered and were concentrated. Compound XX (4.6 g, 90%) was purified by silica gel chromatography.

LC/MS=452 (M$^+$+1)

Preparation of 4-Chloro-2-ethoxy-7-methoxy-8-methyl-quinoline

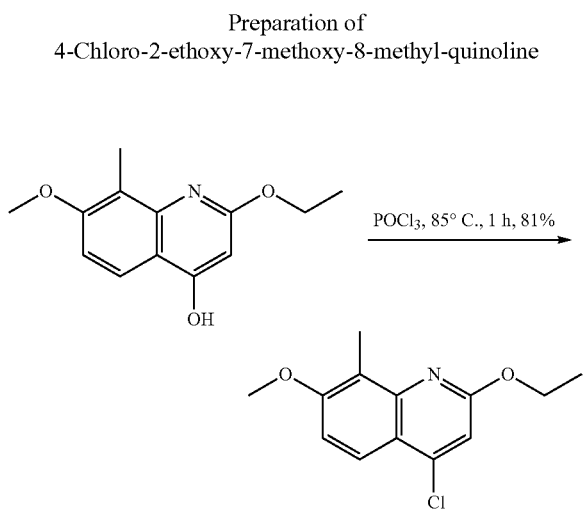

2-Ethoxy-7-methoxy-8-methyl-quinolin-4-ol (1.0 g, 4.3 mmol) was dissolved in POCl$_3$ (21 mL) under a nitrogen atmosphere. The reaction was heated to 85° C. for 1 h. The reaction was cooled to 0° C. and ice was added slowly. After 30 min, pH was adjusted to 6 with 1N NaOH(aq). The solution was extracted with ethyl acetate (2×50 mL). The organic layers were dried with sodium sulfate, filtered and were concentrated. 4-Chloro-2-ethoxy-7-methoxy-8-methyl-quinoline (875 mg, 81%) was purified by silica gel chromatography to afford a white solid.

LC/MS=252 (M$^+$+1)

1-(2-Amino-3-chloro-4-hydroxy-phenyl)-ethanone (6.8 g, 30.77 mmol) was dissolved in DMF (100 mL). To the reaction was added Cs$_2$CO$_3$ (30.08 g, 92.31 mmol). After 30 min, 1-bromo-2-methoxy-ethane (3.47 mL, 36.92 mmol) was added. The reaction was heated to 65° C. for 2 hours. The reaction was cooled to RT and was quenched with water. The solution was extracted with ethyl acetate (3×100 mL). The combined organics were dried with sodium sulfate, filtered and were concentrated. 1-[2-Amino-3-chloro-4-(2-methoxy-ethoxy)-phenyl]-ethanone (3.0 g, 40%) was purified by silica gel chromatography.

LC/MS=244 (M$^+$+1)

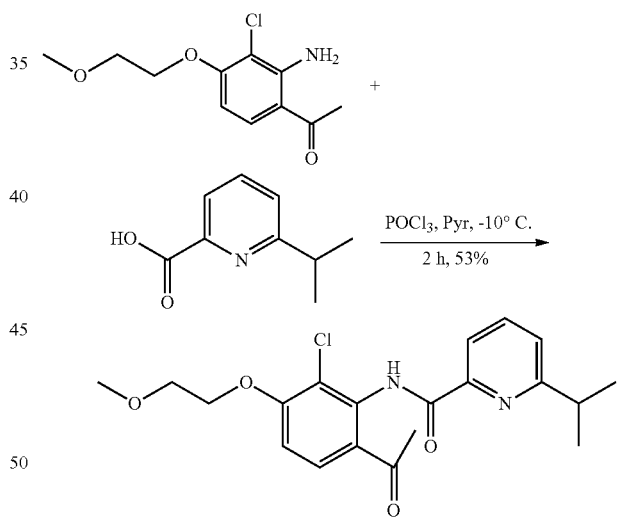

1-[2-Amino-3-chloro-4-(2-methoxy-ethoxy)-phenyl]-ethanone (3.0 g, 12.3 mmol) and 6-isopropyl-pyridine-2-carboxylic acid (2.03 g, 12.3 mmol) were dissolved in pyridine (100 mL) under a nitrogen atmosphere and was cooled to −10° C. POCl$_3$ (1.46 mL, 16.0 mmol) was added dropwise. After 2 hours, the starting acid was consumed. The reaction was quenched with 10 mL H$_2$O and a saturated aqueous bicarbonate solution. The product was extracted with ethyl acetate (2×75 mL). The combined organics were dried with sodium sulfate, filtered and were concentrated. 6-Isopropyl-pyridine-2-carboxylic acid [6-acetyl-2-chloro-3-(2-methoxy-ethoxy)-phenyl]-amide (2.57 g, 53%) was purified by silica gel chromatography.

LC/MS=391 (M$^+$+1)

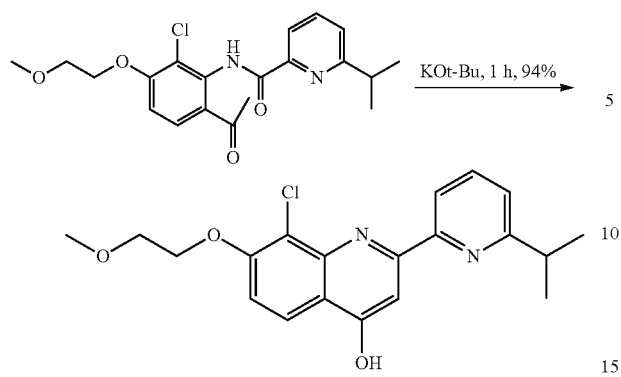

6-Isopropyl-pyridine-2-carboxylic acid [6-acetyl-2-chloro-3-(2-methoxy-ethoxy)-phenyl]-amide (2.42 g, 6.19 mmol) was dissolved in tertbutanol (25 mL) under an atmosphere of nitrogen. Potassium tertbutoxide (1.39 g, 12.38 mmol) was added. The reaction was heated to 80° C. for 1 hour. The reaction was cooled to RT and was neutralized with 1N HCl(aq). The product was extracted with ethyl acetate (2×30 mL). The combined organics were dried with sodium sulfate, filtered and were concentrated. 8-Chloro-2-(6-isopropyl-pyridin-2-yl)-7-(2-methoxy-ethoxy)-quinolin-4-ol (2.16 g, 94%) was purified by silica gel chromatography.
LC/MS=373 (M$^+$+1)

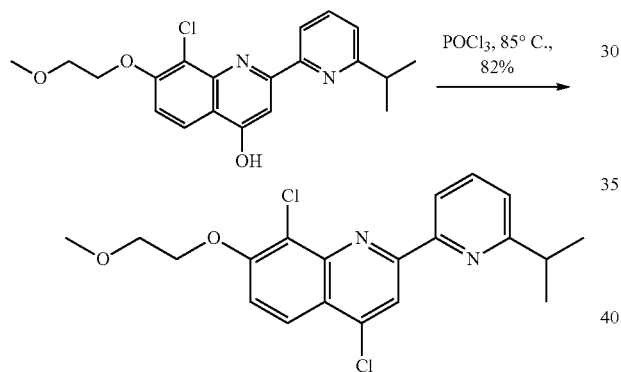

8-Chloro-2-(6-isopropyl-pyridin-2-yl)-7-(2-methoxy-ethoxy)-quinolin-4-ol (2.16 g, 5.8 mmol) was dissolved in POCl$_3$ (20 mL) under an atmosphere of nitrogen. The reaction was heated to 85° C. for 4 hours. The reaction was cooled to 0° C. and quenched with water. A saturated solution of sodium bicarbonate in water was used to neutralize the reaction. The reaction was extracted with ethyl acetate. The organic layer was dried with sodium sulfate, filtered and was concentrated. 4,8-Dichloro-2-(6-isopropyl-pyridin-2-yl)-7-(2-methoxy-ethoxy)-quinoline (1.87 g, 82%) was purified by silica gel chromatography.
LC/MS=391 (M$^+$+1)

Preparation of 4,8-Dichloro-2-(4-isopropyl-thiazol-2-yl)-7-(2-methoxy-ethoxy)-quinoline

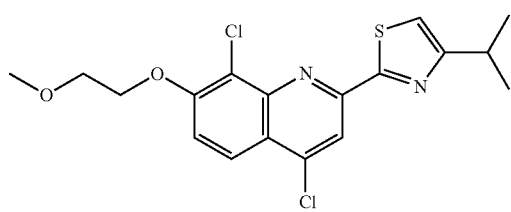 [SMILES: COCCOc1ccc2c(Cl)cc(-c3nc(C(C)C)cs3)nc2c1Cl]

4,8-Dichloro-2-(4-isopropyl-thiazol-2-yl)-7-(2-methoxy-ethoxy)-quinoline was prepared in a similar fashion as 4,8-Dichloro-2-(6-isopropyl-pyridin-2-yl)-7-(2-methoxy-ethoxy)-quinoline except that the lithium salt of 4-isopropyl-thiazole-2-carboxylate was used instead of 6-isopropyl-pyridine-2-carboxylic acid.
LC/MS=397 (M$^+$+1)

Preparation of 4,8-Dichloro-2-(4-isopropyl-thiazol-2-yl)-7-methoxy-quinoline

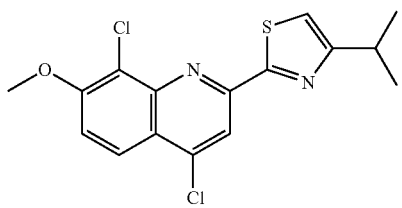 [SMILES: COc1ccc2c(Cl)cc(-c3nc(C(C)C)cs3)nc2c1Cl]

4,8-Dichloro-2-(4-isopropyl-thiazol-2-yl)-7-(2-methoxy-ethoxy)-quinoline was prepared in a similar fashion as 4,8-Dichloro-2-(6-isopropyl-pyridin-2-yl)-7-(2-methoxy-ethoxy)-quinoline except that the lithium salt of 4-isopropyl-thiazole-2-carboxylate was used instead of 6-isopropyl-pyridine-2-carboxylic acid and 1-(2-Amino-3-chloro-4-methoxy-phenyl)-ethanone was used instead of 1-[2-amino-3-chloro-4-(2-methoxy-ethoxy)-phenyl]-ethanone
LC/MS=353 (M$^+$+1)

Preparation of 4,8-Dichloro-2-(2-isopropyl-thiazol-4-yl)-7-methoxy-quinoline

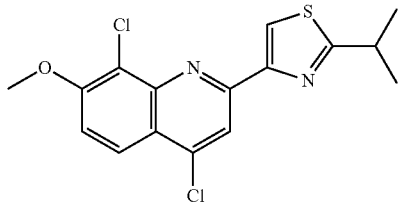 [SMILES: COc1ccc2c(Cl)cc(-c3csc(C(C)C)n3)nc2c1Cl]

4,8-Dichloro-2-(2-isopropyl-thiazol-4-yl)-7-methoxy-quinoline was prepared in a similar fashion as 4,8-dichloro-2-(6-isopropyl-pyridin-2-yl)-7-(2-methoxy-ethoxy)-quinoline except that 2-isopropyl-thiazole-4-carboxylic acid was used instead of 6-isopropyl-pyridine-2-carboxylic acid and 1-(2-Amino-3-chloro-4-methoxy-phenyl)-ethanone was used instead of 1-[2-amino-3-chloro-4-(2-methoxy-ethoxy)-phenyl]-ethanone
LC/MS=353 (M$^+$+1)

Preparation of 4,8-Dichloro-2-(6-isopropyl-pyridin-2-yl)-7-methoxy-quinoline

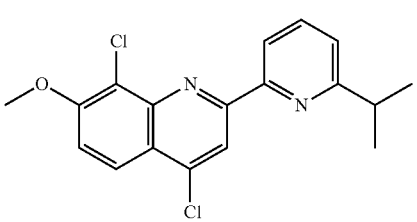 [SMILES: COc1ccc2c(Cl)cc(-c3cccc(C(C)C)n3)nc2c1Cl]

4,8-Dichloro-2-(6-isopropyl-pyridin-2-yl)-7-methoxy-quinoline was prepared in a similar fashion as 4,8-dichloro- 2-(6-isopropyl-pyridin-2-yl)-7-(2-methoxy-ethoxy)-quinoline except that 1-(2-amino-3-chloro-4-methoxy-phenyl)-ethanone was used instead of 1-[2-amino-3-chloro-4-(2-methoxy-ethoxy)-phenyl]-ethanone.
LC/MS=347 (M⁺+1)

Preparation of 4-Chloro-7-(2,2-dimethoxy-ethoxy)-2-(4-isopropyl-thiazol-2-yl)-8-methyl-quinoline

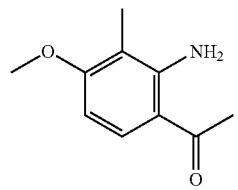

1-(2-Amino-4-methoxy-3-methyl-phenyl)-ethanone (7.8 g, 43.6 mmol) was dissolved in HBr (70 mL, 48% in H₂O). The reaction was heated to 110° C. for 2 days. The reaction was concentrated. The pH was adjusted to 5 with 4N NaOH and extracted with ethyl acetate (3×50 mL). The organic layer was washed with 1N NaOH, dried with sodium sulfate, filtered and was concentrated. 1-(2-Amino-4-hydroxy-3-methyl-phenyl)-ethanone (5.0 g, 70%) was purified by silica gel chromatography.
LC/MS=166 (M⁺+1)

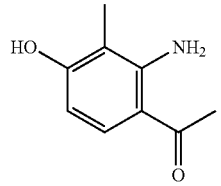

1-(2-Amino-4-hydroxy-3-methyl-phenyl)-ethanone (7.3 g, 44.2 mmol), cesium carbonate (28.8 g, 88.4 mmol) and 2-bromo-1,1-dimethoxy-ethane (7.8 mL, 66.3 mmol) was dissolved in NMP (100 mL) under an atmosphere of nitrogen. The reaction was heated to 50° C. for 6 hours. The reaction was concentrated. The reaction was taken up in ethyl acetate and washed with water. The organic layer was dried with sodium sulfate, filtered and was concentrated. 1-[2-Amino-4-(2,2-dimethoxy-ethoxy)-3-methyl-phenyl]-ethanone (6.29 g, 79%) was purified by silica gel chromatography.
LC/MS=254 (M⁺+1)

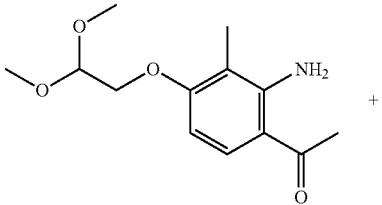

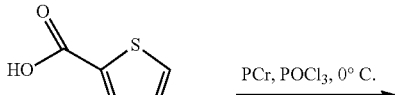

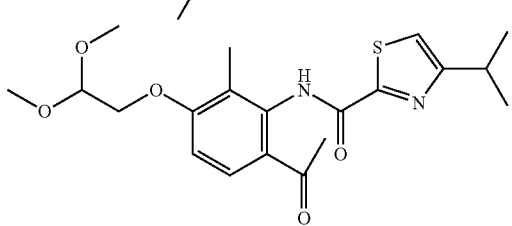

1-[2-Amino-4-(2,2-dimethoxy-ethoxy)-3-methyl-phenyl]-ethanone (3.7 g, 14.6 mmol) and 4-isopropyl-thiazole-2-carboxylic acid (2.5 g, 14.6 mmol) was dissolved in pyridine (50 mL) and was cooled to −40° C. POCl₃ (1.74 mL, 19.0 mmol) was added dropwise. The reaction was allowed to warm to warm to 0° C. The reaction was stirred at 0° C. for 2 hours. The reaction was quenched with 10 mL of water. After 15 minutes, the reaction was taken up in ethyl acetate. The solution was washed with a saturated aqueous sodium bicarbonate solution. The organic layer was dried with sodium sulfate, filtered and was concentrated. 4-Isopropyl-thiazole-2-carboxylic acid [6-acetyl-3-(2,2-dimethoxy-ethoxy)-2-methyl-phenyl]-amide (1.5 g, 25%) was purified by silica gel chromatography.
LC/MS=406 (M⁺)

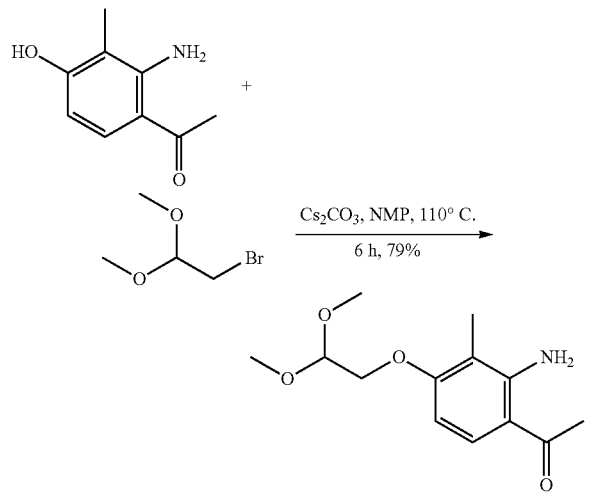

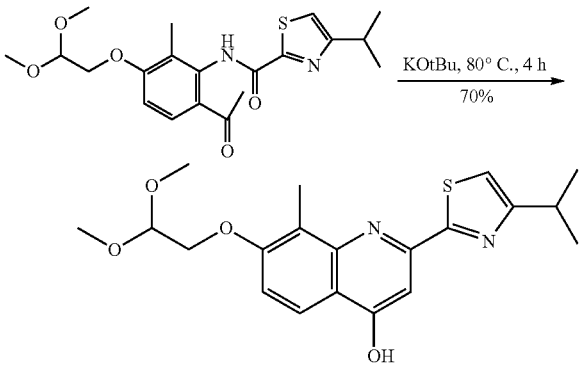

4-Isopropyl-thiazole-2-carboxylic acid [6-acetyl-3-(2,2-dimethoxy-ethoxy)-2-methyl-phenyl]-amide (1.5 g, 3.7 mmol) and potassium tertbutoxide (903 mg, 7.4 mmol) were dissolved in tertbutanol (50 mL) under an atmosphere of nitrogen. The reaction was heated to 80° C. for 4 hours. The reaction was cooled to RT and the pH was adjusted to 5 with 1N HCl. The reaction was extracted with ethyl acetate (2×30 mL). The combined organics were dried with sodium sulfate, filtered and were concentrated. 7-(2,2-Dimethoxy-ethoxy)-2-(4-isopropyl-thiazol-2-yl)-8-methyl-quinolin-4-ol (1.0 g, 70%) was purified by silica gel chromatography.

LC/MS=389 (M⁺+1)

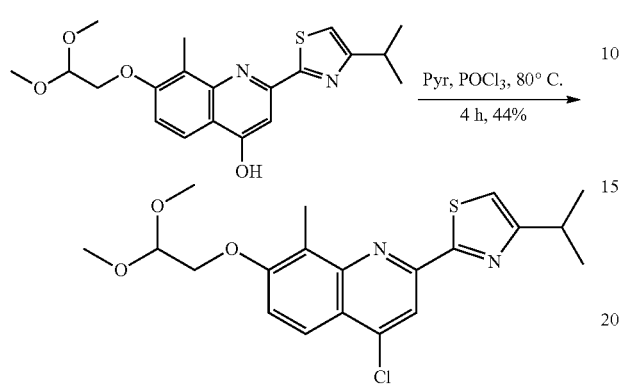

7-(2,2-Dimethoxy-ethoxy)-2-(4-isopropyl-thiazol-2-yl)-8-methyl-quinolin-4-ol (875 mg, 2.3 mmol) was dissolved in pyridine (20 mL). POCl₃ (4.2 ml, 46.0 mmol) was added slowly. The reaction was heated at 80° C. for 4 hours. The reaction was cooled to 0° C. and methanol (5 mL) was added. The reaction was neutralized with a saturated aqueous sodium bicarbonate solution. The product was extracted with ethyl acetate (3×20 mL). The combined organics were dried with sodium sulfate, filtered and was concentrated. 4-Chloro-7-(2,2-dimethoxy-ethoxy)-2-(4-isopropyl-thiazol-2-yl)-8-methyl-quinoline (410 mg, 44%) was purified by silica gel chromatography.

LC/MS=407 (M⁺+1)

Preparation of 4,8-dichloro-2-(3-isopropyl-pyrazol-1-yl)-7-(2-morpholin-4-yl-ethoxy)-quinoline

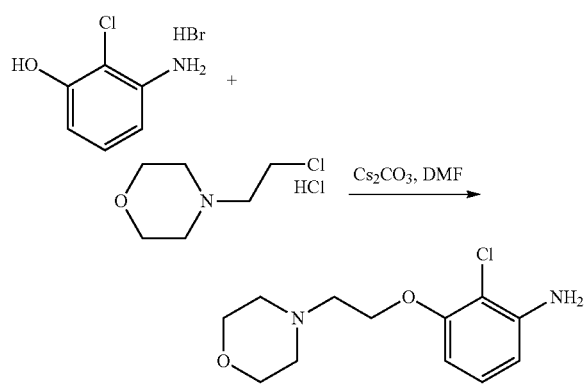

To mixture of 3-amino-2-chloro-phenol HBr salt (3 g, 13 mmol) and 4-(2-chloro-ethyl)-morpholine HCl salt (4 g, 21 mmol) in DMF (30 ml) was added Cs₂CO₃ (17 g, 52 mmol) in one portion. The mixture was stirred at 65° C. for over night, and it was monitored by LC-MS. Major mono-alkylated and minor bis-alkylated products were formed. The crude reaction mixture was diluted with EtOAc (40 ml) and washed with LiCl (5% aqueous) (30 ml), H₂O (30 ml) and brine (30 ml). After being washing with aqueous, most of the bis-alkylated product went into aqueous phase. The organic phase was concentrated down and the residue was purified by flash chromatograph to obtain the desired product in slight yellow color oil form (2.75 g, 10 mmol).

LC/MS=258 (M⁺+1)

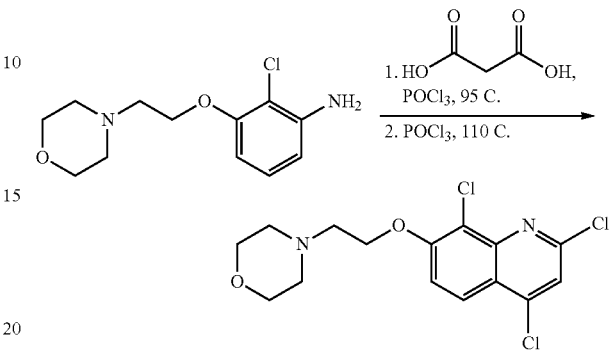

To mixture of 2-chloro-3-(2-morpholin-4-yl-ethoxy)-phenylamine (0.29 g, 1.1 mmol) and malonic acid (0.12 g, 1.1 mmol) was added POCl₃ (0.18 g, 1.21 mmol, 0.12 ml) at room temperature. The mixture was heated to 95° C. with the flask mouth open, along heating, solid started to liquefy and color was changed from yellow to brown. Along the solid being liquefied, foam was getting formed and the reaction was completed when foam stopped forming. The reaction mixture was cooled to room temperature and 3 ml POCl₃ was added, the mixture was then heated to reflux for 3 hours. It was monitored by LC-MS. It was cooled to room temperature and ice water (8 ml) was added slowly and followed by NaOH (10 N) to basify the mixture. CHCl₃ (10 ml×2) was used extract the aqueous. The combined organic phase was washed with NaHCO₃ (sat.), H₂O and brine, and dried with MgSO₄. The organic solvent was stripped off and the residue was purified by flash chromatograph to obtain the product (0.2 g, 0.55 mmol).

LC/MS=362 (M⁺+1)

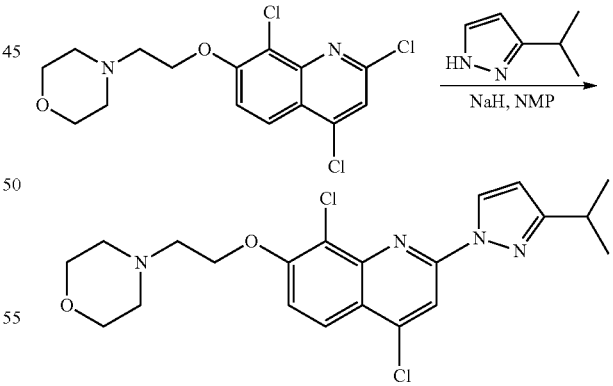

To mixture of 2,4,8-trichloro-7-(2-morpholin-4-yl-ethoxy)-quinoline (0.34 g, 0.95 mmol) and 3-isopropyl-1H-pyrazole (0.63 g, 5.7 mmol) in NMP (3 ml) was added NaH (60% in mineral oil) (0.042 g, 1.05 mmol). The mixture was stirred at room temperature for over night and it monitored by LC-MS. The crude material was purified by pre-HPLC to afford 4,8-dichloro-2-(3-isopropyl-pyrazol-1-yl)-7-(2-morpholin-4-yl-ethoxy)-quinoline (0.204 g, 0.47 mmol).

LC/MS=435 (M⁺+1)

Preparation of Example 1

Method A

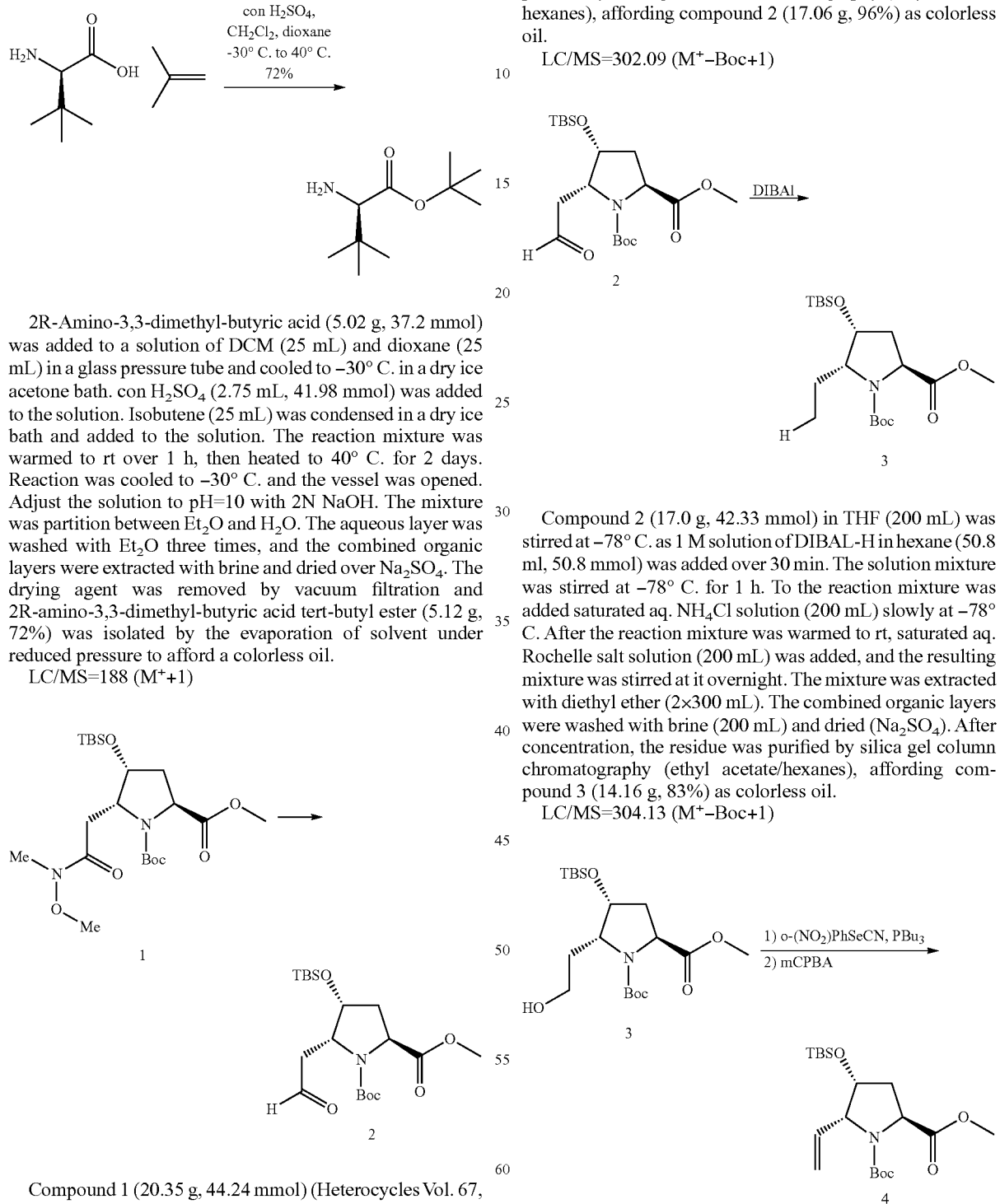

2R-Amino-3,3-dimethyl-butyric acid (5.02 g, 37.2 mmol) was added to a solution of DCM (25 mL) and dioxane (25 mL) in a glass pressure tube and cooled to −30° C. in a dry ice acetone bath. con H$_2$SO$_4$ (2.75 mL, 41.98 mmol) was added to the solution. Isobutene (25 mL) was condensed in a dry ice bath and added to the solution. The reaction mixture was warmed to rt over 1 h, then heated to 40° C. for 2 days. Reaction was cooled to −30° C. and the vessel was opened. Adjust the solution to pH=10 with 2N NaOH. The mixture was partition between Et$_2$O and H$_2$O. The aqueous layer was washed with Et$_2$O three times, and the combined organic layers were extracted with brine and dried over Na$_2$SO$_4$. The drying agent was removed by vacuum filtration and 2R-amino-3,3-dimethyl-butyric acid tert-butyl ester (5.12 g, 72%) was isolated by the evaporation of solvent under reduced pressure to afford a colorless oil.

LC/MS=188 (M$^+$+1)

Compound 1 (20.35 g, 44.24 mmol) (Heterocycles Vol. 67, No. 1, 2006, p. 189; used faster eluting diastereomer) in THF (200 mL) was stirred at −78° C. as 1 M solution of DIBAL-H in hexane (66.4 ml, 66.36 mmol) was added over 30 min. The solution was stirred at −78° C. for 2 h. To the reaction mixture was added saturated aq. NH$_4$Cl solution (200 mL) slowly at −78° C. After the mixture was warmed to rt, saturated aq. Rochelle salt solution (100 mL) and ether (300 mL) were added, and the resulting mixture was stirred at it overnight. The mixture was extracted with diethyl ether (2×300 mL). The combined organic layers were washed with brine (2×200 mL) and dried (Na$_2$SO$_4$). After concentration, the residue was purified by silica gel column chromatography (ethyl acetate/hexanes), affording compound 2 (17.06 g, 96%) as colorless oil.

LC/MS=302.09 (M$^+$−Boc+1)

Compound 2 (17.0 g, 42.33 mmol) in THF (200 mL) was stirred at −78° C. as 1 M solution of DIBAL-H in hexane (50.8 ml, 50.8 mmol) was added over 30 min. The solution mixture was stirred at −78° C. for 1 h. To the reaction mixture was added saturated aq. NH$_4$Cl solution (200 mL) slowly at −78° C. After the reaction mixture was warmed to rt, saturated aq. Rochelle salt solution (200 mL) was added, and the resulting mixture was stirred at it overnight. The mixture was extracted with diethyl ether (2×300 mL). The combined organic layers were washed with brine (200 mL) and dried (Na$_2$SO$_4$). After concentration, the residue was purified by silica gel column chromatography (ethyl acetate/hexanes), affording compound 3 (14.16 g, 83%) as colorless oil.

LC/MS=304.13 (M$^+$−Boc+1)

To compound 3 (14.16 g, 35.26 mmol) in THF (400 mL) were added o-NO$_2$PhSeCN (12.01 g, 52.89 mmol) and PBu$_3$ (13.05 mL, 52.89 mmol) at rt. The reaction mixture was stirred at rt for 2 h under N$_2$ and then cooled to −78° C. before mCPBA (15.65 g, 63.47 mmol) was added to the mixture. The resulting reaction mixture was warmed to rt and stirred for 2.5 h. Upon completion of the reaction, the reaction mixture was diluted with saturated NaHCO₃ and extracted with EtOAc twice. The combined organic extracts were washed with brine, dried (Na₂SO₄), and concentrated. The residue was purified by flash chromatography on silica gel, using ethyl acetate and hexanes as eluents to give the desired product, compound 4 with some impurity. The impure product was dissolved in minimal amount dichloromethane (<10 mL) and diluted with hexanes (~300 mL). The resulting solution was stored in refrigerator overnight and the crystals formed were filtered off. The filtrate was concentrated to give the desired compound 4 (9.6 g, 71%) as orange colored viscous oil.

$^1$H NMR (400 MHz, CDCl₃): δ 5.72-5.84 (m, 1H), 5.03-5.24 (m, 2H), 4.49 (m, 1H), 4.35 (m, 1H), 4.32 (m, 1H), 3.81 and 3.82 (two s, 3H), 2.13 (m, 1H), 1.92 (m, 1H), 1.42 and 1.40 (two s, 9H), 0.87 (s, 9H), 0.06 (s, 3H), 0.05 (s, 3H)

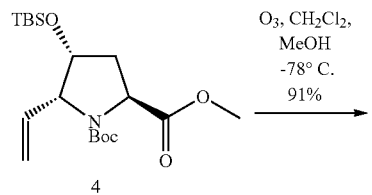

2R-amino-3,3-dimethyl-butyric acid tert-butyl ester (5.36 g, 24 mmol) and compound 5 (7.78 g, 20 mmol) was dissolved in CH₂Cl₂ (200 mL) and stirred at rt for 1 h. The reaction mixture was then cooled to 0° C. with an ice bath and sodium triacetoxyborohydride was added in one portion followed by a few drops of acetic acid. The ice bath was then removed and the solution was allowed to stir for 30 min at rt. The reaction was quenched with H₂O (150 mL). The solution was extracted with H₂O and brine and then dried over Na₂SO₄. Compound 6 (6.75 g, 61%) was isolated as a white solid by silica gel column chromatography.

LC/MS=560 (M⁺+1)

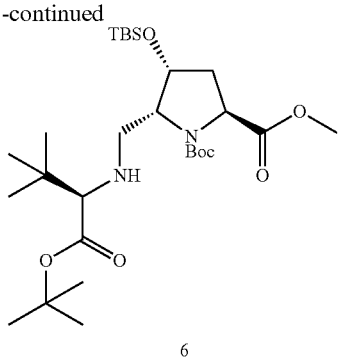

Compound 4 (8.49 g, 21.99 mmol) was added to CH₂Cl₂ (100 mL) and MeOH (60 mL). The reaction mixture was cooled in a dry ice bath to −78° C. and ozone was bubbled through the solution until a color change of yellow to blue was observed (20 min). The ozone was turned off and oxygen was bubbled through the reaction mixture until the solution returned to a yellow color. Dimethyl sulfide (60 mL) was added, the ice bath was removed, and the reaction was allowed to stir for 1 h. Solvents were removed under reduced pressure and the mixture was taken up in EtOAc and partitioned with H₂O. The organic phase was washed with H₂O and brine. The organic phase was then dried over Na₂SO₄. The drying agent was removed by vacuum filtration and compound 5 (7.78 g, 91%) was purified by silica gel column chromatography as a colorless oil.

LC/MS=389 (M⁺+1)

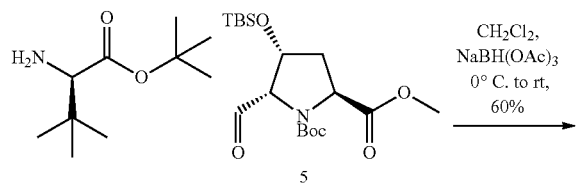

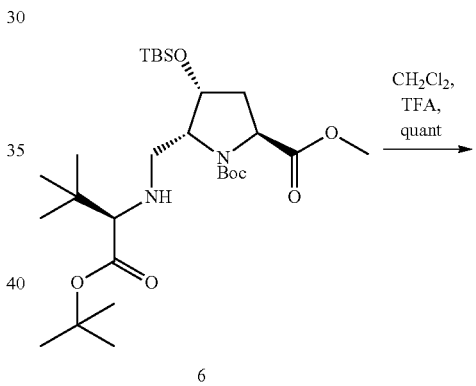

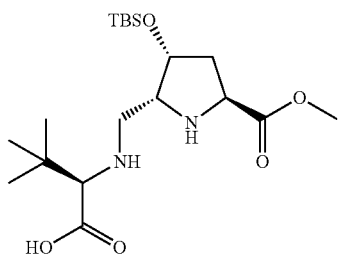

Compound 6 (6.7 g, 11.9 mmol) was dissolved in CH₂Cl₂ (50 mL). TFA (30 mL) was added to this solution in one portion. The reaction was then stirred for 18 h. The reaction was determined to be complete by LCMS. The solvents were removed under reduced pressure, and the crude material was co-evaporated with toluene 3×50 mL and compound 7 was used as is for the next step.

LC/MS=408 (M⁺+1)

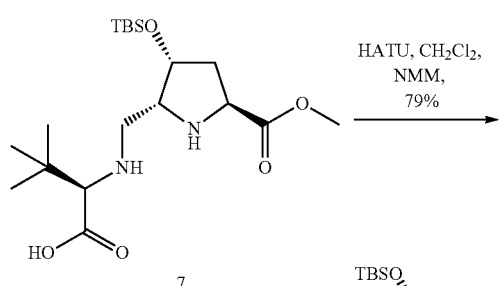

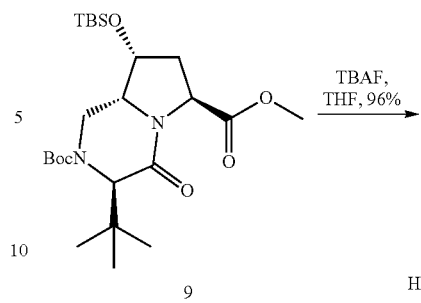

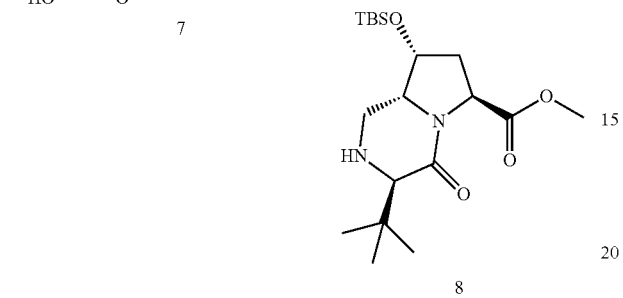

Compound 7 (4.8 g, 11.0 mmol) and HATU (6.27 g, 16.5 mmol) were dissolved in CH$_2$Cl$_2$ (400 mL). To this solution was added NMM (6.0 mL, 55 mmol) in one portion. The reaction was stirred for 5 h. The reaction was then quenched with H$_2$O. The mixture was then partitioned between H$_2$O and CH$_2$Cl$_2$. Aqueous extracted once with CH$_2$Cl$_2$, and then the combined organic phases were extracted with H$_2$O and then dried over Na$_2$SO$_4$. The drying agent was removed by vacuum filtration. Compound 8 (3.33 g, 79%) was isolated as a crystalline white solid by silica gel column chromatography.

LC/MS=385 (M$^+$+1)

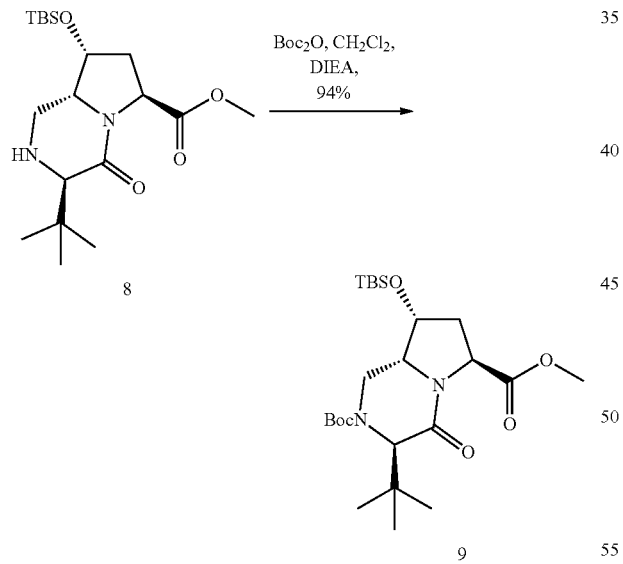

Compound 8 (3.33 g, 8.60 mmol) and ditertbutyldicarbonate (5.63 g, 25.8 mmol) were dissolved in CH$_2$Cl$_2$ (100 mL). Hunig's base (6.15 mL, 34.4 mmol) was added in one portion. The reaction progress was monitored by LC/MS. After 8 h the reaction was nearly complete. The reaction was quenched by the addition of H$_2$O. The aqueous and organic layers were separated and the aqueous layer was extracted with additional CH$_2$Cl$_2$. The combined organic layers were dried over Na$_2$SO$_4$. The drying agent was removed by vacuum filtration. Compound 9 (3.93 g, 94%) was isolated from the filtrate as a crystalline white solid by silica gel column chromatography.

LC/MS=428 (M$^+$+1)

Compound 9 (3.93 g, 8.1 mmol) was dissolved in THF (50 mL). To this solution was added a 1.0M solution of TBAF in THF (12 mL, 12 mmol) in one portion. The reaction was stirred at rt. The reaction progress was monitored by LC/MS. After 1 h the reaction was complete. The reaction was quenched with H$_2$O. The organics were removed under reduced pressure and partitioned between EtOAc and ½ sat brine. The layers were separated and the aqueous layer was back extracted with EtOAc. The combined organic layers were dried over Na$_2$SO$_4$. The drying agent was removed by vacuum filtration. Compound 10 (3.09 g, 98%) was isolated as a crystalline white solid by silica gel column chromatography.

LC/MS=314 (M$^+$+1)

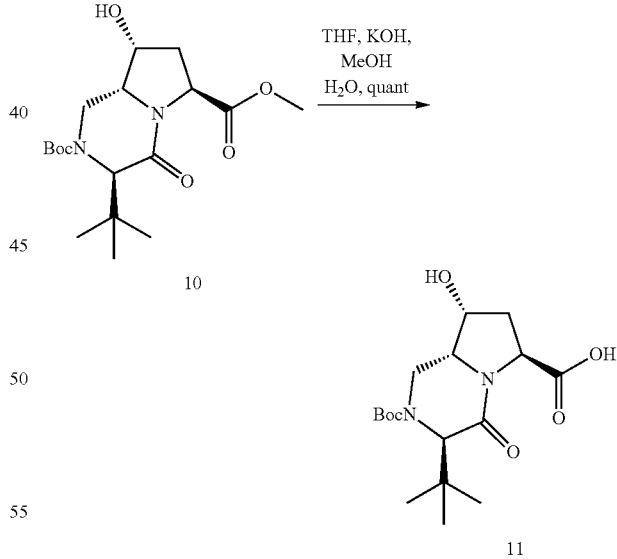

Compound 10 (3.0 g, 8.0 mmol) was dissolved in THF (10 mL) and MeOH (10 mL). This solution was cooled in an ice bath and then a solution of 6M KOH$_{(aq)}$ (7 mL, 42 mmol) was added. The ice bath was removed and the reaction was stirred at rt. The reaction progress was monitored by LC/MS. After 1 h the reaction was complete. The reaction placed in an ice bath and 2N HCl (25 mL) was slowly added. The quenched reaction was concentrated and the resulting white residue was placed on a lypholizer for 72 h. The resulting compound 11 was used as is in the next reaction.

LC/MS=357 (M$^+$+1).

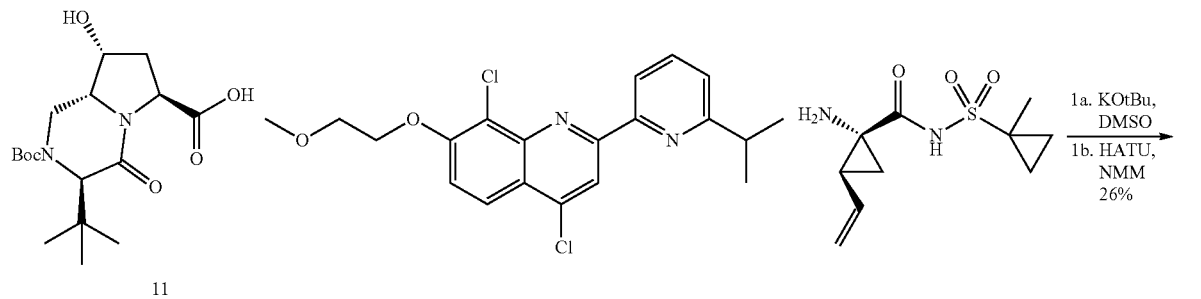

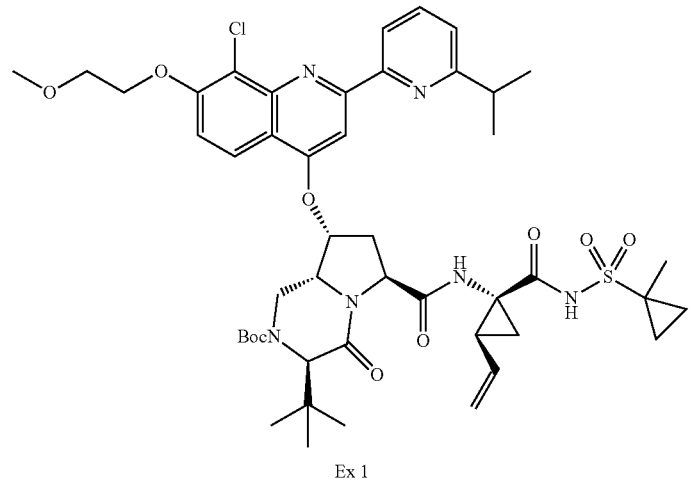

Ex 1

Compound 11 (300 mgs, 0.84 mmol) was dissolved in DMSO (10 mL). To this solution was added tBuOK (235 mg, 2.1 mmol). The reaction was stirred vigorously for 5 min and then 4,8-dichloro-2-(6-isopropyl-pyridin-2-yl)-7-(2-methoxy-ethoxy)-quinoline (344 mg, 0.84 mmol) was added in one portion. The reaction was allowed to stir at it for 10 min. The reaction was monitored by LC/MS. To the reaction mixture was added NMM 4 mmol), followed by the HCl salt of 1-methyl-cyclopropanesulfonic acid ((1R,2S)-1-amino-2-vinyl-cyclopropanecarbonyl)-amide (217 mgs, 0.84 mmol) and HATU (608 mgs, 1.8 mmol). The reaction was monitored by LC/MS and done in 10 min. The reaction was quenched with $H_2O$. The reaction mixture was partitioned between EtOAc and $H_2O$. The layers were separated and the aqueous layer was back extracted with EtOAc. The combined organic layers were dried over $Na_2SO_4$. The drying agent was removed by vacuum filtration and the filtrate was concentrated and then re-dissolved in minimal MeOH. Example 1 (174 mg, 26%) was isolated by reverse phase HPLC as the TFA salt.

LC/MS=937 ($M^+$+1)

$^1$H NMR (400 MHz, $CD_3OD/D_6$-DMSO): δ (ppm) 10.42 (br, 1H), 9.73 (brs, 1H), 8.40 (d, J=7.63 Hz, 1H), 8.05, (s, 1H), 7.95 (dd, J=7.63, 7.82 Hz, 1H), 7.81 (brs, 1H), 7.51 (brs, 2H), 7.41 (d, J=7.82 Hz, 1H), 5.58-5.41 (m, 2H), 5.22-5.17 (m, 1H), 5.10-5.04 (m, 1H), 4.56-4.16 (m, 3H), 3.73 (t, J=4.30 Hz, 2H), 3.15 (septet, J=6.84 Hz, 1H), 2.48-2.40 (m, 1H), 2.29-2.06 (m, 3H), 1.69 (m, 1H), 1.42-0.80 (m, 37H).

Preparation of Example 2

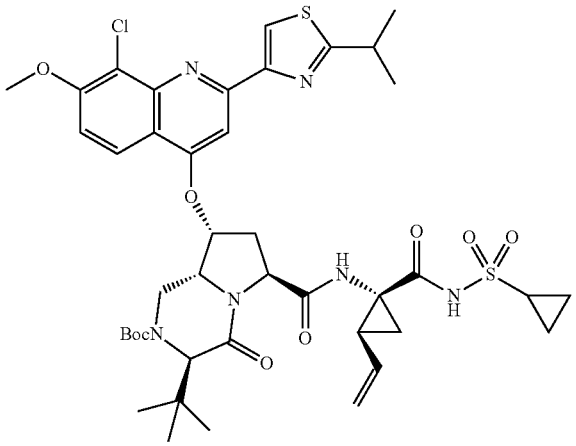

Ex 2

Example 2 was prepared in a manner similar to method A, except, 4,8-dichloro-2-(2-isopropyl-thiazol-4-yl)-7-methoxy-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=885 ($M^+$+1)

$^1$H NMR (400 MHz, $D_6$-DMSO): δ (ppm) 10.603 (s, 1H); 9.045 (s, 1H); 8.345 (s, 1H); 7.817 (brs, 1H); 7.664 (brs, 1H); 7.416 (brs, 1H); 5.579 (m, 2H); 5.206 (d, J=17.21 Hz, 1H); 5.067 (d, J=11.74 Hz, 1H); 4.475 (m, 1H); 4.285 (m, 2H);

3.966 (s, 3H); 3.650 (m, 1H); 3.380 (quint, J=7.04 Hz, 1H); 2.887 (m, 1H); 2.466 (m, 1H); 2.250-2.095 (m, 2H); 1.683 (m, 1H); 1.399-0.982 (m, 30H).

Preparation of Example 3

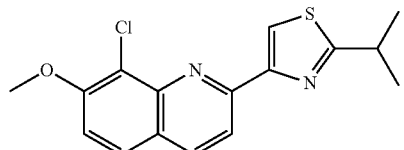

Ex 3

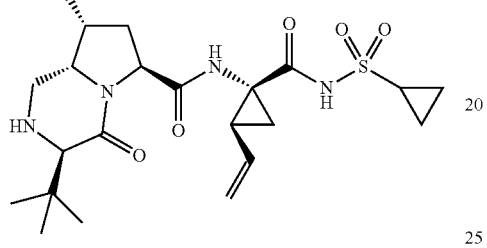

Example 2 (150 mg, 0.149 mmol) was dissolved in CH$_2$Cl$_2$ (2.0 mL) and 4.0N HCl in dioxane (2.0 mL) was added. The mixture was stirred at rt for 1 h. Solvent was removed under reduced pressure. The material was taken up in CH$_3$OH. Example 3 (74 mg, 55%) was isolated by reverse phase HPLC as the TEA salt.

LC/MS=785 (M$^+$+1)

$^1$H NMR (400 MHz, D$_6$-DMSO): δ (ppm) 10.509 (s, 1H); 10.199 (brs, 1H); 8.929 (brs, 1H); 8.732 (s, 1H); 8.346 (s, 1H); 8.191 (d, J=9.19 Hz, 1H); 7.648 (s, 1H); 7.457 (d, J=9.19 Hz, 1H); 5.675 (brs, 1H); 5.523 (m, 1H); 5.171 (d, J=16.83 Hz, 1H); 5.054 (d, J=10.17 Hz, 1H); 4.443 (m, 1H); 4.415 m, 1H); 4.18 (s, 3H); 3.949 (brs, 1H) 3.786 (m, 1H); 3.521 (m, 1H); 3.398 (quint, J=6.85 Hz, 1H); 2.880 (m, 1H); 2.594 (dd, J=7.04, 6.85 Hz, 1H); 2.239 (m, 1H); 2.089 (q, J=8.61 Hz, 1H); 1.678 (m, 1H); 1.405 (d, J=5.68 Hz, 6H); 1.272 (dd, J=5.08, 3.91 Hz, 1H); 1.130 (s, 9H); 1.046 (m, 2H); 0.997 (m, 1H).

Preparation of Example 4

Ex 4

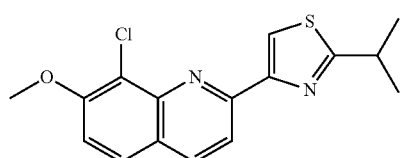

Example 4 was prepared in a manner similar to method A, except, 4,8-dichloro-2-(2-isopropyl-thiazol-4-yl)-7-meth-oxy-quinoline was used in place of 4,8-dichloro-2-(6-isopropyl-pyridin-2-yl)-7-(2-methoxy-ethoxy)-quinoline.

LC/MS=899 (M$^+$+1)

$^1$H NMR (400 MHz, D$_6$-DMSO): δ (ppm) 10.416 (brs, 1H); 8.764 (brs, 1H); 8.336 (s, 1H); 7.793 (brs, 1H); 7.655 (brs, 1H); 7.434 (brs, 1H); 5.532 (m, 2H); 5.204 (d, J=17.02, 1H); 5.062 (d, J=10.17 Hz, 1H); 4.477-4.149 (m, 4H); 3.969 (s, 3H); 3.612 (m, 1H); 3.383 (quint, J=6.84 Hz, 1H); 2.496 (m, 1H); 2.154 (2H); 1.682 (m, 1H); 1.404-1.039 (m, 30H); 0.855 (m, 2H).

Preparation of Example 5

Ex 5

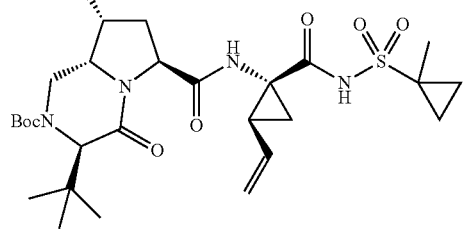

Example 4 (13 mg, 0.014 mmol) was dissolved in CH$_2$Cl$_2$ (0.5 mL) and 4.0N HCl in dioxane (0.5 mL) was added. The mixture was stirred at rt for 1 h. Solvent was removed under reduced pressure. The material was dissolved in acetonitrile (1.0 mL) and H$_2$O (1.0 mL). The material was freeze dried to afford example 5 (11 mg, 87%) as the bis-HCl salt.

LC/MS=799 (M$^+$+1)

Retention time: 2.40 min

LC: Thermo Electron Surveyor HPLC

MS: Finnigan LCQ Advantage MAX Mass Spectrometer

Column: Phenomenex Polar RP 30 mm×4.6 mm

Solvents: Acetonitrile with 0.1% formic acid, Water with 0.1% formic acid

Gradient: 0 min-0.1 min 5% ACN, 0.1 min-1.95 min 5%-100% ACN, 1.95 min-3.50 min 100% ACN, 3.50 min-3.55 min 100%-5% ACN, 3.55 min-4.0 min 5% ACN.

Preparation of Example 6

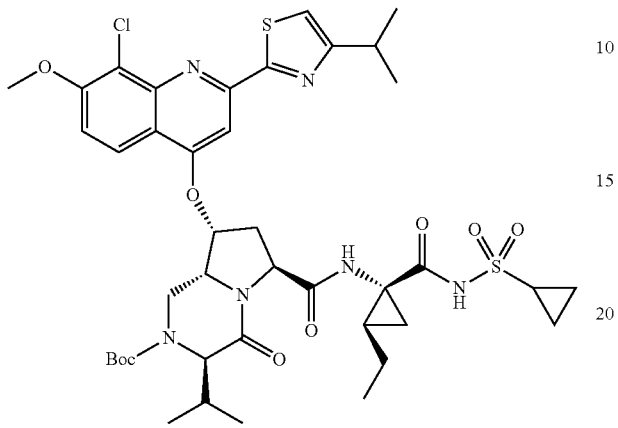

Ex 6

Example 6 was prepared in a similar manner to described in method A, except the HCl salt of cyclopropanesulfonic acid ((1R,2S)-1-amino-2-ethyl-cyclopropanecarbonyl)-amide was used in place of the HCl salt of 1-methyl-cyclopropanesulfonic acid ((1R,2S)-1-amino-2-vinyl-cyclopropanecarbonyl)-amide, 2R-amino-3-methyl-butyric acid tert-butyl ester was used instead of 2R-amino-3,3-dimethyl-butyric acid tert-butyl ester, and 4,8-dichloro-2-(4-isopropyl-thiazol-2-yl)-7-methoxy-quinoline was used instead of 4,8-dichloro-2-(6-isopropyl-pyridin-2-yl)-7-(2-methoxy-ethoxy)-quinoline.

LC/MS=874 (M$^+$+1)

$^1$H NMR (400 MHz, CD$_3$OD): δ (ppm) 9.05 (br, 1H), 7.92 (d, J=9.2 Hz, 1H), 7.70, (s, 1H), 7.32 (d, J=9.2 Hz, 1H), 7.27 (s, 1H), 5.53 (br, 1H), 4.47 (m, 2H), 4.19 (d, J=9.6 Hz, 1H), 4.00 (m, 1H), 3.96 (m, 3H), 3.66 (m, 1H), 3.11 (m, 1H), 2.90 (m, 1H), 2.58 (m, 1H), 2.30 (m, 1H), 2.14 (m, 1H), 1.54-1.12 (m, 24H), 1.09-0.88 (m, 9H).

Preparation of Example 7

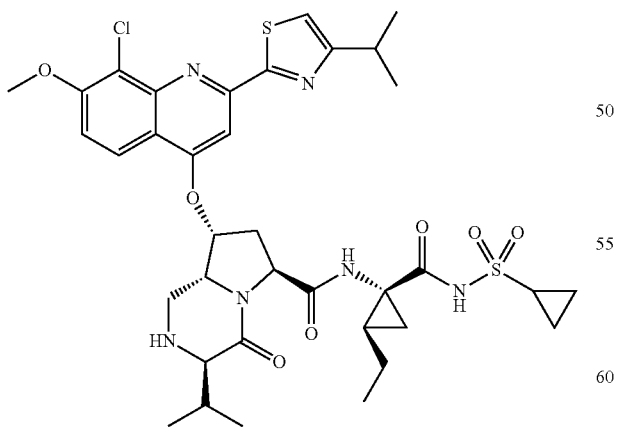

Ex 7

Example 6 (37 mg, 0.037 mmol) was dissolved in DCM (1 mL) and TFA at it and stirred for 1 h. The reaction was concentrated and then triturated with ether. Example 7, (35 mg, 95%) was isolated by filtration as the TFA salt.

LC/MS=774 (M$^+$+1)

$^1$H NMR (400 MHz, CD$_3$OD): δ (ppm) 9.21 (br, 1H), 8.16 (d, J=9.2 Hz, 1H), 7.76, (s, 1H), 7.42 (d, J=9.2 Hz, 1H), 7.30 (s, 1H), 5.60 (br, 1H), 4.57 (m, 2H), 4.19 (m, 1H), 4.01 (m, 3H), 3.66 (m, 2H), 3.15 (m, 1H), 2.90 (m, 2H), 2.40 (m, 1H), 1.60-0.88 (m, 24H),

Preparation of Example 8

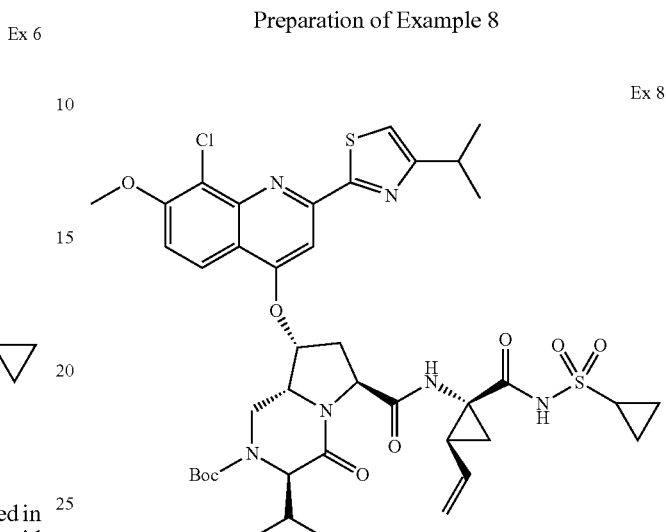

Ex 8

Example 8 was prepared in a similar manner to described in method A, except 2R-amino-3-methyl-butyric acid tert-butyl ester was used instead of 2R-amino-3,3-dimethyl-butyric acid tert-butyl ester, the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide, and 4,8-dichloro-2-(4-isopropyl-thiazol-2-yl)-7-methoxy-quinoline was used instead of 4,8-dichloro-2-(6-isopropyl-pyridin-2-yl)-7-(2-methoxy-ethoxy)-quinoline.

LC/MS=872 (M$^+$+1)

$^1$H NMR (400 MHz, CD$_3$OD): δ (ppm) 9.23 (br, 1H), 8.00 (d, J=9.2 Hz, 1H), 7.75, (s, 1H), 7.42 (d, J=9.2 Hz, 1H), 7.33 (s, 1H), 7.14 (m, 1H), 5.70 (m, 1H), 5.61 (br, 1H), 5.28-5.08 (d, d, 2H), 4.52 (m, 2H), 4.26 (d, J=9.6 Hz, 1H), 4.05 (m, 1H), 4.03 (s, 3H), 3.73 (m, 1H), 3.18 (m, 1H), 2.94 (m, 1H), 2.67 (m, 1H), 2.39 (m, 1H), 2.21 (m, 2H), 1.54-1.12 (m, 18H), 1.16-1.01 (m, 9H).

Preparation of Example 9

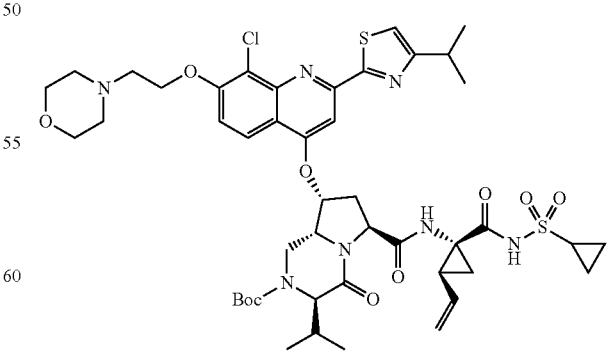

Ex 9

Example 9 was prepared in a similar manner to described in method A, except the HCl salt of 2R-amino-3-methyl-butyric acid tert-butyl ester was used instead of the HCl salt of 2R-amino-3,3-dimethyl-butyric acid tert-butyl ester, the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide, and 4,8-dichloro-2-(4-isopropyl-thiazol-2-yl)-7-(2-morpholin-4-yl-ethoxy)-quinoline was used instead of 4,8-dichloro-2-(6-isopropyl-pyridin-2-yl)-7-(2-methoxy-ethoxy)-quinoline.

LC/MS=971 (M++1)

¹H NMR (400 MHz, CD₃OD): δ (ppm) 7.91 (d, J=9.2 Hz, 1H), 7.77, (s, 1H), 7.38 (d, J=9.2 Hz, 1H), 7.29 (s, 1H), 5.78 (m, 1H), 5.57 (br, 1H), 5.22-5.01 (d, d, 2H), 4.59 (m, 2H), 4.48 (d, J=9.6 Hz, 1H), 4.41-4.34 (m, 2H), 4.26-4.17 (m, 2H), 3.71 (t, 4H), 3.16 (m, 1H), 2.91 (m, 2H), 2.64 (m, 1H), 2.47 (m, 1H), 2.30 (m, 1H), 2.05 (m, 1H), 1.82 (m, 1H), 1.48-0.88 (m, 28H).

Preparation of Example 10

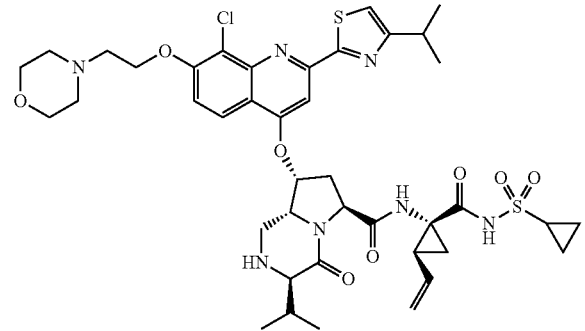

Ex 10

Example 10 was prepared from example 9 by treating with TFA in DCM.

LC/MS=970 (M++1)

¹H NMR (400 MHz, CD₃OD): δ (ppm) 9.23, (dr, 1H), 8.20 (d, J=9.2 Hz, 1H), 7.82, (s, 1H), 7.50 (d, J=9.2 Hz, 1H), 7.33 (s, 1H), 5.72 (br, 1H), 5.65 (m, 1H), 5.27-5.07 (d, d, 2H), 4.68-4.61 (m, 4H), 4.21 (br, 1H), 4.98 (m, 4H), 3.77-4.46 (m, 7H), 3.17 (m, 1H), 2.93 (m, 2H), 2.76 (m, 2H), 2.45 (m, 1H), 2.20 (m, 1H), 1.87 (m, 1H), 1.36 (m, 6H), 1.17-1.05 (m, 12H).

Preparation of Example 11

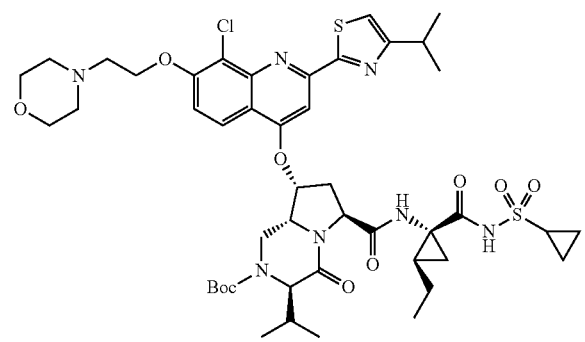

Ex 11

Example 11 was prepared in a similar manner to described in method A, except 2R-amino-3-methyl-butyric acid tert-butyl ester was used instead of 2R-amino-3,3-dimethyl-butyric acid tert-butyl ester, the HCl salt of cyclopropanesulfonic acid ((1R,2S)-1-amino-2-ethyl-cyclopropanecarbonyl)-amide was used in place of the HCl salt of 1-methyl-cyclopropanesulfonic acid ((1R,2S)-1-amino-2-vinyl-cyclopropanecarbonyl)-amide, and 4,8-dichloro-2-(4-isopropyl-thiazol-2-yl)-7-(2-morpholin-4-yl-ethoxy)-quinoline was used instead of 4,8-dichloro-2-(6-isopropyl-pyridin-2-yl)-7-(2-methoxy-ethoxy)-quinoline.

LC/MS=972 (M++1)

¹H NMR (400 MHz, CD₃OD): δ (ppm) 7.92 (d, J=9.2 Hz, 1H), 7.75, (s, 1H), 7.37 (d, J=9.2 Hz, 1H), 7.27 (s, 1H), 5.55 (m, 1H), 4.58 (m, 1H), 4.49 (m, 1H), 4.37 (m, 2H), 4.24 (m, 1H), 4.11 (m, 1H), 3.70 (m, 5H), 3.16 (m, 1H), 2.89 (m, 2H), 2.72 (m, 2H), 2.63 (m, 1H), 2.40 (m, 1H), 2.26 (m, 1H), 1.58-0.88 (m, 36H).

Preparation of Example 12

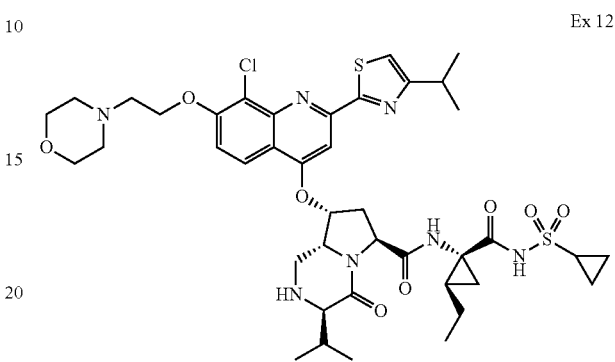

Ex 12

Example 12 was prepared from example 11 by treating with TFA in DCM.

LC/MS=872 (M++1)

¹H NMR (400 MHz, CD₃OD): δ (ppm) 9.21 (s, 1H), 8.20 (d, J=9.2 Hz, 1H), 7.82, (s, 1H), 7.50 (d, J=9.2 Hz, 1H), 7.34 (s, 1H), 5.72 (m, 1H), 4.68 (m, 2H), 4.21 (m, 1H), 4.10-3.45 (m, 11H), 3.16 (m, 1H), 2.96 (m, 1H), 2.77 (m, 2H), 2.44 (m, 1H), 1.61-0.88 (m, 25H).

Preparation of Example 13

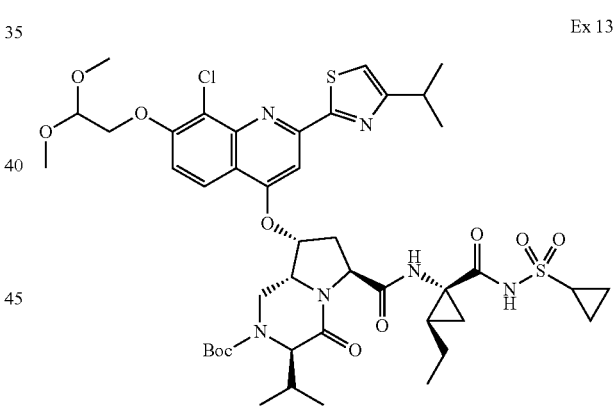

Ex 13

Example 13 was prepared in a similar manner to described in method A, except 2R-amino-3-methyl-butyric acid tert-butyl ester was used instead of 2R-amino-3,3-dimethyl-butyric acid tert-butyl ester, the HCl salt of cyclopropanesulfonic acid ((1R,2S)-1-amino-2-ethyl-cyclopropanecarbonyl)-amide was used in place of the HCl salt of 1-methyl-cyclopropanesulfonic acid ((1R,2S)-1-amino-2-vinyl-cyclopropanecarbonyl)-amide, and 4,8-dichloro-7-(2,2-dimethoxy-ethoxy)-2-(4-isopropyl-thiazol-2-yl)-quinoline was used instead of 4,8-dichloro-2-(6-isopropyl-pyridin-2-yl)-7-(2-methoxy-ethoxy)-quinoline.

LC/MS=947 (M++1)

¹H NMR (400 MHz, CDCl₃): δ (ppm) 9.92 (br, 1H), 7.83 (d, J=9.2 Hz, 1H), 7.81 (s, 1H), 7.59, (s, 1H), 7.20 (d, J=9.2 Hz, 1H), 7.04 (s, 1H), 5.40 (br, 1H), 4.77 (br, 1H), 4.30 (m, 1H), 4.18 (m, 1H), 4.08 (m, 1H), 3.68 (m, 2H), 3.50 (m, 6H), 3.15 (m, 1H), 2.88 (m, 1H), 2.58 (m, 2H), 2.13 (m, 2H), 1.58-0.88 (m, 36H).

Preparation of Example 14

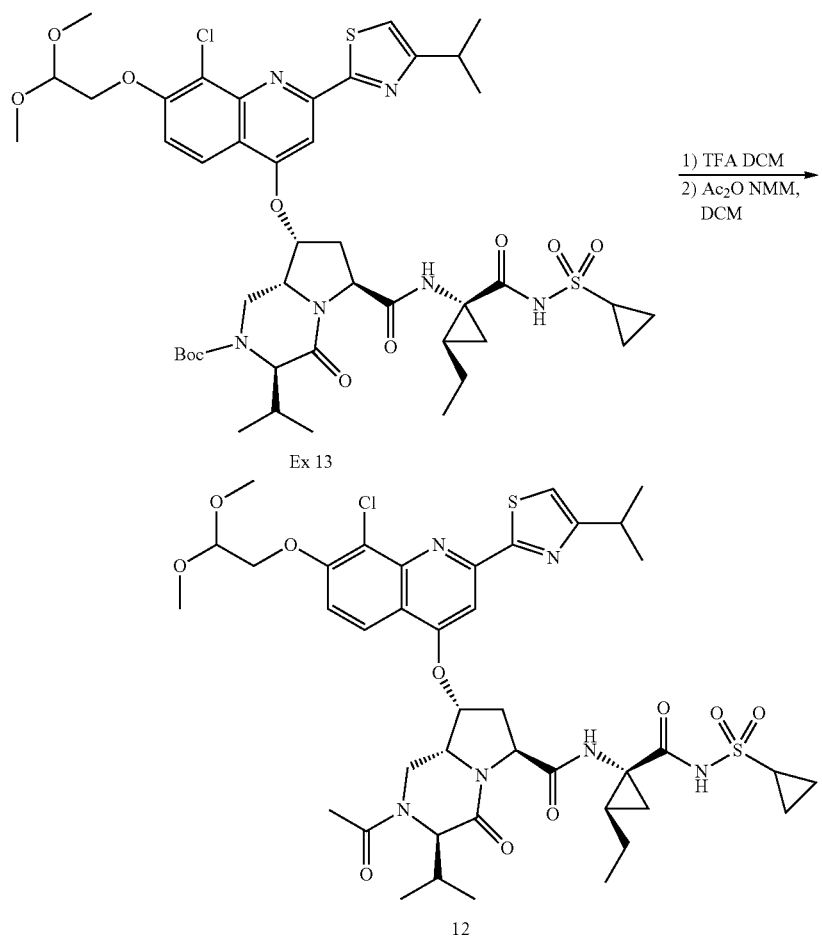

Example 13 (171 mg, 0.18 mmol) was dissolved in CH$_2$Cl$_2$ (2 mL). To this solution was added TFA (0.5 mL). The reaction was stirred for 1 h at rt. The reaction was concentrated; the residue was suspended in toluene and concentrated twice. The crude material was used in the next reaction.

The crude material from the step above was dissolved in CH$_2$Cl$_2$ (2 mL). To this solution was added NMM (1 mL) and Ac$_2$O (0.085 mL). The reaction was stirred overnight at rt. The reaction was concentrated; the residue was suspended in toluene and concentrated twice. This yielded compound 12 that was used in the next reaction.

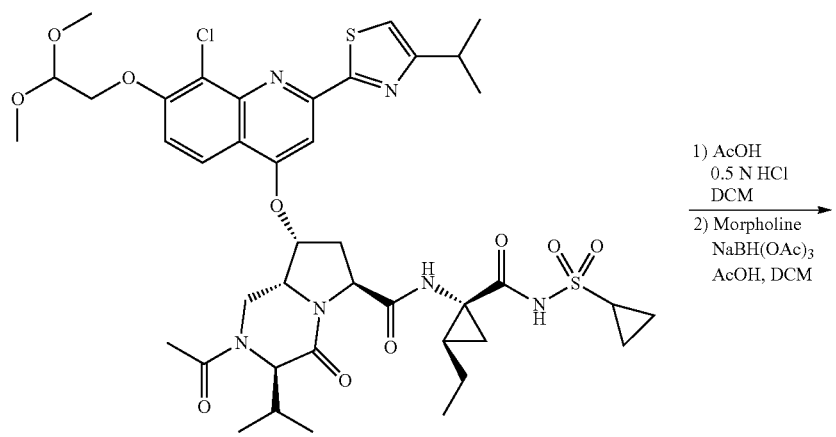

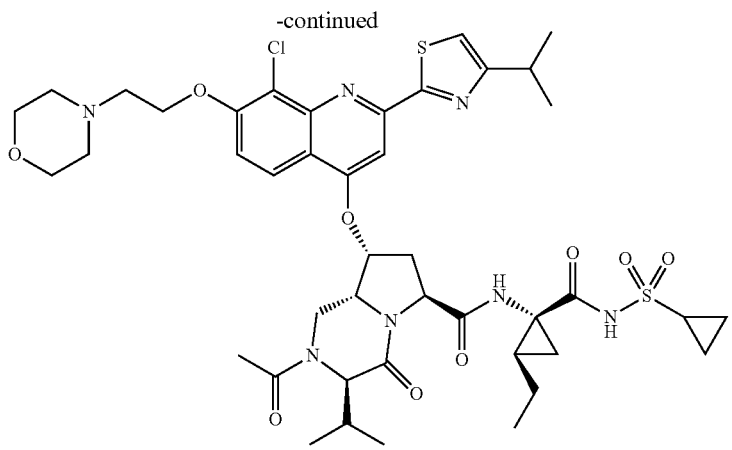

Ex 14

Compound 12 (110 mg, 0.124 mmol) in AcOH (2 mL0 and 1.5N HCl (0.5 mL) was heated to 65° C. for 2 h. The reaction was concentrated and co-evaporated with toluene twice.

To this residue was added DCM (2 mL), morpholine (0.032 mL, 0.372 mmol) and NaBH(OAc)₃ (39 mg, 0.186 mmol). AcOH was added dropwise to adjust pH to 5. The reaction mixture was stirred at rt for 20 min. LC/MS showed the reaction was complete. The reaction was diluted with DCM (20 mL), washed with sat'd NaHCO₃ (10 mL). The organic phase was then dried over Na₂SO₄. The drying agent was removed by vacuum filtration and example 14 (87 mg, 77%) was isolated prep-HPLC.

LC/MS=915 (M⁺+1)

$^1$H NMR (400 MHz, DMSO-d₆): δ (ppm) 10.28 (br, 1H), 8.61 (br, 1H), 7.89 (d, J=9.2 Hz, 1H), 7.73 (s, 1H), 7.57 (d, J=9.2 Hz, 1H), 7.49 (s, 1H), 5.69 (m, 1H), 4.63 (m, 2H), 4.42 (m, 2H), 3.58 (m, 6H), 3.18 (m, 1H), 2.93 (m, 1H), 2.25 (m, 2H), 1.99 (m, 2H), 1.43-0.91 (m, 28H).

Preparation of Example 15

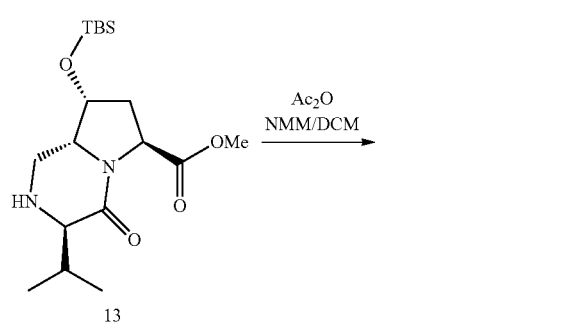

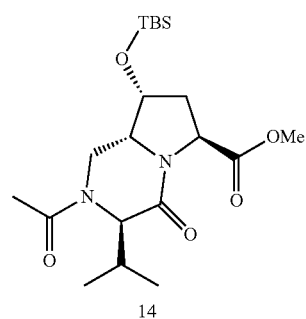

Compound 14 (77 mg, 0.208 mmol), prepared in a similar manner to compound 8, was dissolved in DCM (2 mL) at rt. NMM (0.1 mL) and Ac₂O (0.04 mL, 0.416 mmol) were add. The mixture was stirred at RT for 2 h. It was concentrated by Vacuum. The residue was purified by flash chromatography on silica gel with EtOAc and hexane to give compound 14 (57 mg, 67%).

LC/MS=413 M⁺+1)

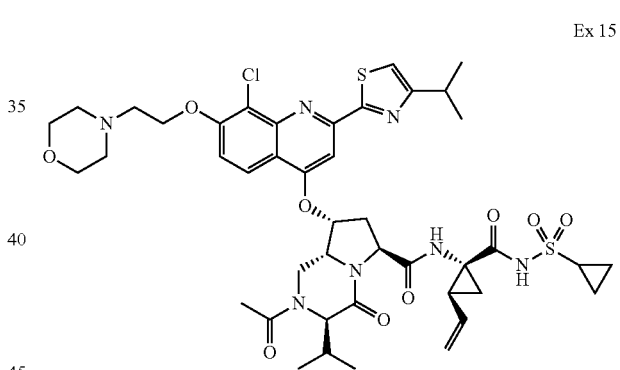

Ex 15

Example 15 was prepared in a similar manner to described in method A, except compound 14 was used, 4,8-dichloro-2-(4-isopropyl-thiazol-2-yl)-7-(2-morpholin-4-yl-ethoxy)-quinoline was used instead of 4,8-dichloro-2-(6-isopropyl-pyridin-2-yl)-7-(2-methoxy-ethoxy)-quinoline and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=913 (M⁺+1)

$^1$H NMR (400 MHz, CD₃OD): δ (ppm) 9.20, 9.06 (s, s, 1H), 7.80-7.75 (m, 2H), 7.48 (m, 1H), 7.34 (m, 1H), 5.72-5.56 (m, 2H), 5.27-5.08 (m, 1H), 4.79 (m, 1H), 4.67 (m, 2H), 4.65-4.47 (m, 2H), 4.25-3.97 (m, 4H), 3.85-3.70 (m, 6H), 3.52-3.40 (m, 3H), 3.20-2.63 (m, 3H), 2.46-1.84 (m, 7H), 1.85 (s, s, 6H), 1.12-0.91 (m, 8H).

Preparation of Example 16

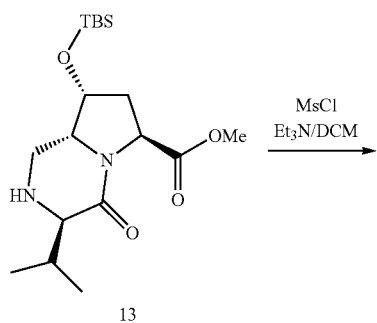

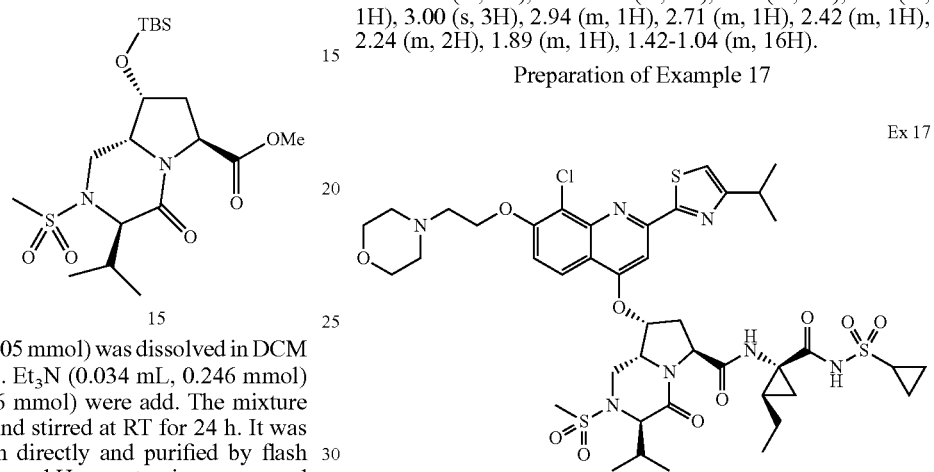

Compound 13 (76 mg, 0.205 mmol) was dissolved in DCM (2 mL) at −78° C. under N$_2$. Et$_3$N (0.034 mL, 0.246 mmol) and MsCl (0.017 mL, 0.226 mmol) were add. The mixture was warmed to RT slowly and stirred at RT for 24 h. It was load on a silica gel column directly and purified by flash chromatography with EtOAc and Hexane to give compound 15 (57 mg, 62%).

LC/MS=449 (M$^+$+1)

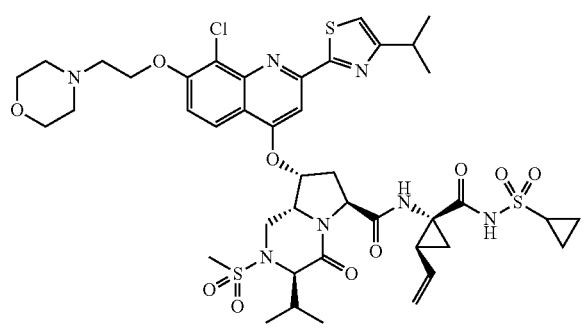

Example 16 was prepared in a similar manner to described in method A, except corn pound 15 was used, 4,8-dichloro-2-(4-isopropyl-thiazol-2-yl)-7-(2-morpholin-4-yl-ethoxy)-quinoline was used instead of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=949 (M$^+$+1)

$^1$H NMR (400 MHz, CD$_3$OD): δ (ppm) 9.20, (s, 1H), 8.23 (m, 1H), 7.81 (s, 1H), 7.50 (m, 1H), 7.32 (m, 1H), 5.74-5.60 (m, 2H), 5.27-5.08 (m, 2H), 4.66 (m, 2H), 4.53 (m, 2H), 4.22-4.08 (m, 3H), 3.88-3.76 (m, 8H), 3.43 (br, 2H), 3.17 (m, 1H), 3.00 (s, 3H), 2.94 (m, 1H), 2.71 (m, 1H), 2.42 (m, 1H), 2.24 (m, 2H), 1.89 (m, 1H), 1.42-1.04 (m, 16H).

Preparation of Example 17

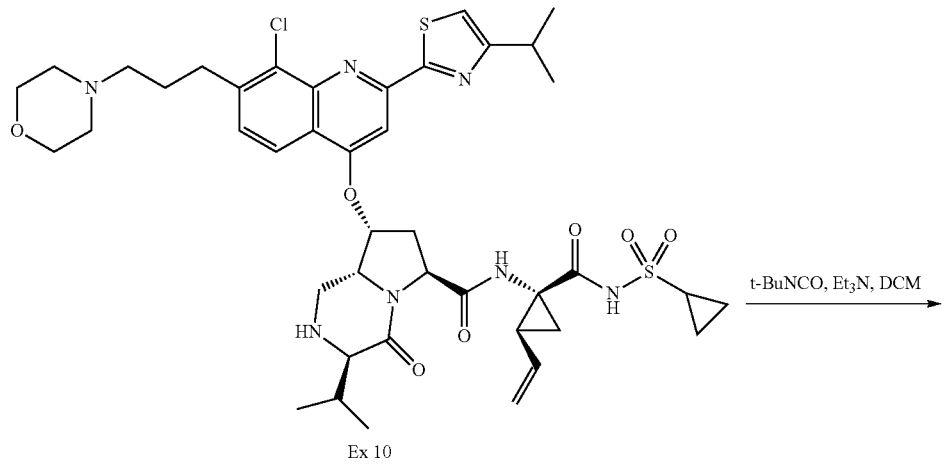

Example 17 was prepared in a similar manner to described in method A, except compound 15 was used, the HCl salt of cyclopropanesulfonic acid ((1R,2S)-1-amino-2-ethyl-cyclopropanecarbonyl)-amide was used in place of the HCl salt of 1-methyl-cyclopropanesulfonic acid ((1R,2S)-1-amino-2-vinyl-cyclopropanecarbonyl)-amide, and 4,8-dichloro-2-(4-isopropyl-thiazol-2-yl)-7-(2-morpholin-4-yl-ethoxy)-quinoline was used instead of 4,8-dichloro-2-(6-isopropyl-pyridin-2-yl)-7-(2-methoxy-ethoxy)-quinoline.

LC/MS=951 (M$^+$+1)

$^1$H NMR (400 MHz, CD$_3$OD): δ (ppm) 9.10, (s, 1H), 8.22 (d, J=9.2 Hz, 1H), 7.79 (s, 1H), 7.45 (d, J=9.2 Hz, 1H), 7.31 (s, 1H), 5.57 (br, 1H), 4.65 (m, 2H), 4.53 (m, 2H), 4.20-4.08 (m, 3H), 3.88-3.76 (m, 8H), 3.43 (br, 2H), 3.19 (m, 1H), 3.00 (s, 3H), 2.94 (m, 1H), 2.71 (m, 1H), 2.40 (m, 1H), 2.24 (m, 1H), 1.59-0.90 (m, 24H).

Preparation of Example 18

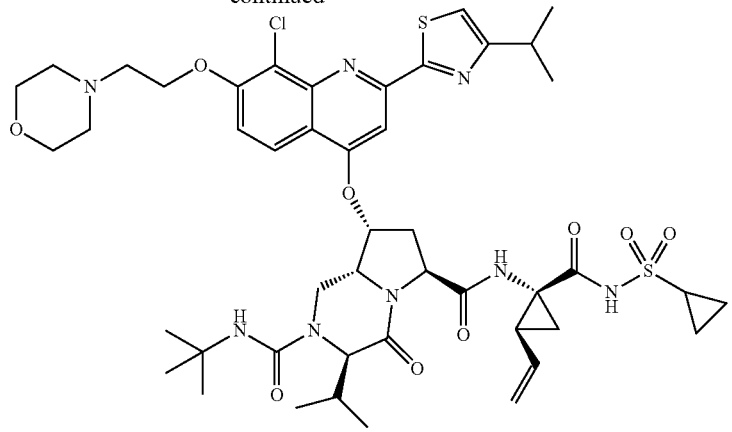

Ex 18

Example 10 (57 mg, 0.066 mmol) was dissolved in DCM (2 mL) at 0° C. under N$_2$. Et$_3$N (0.014 mL, 0.098 mmol) and t-BuNCO (0.010 mL, 0.098 mmol) were add. The mixture was warmed to RT after addition and stirred at RT for 5 h. It was loaded on a silica gel column directly and purified by flash chromatography with EtOAc and Hexane to give example 18 (38 mg, 60%).

LC/MS=970 (M$^+$+1)

$^1$H NMR (400 MHz, CD$_3$OD): δ (ppm) 9.20, (s, 1H), 8.03 (d, J=9.2 Hz, 1H), 7.84 (s, 1H), 7.45 (d, J=9.2 Hz, 1H), 7.34 (s, 1H), 5.74-5.60 (m, 2H), 4.68 (m, 2H), 4.50 (m, 2H), 4.38 (m, 1H), 4.08-3.46 (m, 7H), 3.17 (m, 1H), 2.94 (m, 1H), 2.67 (m, 1H), 2.21 (m, 2H), 1.92 (m, 1H), 1.42-1.04 (m, 22H).

Preparation of Example 19

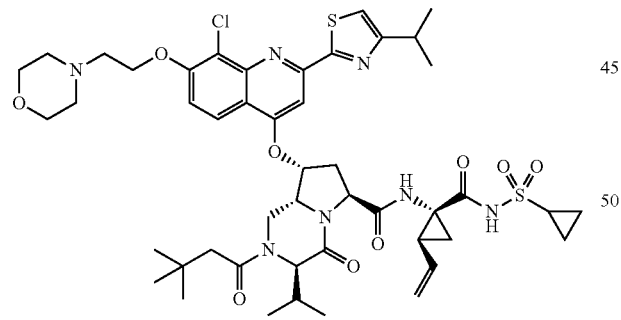

Ex 19

Example 19 was prepared in a similar fashion to example 18, except 3,3-dimethyl-butyryl chloride was used instead of 2-isocyanato-2-methyl-propane.

LC/MS=970 (M$^+$+1)

$^1$H NMR (400 MHz, CD$_3$OD): δ (ppm) 9.22, 9.07 (s, s, 1H), 8.03-7.84 (m, 1H), 7.50-7.34 (m, 2H), 5.72-5.58 (m, 2H), 5.27-5.11 (m, 2H), 4.73-4.43 (m, 4H), 4.31-3.47 (m, 1H), 4.08-3.46 (m, 7H), 3.17 (m, 1H), 2.94 (m, 1H), 2.67 (m, 1H), 2.43-2.14 (m, 3H), 1.86 (m, 1H), 1.42-1.04 (m, 27H).

Preparation of Example 20

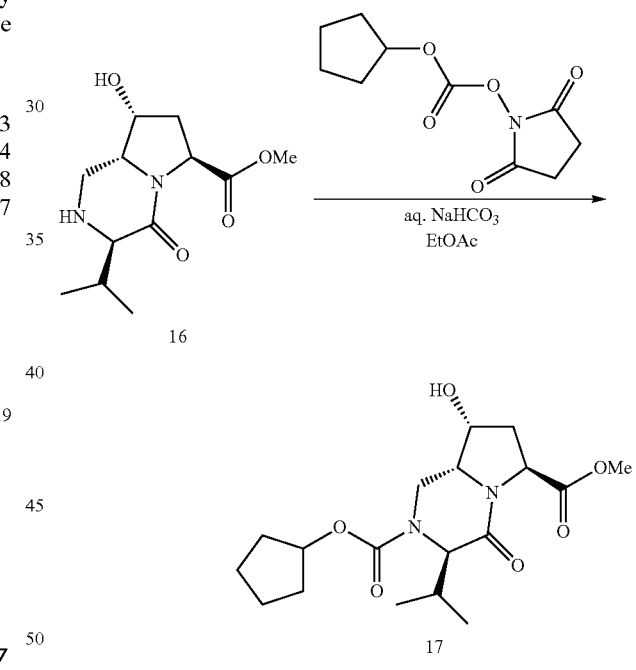

Compound 16 (60 mg, 0.234 mmol), prepared from compound 13 by removal of the TBS protecting group, was dissolved in EtOAc (5 mL) and sat'd NaHCO$_3$ (5 mL) at RT. Carbonic acid cyclopentyl ester 2,5-dioxo-cyclopentyl ester (0.320 mg, 1.406 mmol) was add. The mixture was stirred at RT for 24 h. The layers were separated. The organic layer was washed with brine and dried over Na$_2$SO$_4$, then concentrated. The crude product was load on a silica gel column and purified by flash chromatography with EtOAc and Hexane to give compound 17 (44 mg, 51%).

LC/MS=369 (M$^+$+1)

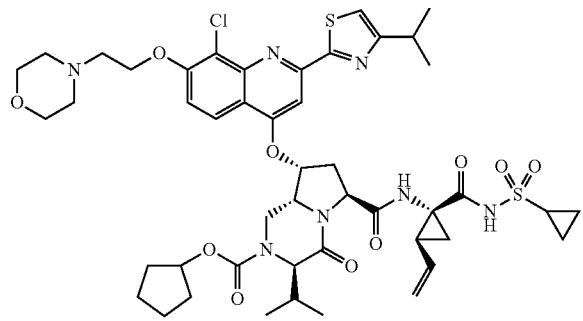

Ex 20

Example 20 was prepared in a similar manner to described in method A, except compound 17 was used, 4,8-dichloro-2-(4-isopropyl-thiazol-2-yl)-7-(2-morpholin-4-yl-ethoxy)-quinoline was used instead of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=983 (M$^+$+1)

$^1$H NMR (400 MHz, CD$_3$OD): δ (ppm) 9.16, 8.75 (s, s, 1H), 8.03 (m, 1H), 7.47 (m, 2H), 7.34 (br, 1H), 5.74-5.63 (m, 2H), 5.28-5.10 (m, 2H), 4.65-4.10 (m, 7H), 3.93-3.47 (m, 9H), 3.20 (m, 1H), 2.92 (m, 1H), 2.65 (m, 1H), 2.40 (m, 1H), 2.21 (m, 2H), 1.88-0.99 (m, 19H).

Preparation of Example 21

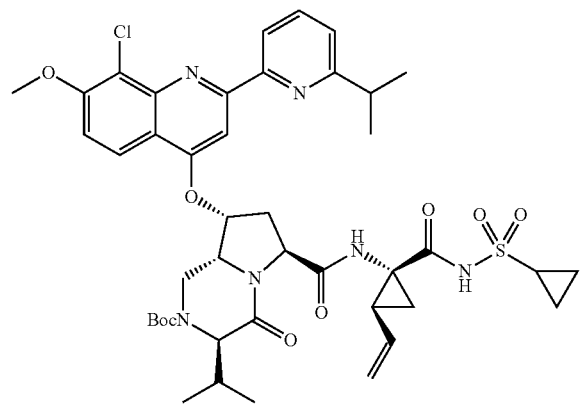

Ex 21

Example 21 was prepared in a similar manner to described in method A, except 2R-amino-3-methyl-butyric acid tert-butyl ester was used instead of 2R-amino-3,3-dimethyl-butyric acid tert-butyl ester, 4,8-dichloro-2-(6-isopropyl-pyridin-2-yl)-7-methoxy-quinoline was used instead of 4,8-dichloro-2-(6-isopropyl-pyridin-2-yl)-7-(2-methoxy-ethoxy)-quinoline and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=866 (M$^+$+1)

$^1$H NMR (400 MHz, CD$_3$OD): δ (ppm) 8.61 (m, 1H), 8.24 (m, 1H), 8.19 (m, 2H), 7.76, (m, 1H), 7.70 (m, 1H), 5.94 (br, 1H), 5.69 (m, 1H), 5.29-5.09 (m, 2H), 4.61 (m, 2H), 4.25 (m, 1H), 4.16 (s, 3H), 4.06 (m, 1H), 3.76 (m, 1H), 3.35 (m, 1H), 2.74 (m, 1H), 2.52 (m, 1H), 2.20 (m, 2H), 1.87 (m, 1H), 1.54-1.03 (m, 25H).

Preparation of Example 22

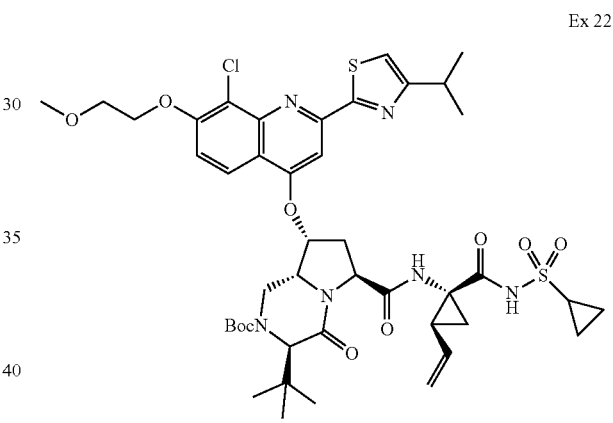

Ex 22

Example 22 was prepared in a similar manner to described in method A, except using 4,8-dichloro-2-(4-isopropyl-thiazol-2-yl)-7-(2-methoxy-ethoxy)-quinoline in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=930 (M$^+$+1)

$^1$H NMR (400 MHz, CD$_3$OD): δ (ppm) 9.16 (br, 1H), 7.88 (d, J=9.2 Hz, 1H), 7.80 (s, 1H), 7.45 (d, J=9.2 Hz, 1H), 7.33 (s, 1H), 5.71 (m, 1H), 5.55 (m, 1H), 5.26 (d, J=16.8 Hz, 1H), 5.10 (d, J=10.8 Hz, 1H), 4.88 (m, 1H), 4.61-4.52 (m, 3H), 4.39-4.31 (m, 4H), 4.17-4.10 (m, 1H), 3.82 (dd, J=4.4 Hz, 8.8 Hz, 2H), 3.71-3.60 (m, 2H), 3.53-3.49 (m, 1H), 3.31 (s, 2H), 3.18 (m, 1H), 3.11 (m, 1H), 2.96 (m, 1H), 2.64 (m, 1H), 2.36 (m, 1H), 2.21 (m, 1H), 1.88 (m, 1H), 1.49 (br, 3H), 1.37 (d, J=6.8 Hz, 6H), 1.26-1.10 (m, 12H), 1.06 (m, 2H).

Preparation of Example 23

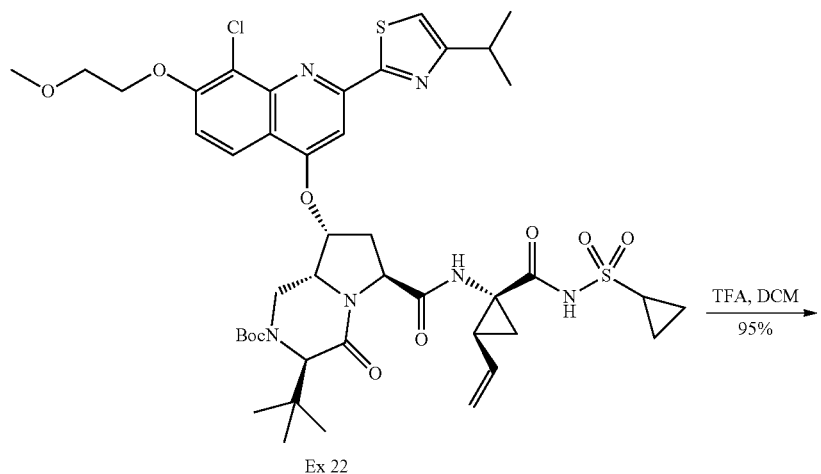

Ex 22

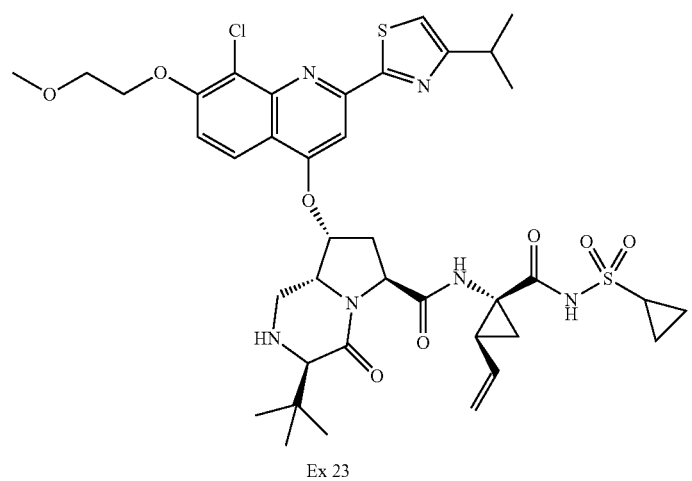

Ex 23

Example 22 (0.22 g, 0.24 mmol) was dissolved in DCM (2 ml) at room temperature, followed by the addition of TFA (2 ml). The mixture was stirred for 2 h and monitored by LC-MS. After prep-HPLC purification example 23, as the TFA salt (0.24 g, 0.23 mmol), was obtained in white solid form.

LC/MS=830 (M$^+$+1)

$^1$H NMR (400 MHz, CD$_3$OD/D$_6$-DMSO): δ (ppm) 9.14 (br, 1H), 8.13 (d, J=9.2 Hz, 1H), 7.80 (s, 1H), 7.48 (d, J=9.2 Hz, 1H), 7.34 (s, 1H), 5.72 (m, 1H), 5.64 (m, 1H), 5.24 (d, J=17.2 Hz, 1H), 5.10 (d, J=10.48 Hz, 1H), 4.88 (m, 1H), 4.63 (m, 1H), 4.53 (m, 1 h), 4.38 (m, 2H), 4.13 (m, 1H), 4.03 (s, 1H), 3.94 (m, 1H), 3.84 (m, 2H), 3.71-3.61 (m, 4H), 3.53-3.48 9 m, 3H), 3.19 (m, 1H), 2.77 (m, 1H), 2.37 (m, 1H), 2.17 (m, 1H), 1.88 (m, 1H), 1.38-1.00 (m, 15H).

Preparation of Example 24

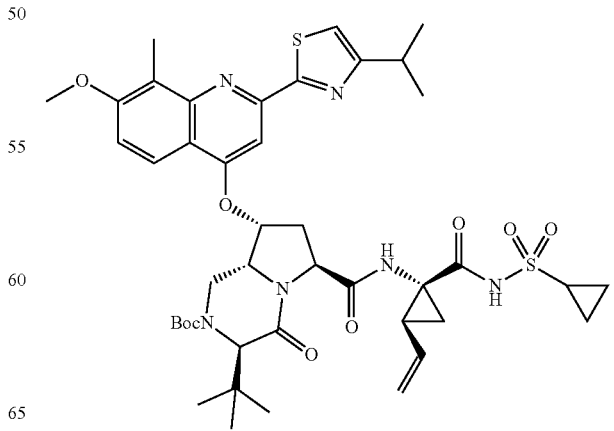

Ex 24

Example 24 was prepared in a similar manner to that described in method A, except using 4,8-dichloro-2-(4-isopropyl-thiazol-2-yl)-7-methoxy-quinoline in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=866 (M$^+$+1)

$^1$H NMR (400 MHz, CD$_3$OD): δ (ppm) 7.84 (d, J=9.6 Hz, 1H), 7.70 (m, 1H), 7.31 (m, 2H), 5.68 (m, 1H), 5.41 (m, 1H), 5.26 (d, J=16.8 Hz, 1H), 5.096 (d, J=12 Hz, 1H), 4.59-4.53 (m, 2H), 4.40-4.30 (m, 4H), 3.96 (s, 3H), 3.76-3.64 (m, 3H), 3.21-3.11 (m, 2H), 2.95 (m, 1H), 2.62 (m, 4H), 2.36 (m, 1H), 2.20 (m, 1H), 1.88 (m, 1H), 1.50-1.07 (m, 27H).

Preparation of Example 25

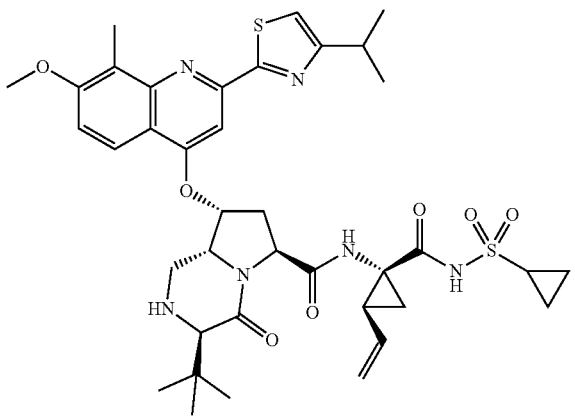

Ex 25

Example 25 was prepared from example 24 via removal of the Boc group, in a manner similar to that previously described.

LC/MS=766 (M$^+$+1)

$^1$H NMR (400 MHz, CD$_3$OD): δ (ppm) 9.13 (s, 1H), 8.05 (d, J=9.2 Hz 1H), 7.68 (s, 1H), 7.38 (d, J=9.2 Hz, 1H), 7.29 (s, 1H), 5.68 (br, 1H), 5.56 (m, 1H), 5.25-5.21 9 m, 1H), 5.07 (m, 1H), 4.87 (m, 1H), 4.67-4.57 (m, 2H), 4.18-3.97 (m, 5H), 3.54-3.49 (m, 1H), 3.18 (m, 1H), 2.91 (m, 1H), 2.83 (m, 1H), 2.60 (s, 3H), 2.40-2.33 (m, 1H), 2.20-2.13 (m, 1H), 1.85 (m, 1H), 1.42-1.02 (m, 17H).

Preparation of Example 26

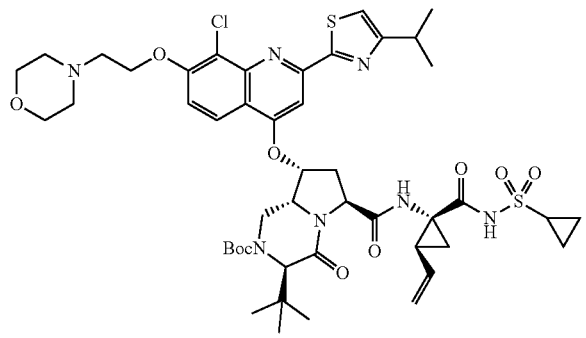 [SMILES: C=C[C@@H]1C[C@]1(NC(=O)[C@@H]1C[C@@H](Oc2cc(-c3nc(C(C)C)cs3)nc3c(Cl)c(OCCN4CCOCC4)ccc23)[C@H]2CN(C(=O)OC(C)(C)C)[C@H](C(C)(C)C)C(=O)N21)C(=O)NS(=O)(=O)C1CC1]

Example 26 was prepared in a similar manner to that described in method A, except using 4,8-dichloro-2-(4-isopropyl-thiazol-2-yl)-7-(2-morpholin-4-yl-ethoxy)-quinoline in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=984 (M$^+$+1)

$^1$H NMR (400 MHz, CD$_3$OD): δ (ppm) 7.94 (m, 1H), 7.84 (m, 1H), 7.48-7.38 (m, 1H), 7.34 (s, 1H), 5.73-5.54 (m, 2H), 5.26 (m, 1H), 5.10 (m, 1H), 4.88 (m, 3H), 4.84-4.33 (m, 5H), 4.16-4.10 (m, 3H), 3.86-3.38 (m, 7H), 3.18 (m, 1H), 2.95 (m, 1H), 2.65 (m, 1H), 2.40 (m, 1H), 2.20 (m, 1H), 1.88 (m, 1H), 1.48-1.02 (m, 29H).

Preparation of Example 27

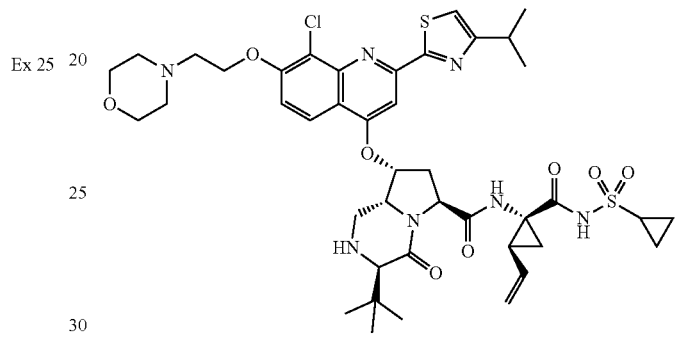

Ex 27

Example 27 was prepared from example 26 via removal of the Boc group, in a manner similar to that previously described.

LC/MS=884 (M$^+$+1)

$^1$H NMR (400 MHz, CD$_3$OD/D$_6$-DMSO): δ (ppm) 8.20 (d, J=9.2 Hz, 1H), 7.85 (s, 1H), 7.52 (d, J=9.2 Hz, 1H), 7.36 (s, 1H), 5.78-5.61 (m, 2H), 5.24 (m, 1H), 5.10 (m, 1H), 4.68-4.51 (m, 4H), 3.98-3.89 (m, 6H), 3.77 (m, 2H), 3.62 (m, 4H), 3.18 (m, 1H), 2.94 (m, 1H), 2.77 (m, 1H), 2.39 (m, 1H), 2.16 (m, 1H), 1.88 (m, 1H), 1.38-1.05 (m, 20H).

Preparation of Example 28

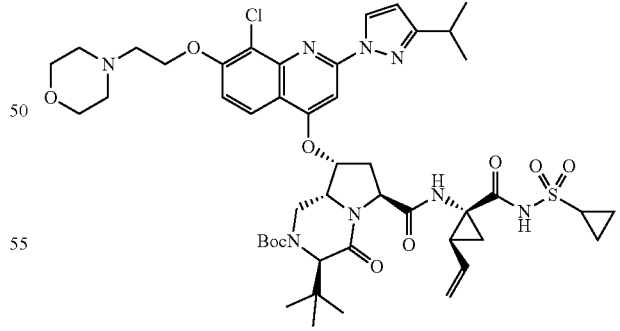

Ex 28

Example 28 was prepared in a similar manner to that described in method A, except using 4,8-dichloro-2-(3-isopropyl-pyrazol-1-yl)-7-(2-morpholin-4-yl-ethoxy)-quinoline in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=968 (M$^+$+1)

$^1$H NMR (400 MHz, CD$_3$OD): δ (ppm) 8.72 (d, J=2.4 Hz, 1H), 7.89 (d, J=9.2 Hz, 1H), 7.66 (s, 1H), 7.33 (d, J=9.2 Hz, 1H), 6.47 (d, J=2.4 Hz, 1H), 5.71-5.51 (m, 2H), 5.26 (m, 1H), 5.11 (m, 1H), 4.63-4.35 (m, 4H), 4.20-3.40 (m, 12H), 3.08 (m, 1H), 2.95 (m, 1H), 2.63 (m, 1H), 2.36 (m, 1H), 2.20 (m, 1H), 1.88 (m, 1H), 1.50-1.04 (m, 28H).

Preparation of Example 29

Ex 29

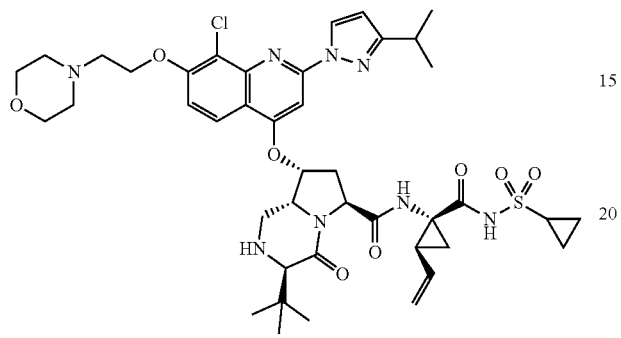

Example 29 was prepared from example 28 via removal of the Boc group, in a manner similar to that previously described.

LC/MS=867 (M$^+$+1)

$^1$H NMR (400 MHz, CD$_3$OD/D$_6$-DMSO): δ (ppm) 8.72 (d, J=2.4 Hz, 1H), 8.15 (d, J=9.2 Hz, 1H), 7.63 (s, 1H), 7.42 (d, J=9.2 Hz, 1H), 6.46 (d, J=2.4 Hz, 1H), 5.70-5.58 (m, 2H), 5.25 (m, 1H), 5.09 (m, 1H), 4.67-4.55 (m, 4H), 4.09-3.62 (m, 12H), 3.07 (m, 1H), 2.94 (m, 1H), 2.79 (m, 1H), 2.38 (m, 1H), 2.17 (m, 1H), 1.87 (m, 1H), 1.36-1.04 (m, 19H).

Preparation of Example 30

Ex 30

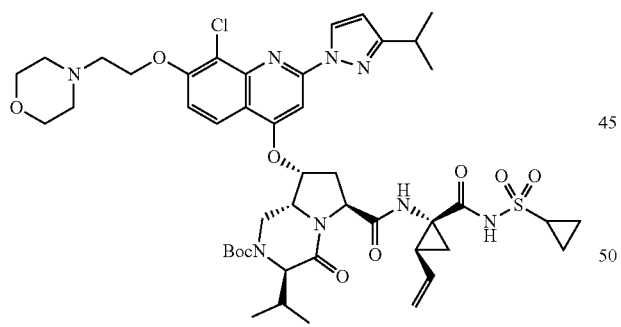

Example 30 was prepared in a similar manner to that described in method A, except using 4,8-dichloro-2-(3-isopropyl-pyrazol-1-yl)-7-(2-morpholin-4-yl-ethoxy)-quinoline in place of 4,8-dichloro-2-(6-isopropyl-pyridin-2-yl)-7-(2-methoxy-ethoxy)-quinoline, the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide, and 2R-amino-3-methyl-butyric acid tert-butyl ester was used in place of 2R-amino-3,3-dimethyl-butyric acid tert-butyl ester.

LC/MS=954 (M$^+$+1)

$^1$H NMR (400 MHz, CD$_3$OD): δ (ppm) 8.72 (d, J=2.4 Hz, 1H), 7.99 (d, J=9.2 Hz, 1H), 7.64 (s, 1H), 7.373 (d, J=9.2 Hz, 1H), 6.46 (d, J=2.4 Hz, 1H), 5.75-5.60 (m, 2H), 5.26 (m, 1H), 5.11 (m, 1H), 4.87 (m, 1H), 4.60-4.45 (m, 4H), 4.27-3.82 (m, 5H), 3.71-3.47 (m, 11H), 3.08 (m, 1H), 2.94 (m, 1H), 2.39 (m, 1H), 1.88 (m, 1H), 1.48-0.99 (m, 23H).

Preparation of Example 31

Ex 31

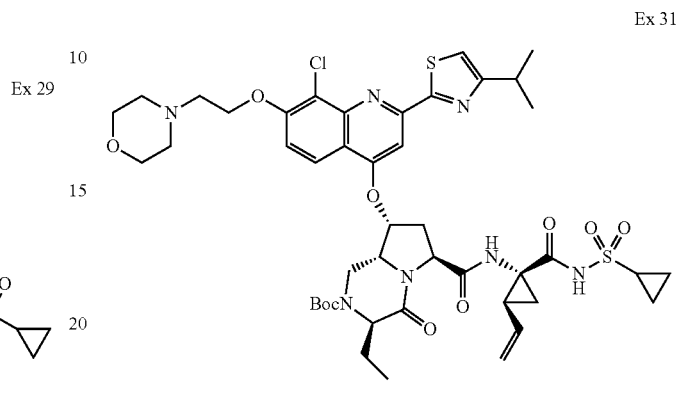

Example 31 was prepared in a similar manner to that described in method A, except using 4,8-dichloro-2-(4-isopropyl-thiazol-2-yl)-7-(2-morpholin-4-yl-ethoxy)-quinoline instead of 4,8-dichloro-2-(6-isopropyl-pyridin-2-yl)-7-(2-methoxy-ethoxy)-quinoline, the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide, and 2R-amino-butyric acid tert-butyl ester was used in place of 2R-amino-3,3-dimethyl-butyric acid tert butyl ester.

LC/MS=956 (M$^+$+1)

$^1$H NMR (400 MHz, CD$_3$OD): δ (ppm) 8.00 (d, J=9.2 Hz, 1H), 7.85 (s, 1H), 7.55 (d, J=9.2 Hz, 1H), 7.34 (s, 1H), 5.65 (m, 2H), 5.28 (m, 1H), 5.11 (m, 1H), 4.88 (m, 3H), 4.67-4.53 (m, 4H), 4.31 (m, 1H), 4.17-4.10 (m, 3H), 3.78-3.33 (m, 8H), 3.16 (m, 1H), 2.95 (m, 1H), 2.68 (m, 1H), 2.41 (m, 1H), 2.23 (m, 1H), 2.11 (m, 1H), 1.88 (m, 1H), 1.48-1.02 (m, 22H).

Preparation of Example 32

Ex 32

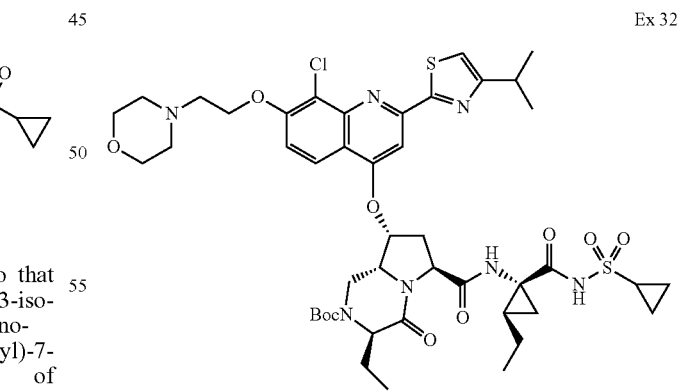

Example 32 was prepared in a similar manner to that described in method A, except using 4,8-dichloro-2-(4-isopropyl-thiazol-2-yl)-7-(2-morpholin-4-yl-ethoxy)-quinoline in place of 4,8-dichloro-2-(6-isopropyl-pyridin-2-yl)-7-(2-methoxy-ethoxy)-quinoline, the HCl salt of cyclopropanesulfonic acid ((1R,2S)-1-amino-2-ethyl-cyclopropanecarbonyl)-amide was used in place of the HCl salt of 1-methylcyclopropanesulfonic acid ((1R,2S)-1-amino-2-vinyl-cyclopropanecarbonyl)-amide, and 2R-amino-butyric acid tert-butyl ester was used in place of 2R-amino-3,3-dimethyl-butyric acid tert butyl ester.

LC/MS=958 (M$^+$+1)

$^1$H NMR (400 MHz, CD$_3$OD): δ (ppm) 8.00 (d, J=9.2 Hz, 1H), 7.85 (s, 1H), 7.55 (d, J=9.2 Hz, 1H), 7.34 (s, 1H), 5.65 (m, 1H), 4.67-4.53 (m, 4H), 4.32-4.30 (m, 2H), 3.84-3.46 (m, 6H), 3.22-3.11 (m, 3H), 2.95 (m, 1H), 2.66 (m, 1H), 2.41 (m, 1H), 2.09 (m, 1H), 1.86 (m, 1H), 1.60-0.94 (m, 34H).

Preparation of Example 33

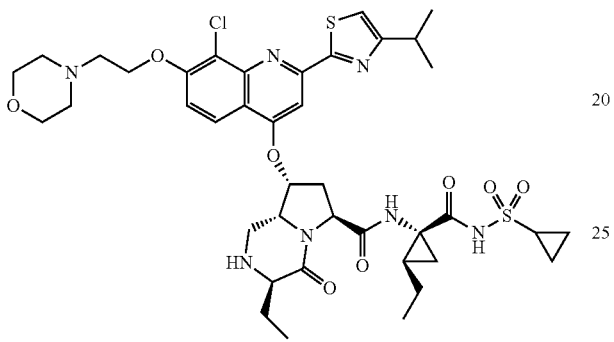

Ex 33

Example 33 was prepared from example 32 via removal of the Boc group, in a manner similar to that previously described.

LC/MS=858 (M$^+$+1)

$^1$H NMR (400 MHz, CD$_3$OD/D$_6$-DMSO): δ (ppm) 8.04 (d, J=9.2 Hz, 1H), 7.86 (s, 1H), 7.55 (d, J=9.2 Hz, 1H), 7.36 (s, 1H), 5.74 (m, 1H), 4.67-4.57 (m, 4H), 4.08-3.77 (m, 7H), 3.67-3.46 (m, 5H), 3.22-3.11 (m, 2H), 2.95 (m, 1H), 2.74 (m, 1H), 2.48 (m, 1H), 2.09 (m, 1H), 2.07 (m, 1H), 1.63-0.94 (m, 19H).

Preparation of Example 34

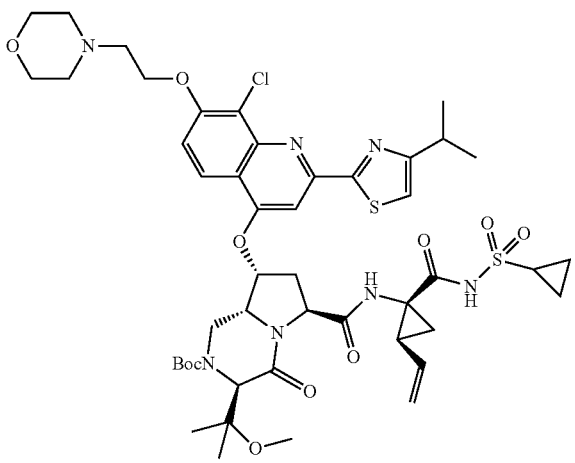

Ex 34

Example 34 was prepared in a manner similar to that described in method A, except 2R-amino-3-methoxy-3-methyl-butyric acid tert-butyl ester was used in place of 2R-amino-3,3-dimethyl-butyric acid tert-butyl ester, 4,8-dichloro-2-(4-isopropyl-thiazol-2-yl)-7-(2-morpholin-4-yl-ethoxy)-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=1001 (M$^+$+1).

$^1$H NMR (400 MHz, CD$_3$OD): δ (ppm) 8.91 (brs, 1H), 7.99 (m, 1H), 7.86 (d, J=9.6 Hz, 1H), 7.47 (m, 1H), 7.34 (s, 1H), 5.80-5.62 (m, 1H), 5.56 (m, 1H), 5.29-5.25 (m, 1H), 5.12-5.09 (m, 1H), 4.68-4.60 (m, 2H), 4.51-4.43 (m, 3H), 4.27 (m, 1H), 4.09 (brs, 2H), 3.84-3.67 (m, 6H), 3.46 (brs, 2H), 3.25 (s, 3H), 3.18 (m, 1H), 2.95 (m, 1H), 2.65-2.58 (m, 1H), 2.44 (m, 1H), 2.22 (m, 1H), 1.88 (m, 1H), 1.49-1.08 (m, 27H).

Preparation of Example 35

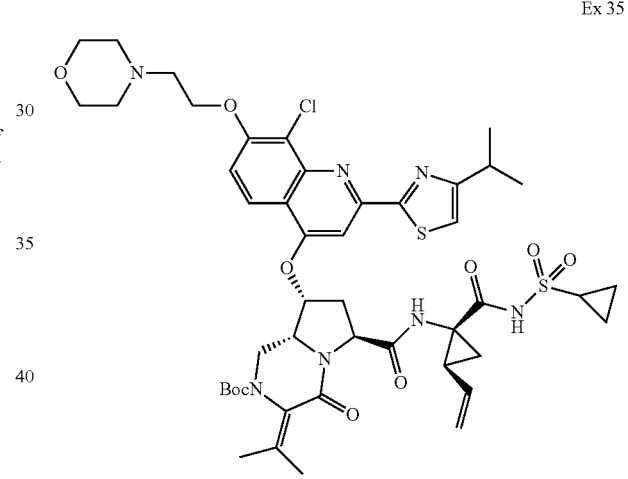

Ex 35

Example 35 was prepared in a manner similar to that described in method A, except 2R-amino-3-methoxy-3-methyl-butyric acid tert-butyl ester was used in place of 2R-amino-3,3-dimethyl-butyric acid tert-butyl ester, 4,8-dichloro-2-(4-isopropyl-thiazol-2-yl)-7-(2-morpholin-4-yl-ethoxy)-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=969 (M$^+$+1).

$^1$H NMR (400 MHz, CD$_3$OD): δ (ppm) 9.25 (brs, 1H), 8.05 (d, J=9.2 Hz, 1H), 7.83 (s, 1H), 7.53 (d, J=9.2 Hz, 1H), 7.34 (s, 1H), 5.72-5.60 (m, 1H), 5.29-5.25 (m, 1H), 5.12-5.09 (m, 1H), 4.65-4.46 (m, 4H), 4.08 (brs, 2H), 3.85-3.76 (m, 4H), 3.46 (brs, 2H), 3.20 (m, 2H), 2.93 (m, 1H), 2.69-2.63 (m, 1H), 2.34 (s, 3H), 2.22 (m, 1H), 1.90 (m, 2H), 1.55-1.01 (m, 27H).

Preparation of Example 36

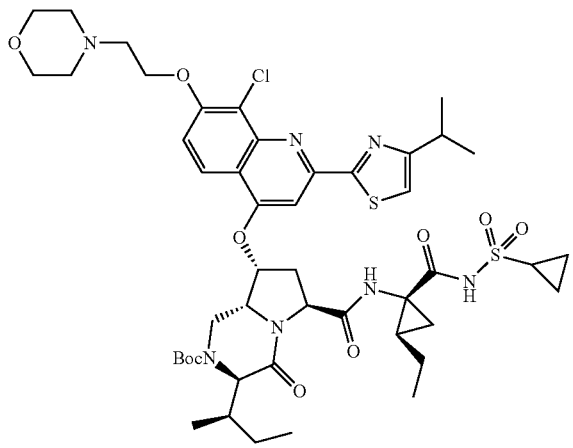

Ex 36

Example 36 was prepared in a manner similar to that described in method A, except the 2R-amino-3R-methyl-pentanoic acid tert-butyl ester was used in place of 2R-amino-3,3-dimethyl-butyric acid tert-butyl ester, 4,8-dichloro-2-(4-isopropyl-thiazol-2-yl)-7-(2-morpholin-4-yl-ethoxy)-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-ethyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=987 (M$^+$+1)

$^1$H NMR (400 MHz, CD$_3$OD): δ (ppm) 9.06 (s, 1H), 8.02 (d, J=9.2 Hz, 1H), 7.82 (s, 1H), 7.45 (d, J=9.2 Hz, 1H), 7.33 (s, 1H), 5.61 (brs, 1H), 4.91 (m, 2H), 4.68 (m, 2H), 4.55 (m, 2H), 4.32 (m, 1H), 4.19-4.09 (m, 4H), 3.89-3.58 (m, 8H), 3.52 (m, 3H), 3.17 (m, 1H), 2.96 (m, 1H), 2.67 (m, 1H), 2.38 (m, 1H), 2.00 (m, 1H), 1.57-0.95 (m, 30H).

Preparation of Example 37

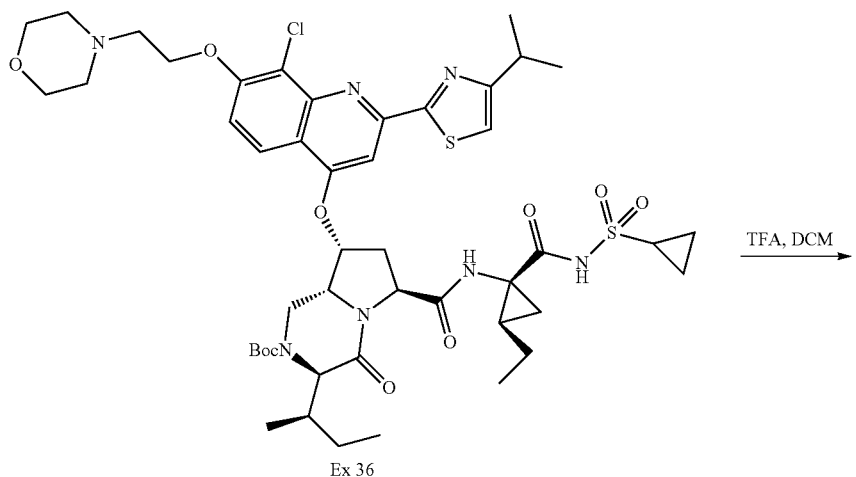

Ex 36

TFA, DCM

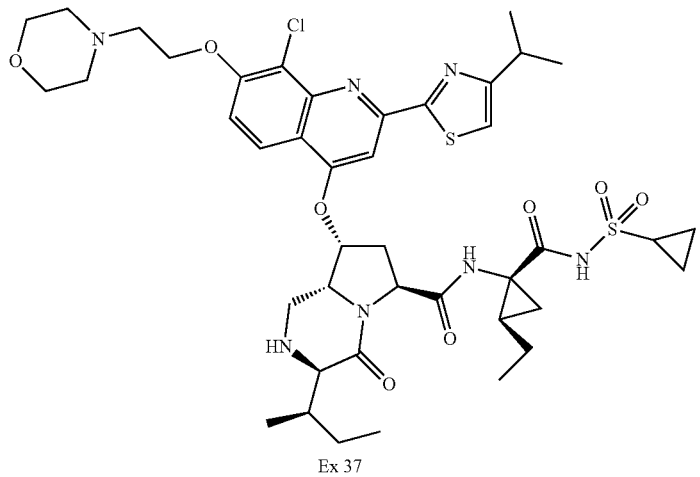

Ex 37

Example 36 was dissolved in DCM and TFA (1:1) and stirred at room temperature for 1 hour to afford example 37 as the TFA salt.

LC/MS=887 (M⁺+1)

$^1$H NMR (400 MHz, CD$_3$OD): δ (ppm) 9.13 (s, 1H), 8.23 (d, J=9.2 Hz, 1H), 7.83 (s, 1H), 7.53 (d, J=9.2 Hz, 1H), 7.35 (s, 1H), 5.73 (br, 1H), 4.59-4.47 (m, 6H), 4.25 (m, 1H), 4.16-4.10 (m, 5H), 3.89-3.56 (m, 8H), 3.41 (m, 3H), 3.19 (m, 1H), 2.96 (m, 1H), 2.75 (m, 1H), 2.42 (m, 1H), 1.61-0.93 (m, 21H).

Preparation of Example 38

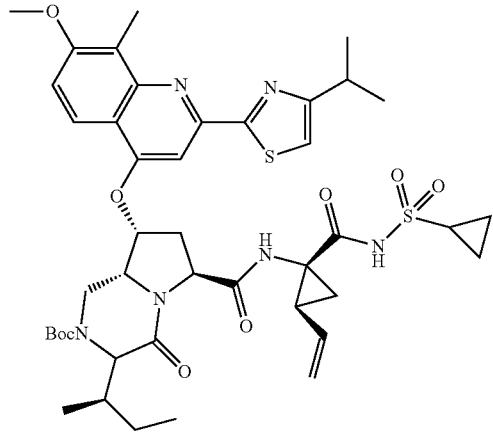

Ex 38

Example 38 was prepared in a manner similar to that described in method A, except the 2R-amino-3R-methyl-pentanoic acid tert-butyl ester was used in place of 2R-amino-3,3-dimethyl-butyric acid tert-butyl ester, 4-chloro-2-(4-isopropyl-thiazol-2-yl)-7-methoxy-8-methyl-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=865 (M⁺+1).

$^1$H NMR (400 MHz, CD$_3$OD): δ (ppm) 9.24 (br, 1H), 7.99 (d, J=9.2 Hz, 1H), 7.72 (s, 1H), 7.40 (m, 2H), 5.72-5.64 (m, 2H), 5.28-5.24 (m, 1H), 5.11-5.08 (m, 1H), 4.56 (m, 2H), 4.35 (m, 1H), 4.08 (m, 1H), 3.98 (s, 3H), 3.71 9 m, 1H), 3.22 (m, 1H), 2.94 (m, 1H), 2.68 (m, 1H), 2.61 (s, 3H), 2.39 (m, 1H), 2.21 (m, 1H), 2.01 (m, 1H), 1.87 (m, 1H), 1.42-0.95 (m, 28H).

Preparation of Example 39

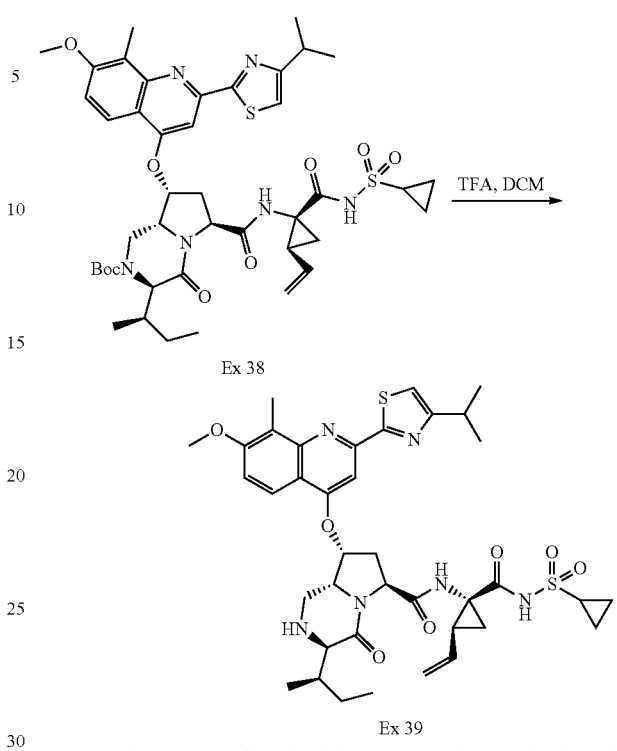

Ex 38

Ex 39

Example 38 was dissolved in DCM and TFA (1:1) and stirred at room temperature for 1 hour to afford example 39 as the TFA salt.

LC/MS=765 (M⁺+1).

$^1$H NMR (400 MHz, CD$_3$OD): δ (ppm) 9.29 (br, 1H), 8.09 (d, J=9.2 Hz, 1H), 7.70 (s, 1H), 7.40 (d, J=9.2 Hz, 1H), 7.29 (s, 1H), 5.72-5.63 (m, 2H), 5.27-5.24 (m, 1H), 5.10-5.08 (m, 1H), 4.56 (m, 2H), 4.35 (m, 1H), 4.08 (m, 1H), 3.98 (s, 3H), 3.71 (m, 1H), 3.22 (m, 1H), 2.94 (m, 1H), 2.68 (m, 1H), 2.62 (s, 3H), 2.39 (m, 1H), 2.21 (m, 1H), 2.01 (m, 1H), 1.87 (m, 1H), 1.42-0.95 (m, 19H).

Preparation of Example 40

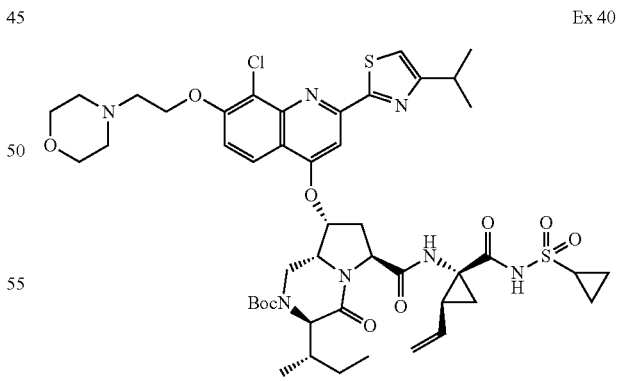

Ex 40

Example 40 was prepared in a manner similar to that described in method A, except the 2R-amino-3S-methyl-pentanoic acid tert-butyl ester was used in place of 2R-amino-3,3-dimethyl-butyric acid tart-butyl ester, 4,8-dichloro-2-(4-isopropyl-thiazol-2-yl)-7-(2-morpholin-4-yl-ethoxy)-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=985 (M$^+$+1).

$^1$H NMR (400 MHz, CD$_3$OD): δ (ppm) 9.18 (br, 1H), 8.06 (d, J=92 Hz, 1H), 7.84 (s, 1H), 7.47 (d, J=9.2 Hz, 1H), 7.34 (s, 1H), 5.75-5.62 (m, 2H), 5.27-5.24 (m, 1H), 5.11-5.09 (m, 1H), 4.65 (m, 2H), 4.52 (m, 2H), 4.35 (m, 1H), 4.09 (br, 2H), 3.84-3.64 (m, 8H), 3.46 (br, 2H), 3.18 (m, 1H), 2.97 (m, 1H), 2.70 (m, 1H), 2.43 (m, 1H), 2.23 (m, 1H), 2.01 (m, 1H), 1.87 (m, 1H), 1.65 (m, 1H), 1.49-0.85 (m, 27H).

Preparation of Example 41

Example 40 was dissolved in DCM and TFA (1:1) and stirred at room temperature for 1 hour to afford example 41 as the TFA salt.

LC/MS=885 (M$^+$+1)

$^1$H NMR (400 MHz, CD$_3$OD): δ (ppm) 9.33 (br, 1H), 8.24 (d, J=9.2 Hz, 1H), 7.85 (s, 1H), 7.53 (d, J=9.2 Hz, 1H), 7.36 (s, 1H), 5.75-5.64 (m, 2H), 5.28-5.24 (m, 1H), 5.11-5.08 (m, 1H), 4.67-4.53 (m, 4H), 4.29 (m, 1H), 4.10 (br, 2H), 3.96-3.63 (m, 6H), 3.45 (m, 3H), 3.18 (m, 1H), 2.92 (m, 1H), 2.81 (m, 1H), 2.46 (m, 1H), 2.41 (m, 1H), 2.22 (m, 1H), 1.92 (m, 1H), 1.63 (m, 1H), 1.46 (m, 1H), 1.38-1.05 (m, 18H).

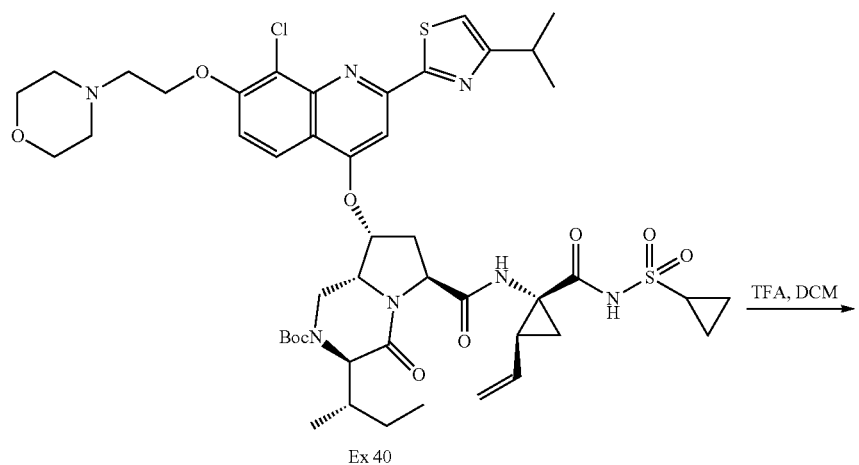

Ex 40

TFA, DCM

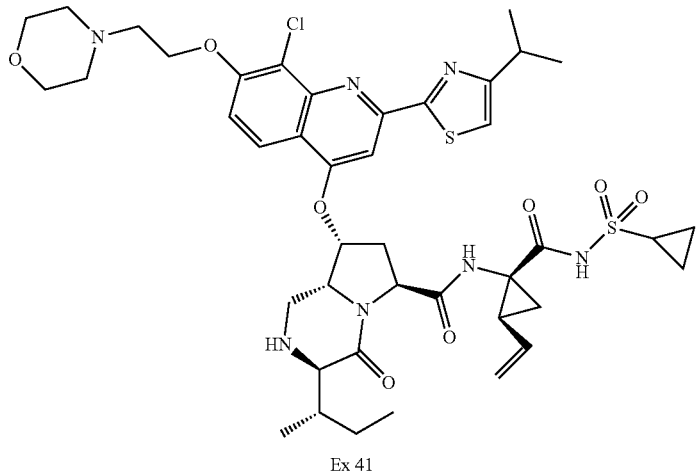

Ex 41

Preparation of Example 42

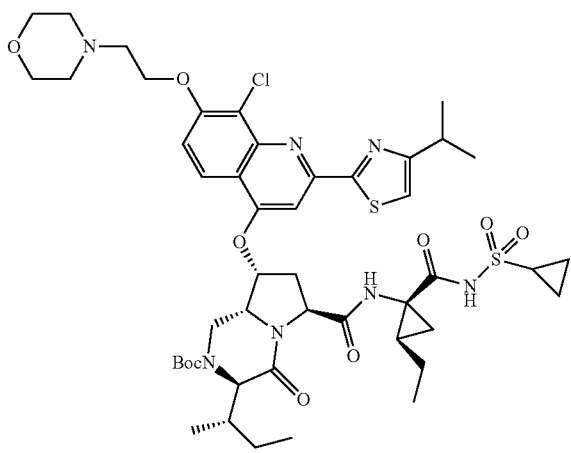 [SMILES: CC[C@@H]1C[C@]1(NC(=O)[C@@H]1C[C@@H](Oc2cc(-c3nc(C(C)C)cs3)nc3c(Cl)c(OCCN4CCOCC4)ccc23)[C@H]2CN(C(=O)OC(C)(C)C)[C@H]([C@@H](C)CC)C(=O)N21)C(=O)NS(=O)(=O)C1CC1]

Example 42 was prepared in a manner similar to that described in method A, except 2R-amino-3S-methyl-pentanoic acid tert-butyl ester was used in place of 2R-amino-3,3-dimethyl-butyric acid tert-butyl ester, 4,8-dichloro-2-(4-isopropyl-thiazol-2-yl)-7-(2-morpholin-4-yl-ethoxy)-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-ethyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=987 (M$^+$+1)

$^1$H NMR (400 MHz, CD$_3$OD): δ (ppm) 9.08 (s, 1H), 8.04 (d, J=9.2 Hz, 1H), 7.83 (s, 1H), 7.46 (d, J=9.2 Hz, 1H), 7.33 (s, 1H), 5.61 (br, 1H), 4.65 (m, 2H), 4.54 (m, 2H), 4.38 (m, 1H), 4.13 (m, 2H), 3.89-3.63 (m, 8H), 3.42 (m, 3H), 3.17 (m, 1H), 2.97 (m, 1H), 2.63 (m, 1H), 2.38 (m, 1H), 2.00 (m, 1H), 1.70-0.95 (m, 34H).

Preparation of Example 43

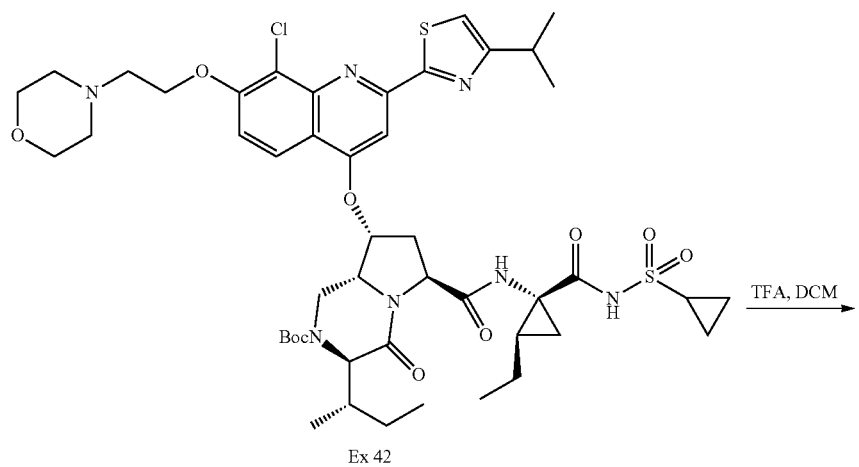

Ex 42

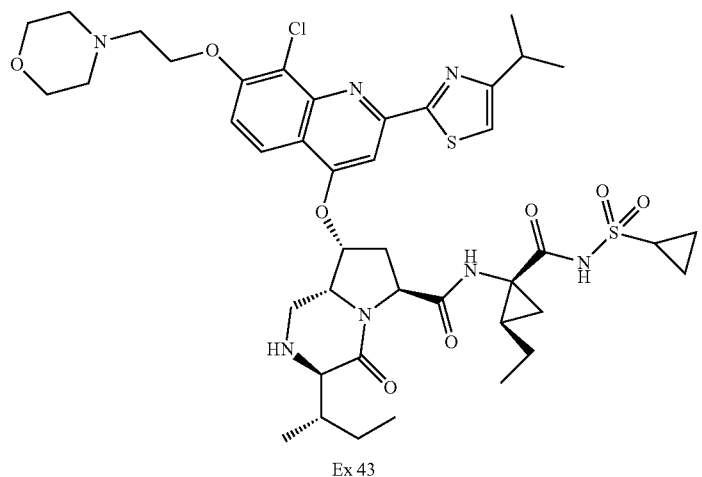

Ex 43

Example 42 was dissolved in DCM and TFA (1:1) and stirred at room temperature for 1 hour to afford example 43 as the TFA salt.

LC/MS=887 (M$^+$+1)

$^1$H NMR (400 MHz, CD$_3$OD): δ (ppm) 9.17 (s, 1H), 8.14 (d, J=9.2 Hz, 1H), 7.76 (s, 1H), 7.44 (d, J=9.2 Hz, 1H), 7.27 (s, 1H), 5.66 (br, 1H), 4.59-4.47 (m, 5H), 4.23 (m, 1H), 4.01 (br, 2H), 3.89-3.56 (m, 8H), 3.41 (m, 3H), 3.17 (m, 1H), 2.93 (m, 1H), 2.68 (m, 1H), 2.45 (m, 1H), 2.39 (m, 1H), 1.61-0.86 (m, 24H).

Preparation of Example 44

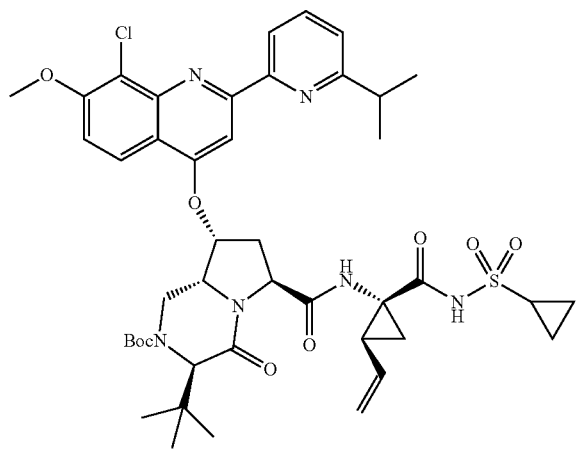

Ex 44

Example 44 was prepared in a manner similar to that described in method A, except the 4,8-dichloro-2-(6-isopropyl-pyridin-2-yl)-7-methoxy-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=879 (M$^+$+1)

$^1$H NMR (300 MHz, CD$_3$OD): δ (ppm) 8.57 (d, J=7.63 Hz, 1H), 8.12, (br, 1H), 7.95-7.82 (m, 2H), 7.40 (m, 2H), 5.80-5.58 (m, 2H), 5.32-5.22 (m, 1H), 5.18-5.11 (m, 1H), 4.60 (m, 2H), 4.43 (m, 2H), 4.01 (s, 3H), 3.73 (br, 1H), 3.21 (m, 1H), 2.98 (m, 1H), 2.45-2.30 (m, 1H), 2.25 (m, 3H), 1.95 (m, 1H), 1.58-1.02 (m, 29H).

Preparation of Example 45

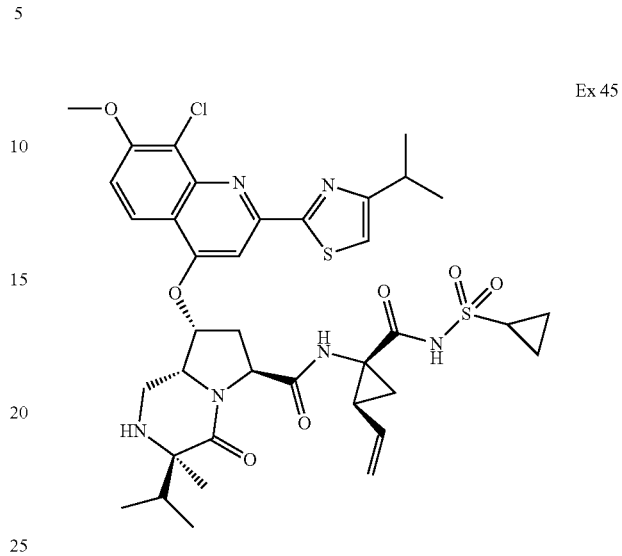

Ex 45

Example 45 was prepared in a manner similar to that described in method A, except the 2R-amino-2,3-dimethyl-butyric acid was used in place of 2R-amino-3,3-dimethyl-butyric acid tert-butyl ester, 4-chloro-2-(4-isopropyl-thiazol-2-yl)-7-methoxy-8-methyl-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=784 (M$^+$+1).

$^1$H NMR (400 MHz, CD$_3$OD): δ (ppm) 9.31 (br, 1H), 8.05 (d, J=9.2 Hz, 1H), 7.79 (s, 1H), 7.51 (d, J=9.2 Hz, 1H), 7.33 (s, 1H), 5.75-5.64 (m, 2H), 5.28-5.24 (m, 1H), 5.11-5.08 (m, 1H), 4.83-4.53 (m, 2H), 4.04 (s, 3H), 3.96 (m, 1H), 3.67 (m, 1H), 3.29 (m, 1H), 2.94 (m, 1H), 2.79-2.73 (m, 1H), 2.58 (m, 1H), 2.46 (m, 1H), 2.19 (m, 1H), 1.88 (m, 1H), 1.74 (s, 3H), 1.38 (d, J=6.8 Hz, 6H), 1.25-1.04 (m, 14H).

Example 46 was dissolved in DCM and TFA (1:1) and stirred at room temperature for 1 hour to afford example 47 as the TFA salt.

LC/MS=885 (M$^+$+1).

$^1$H NMR (300 MHz, CD$_3$OD): δ (ppm) 8.25 (d, J=9.3 Hz, 1H), 7.86 (s, 1H), 7.54 (d, J=9.3 Hz, 1H), 7.37 (s, 1H), 5.68-5.59 (m, 2H), 5.30-5.25 (m, 1H), 5.14-5.10 (m, 1H), 4.70-4.58 (m, 4H), 4.25 (m, 1H), 4.14 (br, 2H), 3.98-3.69 (m, 8H), 3.47 (br, 2H), 3.22 (m, 1H), 2.86 (m, 1H), 2.70 (m, 1H), 2.46 (m, 1H), 2.27 (m, 1H), 2.01 (m, 1H), 1.89 (m, 1H), 1.56-0.87 (m, 19H).

Preparation of Example 48

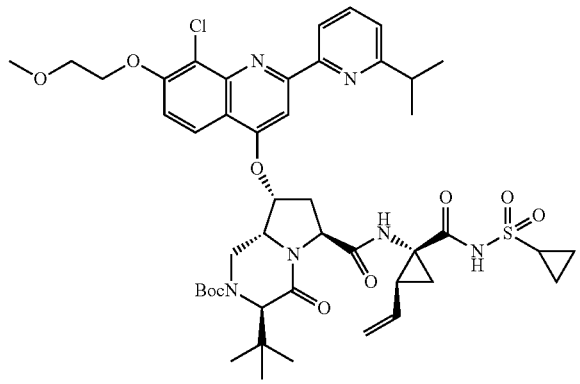

Ex 48

Example 48 was prepared in a manner similar to that described in method A, except that and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=924 (M$^+$+1)

$^1$H NMR (400 MHz, (CD$_3$)$_2$SO): δ 10.58 (s, 1H), 8.90 (s, 1H), 8.48 (d, J=7.6 Hz, 1H), 8.16-8.08 (m, 2H), 7.96 (t, J=7.6 Hz, 1H), 7.59 (d, J=9.6 Hz, 1H), 7.44 (d, J=8.0 Hz, 1H), 5.65-5.56 (m, 2H), 5.22 (d, J=17.2 Hz, 1H), 5.09 (d, J=12.0 Hz, 1H), 4.48-4.33 (m, 4H), 3.75 (t, J=4.4 Hz, 2H), 3.36 (s, 3H), 3.17 (quint, J=6.8 Hz, 1H), 2.93 (quint, J=4.4 Hz, 1H), 2.57-2.49 (m, 2H), 2.33-2.24 (m, 1H), 2.14 (quart, J=8.4 Hz, 1H), 1.72 (dd, J=8.0 Hz, 5.6 Hz, 1H), 1.45-1.34 (m, 10H), 1.28-1.02 (m, 16H)

Preparation of Example 46

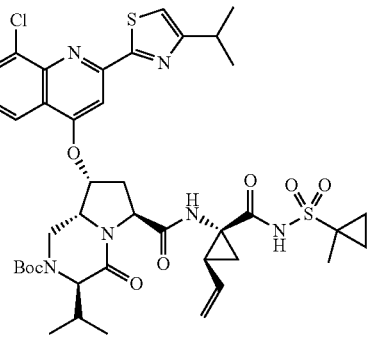

Ex 46

Example 46 was prepared in a manner similar to that described in method A, except 2R-amino-3-methyl-butyric acid tert-butyl ester was used in place of 2R-amino-3,3-dimethyl-butyric acid tert-butyl ester, and 4,8-dichloro-2-(4-isopropyl-thiazol-2-yl)-7-(2-morpholin-4-yl-ethoxy)-quinoline was used in place of 4,8-dichloro-2-(6-isopropyl-pyridin-2-yl)-7-(2-methoxy-ethoxy)-quinoline.

LC/MS=985 (M$^+$+1)

$^1$H NMR (300 MHz, CD$_3$OD): δ (ppm) 9.17 (brs, 1H), 8.07 (d, J=9.3 Hz, 1H), 7.86 (s, 1H), 7.49 (d, J=9.3 Hz, 1H), 7.36 (s, 1H), 5.75-5.61 (m, 2H), 5.31-5.25 (m, 1H), 5.14-5.10 (m, 1H), 4.67-4.52 (m, 4H), 4.31 (m, 1H), 4.14 (br, 2H), 3.88-3.64 (m, 8H), 3.45 (brs, 2H), 3.18 (m, 1H), 2.97 (m, 1H), 2.70 (m, 1H), 2.43 (m, 1H), 2.23 (m, 1H), 2.01 (m, 1H), 1.87 (m, 1H), 1.62-0.89 (m, 28H).

Preparation of Example 47

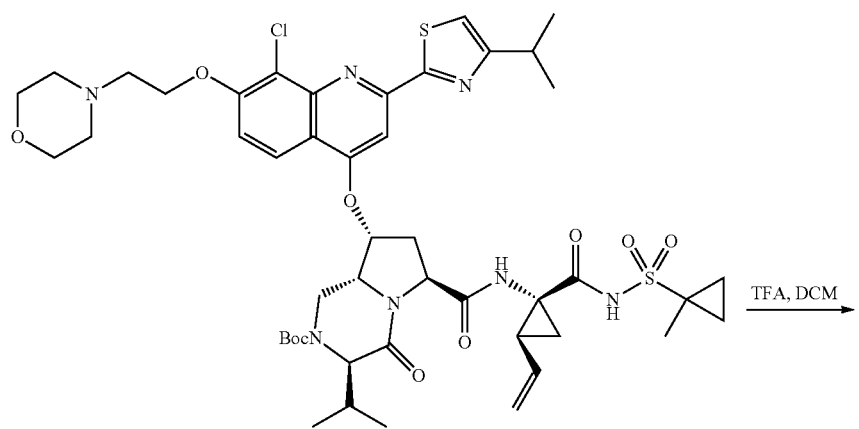

Ex 46

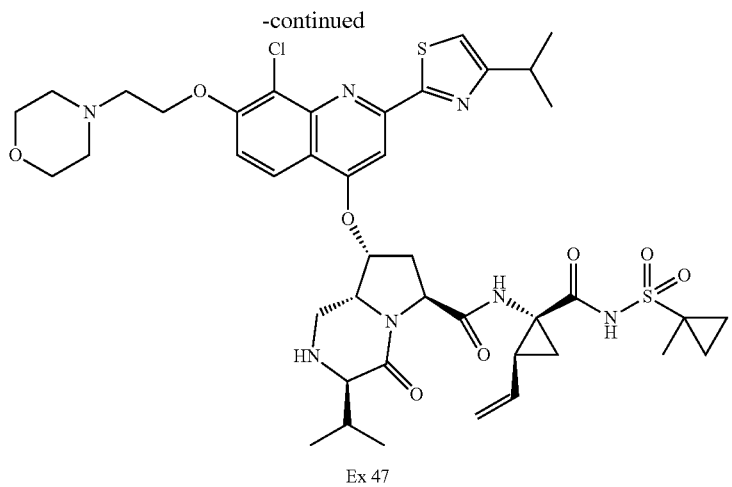

Ex 47

Preparation of Example 49

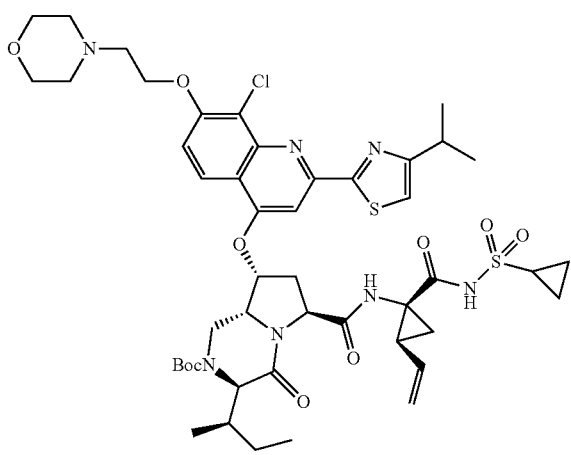

Ex 49

Example 49 was prepared in a manner similar to that described in method A, except the (R)-2-amino-(R)-3-methyl-pentanoic acid tert-butyl ester was used in place of the tert-butyl ester of (R)-tertbutyl glycine, 4,8-dichloro-2-(4-isopropyl-thiazol-2-yl)-7-(2-morpholin-4-yl-ethoxy)-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=985 (M$^+$+1).

$^1$H NMR (400 MHz, CD$_3$OD): δ (ppm) 9.17 (br, 1H), 8.06 (d, J=9.2 Hz, 1H), 7.84 (s, 1H), 7.47 (d, J=9.2 Hz, 1H), 7.34 (s, 1H), 5.75-5.62 (m, 2H), 5.27-5.24 (m, 1H), 5.11-5.09 (m, 1H), 4.65 (m, 2H), 4.52 (m, 2H), 4.35 (m, 1H), 4.09 (br, 2H), 3.84-3.64 (m, 8H), 3.46 (br, 2H), 3.18 (m, 1H), 2.97 (m, 1H), 2.70 (m, 1H), 2.43 (m, 1H), 2.23 (m, 1H), 2.01 (m, 1H), 1.87 (m, 1H), 1.49-1.08 (m, 28H).

Preparation of Example 50

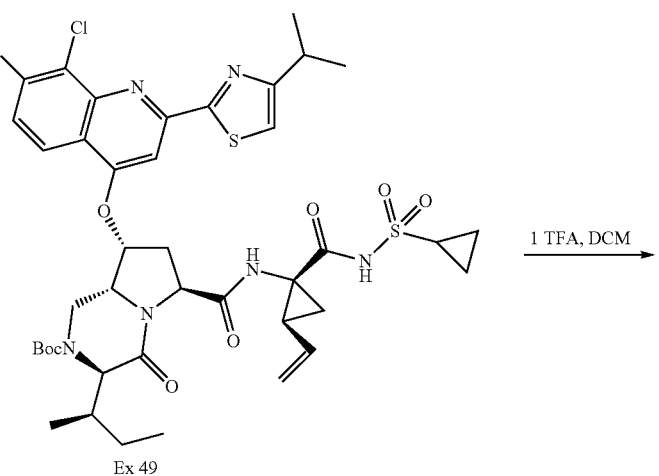

Ex 49

1 TFA, DCM →

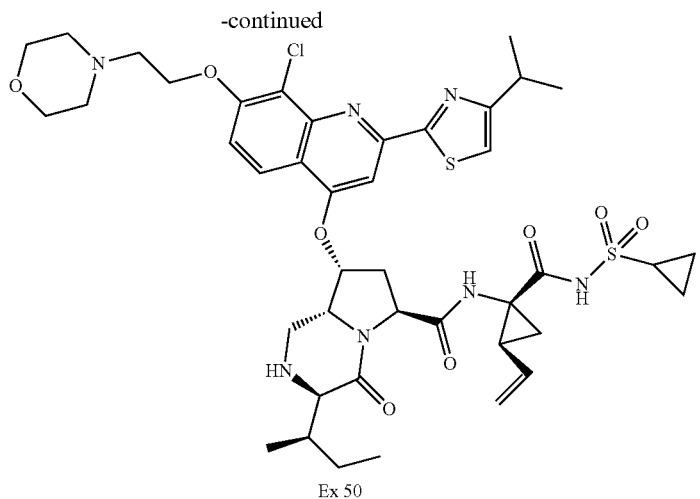

Ex 50

Example 49 was dissolved in DCM and TFA (1:1) and stirred at room temperature for 1 hour to afford example 50 as the TFA salt.

LC/MS=885 (M⁺+1).

¹H NMR (400 MHz, CD₃OD): δ (ppm) 9.23 (br, 1H), 8.20 (d, J=9.2 Hz, 1H), 7.83 (s, 1H), 7.52 (d, J=9.2 Hz, 1H), 7.34 (s, 1H), 5.73-5.64 (m, 2H), 5.27-5.23 (m, 1H), 5.10-5.08 (m, 1H), 4.67-4.58 (m, 4H), 4.27 (m, 1H), 4.08 (br, 2H), 3.96-3.63 (m, 6H), 3.45 (m, 3H), 3.18 (m, 1H), 2.92 (m, 1H), 2.81 (m, 1H), 2.46 (m, 1H), 2.41 (m, 1H), 2.22 (m, 1H), 1.92 (m, 1H), 1.63 (m, 1H), 1.46 (m, 1H), 1.36-0.89 (m, 18H).

Preparation of Example 51

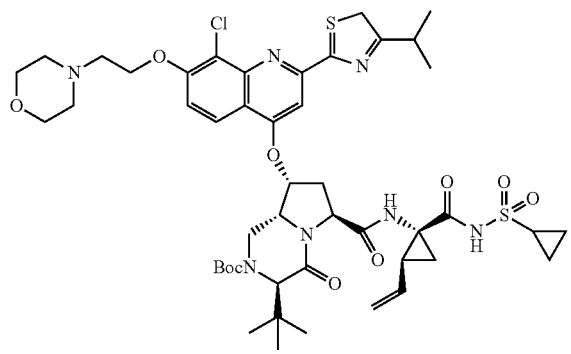

Ex 51

Example 51 was prepared in a manner similar to that described in method A, except that 4,8-dichloro-2-(2-isopropyl-thiazol-4-yl)-7-(2-morpholin-4-yl-ethoxy)-quinoline was used instead of 4,8-dichloro-2-(6-isopropyl-pyridin-2-yl)-7-(2-methoxy-ethoxy)-quinoline and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=984 (M⁺)

¹H NMR (400 MHz, CD₃OD): δ 8.33 (d, J=8.4 Hz, 1H), 7.88 (t, J=7.4 Hz, 1H), 7.76 (s, 1H), 7.40-7.25 (m, 1H), 5.61 (quint, J=8.4 Hz, 1H), 5.51 (d, J=14.0 Hz, 1H), 5.18 (d, J=16.0 Hz, 1H), 5.03 (d, J=11.6 Hz, 1H), 4.60-4.29 (m, 6H), 4.02-3.99 (m, 1H), 3.69 (t, J=4.8 Hz, 2H), 3.36 (quint, J=7.2 Hz, 1H), 2.91-2.83 (m, 1H), 2.32-2.29 (m, 1H), 2.12 (quart, J=8.8 Hz, 1H), 1.83-1.78 (m, 1H), 1.41-1.37 (m, 13H), 1.22-0.95 (m, 25H)

Preparation of Example 52

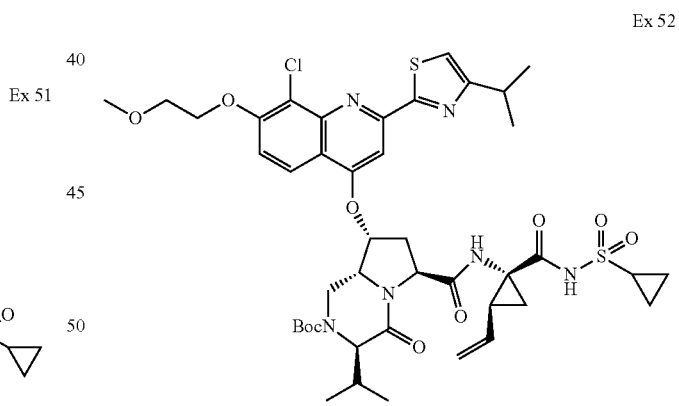

Ex 52

Example 52 was prepared in a manner similar to that described in method A, except that 4,8-dichloro-2-(4-isopropyl-thiazol-2-yl)-7-(2-methoxy-ethoxy)-quinoline was used instead of 4,8-dichloro-2-(6-isopropyl-pyridin-2-yl)-7-(2-methoxy-ethoxy)-quinoline, the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide, and 2R-amino-3-methyl-butyric acid tert-butyl ester was used instead of 2R-amino-3,3-dimethyl-butyric acid tert-butyl ester.

LC/MS=915 (M+)

¹H NMR (400 MHz, (CD₃)₂SO): δ 10.51 (s, 1H), 8.90 (s, 1H), 7.92 (d, J=9.2 Hz, 1H), 7.66 (s, 1H), 7.53 (d, J=9.6 Hz, 1H), 7.50 (s, 1H), 5.67 (s, 1H), 5.63-5.53 (m, 1H), 5.19 (d, J=17.2 Hz, 1H), 5.06 (d, J=12.0 Hz, 1H), 4.41-4.36 (m, 5H), 4.00 (d, J=8.4 Hz, 1H), 3.72 (t, J=6.3 Hz, 2H), 3.68-3.63 (m, 1H), 3.32 (s, 3H), 3.13 (quint, J=6.8 Hz, 1H), 2.93-2.87 (m, 1H), 2.53-2.47 (m, 1H), 2.25 (t, J=10.4 Hz, 1H), 2.12 (quart, J=8.8 Hz, 2H), 1.71-1.67 (m, 1H), 1.32-1.19 (m, 15H), 1.08-0.99 (m, 4H), 0.94 (d, J=6.4 Hz, 3H), 0.90 (d, J=6.4 Hz, 3H)

Preparation of Example 53

Example 52 (20 mg, 0.019 mmol) was dissolved in DCM (5 mL). Trifluoroacetic acid (1 mL) was added. After 1 hour, the reaction was concentrated. Example 53 (17 mg, 93%) was purified by HPLC.

LC/MS=815 (M+)

¹H NMR (400 MHz, CD₃OD): δ 8.14 (d, J=9.6 Hz, 1H), 7.80 (s, 1H), 7.48 (d, J=9.2 Hz, 1H), 7.34 (s, 1H), 5.73-5.64 (m, 2H), 5.26 (d, J=17.2 Hz, 1H), 5.10 (d, J=10.4 Hz, 1H), 4.64-4.60 (m, 1H), 4.53-4.51 (m, 1H), 4.38 (t, J=5.2 Hz, 2H), 4.17 (d, J=4.8 Hz, 1H), 3.98-3.94 (m, 1H), 3.84 (t, J=5.2 Hz, 2H), 3.66 (t, J=12.0 Hz, 1H), 3.47 (s, 3H), 3.18 (quint, J=6.8 Hz, 2H), 2.972-2.914 (m, 1H), 2.77 (quart, J=7.2 Hz, 2H),

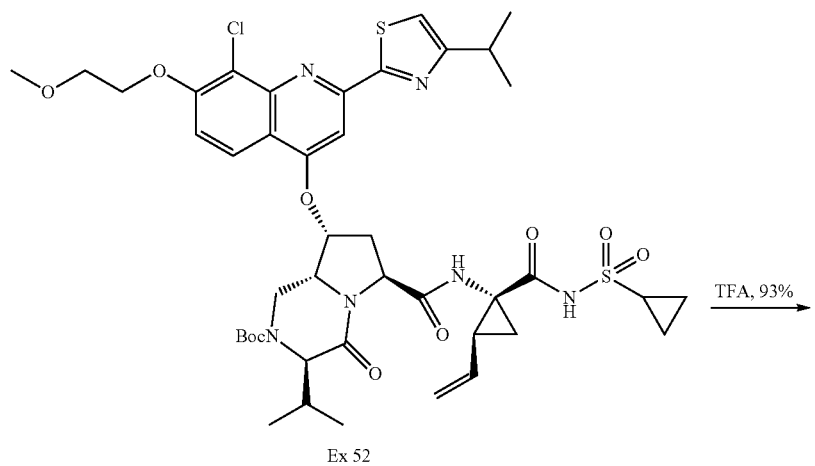

Ex 52

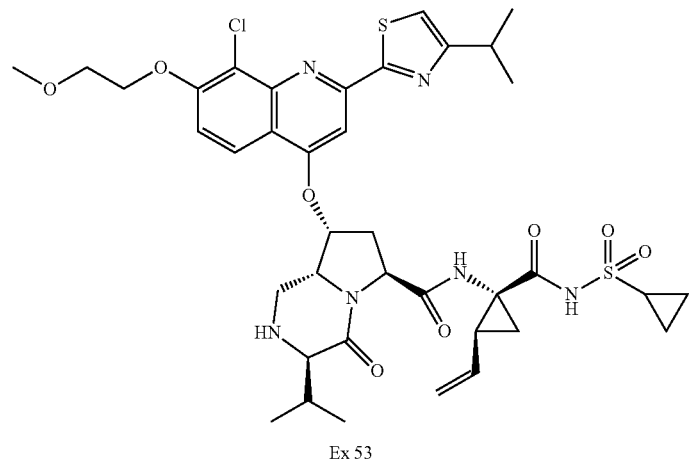

Ex 53

2.45-2.41 (m, 1H), 2.19 (quart, J=8.8 Hz, 1H), 1.91-1.87 (m, 1H), 1.37 (d, J=6.8 Hz, 6H), 1.20-1.22 (m, 2H), 1.16 (d, J=7.6 Hz, 3H), 1.11-1.05 (m, 5H)

Preparation of Example 54

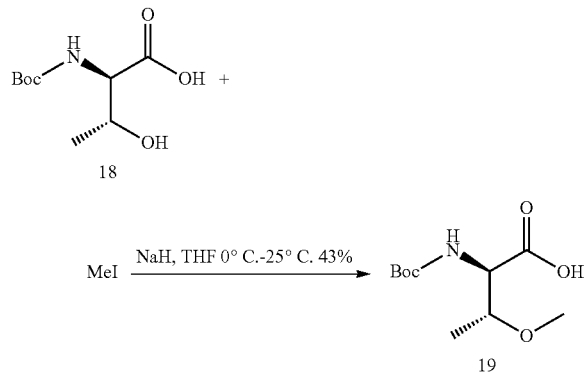 [SMILES: "MeI" ; C[C@@H](O)[C@@H](NC(=O)OC(C)(C)C)C(=O)O ; CO[C@H](C)[C@@H](NC(=O)OC(C)(C)C)C(=O)O]

Sodium hydride (3.2 g, 80.0 mmol, 60% in oil) was suspended in THF (100 mL) and cooled to 0° C. in an ice bath under an atmosphere of N$_2$. Compound 18 (4.38 g, 20.0 mmol) was added as a solution in THF (50 mL) over 15 minutes followed by a THF wash (50 mL). The reaction was allowed to warm to rt and stirred for 1 h. The reaction mixture was then cooled to 0° C. with an ice bath and iodomethane (6.24 g, 100.0 mmol) was added over 15 minutes. The ice bath was removed and the reaction was stirred for 18 h at rt. Solvents were removed under reduced pressure and the reaction was taken up in H$_2$O. The reaction was cooled to 0° C. in an ice bath and the pH was adjusted to 3-4 with HCl (1N in H$_2$O). The solution was extracted with EtOAc (3×50 mL). The combined organics were dried over Na$_2$SO$_4$, filtered and concentrated under reduced pressure. Compound 19 (2.02 g, 43%) was purified by silica gel chromatography to afford a white solid.

$^1$H NMR (400 MHz, CD$_3$OD): δ 4.35 (d, J=4.4 Hz, 1H), 3.69 (quint, J=5.6 Hz, 1H), 3.35 (s, 3H), 1.45 (s, 9H), 1.17 (d, J=6.0 Hz, 3H)

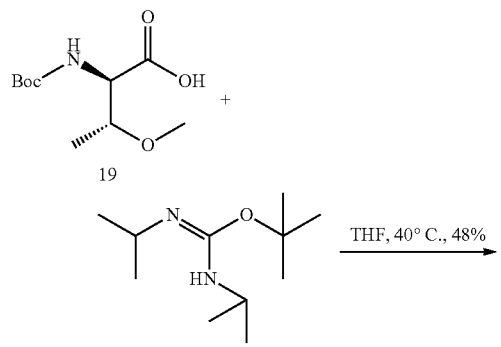

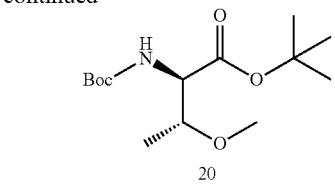

Compound 19 (2.02 g, 8.7 mmol) was added to THF (100 mL) under an atmosphere for N$_2$. To the reaction was added 2-tert-butyl-1,3-diisopropyl-isourea (1.7 g, 8.7 mmol) as prepared in JOC 2004, 69, 7, 2506. The reaction was heated to 40° C. for 20 h. The reaction was cooled to rt and filtered. The solvent was removed under reduced pressure. Compound 20 (1.2 g, 48%) was purified by silica gel chromatography to afford a clear oil.

$^1$H NMR (400 MHz, CD$_3$OD): δ 4.20 (d, J=4.8 Hz, 1H), 3.63 (quint, J=6.0 Hz, 1H), 3.33 (s, 3H), 1.46 (d, J=8.4 Hz, 18H), 1.16 (d, J=6.4 Hz, 3H)

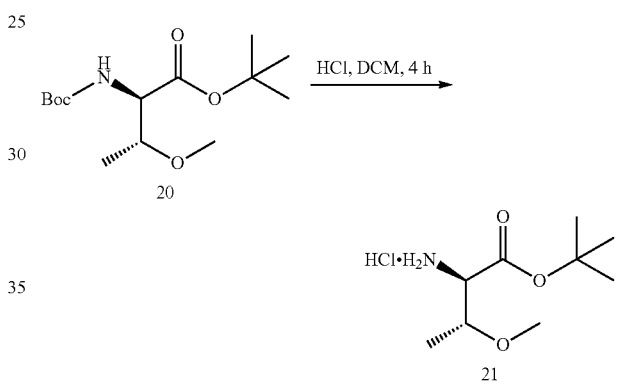

Compound 20 (1 g, 3.4 mmol) was dissolved in CH$_2$Cl$_2$ under an atmosphere of N$_2$. HCl (6.9 mL, 27.6 mmol, 4N in dioxane) was added over 2 minutes. The reaction was stirred at rt for 4 hr. The solvent was removed under reduced pressure to yield compound 21.

$^1$H NMR (400 MHz, CD$_3$OD): δ 4.15 (d, J=3.2 Hz, 1 h), 3.89-3.83 (m, 1H), 3.40 (s, 3H), 1.53 (s, 9H), 1.27 (d, J=6.8 Hz, 3H)

Ex 54

Example 54 was prepared in a manner similar to that described in method A, except that 4,8-dichloro-2-(4-isopropyl-thiazol-2-yl)-7-(2-morpholin-4-yl-ethoxy)-quinoline was used instead of 4,8-dichloro-2-(6-isopropyl-pyridin-2-yl)-7-(2-methoxy-ethoxy)-quinoline, the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide, and compound 21 was used instead of 2R-amino-3,3-dimethyl-butyric acid tert-butyl ester.

LC/MS=896 (M+)

$^1$H NMR (400 MHz, (CD$_3$)$_2$SO): δ 11.14 (s, 1H), 8.11 (d, J=9.2 Hz, 1H), 7.91 (s, 1H), 7.71 (s, 1H), 7.56 (d, J=9.6 Hz, 1H), 7.52 (s, 1H), 5.78 (s, 1H), 5.52-5.43 (m, 1H), 5.24 (d, J=17.2 Hz, 1H), 5.10 (d, J=12.0 Hz, 1H), 4.61-4.63 (br, 2H), 4.52-4.50 (m, 1H), 4.33 (t, J=8.0 Hz, 1H), 4.03-3.99 (m, 2H), 3.82-3.67 (m, 6H), 3.40 (s, 3H), 3.35-3.29 (m, 2H), 3.12 (quint, J=6.8 Hz, 1H), 2.88 (quint, J=5.6 Hz, 1H), 2.56-2.47 (m, 4H), 2.07 (quart, J=8.8 Hz, 1H), 1.764-1.726 (m, 1H), 1.36 (s, 9H), 1.31 (d, J=6.8 Hz, 6H), 1.22 (d, J=6.4 Hz, 3H), 1.18-0.99 (m, 5H)

Preparation of Example 55

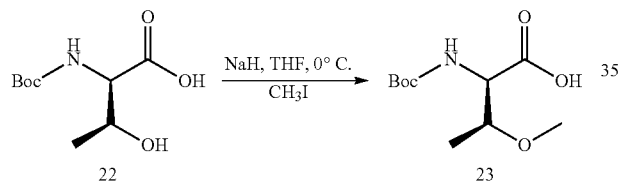

Sodium hydride (1.76 g, 44 mmol, 60% in oil) was suspended in THF (100 mL) and cooled to 0° C. in an ice bath under an atmosphere of N$_2$. Compound 22 (4.38 g, 20.0 mmol) was added as a solution in THF (50 mL), over 15 min followed by a THF (50 mL) wash. The reaction was allowed to warm to rt and stirred for 1 h. The reaction mixture was then cooled to 0° C. in an ice bath, and CH$_3$I (3.11 mL, 50.0 mmol) was added over 10 min. The ice bath was removed and the reaction was stirred for 18 h at rt. Quench with 10 mL H$_2$O, and then remove solvents under reduced pressure. Adjust pH to 3 with 2N HCl$_{(aq)}$. Partition the aqueous with EtOAc, and wash with 2×50 mL EtOAc. Combine organics and dry over Na$_2$SO$_4$, filter, and remove solvent under reduced pressure. Compound 23 was carried forward without purification.

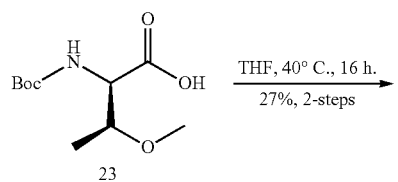

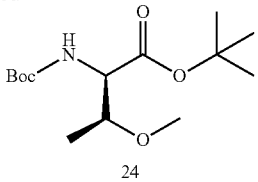

Compound 23 (2.91 g, 12.48 mmol) was taken up in THF (100 mL) under an atmosphere of N$_2$. To the reaction mixture was added 2-tert-butyl-1,3-diisopropyl-isourea (4.99 g, 25.0 mmol) as prepared in JOG 2004, 69, 7, 2506. The reaction was heated to 40° C. for 16 h. The reaction was cooled to rt then solids were filtered. The solvent was removed under reduced pressure. Compound 24 was isolated by silica gel chromatography as a colorless oil.

$^1$H NMR (400 MHz, D$_6$-DMSO): δ (ppm) 6.459 (d, J=8.81 Hz, 1H); 3.926 (dd, J=3.91, 8.61 Hz, 1H); 3.668, (quint, (J=4.11 Hz, 1H); 3.178 (s, 3H); 1.372 (s, 9H), 1.350 (s, 9H); 1.067 (d, J=6.26, 3H).

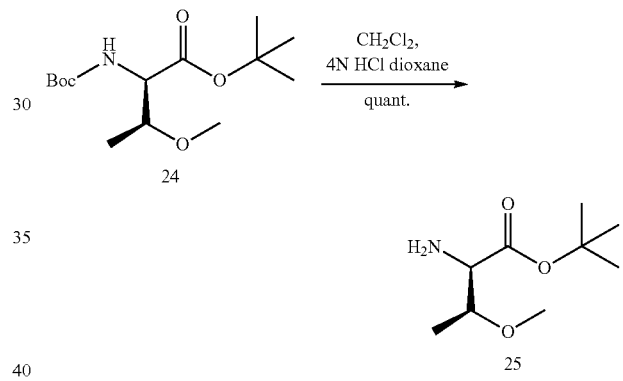

Compound 24 was taken up in CH$_2$Cl$_2$ (10 mL) and 4N HCl in dioxane (10 mL) and allowed to stir at rt for 1 h. the reaction was determined to be complete by crude $^1$H NMR. Solvent was removed under reduced pressure and compound 25 (1.22 g) was co-evaporated with toluene (3×50 mL) and carried forward without purification as the HCl salt.

Ex 55

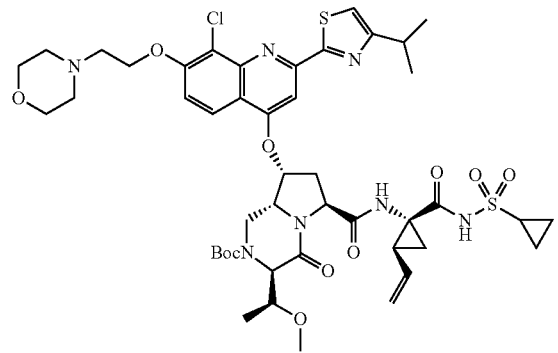

Example 55 was prepared in a manner similar to method A, except compound 25 was used in place of 2R-amino-3,3-dimethyl-butyric acid tert-butyl ester, 4,8-dichloro-2-(4-isopropyl-thiazol-2-0)-7-(2-morpholin-4-yl-ethoxy)-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.
LC/MS=987 (M⁺+1)

¹H NMR (400 MHz, CDCl₃): 5 (ppm) 7.907 (brd, J=6.5 Hz, 1H); 7.800 (s, 1H); 7.192 (m, 2H); 5.695 (m, 2H); 5.411 (brs, 1'-1); 5.273 (brd, J=16.83 Hz, 1H); 5.088 (m, 1H); 4.746 (m, 1H); 4.617 (m, 3H); 4.325 (m, 2H); 4.085-3.931 (m, 5H); 3.815 (m, 3H); 3.657 (brs, 2H); 3.323 (m, 6H); 2.947 (m, 1H); 2.693 (m, 1H); 2.546 (m, 1H); 2.096 (m, 1H); 1.957 (m, 1H); 1.392-1.032 (m, 25H).

Preparation of Example 56

Example 56 was prepared in a manner similar to that described in method A, except that 4,8-dichloro-2-(4-isopropyl-thiazol-2-yl)-7-(2-morpholin-4-yl-ethoxy)-quinoline was used instead of 4,8-dichloro-2-(6-isopropyl-pyridin-2-yl)-7-(2-methoxy-ethoxy)-quinoline, the HCl salt of cyclopropanesulfonic acid ((1R,2S)-1-amino-2-ethyl-cyclopropanecarbonyl)-amide was used in place of the HCl salt of 1-methyl-cyclopropanesulfonic acid ((1R,2S)-1-amino-2-vinyl-cyclopropanecarbonyl)-amide and the HCl salt of 2R-amino-3-phenyl-propionic acid tert-butyl ester was used instead of 2R-amino-3,3-dimethyl-butyric acid tert-butyl ester.

LC/MS=1021 (M⁺+1)

¹H NMR (400 MHz, (CD₃)₂SO): δ 10.54 (s, 1H), 8.96 (s, 1H), 7.70-7.51 (m, 4H), 7.32-7.13 (m, 5H), 5.66 (s, 1H), 4.73-4.65 (m, 4H), 4.42-4.32 (m, 2H), 4.18-4.01 (m, 4H), 3.73-3.69 (m, 1H), 3.35-3.31 (m, 2H), 3.19-3.12 (m, 3H), 2.96 (br, 1H), 2.34-2.32 (m, 1H), 1.53-0.92 (m, 30H)

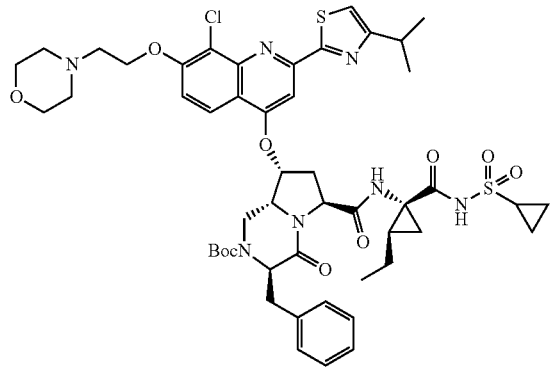

Ex 56

Preparation of Example 57

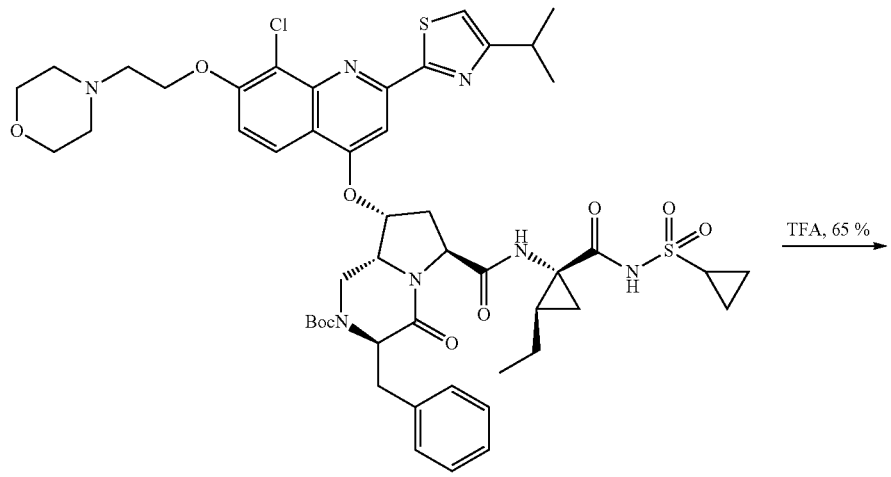

Ex 56

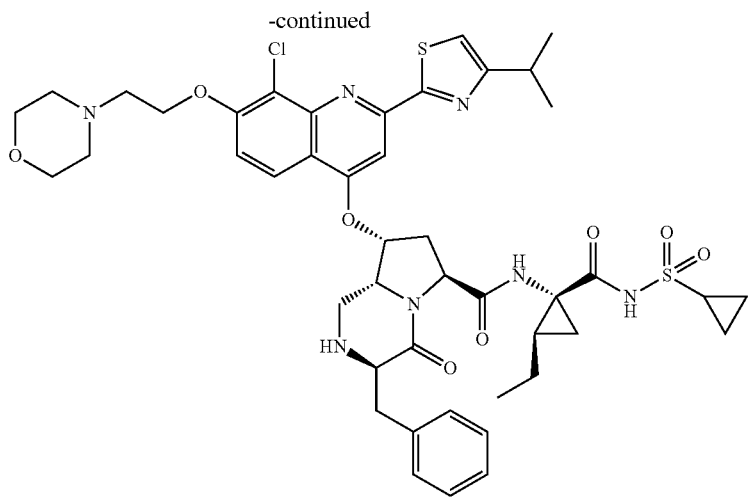

Ex 57

Example 56 (15 mg, 0.015 mmol) was dissolved in DCM (5 mL).

Trifluoroacetic acid (1 mL) was added. After 1 hour, the reaction was concentrated. Example 57 (10 mg, 65%) was purified by HPLC.

LC/MS=920 (M+)

$^1$H NMR (400 MHz, (CD$_3$)$_2$SO): δ 10.52 (s, 1H), 8.97 (s, 1H), 7.70-7.51 (m, 4H), 7.32-7.13 (m, 5H), 5.66 (s, 1H), 4.75-4.66 (m, 4H), 4.43-4.33 (m, 2H), 4.18-4.02 (m, 4H), 3.74-3.69 (m, 1H), 3.37-3.32 (m, 2H), 3.18-3.12 (m, 3H), 2.97-2.95 (m, 1H), 2.34-2.32 (m, 1H), 1.55-0.91 (m, 21H)

Preparation of Example 58

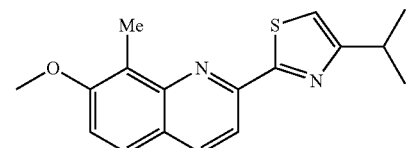

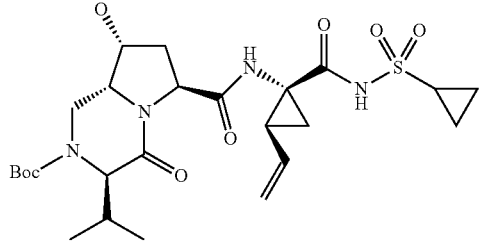

Ex 58

Example 58 was prepared in a manner similar to that described in method A, except 2R-amino-3-methyl-butyric acid tart-butyl ester was used in place of 2R-amino-3,3-dimethyl-butyric acid tert-butyl ester, 4-chloro-2-(4-isopropyl-thiazol-2-yl)-7-methoxy-8-methylquinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of HCl salt of 1-methyl-cyclopropanesulfonic acid ((1R,2S)-1-amino-2-vinyl-cyclopropanecarbonyl)-amide.

LC/MS=851.73 (M+ +1)

$^1$H NMR (400 MHz, CD$_3$OD): δ 9.19 (s, 1H), 7.94 (d, J=9.6 Hz, 1H), 7.69 (s, 1H), 7.37 (s, 1H), 7.36 (d, J=9.6 Hz, 1H), 5.58 (ddd, J=17.2, 10, 8.8 Hz, 1H), 5.59 (brs, 1H), 5.25 (dd, J=17.2, 1.2 Hz, 1H), 5.09 (dd, J=10.4, 1.2 Hz, 1H), 4.45-4.57 (m, 2H), 4.25 (d, J=9.6 Hz, 1H), 4.07 (brs, 1H), 3.96 (s, 3H), 3.69 (dd, J=12.8, 6.8 Hz, 1H), 3.21 (heptet, J=6.9 Hz, 1H), 2.92 (m, 1H), 2.66 (dd, J=14, 7.2 Hz, 1H), 2.58 (s, 3H), 2.39 (m, 1H), 2.14-2.23 (m, 2H), 1.85 (dd, J=8.4, 5.6 Hz, 1H), 1.14-1.51 (br, 16H), 1.37 (d, J=6.8 Hz, 6H), 1.18-1.23 (m, 2H), 0.80-1.07 (m, 8H)

Preparation of Example 59

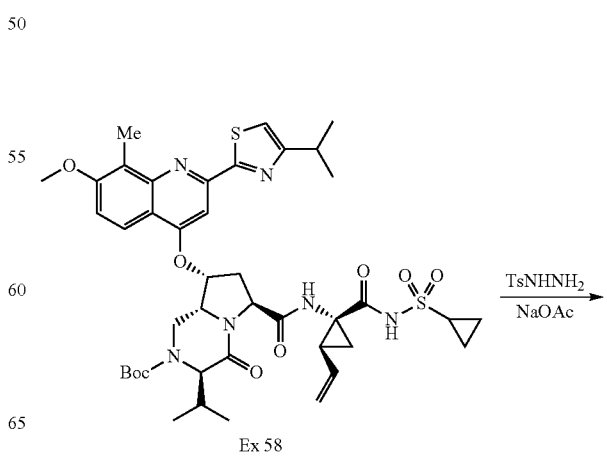

Ex 58

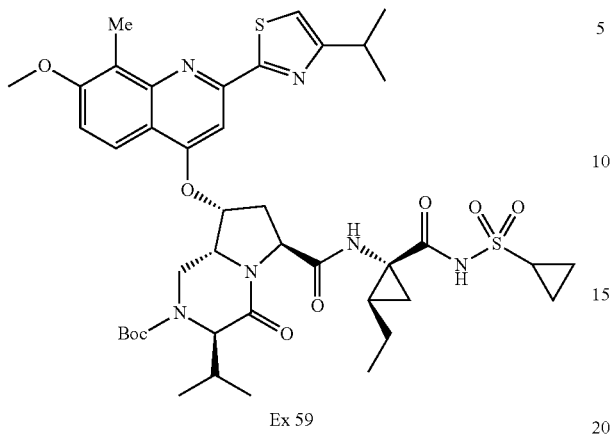

Ex 59

Example 58 (48 mg, 0.056 mmol), tosylhydrazide (157 mg, 0.849 mmol), and sodium acetate (140 mg, 1.70 mmol) in dimethoxyethane (1.5 mL) and water (0.15 mL) were refluxed at 95° C. bath for 2 h and then cooled to rt. After the mixture was diluted with water, the product was extracted with ethyl acetate (×2). The extracts were washed with water (×1), combined, dried (MgSO$_4$), and concentrated. Example 59 (32 mg, 67%) was isolated by reverse phase HPLC as the TFA salt.

LC/MS=853.74 (M$^+$+1)

$^1$H NMR (400 MHz, CD$_3$OD): δ 9.12 (s, 1H), 7.92 (d, J=9.2 Hz, 1H), 7.67 (s, 1H), 7.33 (d, J=9.2 Hz, 1H), 7.29 (s, 1H), 5.55 5.59 (br, 1H), 4.45-4.57 (m, 2H), 4.26 (d, J=9.6 Hz, 1H), 4.07 (br, 1H), 3.95 (s, 3H), 3.69 (dd, J=12.8, 6.8 Hz, 1H), 3.17 (heptet, J=6.8 Hz, 1H), 2.96 (m, 1H), 2.64 (dd, J=14, 7.2 Hz, 1H), 2.59 (s, 3H), 2.35 (m, 1H), 2.20 (m, 1H), 1.37 (d, J=6.8 Hz, 1H), 1.10-1.62 (m, 23H), 1.05 (d, J=6.8 Hz, 3H), 1.01 (d, J=6.8 Hz, 3H), 0.90-0.96 (m, 3H)

Preparation of Example 60

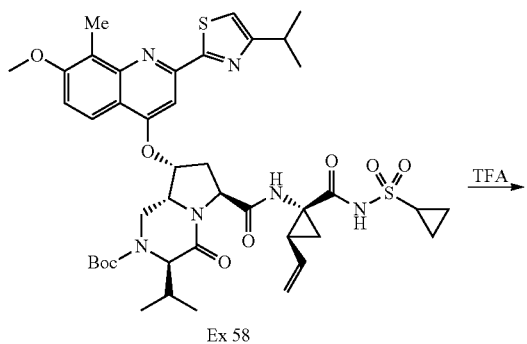

Ex 58 →[TFA]

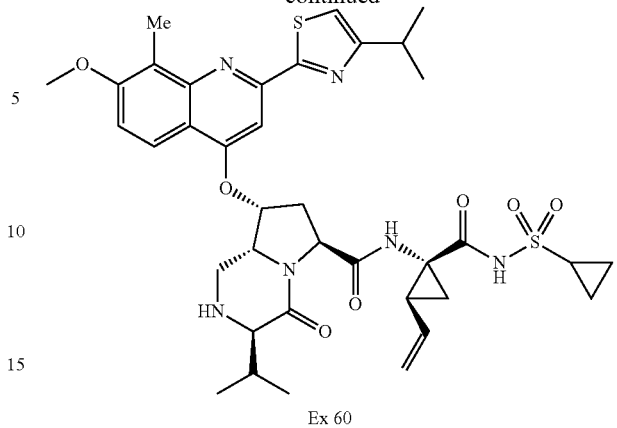

Ex 60

Example 58 (167 mg, 0.113 mmol) in dichloromethane (2 mL) and trifluoroacetic acid (0.5 mL) was stirred at rt for 2 h. After the solution was concentrated, the residue was dissolved in aqueous acetonitrile and freeze-dried to obtain example 60 (158 mg, 93%) as the TFA salt.

LC/MS=751.61 (M$^+$+1)

$^1$H NMR (400 MHz, CD$_3$OD): δ 9.32 (s, 1H), 8.27 (d, J=8.8 Hz, 1H), 7.85 (s, 1H), 7.60 (s, 1H), 7.55 (d, J=8.8 Hz, 1H), 5.89 (br, 1H), 5.63-5.72 (m, 1H), 5.27 (d, J=16.8 Hz, 1H), 5.10 (d, J=11.2 Hz, 1H), 4.58-4.69 (m, 2H), 4.09 (br, 1H), 4.04 (s, 3H), 3.75 (br, 1H), 3.54-3.58 (m, 1H), 2.90-2.98 (m, 1H), 2.72-2.85 (br m, 2H), 2.63 (s, 3H), 2.50 (br t, J=−12 Hz, 1H), 2.23 (br q, J=8.4 Hz, 1H), 1.88 (dd, J=7.6, 5.6 Hz, 1H), 141 (d, J=7.2 Hz, 6H), 1.35-1.45 (m, 2H), 1.18 (d, J=7.2 Hz, 3H), 1.11 (d, J=7.2 Hz, 3H), 1.14-1.28 (m, 2H), 1.00-1.08 (m, 2H)

Preparation of Example 61

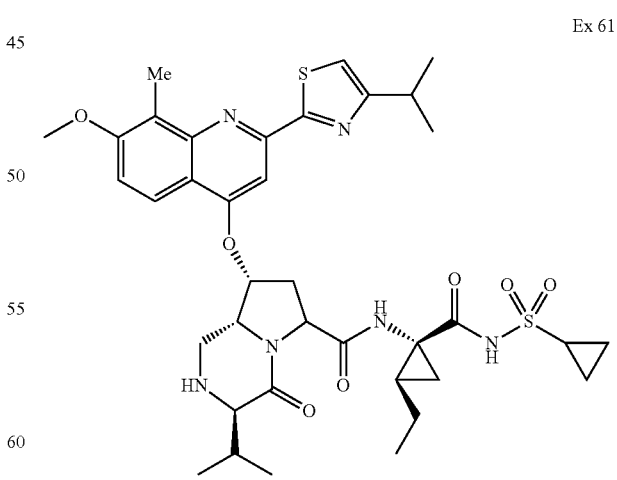

Ex 61

Example 61 was prepared from example 59 via removal of the Boc protecting group, in a manner similar to that previously described.

LC/MS=753.60 (M'+1)

¹H NMR (400 MHz, CD₃OD): δ 9.24 (s, 1H), 8.07 (d, J=9.2 Hz, 1H), 7.70 (s, 1H), 7.38 (d, J=9.2 Hz, 1H), 7.28 (s, 1H), 5.70 (br, 1H), 4.63 (dd, J=10.4, 7.2 Hz, 1H), 4.55 (dt, J=11.2, 3.2 Hz, 1H), 4.22 (d, J=3.6 Hz, 1H), 4.01 (d, J=3.2 Hz, 1H), 3.98 (s, 3H), 3.68 (t, J=12 Hz, 1H), 3.17 (heptet, J=6.8 Hz, 1H), 2.96 (m, 1H), 2.75 (dd, J=14.4, 7.2 Hz, 1H), 2.76 (m, 1H), 2.61 (s, 3H), 2.41 (m, 1H), 1.41-1.62 (m, 4H), 1.37 (d, J=7.2 Hz, 6H), 1.19-1.27 (m, 2H), 1.17 (d, J=7.2 Hz, 3H), 1.10 (d, J=7.2 Hz, 3H), 1.03-1.18 (m, 3H), 0.93 (t, J=7.2 Hz, 3H)

Preparation of Example 62

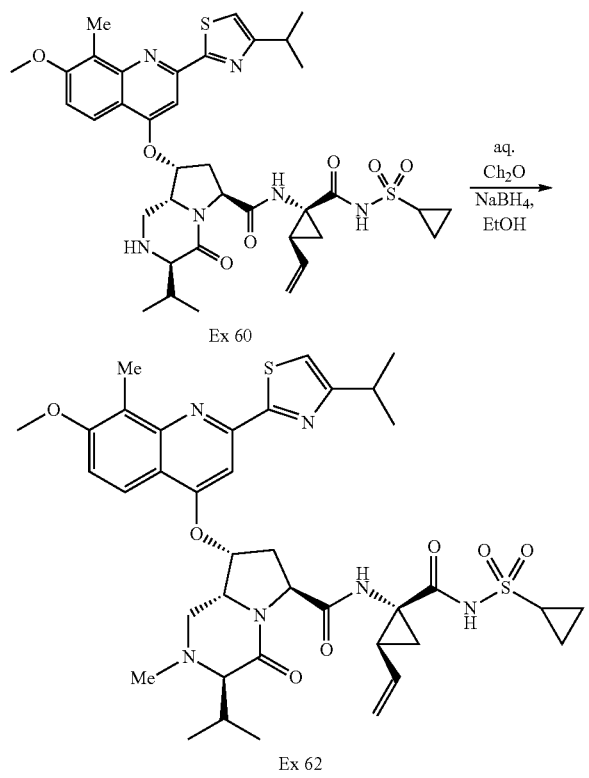

Example 60 (158 mg, 0.162 mmol) and paraformaldehyde (10.8 mg) in ethanol (2 mL) was stirred at 0° C. as NaBH₄ (20 mg) was added. Mixture of acetic acid in ethanol (1:10) was added dropwise. After 20 min, several drops of 37% aq. formaldehyde, NaBH₄, and acetic acid/ethanol mixture were added. Addition of these three was continued until the methylation was >95% completed by HPLC. The mixture was concentrated to ½ volume, diluted with DMF, and filtered through celite pad. The filtrate was concentrated and the residue was dissolved in water and the product was extracted with ethyl acetate (×2). The organic extracts were washed with water (×1) combined, dried (MgSO₄) and concentrated. Example 62 (92 mg, 57%) was isolated by reverse phase HPLC as the TFA salt.

LC/MS=765.61 (M⁺+1)

¹H NMR (400 MHz, CD₃OD): δ 9.19 (s, 1H), 8.09 (d, J=9.2 Hz, 1H), 7.68 (s, 1H), 7.37 (d, J=9.2 Hz, 1H), 7.28 (s, 1H), 5.70 (br t, J=3.2 Hz, 1H), 5.63 (ddd, J=16.8, 10.4, 7.6 Hz, 1H), 5.23 (dd, J=16.8, 1.2 Hz, 1H), 5.08 (dd, J=10.4, 1.2 Hz, 1H), 4.57-4.65 (m, 2H), 4.04 (dd, J=12, 1.2 Hz, 1H), 3.96 (s, 3H), 3.80 (t, J=11.6 Hz, 1H), 3.17 (s, 3H), 3.17 (heptet, J=6.8 Hz, 1H), 2.92 (m, 1H), 2.76 (dd, J=14.4, 7.2 Hz, 1H), 2.60 (s, 3H), 2.48 (m, 1H), 2.41 (m, 1H), 2.18 (q, J=8.6 Hz, 1H), 1.85 (dd, J=8, 5.2 Hz, 1H), 1.37 (d, J=7.2 Hz, 6H), 1.35 (d, J=7.2 Hz, 3H), 1.18 (d, J=7.2 Hz, 3H), 1.14-1.26 (m, 3H), 0.98-1.12 (m, 3H)

Preparation of Example 63

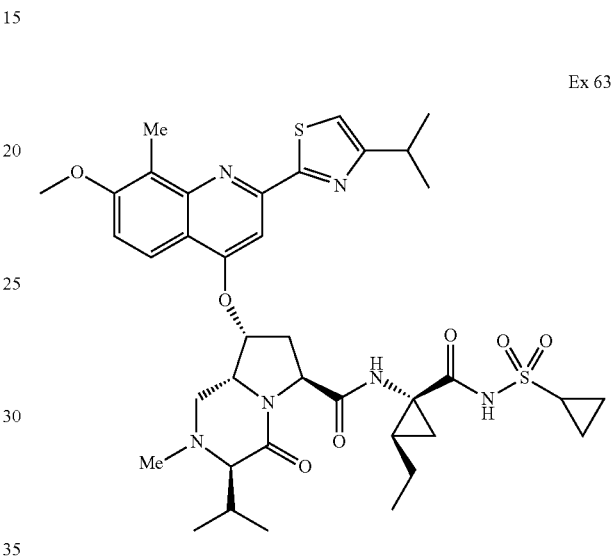

Example 63 was prepared from example 62 via a diimide reduction, similar to that described in the synthesis of example 59.

LC/MS=767.63 (M⁺ 1)

¹H NMR (400 MHz, CD₃OD): δ 9.06 (s, 1H), 8.02 (d, J=9.2 Hz, 1H), 7.61 (s, 1H), 7.30 (d, J=9.2 Hz, 1H), 7.19 (s, 1H), 5.62 (br t, J=3.2 Hz, 1H), 4.47-4.56 (m, 2H), 3.94 (dd, J=12.4, 2.8 Hz, 1H), 3.90 (s, 3H), 3.85 (d, J=2 Hz, 1H), 3.69 (t, J=11.8 Hz, 1H), 3.08 (s, 3H), 3.09 (heptet, J=6.8 Hz, 1H), 2.88 (m, 1H), 2.66 (dd, J=14.4, 7.2 Hz, 1H), 2.53 (s, 3H), 2.42 (m, 1H), 2.31 (m, 1H), 1.3-1.53 (m, 4H), 1.29 (d, J=6.8 Hz, 6H), 1.27 (d, J=6.8 Hz, 3H), 1.11-1.17 (m, 2H), 1.09 (d, J=6.8 Hz, 3H), 1.00-1.06 (m, 1H), 0.94-1.00 (m, 2H), 0.84 (t, =6.8 Hz, 3H)

Preparation of Example 64

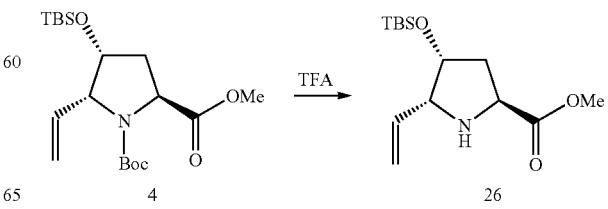

Compound 4 (1.50 g, 3.89 mmol) was dissolved in dichloromethane (5 mL) and stirred at 0° C. as trifluoroacetic acid (5 mL) was added. The solution was stirred at rt for 2 h and concentrated. After the residue was dissolved in dissolved in aqueous NaHCO$_3$ solution, the product was extracted with dichloromethane (×2) and the combined extracts were dried (MgSO$_4$) and concentrated. The residue was purified by silica gel column chromatography (ethyl acetate/hexanes) to obtain compound 26 (858 mg, 77%).

LC/MS=285.89 (M$^+$+1)

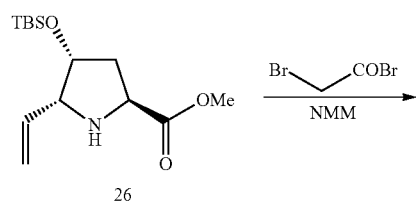

26

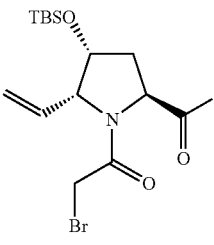

27

Compound 26 (858 mg, 3.01 mmol) in THF (5 mL) was stirred at 0° C. as bromoacetyl bromide (0.32 mL, 3.68 mmol) and N-methylmorpholine (0.5 mL, 4.55 mmol) were added. After stirring at 0° C. for 1 h, the resulting mixture was diluted with water and the product was extracted with ethyl acetate (×2). The combined extracts were dried (MgSO$_4$) and concentrated. The residue was purified by silica gel column chromatography (ethyl acetate/hexanes) to obtain compound 27 (1.214 mg, 99%).

LC/MS=405.81 (M$^+$+1)

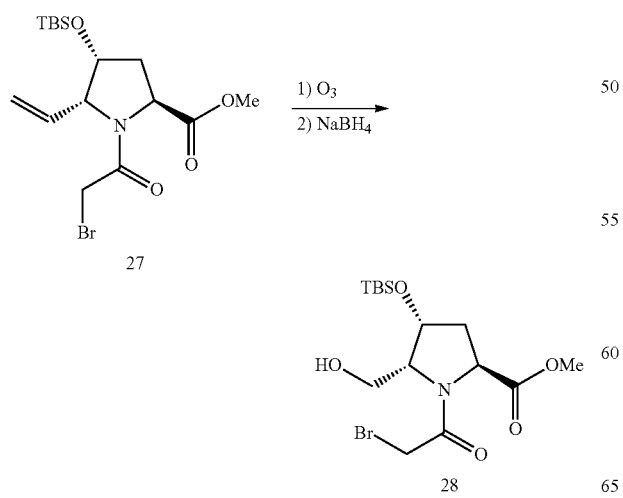

27

28

Compound 27 (1.204 g, 2.99 mmol) in methanol (25 mL) was stirred at 78° C. as ozone was bubbled through the solution until blue was observed. The ozone was turned off and oxygen was bubbled through the reaction mixture until the blue color disappeared. To the suspension was added NaBH$_4$ (335 mg, 8.86 mmol) and the mixture was warmed to 0° C. After 15 min, the mixture was acidified with acetic acid (~2 mL) and concentrated. The residue was dissolved in water and the product was extracted with ethyl acetate (×2). After the combined extracts were dried (MgSO$_4$) and concentrated, the residue was purified by silica gel column chromatography (ethyl acetate/hexanes) to obtain compound 28 (851 mg, 69%).

LC/MS=409.98 (M$^+$+1)

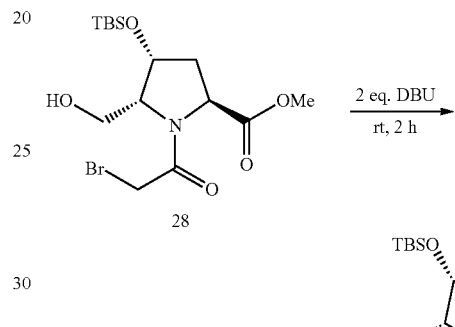

28

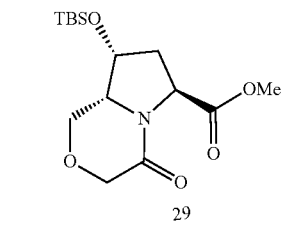

29

Compound 28 (842 mg, 2.05 mmol) and DBU (1.55 mL, 10.37 mmol) in THF (20 mL) was stirred at rt for 30 min and diluted with dichloromethane. The solution was concentrated. the residue was purified by silica gel column chromatography (ethyl acetate/hexanes) to obtain compound 29 (432 mg, 64%).

LC/MS=330.07 (M$^+$+1)

I.

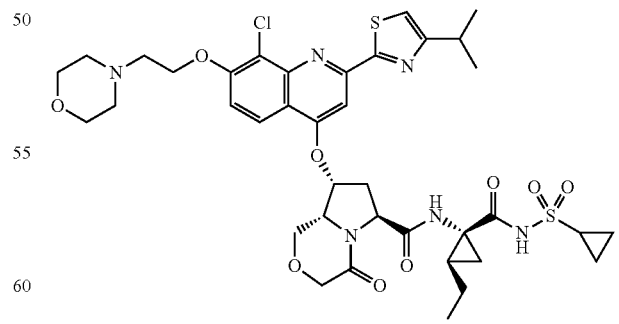

Example 64 was prepared in a manner similar to that described in method A, except compound 29 was used, 4,8-dichloro-2-(4-isopropyl-thiazol-2-yl)-7-(2-morpholin-4-yl-ethoxy)-quinoline was used in place of 4,8-dichloro-2-(6- isopropyl-pyridin-2-yl)-7-(2-methoxy-ethoxy)-quinoline, and the HCl salt of cyclopropanesulfonic acid ((1R,2R)-1-amino-2-ethyl-cyclopropanecarbonyl)-amide was used in place of HCl salt of 1-methyl-cyclopropanesulfonic acid ((1R,2S)-1-amino-2-vinyl-cyclopropanecarbonyl)-amide.

LC/MS=831.31 (M$^+$+1)

$^1$H NMR (400 MHz, CD$_3$OD): δ 9.19 (s, 1H), 8.10 (d, J=9.2 Hz, 1H), 7.79 (s, 1H), 7.51 (d, J=9.2 Hz, 1H), 7.33 (s, 1H), 5.62 (br t, J=2.8 Hz, 1H), 4.67 (t, J=4.8 Hz, 2H), 4.63 (dd, J=9.6, 8 Hz, 1H), 4.43 (br dt, J=9.6, 3.6 Hz, 1H), 4.36 (dd, J=11.6, 4.4 Hz, 1H), 4.29 (d, J=16.8 Hz, 1H), 4.16 (d, J=16.8 Hz, 1H), 4.10 (br, 2H), 3.87 (br, 2H), 3.86 (t, J=10.6 Hz, 1H), 3.78 (t, J=4.8 Hz, 2H), 3.77 (br, 2H), 3.47 (br, 2H), 3.18 (heptet, J=7 Hz, 1H), 2.95 (m, 1H), 2.71 (dd, J=14.4, 7.6 Hz, 1H), 2.43 (m, 2H), 1.44-1.63 (m, 4H), 1.38 (d, J=6.8 Hz, 6H), 1.10-1.28 (m, 3H), 1.04-1.10 (m, 2H), 0.97 (t, J=7.2 Hz, 3H)

Preparation of Example 65

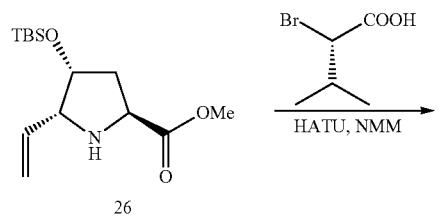

26

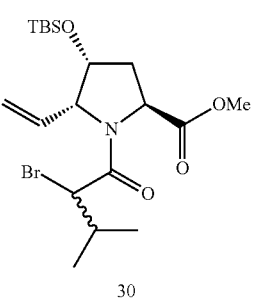

30

Compound 26 (401 mg, 1.41 mmol), HATU (804 mg, 2.12 mmol) and the bromoacid (281 mg, 1.55 mmol) in DMF (3 mL) was stirred at rt as N-methylmorpholine (0.39 mL, 3.55 mmol) was added. After stirring at rt for 1.5 h, additional acid (281 mg, 1.55 mmol), N-methylmorpholine (0.39 mL, 3.55 mmol), and DMF (3 mL) were added and the resulting mixture was stirred at it overnight. The mixture was diluted with 5% aqueous LiCl (30 mL) and the product was extracted with ethyl acetate (×2). The extracts were washed with water (×2), combined, dried (MgSO$_4$) and concentrated. The residue was purified by silica gel column chromatography (ethyl acetate/hexanes) to obtain the major isomers of the compound 30 (370 mg, 59%) and the minor isomer (contained ~20% of the major isomer, 168 mg, 27%).

The major isomer LC/MS=447.91 (M$^+$+1)

The minor isomer LC/MS=448.15 (M$^+$+1)

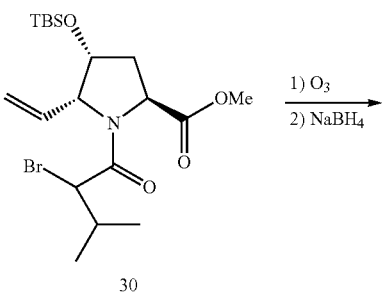

30

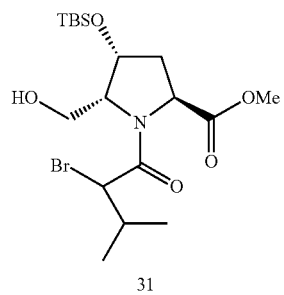

31

The major isomer of compound 30 was ozonized and reduced with NaBH$_4$ as described previously for compound 28. The product was purified by silica gel column chromatography (ethyl acetate/hexanes) to obtain compound 31 (317 mg, 85%).

LC/MS=452.11 (M$^+$+1)

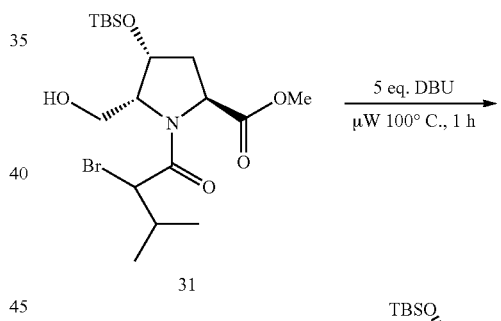

31

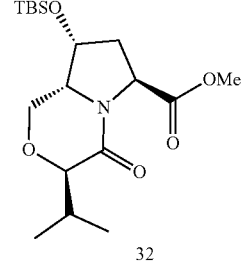

32

Compound 31 (317 mg, 0.700 mmol) in THF (20 mL) was stirred at it as DBU (0.51 mL, 3.41 mmol) was added. The mixture was heated at 100° C. for 1 h at microwave reactor. After the mixture was concentrated, the residue was dissolved in ethyl acetate, washed with water (50 mL) containing 1N HCl (5 mL), and the water (50 mL). The aqueous fractions were extracted with ethyl acetate (×1) and the combined organic fractions were dried (MgSO$_4$) and concentrated. The residue was purified by silica gel column chromatography (ethyl acetate/hexanes) to obtain compound 32 (83 mg, 32%).

LC/MS=372.06 (M$^+$+1)

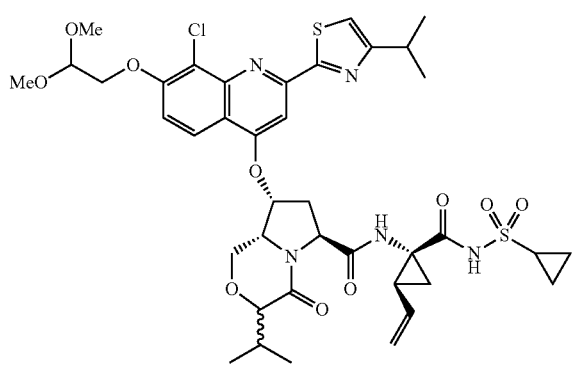

Example 65 (85:15 mixture) was prepared in a manner similar to that described in method A, except compound 32 was used, 4,8-dichloro-7-(2,2-dimethoxy-ethoxy)-2-(4-isopropyl-thiazol-2-yl)-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of HCl salt of 1-methyl-cyclopropanesulfonic acid ((1R,2S)-1-amino-2-vinyl-cyclopropanecarbonyl)-amide.

LC/MS=846.19 (M$^+$+1)

$^1$H NMR (400 MHz, CD$_3$OD): δ 9.23 (s, 0.85H), 9.24 (s, 0.15H), 7.95 (d, J=9.2 Hz, 0.15H), 7.89 (d, J=9.2 Hz, 0.85H), 7.69 (s, 0.15H), 7.67 (s, 0.85H), 7.37 (d, J=9.2 Hz, 0.15H), 7.32 (d, J=9.2 Hz, 0.85H), 7.30 (s, 1H), 5.60 (m, 1H), 5.57 (br, 0.15H), 5.52 (br, 0.85H), 5.28 (dd, J=17.2, 1.2 Hz, 0.85H), 5.27 (br d, J=16.8 Hz, 0.15H), 5.11 (dd, J=10.4, 1.2 Hz, 1H), 4.77 (t, J=5 Hz, 1H), 4.62 (t, J=8.4 Hz, 0.85H), 4.54-4.61 (m, 0.15H), 4.38 (br, 0.15H), 4.34 (br, 0.85H), 4.10-4.24 (m, 5H), 4.06 (br, 0.15H), 4.00 (d, J=4.4 Hz, 0.85H), 3.49 (s, 6H), 3.17 (heptet, J=6.9 Hz, 1H), 2.92 (m, 1H), 2.70 (dd, J=14.4, 7.6 Hz, 1H), 2.33-2.50 (m, 2H), 2.23 (q, J=8.8 Hz, 0.85H), 2.15-2.24 (m, 0.15H), 1.88 (dd, J=8.4, 5.6 Hz, 1H), 1.37 (d, J=6.8 Hz, 6H), 1.34-1.42 (m, 1H), 1.15-1.28 (m, 3H), 1.14 (d, J=6.8 Hz, 2.55H), 1.08 (d, J=6.8 Hz, 0.45H), 1.06 (d, J=6.4 Hz, 2.55H), 0.93 (d, J=6.4 Hz, 0.45H).

Preparation of Examples 66 and 67

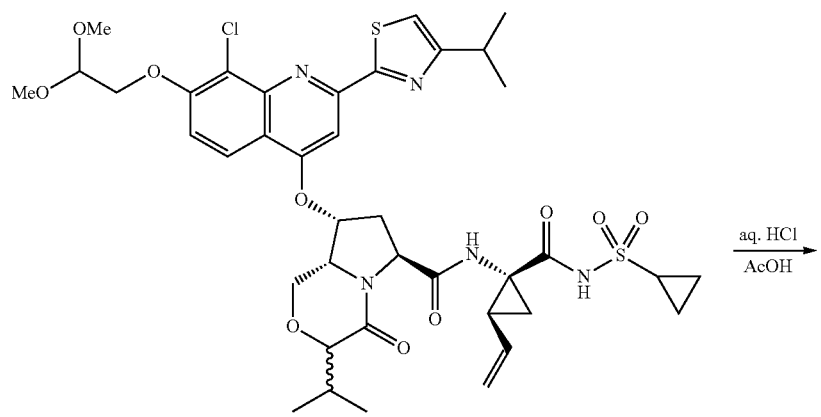

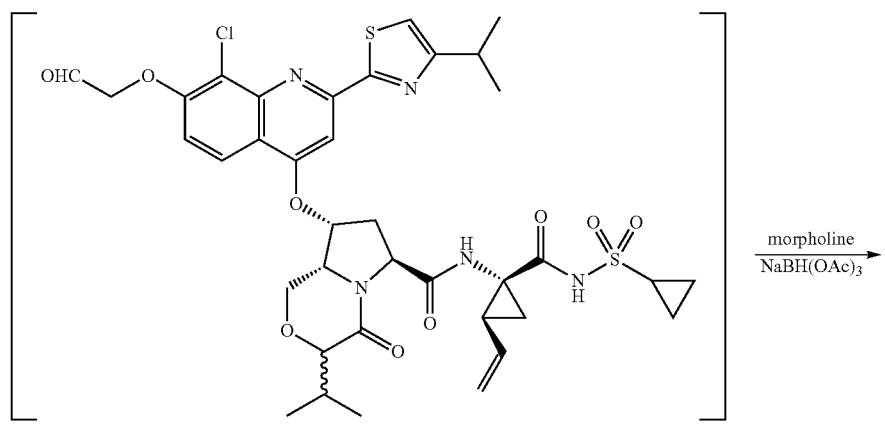

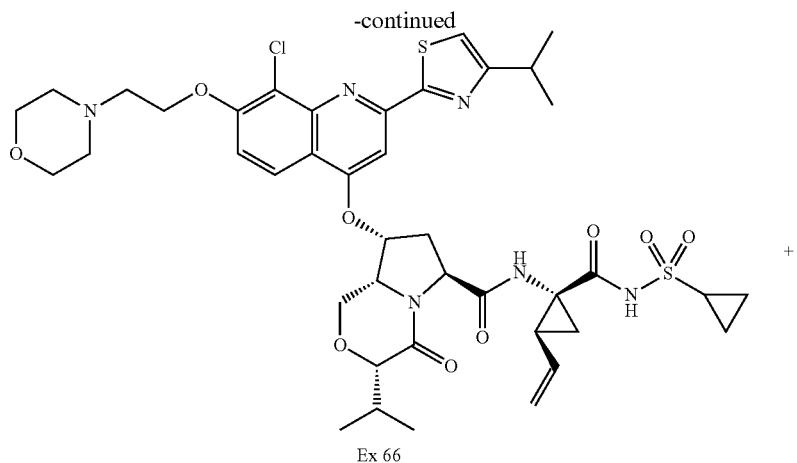

Ex 66

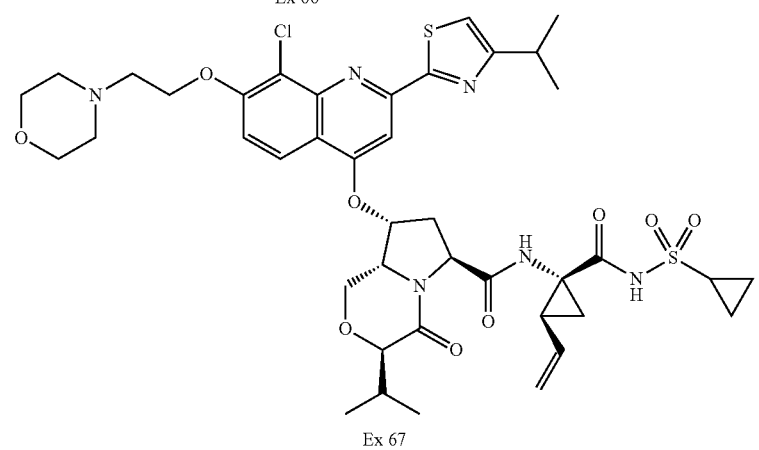

Ex 67

Example 65 (105 mg, 0.11 mmol) in acetic acid (4 mL) was stirred at rt as 1.4 N HCl (1.5 mL) was added. The solution was stirred at 60° C. for 1 h. The solution was concentrated and the residue was treated with saturated NaHCO₃ solution and ethyl acetate. The insoluble viscous material was collected by dissolving with methanol and combined with the organic fraction. After the combined material was concentrated, it was dissolved in methanol again, filtered through celite pad, and concentrated. The residue was co-evaporated with toluene (×2) and the crude aldehyde was used as is for the next step.

LC/MS=800.13 (M⁺+1), 818.16 (M⁺+H₂O+1), 832.19 (M⁺+CH₃OH+1)

The crude aldehyde and sodium triacetoxyborohydride (37 mg, 0.174 mmol) in dichloromethane (5 mL) was stirred at 0° C. as morpholine (20 □L, 0.230 mmol) followed by acetic acid (3 □L) were added. After 30 min, additional acetic acid (3 □L) was added. The mixture was stirred at 0° C. for 30 min and additional morpholine (20 □L, 0.230 mmol) was added. After 30 min, the mixture was concentrated. Example 66 (69 mg, 64%) and example 67 (15 mg, 14%) were isolated by reverse phase HPLC as the bis-TEA salts.

Ex 66

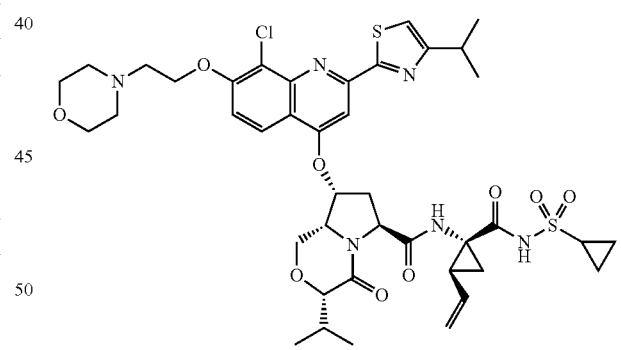

LC/MS=871.33 (M⁺+1)

¹H NMR (400 MHz, CD₃OD): δ 9.21 (s, 1H), 8.03 (d, J=9.2 Hz, 1H), 7.78 (s, 1H), 7.47 (d, J=9.2 Hz, 1H), 7.32 (s, 1H), 5.65 (dt, J=16.8, 9.2 Hz, 1H), 5.55 (br, 1H), 5.28 (d, J=16.8 Hz, 1H), 5.10 (d, J=11.2 Hz, 1H), 4.59-4.67 (m, 3H), 4.33 (br, 1H), 4.17 (dd, J=11.6, 5.2 Hz, 1H), 4.11 (dd, J=11.6, 7.6 Hz, 1H), 4.1 (br, 2H), 3.98 (d, J=4 Hz, 1H), 3.85 (br, 2H), 3.76 (t, J=4.6 Hz, 2H), 3.75 (br, 2H), 3.46 (br, 2H), 3.17 (heptet, J=6.8 Hz, 1H), 2.91 (m, 1H), 2.69 (dd, J=14.4, 7.6 Hz, 1H), 2.44 (m, 2H), 2.24 (q, J=8.8 Hz, 1H), 1.88 (dd, J=8, 5.6 Hz, 1H), 1.37 (d, J=7.2 Hz, 6H), 1.33-1.39 (m, 1H) 1.14-1.27 (m, 2H), 1.12 (d, J=6.8 Hz, 3H), 1.04 (d, J=6.4 Hz, 3H), 1.00-1.09 (m, 2H)

Ex 67

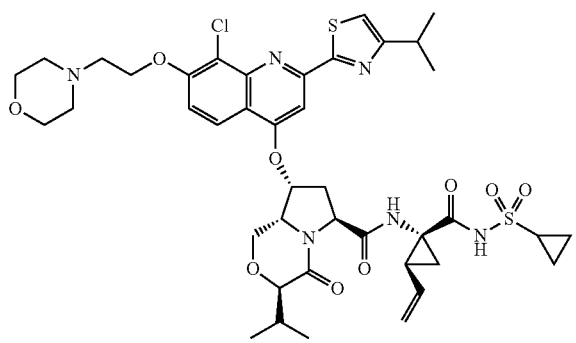

LC/MS=871.38 (M⁺+1)

¹H NMR (400 MHz, CD₃OD): δ 9.24 (s, 1H), 8.08 (d, J=9.2 Hz, 1H), 7.80 (s, 1H), 7.51 (d, J=9.2 Hz, 1H), 7.33 (s, 1H), 5.69 (ddd, J=17.2, 10.4, 9.2 Hz, 1H), 5.63 (br, 1H), 5.26 (dd, J=17.2, 1.2 Hz, 1H), 5.09 (d, J=10.4, 1.2 Hz, 1H), 4.66 (br t, J=4.6 Hz, 2H), 4.57 (dd, J=10, 6.8 Hz, 1H), 4.39 (m, 1H), 4.34 (dd, J=11.2, 4 Hz, 1H), 4.09 (br, 2H), 4.04 (d, J=2 Hz, 1H), 3.86 (br, 2H), 3.85 (t, J=10.4 Hz, 2H), 3.77 (t, J=4.8 Hz, 2H), 3.75 (br, 2H), 3.46 (br, 2H), 3.17 (heptet, J=6.8 Hz, 1H), 2.93 (m, 1H), 2.68 (dd, J=14.4, 7.2 Hz, 1H), 2.35-2.47 (m, 2H), 2.19 (q, J=8.8 Hz, 1H), 1.88 (dd, J=8, 5.6 Hz, 1H), 1.37 (d, J=7.2 Hz, 6H), 1.15-1.27 (m, 2H), 1.06 (d, J=6.8 Hz, 3H), 1.00-1.09 (m, 2H), 0.92 (d, J=6.8 Hz, 3H), Preparation of Example 68

Ex 68

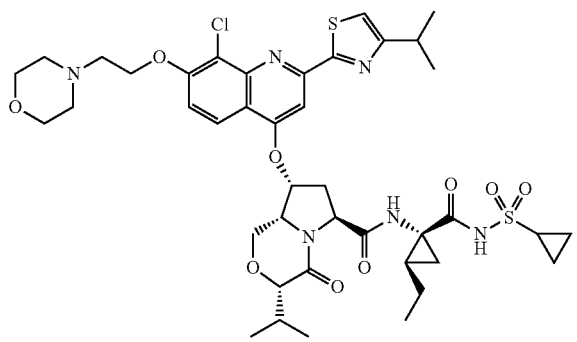

Example 68 was prepared from example 66 via a diimide reduction, similar to that previously described.

LC/MS=873.31 (M⁺+1)

¹H NMR (400 MHz, CD₃OD): δ 9.17 (s, 1H), 8.07 (d, J=9.2 Hz, 1H), 7.82 (s, 1H), 7.51 (d, J=9.2 Hz, 1H), 7.35 (s, 1H), 5.58 (br, 1H), 4.67 (t, J=4.8 Hz, 2H), 4.62 (t, J=8.4 Hz, 1H), 4.35 (m, 1H), 4.19 (dd, J=11.6, 5.6 Hz, 1H), 4.13 (dd, J=11.6, 7.2 Hz, 1H), 4.13 (br, 2H), 4.00 (d, J=4 Hz, 1H), 3.86 (br, 2H), 3.78 (t, J=4.6 Hz, 2H), 3.76 (br, 2H), 3.46 (br, 2H), 3.19 (heptet, J=6.8 Hz, 1H), 2.96 (m, 1H), 2.68 (dd, J=14.4, 7.6 Hz, 1H), 2.39-2.50 (m, 2H), 1.45-1.64 (m, 4H), 1.39 (d, J=6.8 Hz, 6H), 1.20-1.34 (m, 2H), 1.14 (d, J=6.8 Hz, 3H), 1.04-1.19 (m, 3H), 1.06 (d, J=6.8 Hz, 3H), 0.98 (t, J=7 Hz, 3H)

Preparation of Examples 69 and 70

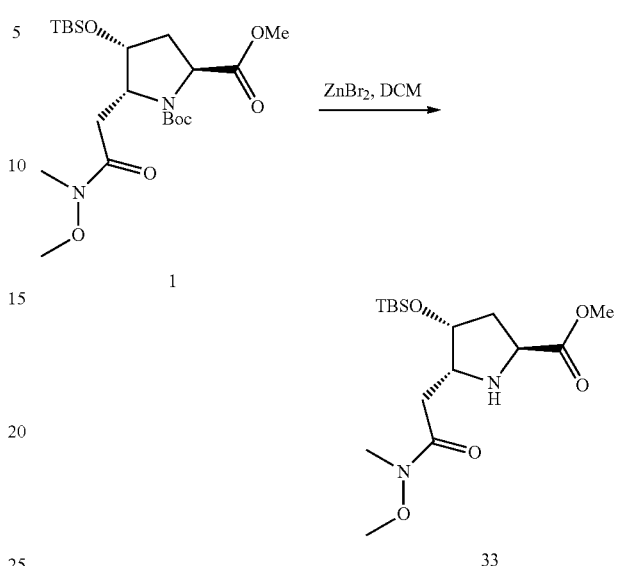

Compound 1 (3 g, 6.53 mmol) was dissolved in DCM (30 ml) at r.t., followed by the addition of ZnBr₂ (3 g, 13.3 mmol) solution in DCM slowly. The reaction mixture was stirred for overnight. The reaction was monitored by LC-MS, 25% compound XX was still left according to the UV trace on LC-MS, so one more equivalent ZnBr₂ (1.5 g, 6.6 mmol) in DCM was added to the reaction mixture. And it was stirred at r.t. for another 4 hours. Reaction mixture was washed with NaHCO₃ (sat.), Brine and dried with MgSO₄. Solvent was removed under reduced pressure; compound 33 (1.9 g) was used crude in next step.

LC/MS=561 (M⁺+1)

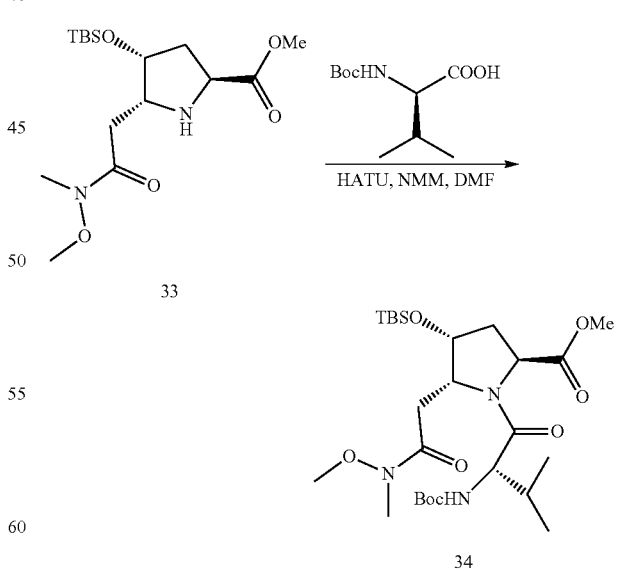

Crude compound 33 (1.9 g) was dissolved in DMF (20 ml), followed by the addition of 2-tert-Butoxycarbonylamino-3-methyl-butyric acid (1.7 g, 7.84 mmol), HATU (6.2 g, 16.3 mmol), and NMM (2.64 g, 26 mmol). The reaction mixture was stirred at r.t. for overnight. Reaction solution was diluted with EtOAc (30 ml), and it was washed with LiCl (5%) (20 ml), NH$_4$Cl (sat.) (20 ml), NaHCO$_3$ (sat.) (20 ml) and brine. The organic phase was dried with MgSO$_4$ and solvent was stripped down under reduced pressure. The crude material was purified by flash chromatograph to afford compound 34 (1.2 g, 2.2 mmol).

LC/MS=937 (M$^+$+1)

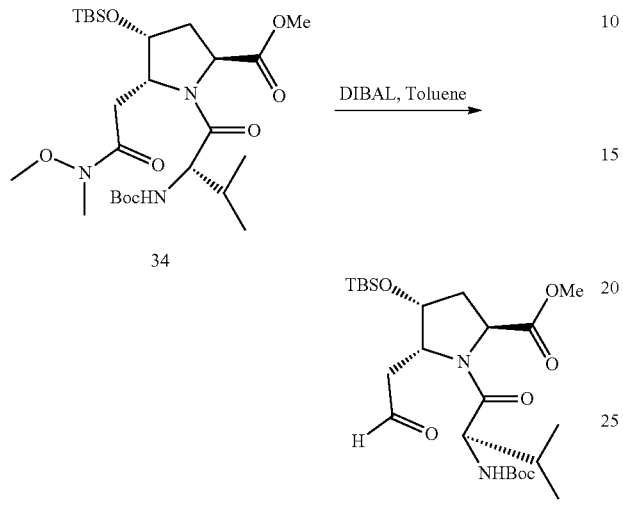

34

At −78° C., DIBAL (1.5 M in toluene) (1 ml) was added drop-wise to solution of compound 34 (0.8 g, 1.43 mmol) in toluene (8 ml). The mixture was stirred at −78 C for 6 h. The reaction mixture was quenched with NH$_4$Cl (sat.) (8 ml) at −78° C., the mixture was stirred for 30 minutes and the temperature was allowed to warm up to room temperature gradually. Organic phase was separated from aqueous and washed with H$_2$O and brine. Solvent was stripped down under reduced pressure and the residue was purified by flash chromatograph to afford compound 35 (0.4 g, 0.8 mmol, and yield 56%).

LC/MS=502 (M$^+$+1)

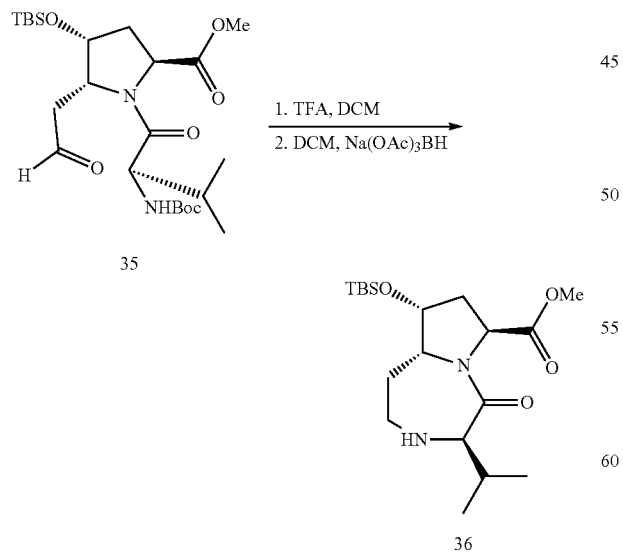

Compound 35 (0.2 g, 0.4 mmol) was dissolved in DCM (2 ml), followed by the addition of TEA (1.5 ml). The reaction mixture was stirred at room temperature for half hour. Solvent was stripped off under reduced pressure and it was dried under high vacuum. The crude material was used directly in next step.

The crude material was dissolved in DCM (2 ml) and stirred at rt for 1 h. The reaction mixture was then cooled to 0° C. with an ice bath and sodium triacetoxyborohydride was added in one portion. The ice bath was then removed and the solution was allowed to stir for 30 min at rt. The reaction was quenched with H$_2$O (150 mL). The solution was extracted with H$_2$O and brine and then dried over Na$_2$SO$_4$. The crude compound 36 was used directly in next step.

LC/MS=386 (M$^+$+1)

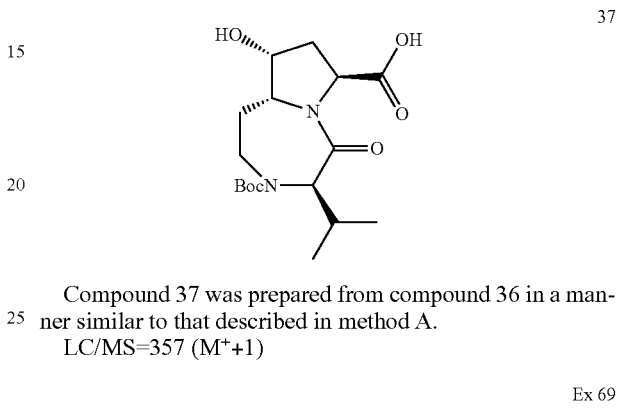

37

Compound 37 was prepared from compound 36 in a manner similar to that described in method A.

LC/MS=357 (M$^+$+1)

Ex 69

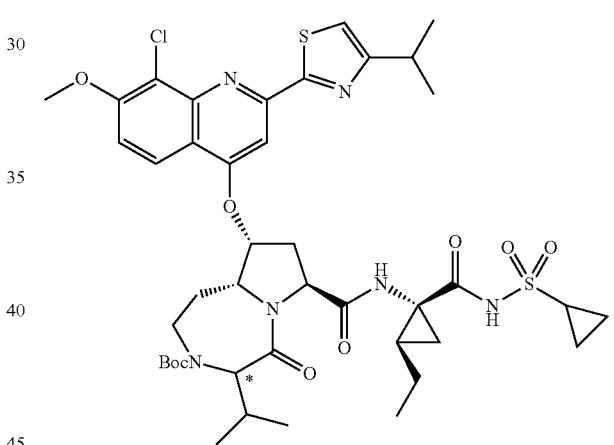

Ex 70

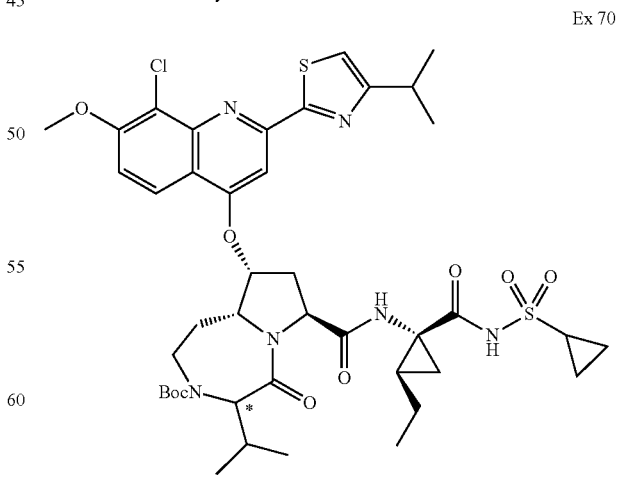

Examples 69 and 70 were prepared in a similar manner to that described in method A, except using compound 37, 4,8-dichloro-2-(4-isopropyl-thiazol-2-yl)-7-methoxy-quinoline in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-ethyl-cyclopropanecarbonyl)-amide was used in place of the HCl salt of 1-methyl-cyclopropanesulfonic acid ((1R,2S)-1-amino-2-vinyl-cyclopropanecarbonyl)-amide. Examples 69 and 70 formed due to epimerization of the iPr bearing carbon during the installation of the quinoline piece. The resulting mixture of diastereomers was carried on until the end of the synthesis, at which point the two diastereomers were separated by reverse phase HPLC.

Example 69

LC/MS=868 (M$^+$+1)

$^1$H NMR (400 MHz, CDCl$_3$): δ (ppm) 7.98 (m, 1H), 7.83 (m, 1H), 7.33 (m, 2H), 5.59 (bs, 1H), 4.46 (m, 3H), 4.02 (s, 3H), 3.32 (m, 1H), 2.90 (m, 2H), 2.63 (s, 3H), 2.49 (m, 2H), 1.94 (m, 21H), 1.62-0.84 (m, 36H)

Example 70

LC/MS=868 (M$^+$+1)

$^1$H NMR (400 MHz, CD$_3$OD): δ (ppm) 8.10-7.640 (m, 3H), 7.47-7.28 (m, 1H), 5.80-5.61 (m, 1H), 4.79-4.48 (m, 2H), 4.25 (m, 1H), 4.03 (s, 3H), 3.34 (m, 1H), 3.14-2.51 (m, 6H), 2.38-1.78 (m, 2H), 1.62-0.80 (m, 43H), Preparation of Example 71

Ex 71

Example 71 was prepared from example 69 via removal of the Boc group, in a manner similar to that previously described.

LC/MS=767 (M$^+$+1)

$^1$H NMR (400 MHz, CD$_3$Cl3): δ (ppm) 9.92 (br, 1H), 8.82 (m, 1H), 8.20 (m, 1H), 7.69, (s, 1H), 7.48 (s, 1H), 5.95 (br, 1H), 4.77 (m, 2H), 4.07 (s, 3H), 3.97 (m, 1H), 3.62 (m, 1H), 3.27 (m, 1H), 2.88 (m, 1H), 2.65-2.40 (m, 7H), 1.54-0.84 (m, 22H)

Preparation of Example 72

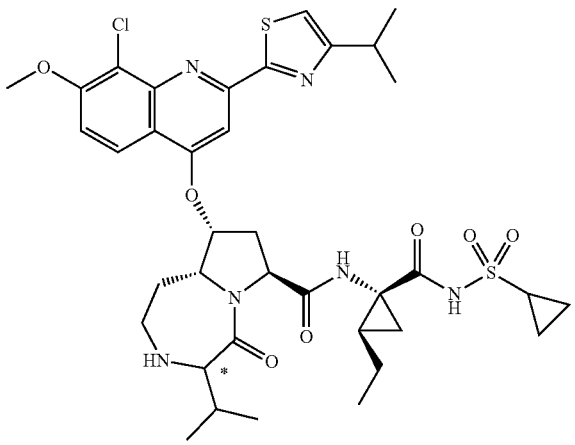

Ex 72

Example 72 was prepared from example 70 via removal of the Boc group, in a manner similar to that previously described.

LC/MS=767 (M$^+$+1)

$^1$H NMR (400 MHz, CD$_3$Cl3): δ (ppm) 10.04 (br, 1H), 8.59 (m, 1H), 8.23 (m, 1H), 7.66, (s, 1H), 7.51 (s, 1H), 5.96 (br, 1H), 4.94 (m, 1H), 4.73 (m, 1H), 4.09 (s, 3H), 3.97 (m, 1H), 3.75 (m, 1H), 3.50 (m, 1H), 3.27 (m, 1H), 2.92 (m, 1H), 2.65-2.18 (m, 7H), 1.62-0.89 (m, 22H)

Preparation of Example 73

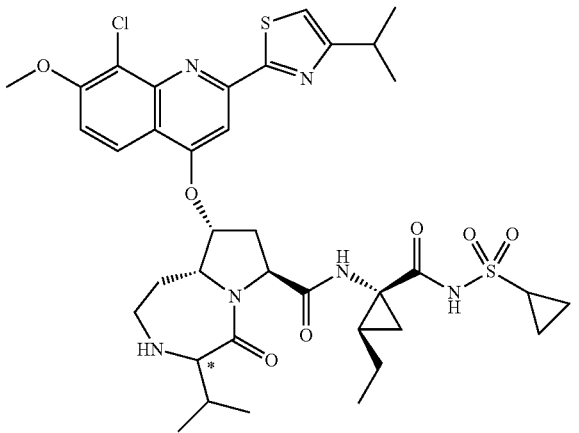

Compound 5 (387 mg, 0.99 mmol), compound 38 (787 mg, 2.99 mmol) were taken up in CH$_2$Cl$_2$. The mixture was cooled to 0° C. in a ice bath and stirred for 1 h. NaBH(OAc)$_3$ was added to the reaction mixture and monitored by LC/MS. The reaction was determined to be complete in 15 min by LC/MS. Quench with H₂O. Extract with CH₂Cl₂, and dry over Na₂SO₄. Remove solids by filtration. Solvent was removed under reduced pressure. Compound 39 (496 mg, 92%) was isolated by silica gel chromatography as a white solid.

LC/MS=545 (M⁺1)

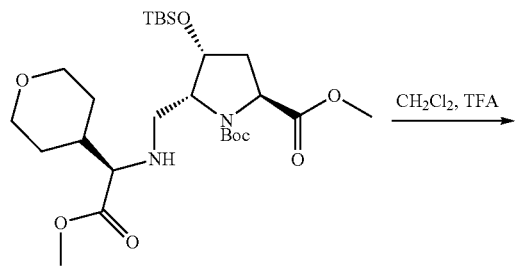

39

Compound 39 (490 mg, 0.899 mmol) was taken up in CH₂Cl₂ (2.0 mL) and TFA (2.0 mL). The reaction mixture was stirred at rt for 16 h. The reaction was determined to be complete by LC/MS. Solvent was removed under reduced pressure and toluene (3×10 mL) was co-evaporated to afford compound 40 as a yellow oil.

LC/MS=445 (M⁺1)

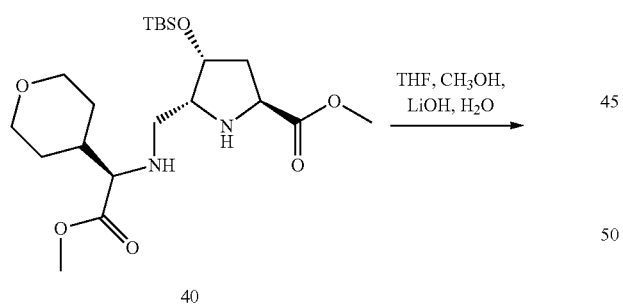

40

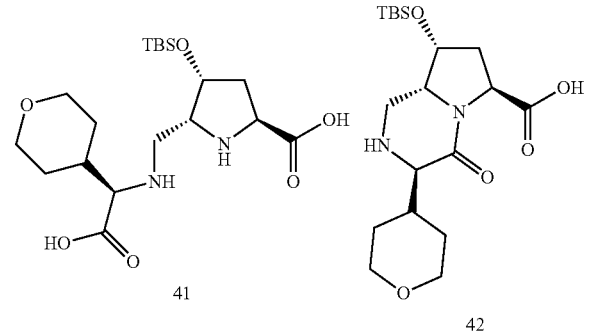

Compound 40 (502 mg, 0.899 mmol) was taken up in THF (5.0 mL) and CH₃OH (3.0 mL). LiOH·H₂O (188 mg, 4.49 mmol) was dissolved in H₂O (3.0 mL). The aqueous solution was added to the organic solution and the reaction progress was monitored by LC/MS. At 6 h, the reaction was determined to be a mixture of acyclic bis-acid and bicyclic monoacid in a 1:2 ratio with no observed compound 40. Adjust pH to 5 with 2N HCl₍aq₎. Remove solvent under reduced pressure and partition between EtOAc and H₂O. Dry organics over Na₂SO₄, filter and removed solvent under reduced pressure. The mixture of products were carried forward without purification.

LC/MS=417 (M⁺1), 399 (M⁺1)

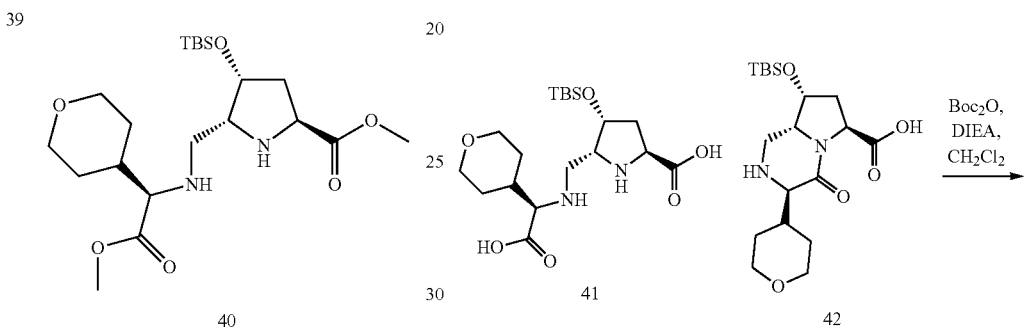

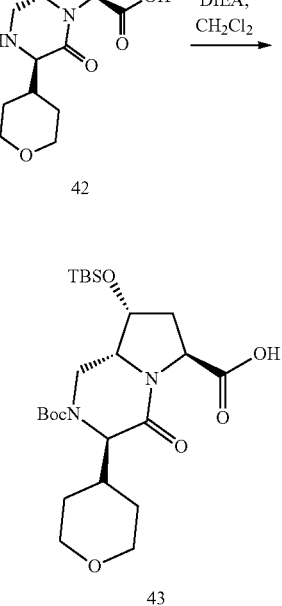

43

Compounds 41 & 42 (0.517 mmol) were taken up in CH₂Cl₂ (10 mL). Di-tert-butyl-dicarbonate, (0.225 mg, 1.03 mmol) was added to the reaction mixture followed by DIEA (4204, 2.34 mmol). The reaction was stirred for 6 h, with progress monitored by LC/MS. Only compound 42 reacted with di-tert-butyl-dicarbonate. Solvent was removed under reduced pressure and the crude material was taken up in EtOAc (20 mL). H₂O (10 mL) was added followed by the addition of 2N HCl₍aq₎ to a pH=2. Aqueous was washed with EtOAc (30 mL), organics combined and dried over Na₂SO₄, filtered and solvent removed under reduced pressure. Compound 43 was carried forward without purification.

LC/MS=499 (M⁺1)

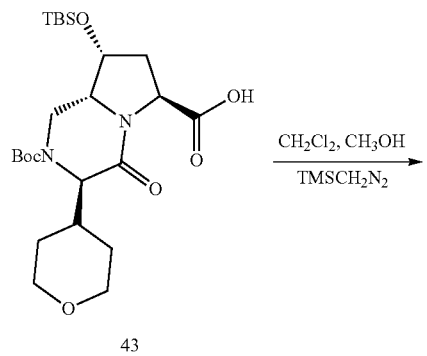

43

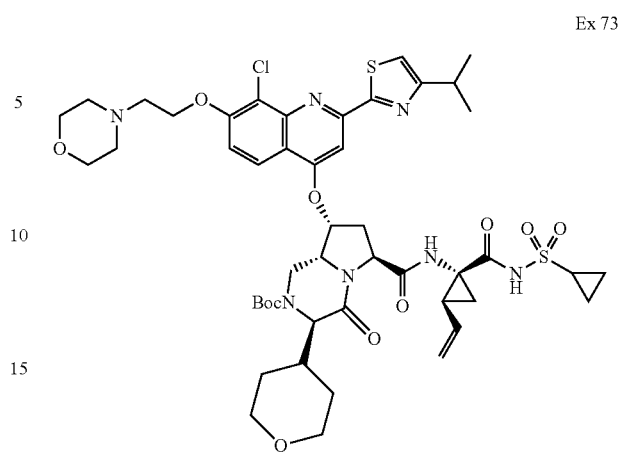

Ex 73

Example 73 was prepared in a manner similar to method A, except compound 44 was used, 4,8-dichloro-2-(4-isopropyl-thiazol-2-yl)-7-(2-morpholin-4-yl-ethoxy)-quinoline was used in place of 4,8-dichloro-2-(6-isopropyl-pyridin-2-yl)-7-(2-methoxy-ethoxy)-quinoline, and the HCl salt of cyclopropanesulfonic acid ((1R,2S)-1-amino-2-vinyl-cyclopropanecarbonyl)-amide was used in place of the HCl salt of 1-methyl-cyclopropanesulfonic acid ((1R,2S)-1-amino-2-vinyl-cyclopropanecarbonyl)-amide.

LC/MS=1012 (M$^+$+1)

$^1$H NMR (400 MHz, CD$_3$OD): δ (ppm) 9.926 (s, 1H); 8.069 (d, J=9.0 Hz, 1H); 7.851 (s, 1H); 7.51 (d, J=9.0 Hz, 1H); 7.343 (s, 1H); 5.657 (m, 2H); 5.282 (d, J=17.02 Hz, 1H); 5.114 (d, J=11.93 Hz, 1H); 4.650 (brt, J=3.33 Hz, 2H); 4.545 (m, 2H); 4.362 (m, 1H); 4.18-3.765 (m, 10H); 3.424 (m, 4H); 3.288 (m, 2H); 3.183 (quint, J=4.65 Hz, 1H); 2.956 (m, 1H); 2.685 (m, 1H); 2.423 (m, 1H); 2.213, (m, 2H); 1.880 (m, 1H); 1.522-1.205 (m, 22H); 1.062 (m, 3H).

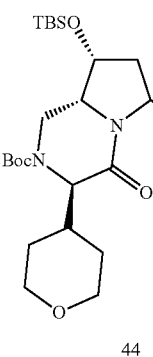

44

Compound 43 (309 mg, 0.517 mmol) was taken up in CH$_2$Cl$_2$ (5.0 mL) and CH$_3$OH (1.0 mL). TMSCH$_2$N$_2$ (0.775 mL, 2.0M hexanes) was added very slowly to the solution. Reaction progress was monitored by LC/MS, and was determined complete after 5 min. Solvents were removed under reduced pressure and the material was partitioned between EtOAc and H$_2$O. The organics were dried over Na$_2$SO$_4$, filtered and solvent removed under reduced pressure. Compound 44 (105 mg, 40% 3-steps) was isolated by silica gel chromatography as a white solid.

LC/MS=513 (M$^+$1)

Preparation of Example 74

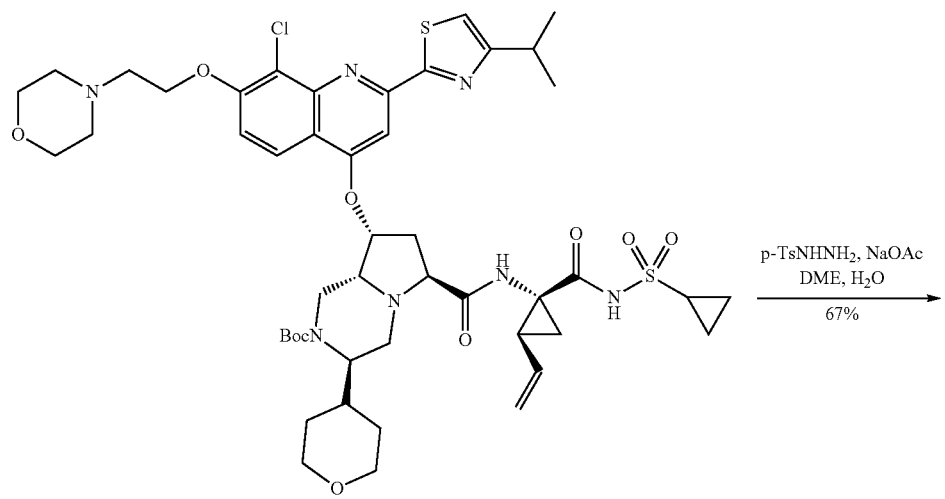

Ex 73

-continued

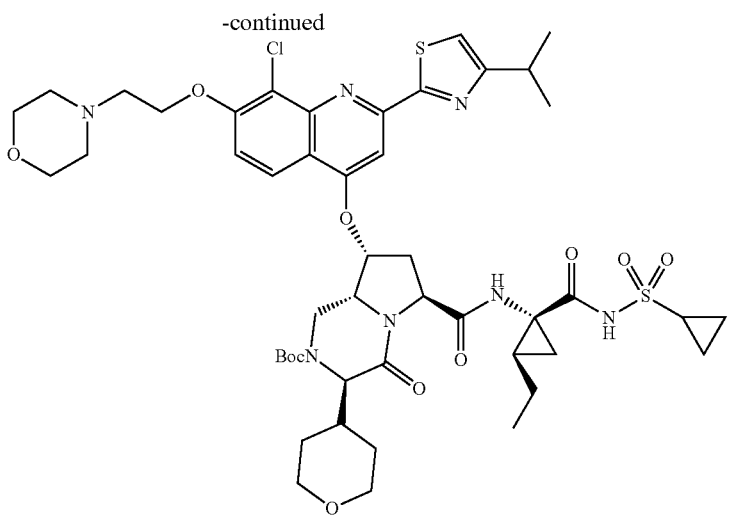

Ex 74

Example 73 (10 mg, 0.0088 mmol) was taken up in dimethoxyethane (0.1 mL) and H₂O (0.02 mL). p-Toluenesulfonylhydrazide (8.0 mg, 0.04 mmol) and NaOAc (6.56 mg, 0.08 mmol) were added and the reaction was heated to 95° C. for 1 h. The reaction was determined complete by LC/MS. The reaction mixture was diluted with 1.0 mL acetonitrile and example 74 was isolated by reverse phase HPLC as the TFA salt.

LC/MS=1014 (M⁺+1)

¹H NMR (400 MHz, CDCl₃): δ (ppm) 9.983 (brs, 1H); 8.139 (brs, 1H); 7.709 (m, 2H); 7.161 (s, 1H); 6.978 (brs, 1H); 5.503 (brs, 1H); 4.545-4.335 (m, 6H); 3.998 (m, 7H); 3.745 (m, 5H); 3.517 (brs, 1H); 3.268 (m, 2H); 3.268-3.155 (m, 3H); 2.974 (m, 1H); 2.511 (m, 2H); 2.046 (m, 1H); 1.656-1.235 (m, 23H); 1.141 (m, 1H); 1.053 (brd, J=7.43 Hz, 2H); 0.899 (m, 3H)

Preparation of Example 75

Method B:

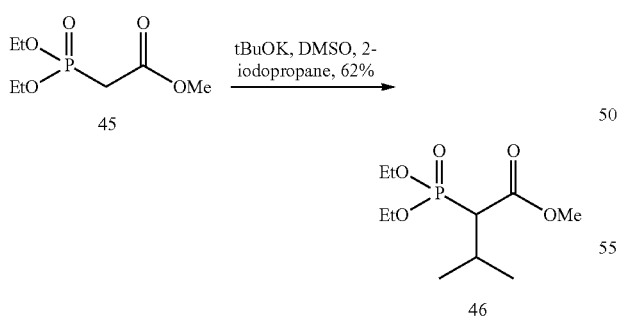

Compound 45 (9 g, 42.8 mmol) was added to a solution of tBuOK (6.7 g, 60 mmol) in DMSO (25 mL). Reaction warms during this addition. Reaction progress was monitored by LC/MS. After 3 h the reaction was quenched by the slow addition of pH 7 phosphate buffered saline (10 mL). The mixture was then partitioned between CH₂Cl₂ and H₂O. The aqueous layer was washed with CH₂Cl₂ three times, and the combined organic layers were extracted with brine and dried over Na₂SO₄. The drying agent was removed by vacuum filtration and compound 46 (6.67 g, 62%) was isolated from the filtrate by silica gel column chromatography as a clear colorless oil.

LC/MS=252.96 (M⁺+1)

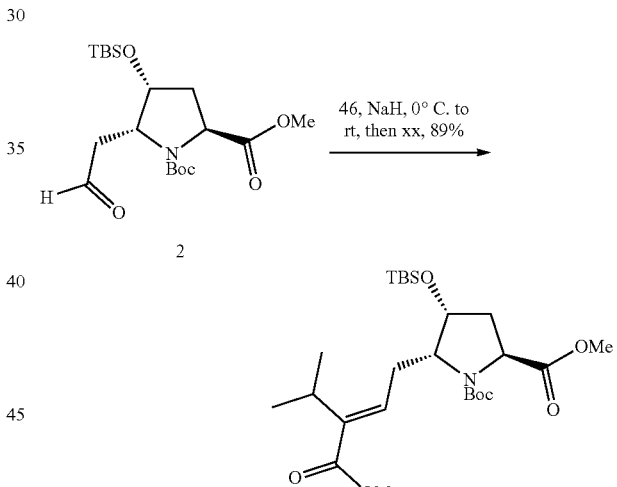

Compound 46 (4.27 g, 16.9 mmol) was added to a slurry of NaH (642 mg, 16.07 mmol) in THF (64.5 mL), which had been cooled in an ice bath. The ice bath was removed and the reaction was allowed to stir for 30 min. To this clear colorless solution was added a solution of compound 2 (4.3 g, 10.71 mmol) in THF (21.5 mL). The resulting clear, slightly yellow reaction was allowed to stir for 2 h. The reaction progress was monitored by TLC. The reaction was quenched by the addition of H₂O (10 mL) and this mixture was then partitioned between EtOAc and H₂O. The organic phase was washed with H₂O and brine. The organic phase was then dried over Na₂SO₄. The drying agent was removed by vacuum filtration and compound 47 (4.8 g, 89%) was isolated from the filtrate by silica gel column chromatography as a 4.5:1 mixture of isomers about the olefin.

LC/MS=499.74 (M⁺+1)

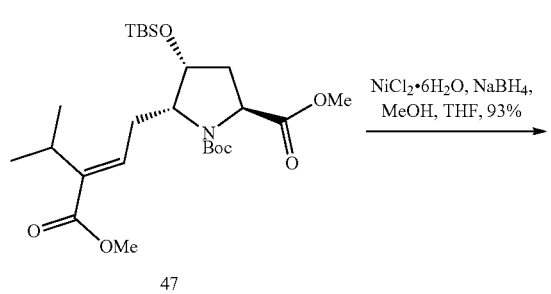

47

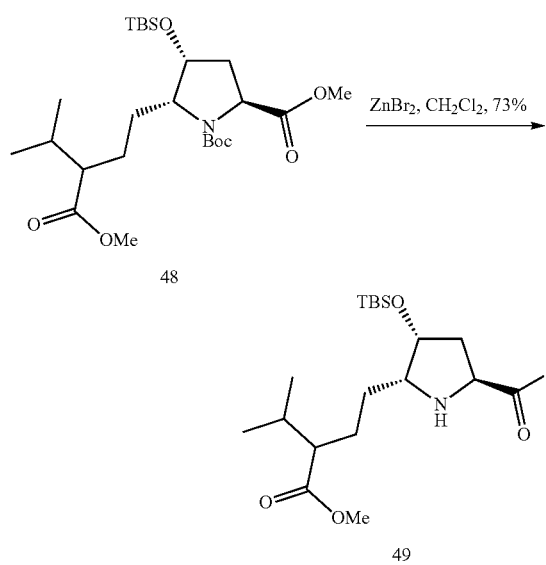

48

Compound 47 (3.04 g, 9.6 mmol) was dissolved in MeOH (24 mL) and THF (8 mL). This solution was cooled in an ice bath and then NiCl$_2$·6H$_2$O (1.43 g, 6 mmol) was added, followed by NaBH$_4$ (454 mg, 12 mmol) portion-wise over 20 min. The progress of the reaction was monitored by LC/MS. Additional NiCl$_2$·6H$_2$O and NaBH$_4$ were added in portions, with monitoring by LC/MS, until the reaction was complete. The reaction was then filtered through Celite, eluting with Et$_2$O. The filtrate was extracted with H$_2$O and brine and then dried over Na$_2$SO$_4$. Compound 48 (2.8 g, 93%) was isolated as a clear colorless oil by silica gel column chromatography.

LC/MS=402.18 (M$^+$+1−Boc)

Compound 48 (2.8 g, 5.58 mmol) was dissolved in CH$_2$Cl$_2$ (28 mL). ZnBr$_2$ was added to this solution in one portion. The reaction was then stirred for 18 h. The reaction was determined to be complete by TLC. The reaction was quenched with sat. NaHCO$_{3(aq.)}$. The reaction was then partitioned between CH$_2$Cl$_2$ and H$_2$O. The aqueous phase was brought to pH 8-10 with sat. NaHCO$_{3(aq.)}$ and then extracted with CH$_2$Cl$_2$. The combined organic phase was extracted with brine and then dried over Na$_2$SO$_4$. The drying agent was removed by vacuum filtration and compound 49 (1.9 g, 85%) was isolated from the filtrate by silica gel column chromatography.

LC/MS=402.2 (M$^+$+1)

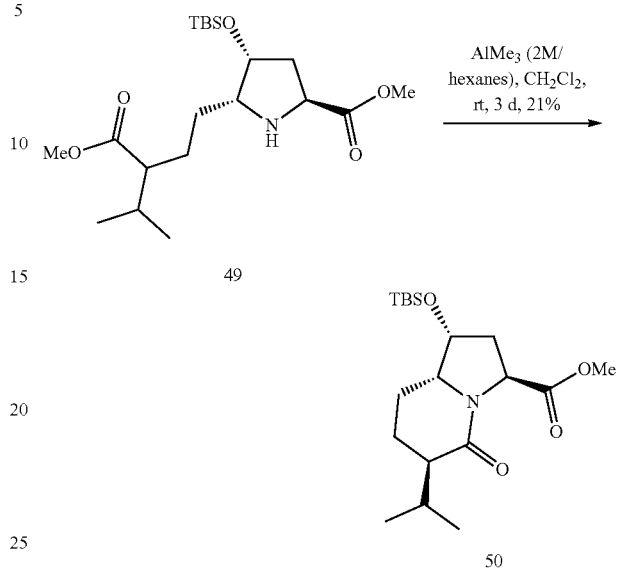

49

Compound 49 (1.9 g, 4.73 mmol) was dissolved in CH$_2$Cl$_2$ (100 mL). This solution was cooled in an ice bath and a 2M solution of AlMe$_3$ in hexanes (2.84 mL, 5.68 mmol) was slowly added. The ice bath was then removed and the reaction was stirred for 48 h. The reaction was then quenched with sat. NH$_4$Cl$_{(aq.)}$. The mixture was then partitioned between sat. NH$_4$Cl$_{(aq.)}$ and CH$_2$Cl$_2$. Aqueous extracted once with CH$_2$Cl$_2$, and then the combined organic phases were extracted with H$_2$O and then dried over Na$_2$SO$_4$. Compound 50 (369 mg, 21%) was isolated as a crystalline white solid by silica gel column chromatography.

LC/MS=370.15 (M$^+$+1)

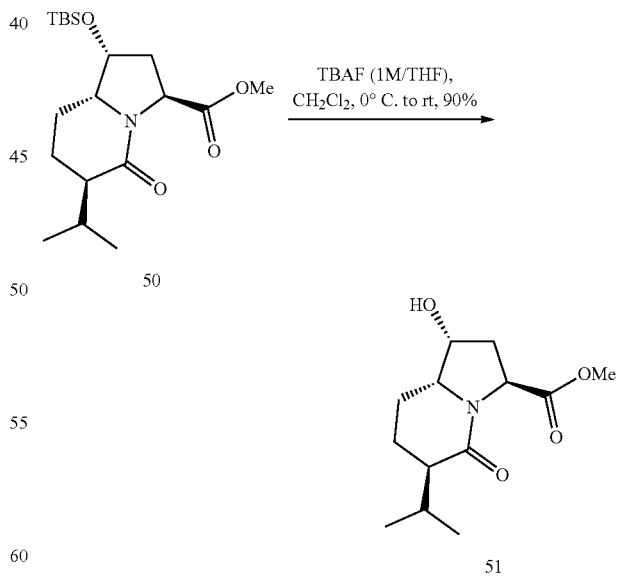

50

51

Compound 50 (350 mg, 0.947 mmol) was dissolved in CH$_2$Cl$_2$ (9.5 mL). This solution was placed in an ice bath and a 1M solution of TBAF in THF (1.42 mL) was added. After 45 min another more 1M TBAF in THF (1.5 mL) was added. The reaction progress was monitored by TLC. After 8 h the reaction was nearly complete. The reaction was quenched by the addition of H₂O. The aqueous and organic layers were separated and the aqueous layer was extracted with additional CH₂Cl₂. The combined organic layers were dried over Na₂SO₄. The drying agent was removed by vacuum filtration. Compound 51 (217 mg, 90%) was isolated from the filtrate as a crystalline white solid by silica gel column chromatography. It was determined that compound 51 is a single diastereomer by X-ray crystallography (See FIG. 1).

LC/MS=256.17 (M⁺+1)

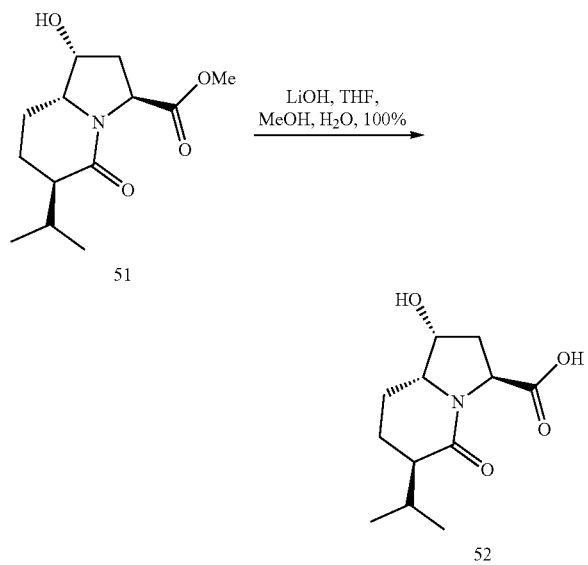

Compound 51 (217 mg, 0.85 mmol) was dissolved in THF (4.26 mL) and MeOH (2.83 mL). This solution was cooled in an ice bath and then a solution of LiOH (178 mg, 4.25 mmol) in H₂O (1.42 mL) was added. The ice bath was removed and the reaction was stirred at rt. The reaction progress was monitored by LC/MS. After 1 h the reaction was complete. The reaction placed in an ice bath and 2N HCl (2.5 mL) was slowly added. The quenched reaction was concentrated and the resulting white residue was placed on a lypholizer for 72 h. The resulting compound 52 was used as is in the next reaction.

LC/MS=242.07 (M⁺+1)

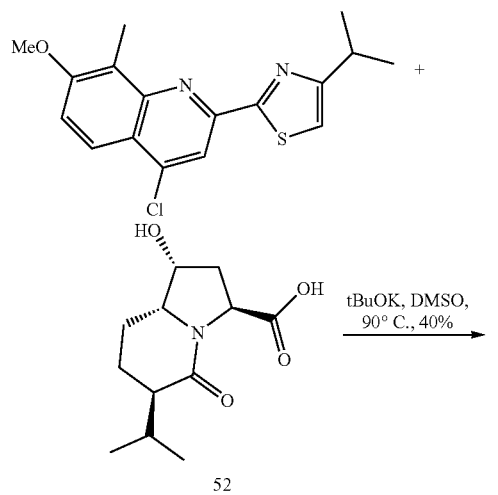

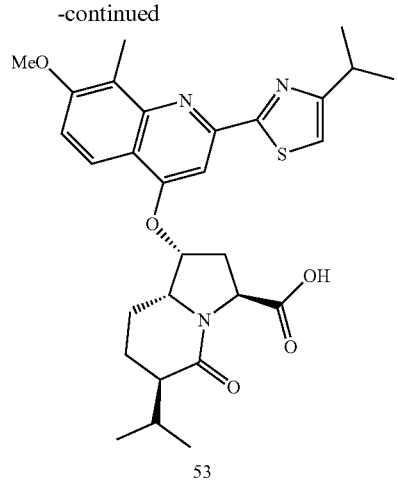

Compound 52 (0.85 mmol) was dissolved in DMSO (8 mL). To this solution was added tBuOK (381 mg, 3.4 mmol). The reaction was stirred vigorously for 45 min and then 4-chloro-2-(4-isopropyl-thiazol-2-yl)-7-methoxy-8-methyl-quinoline (283 mg, 0.85 mmol) was added in one portion. The reaction was then placed in a 90° C. oil bath and stirred for 3 h. The reaction was then removed from the oil bath and quenched by the drop-wise addition of a 20% (v/v) solution of AcOH in H₂O. The reaction was then partitioned between EtOAc and H₂O. The layers were separated and the aqueous layer was back extracted with EtOAc. The combined organic layers were dried over Na₂SO₄. The drying agent was removed by vacuum filtration and the filtrate was concentrated and then re-dissolved in minimal MeOH. Compound 53 (224 mg, 40%) was isolated by reverse phase HPLC as the TFA salt.

LC/MS=538.17 (M⁺+1)

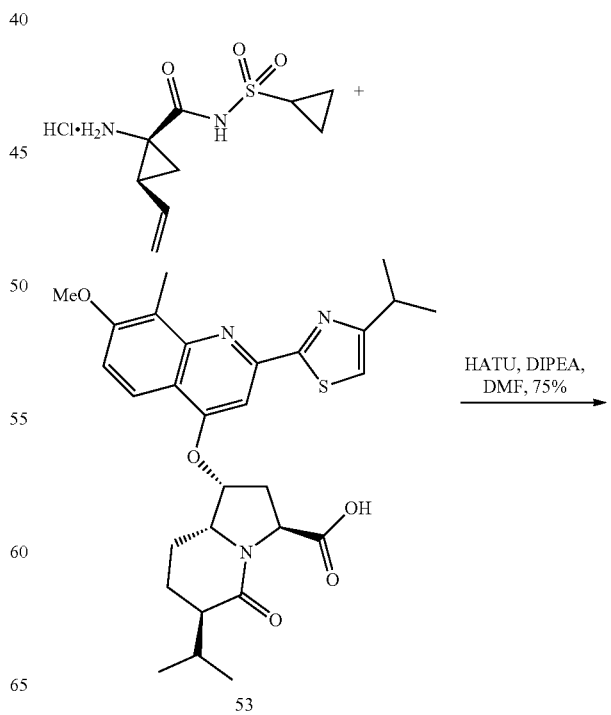

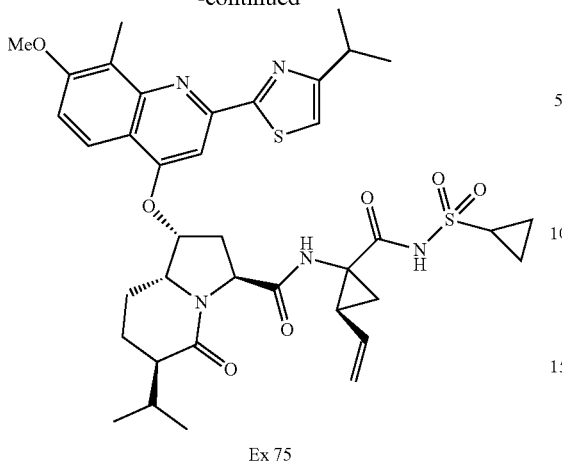

Ex 75

Compound 53 (224 mg, 0.344 mmol) and HATU (327 mg, 0.86 mmol) were combined in a flask and then dissolved with a solution of the HCl salt of cyclopropanesulfonic acid ((1R,2S)-1-amino-2-vinyl-cyclopropanecarbonyl)-amide (184 mg, 0.688 mmol) in DMF (4 mL). To this resulting mixture was added DIPEA (582 μL, 2.41 mmol) and the reaction was stirred for 45 min. The reaction was monitored by LC/MS. The reaction was filtered and example 75 (204 mg, 69%) was isolated from the filtrate by reverse phase HPLC as the TFA salt. This material was lyophilized to yield a yellow solid.

LC/MS=750.33 (M$^+$+1)

$^1$H NMR (400 MHz, CD$_3$OD): δ 9.16 (s, 1H), 8.22 (d, J=9.2 Hz, 1H), 7.73 (s, 1H), 7.44 (d, J=9.2 Hz, 1H), 7.34 (s, 1H), 5.75 (dt, J=16, 8.8 Hz, 1H), 5.50 (s, 1H), 5.30 (dd, J=17.2, 1.2 Hz, 1H), 5.13 (dd, J=10.4, 1.6 Hz, 1H), 4.51 (dd, J=10.4, 7.2 Hz, 1H), 4.19 (d, J=10.8 Hz, 1H), 4.02 (s, 3H), 3.69 (m, 1H), 3.21 (sept, J=6.8 Hz, 1H), 2.99 (ddd, J=12.8, 8, 4.8 Hz, 1H), 2.66 (s, 3H), 2.63 (m, 2H), 2.45 (m, 1H), 2.31 (ddd, J=14, 10.8, 3.2 Hz, 1H), 2.21 (quart, J=8.8 Hz, 1H), 2.19 (m, 1H), 2.01 (m, 1H), 1.89 (m, 2H), 1.74 (m, 1H), 1.41 (d, J=6.8 Hz, 6H), 1.26 (m, 3H), 1.09 (d, J=8.4 Hz, 2H), 1.02 (d, J=6.8 Hz, 3H), 0.90 (d, J=6.8 Hz, 3H)

Preparation of Example 76

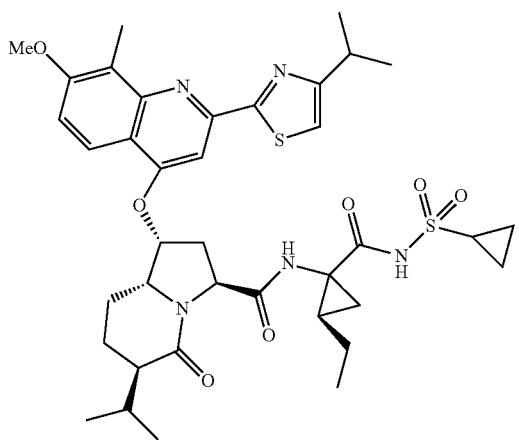

Ex 76

Example 76 was prepared in a similar fashion to example 75 in method B, except the HCl salt of cyclopropanesulfonic acid ((1R,2S)-1-amino-2-ethyl-cyclopropanecarbonyl)-amide was used instead of the HCl salt of cyclopropanesulfonic acid ((1R,2S)-1-amino-2-vinyl-cyclopropanecarbonyl)-amide.

LC/MS=752.54 (M$^+$+1)

$^1$H NMR (400 MHz, D$_6$-DMSO):): δ 10.47 (s, 1H), 8.93 (s, 1H), 7.94 (d, J=9.2 Hz, 1H), 7.58 (s, 1H), 7.47 (s, 1H), 7.46 (d, J=9.6 Hz, 1H), 5.54 (s, 1H), 4.36 (dd, J=10.8, 7.2 Hz, 1H), 4.05 (d, J=10.8 Hz, 1H), 3.14 (sept, J=6.8 Hz, 1H), 2.94 (ddd, J=12.4, 7.6, 4.4 Hz, 1H), 2.59 (s, 3H), 2.41 (dd, J=16.6, 6.8 Hz, 1H), 2.33 (m, 1H), 2.17 (ddd, J, 13.6, 10.4, 3.2, 1H), 2.05 (m, 1H), 1.86 (m, 1H), 1.46-1.79 (m, 4H), 1.38 (m, 4H), 1.33 (d, J=6.8 Hz, 6H), 1.06 (m, 5H), 0.91 (d, J=7.2 Hz, 3H), 0.87 (m, 3H), 0.78 (d, J=6.8 Hz, 3H)

Preparation of Example 77

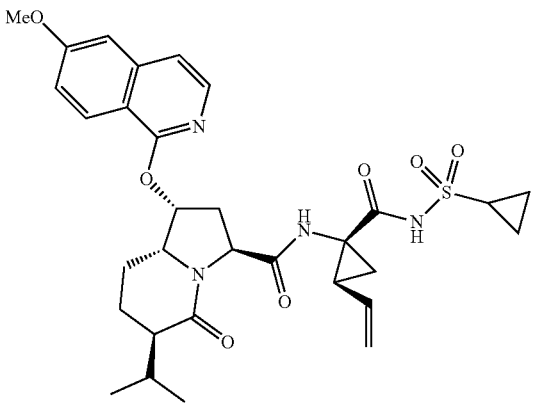

Ex 77

Example 77 was prepared in a similar fashion to example 75 in method B, using 1-chloro-6-methoxy-isoquinoline in place of 4-chloro-2-(4-isopropyl-thiazol-2-yl)-7-methoxy-8-methyl-quinoline.

LC/MS=611.18 (M$^+$+1)

$^1$H NMR (400 MHz, D$_6$-DMSO): δ 10.55 (s, 1H), 9.06 (s, 1H), 8.00 (d, J=9.2 Hz, 1H), 7.93 (d, J=5.6 Hz, 1H), 7.33 (d, J=2.8 Hz, 1H), 7.32 (s, 1H), 7.24 (dd, J=9.2, 2.4 Hz, 1H), 5.83 (s, 1H), 5.64 (dt, J=17.2, 9.6 Hz, 1H), 5.25 (dd, J=17.6, 1.6 Hz, 1H), 5.1 (dd, J=10.4, 1.6 Hz, 1H), 4.39 (dd, J=10.8, 7.2, 1H), 3.99 (m, 1H), 3.90 (s, 3H), 2.92 (ddd, J=17.6, 8, 4.8 Hz, 1H), 2.48 (m, 1H), 2.36 (dd, J=13.6, 7.2 Hz, 1H), 2.30 (m, 1H), 2.12 (m, 2H), 1.96 (m, 11-1), 1.81 (m, 1H), 1.73 (dd, J=8, 5.2 Hz, 1H), 1.56 (dquart, J=18.4, 10 Hz, 2H), 1.34 (dd, J=9.6, 5.2 Hz, 1H), 1.01-1.12 (m, 4H), 0.89 (d, J=6.8 Hz, 3H), 0.76 (d, J=6.8 Hz, 3H)

Preparation of Example 78

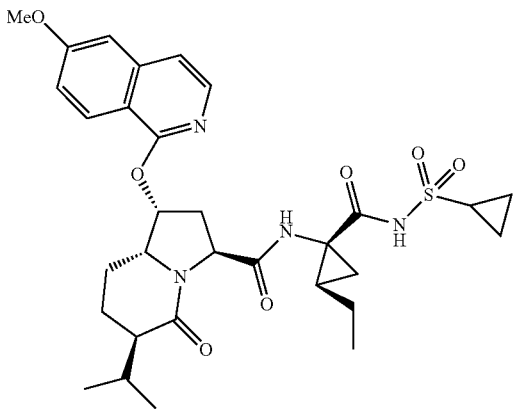

Example 77 (59 mg, 0.096 mmol) was dissolved in DME (2 mL). To this solution was added H$_2$O (200 μL), pTsSO$_2$NHNH$_2$ (135 mg, 0.725 mmol), and NaOAc (119 mg, 1.45 mmol). The reaction was placed in a 95° C. oil bath and the reaction progress was monitored by LC/MS. After 1 h 30 min the reaction was complete. The reaction was cooled to rt, filtered and example 78 (21 mg, 30%) was isolated from the filtrate by reverse phase HPLC as the TFA salt.

LC/MS=613.12 (M$^+$+1)

$^1$H NMR (400 MHz, D$_6$-DMSO): δ 10.50 (s, 1H), 8.97 (s, 1H), 7.99 (d, J=9.2 Hz, 1H), 7.93 (d, J=6 Hz, 1H), 7.33 (d, J=1.6 Hz, 1-1), 7.32 (s, 1H), 7.23 (dd, J=9.2, 2.8 Hz, 1H), 5.83 (s, 1H), 4.40 (dd, J=10.8, 7.2 Hz, 1H), 3.99 (m, 1H), 3.90 (s, 3H), 2.94 (ddd, J=15.6, 12.8, 4.8 Hz, 1H), 2.47 (m, 1H), 2.34 (quart, J=6.8 Hz, 1H), 2.29 (m, 1H), 2.11 (ddd, J=14, 10.8, 3.2 Hz, 1H), 1.97 (m, 1H), 1.81 (m, 1H), 1.49-1.60 (m, 3H), 1.35-1.45 (m, 3H), 1.02-1.13 (m, 5H), 0.88 (dd, J=6.8, 5.6 Hz, 6H), 0.76 (d, J=6.4 Hz, 3H

Preparation of Example 79

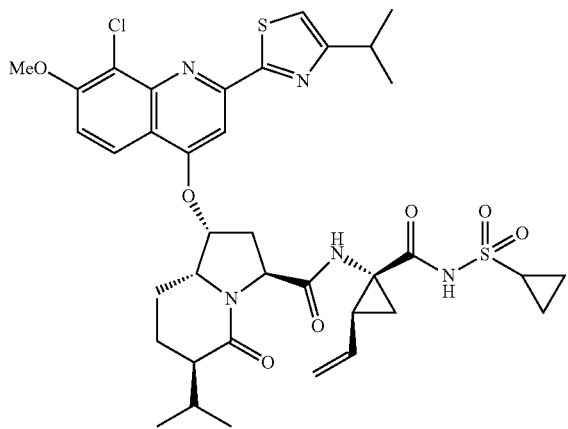

Example 79 was prepared in a similar fashion to that described in method 8, except that 4,8-dichloro-2-(4-isopropyl-thiazol-2-yl)-7-methoxy-quinoline was used instead of 4-chloro-2-(4-isopropyl-thiazol-2-yl)-7-methoxy-8-methyl-quinoline.

LC/MS=770 (M$^+$+1)

$^1$H NMR (400 MHz, (CD$_3$)$_2$SO): δ 10.53 (s, 1H), 8.99 (s, 1H), 8.01 (d, J=9.2 Hz, 1H), 7.63 (s, 1H), 7.56 (d, J=9.2 Hz, 1H), 7.50 (s, 1H), 5.63-5.54 (m, 2H), 5.19 (d, J=17.2 Hz, 1H), 5.05 (d, J=12 Hz, 1H), 4.36-4.29 (m, 1H), 4.00 (s, 3H), 3.12 (quint, J=6.4 Hz, 1H), 2.92-2.86 (m, 1H), 2.51-2.41 (m, 1H), 2.33-2.01 (m, 4H), 1.85-1.80 (m, 1H), 1.72-1.67 (m, 2H), 1.56 (quart, J=12.8 Hz, 1H), 1.30 (d, J=7.2 Hz, 6H), 1.08-0.944 (m, 5H), 0.88 (d, J=7.2 Hz, 3H), 0.744 (d, J=7.2 Hz, 3H)

Preparation of Example 80

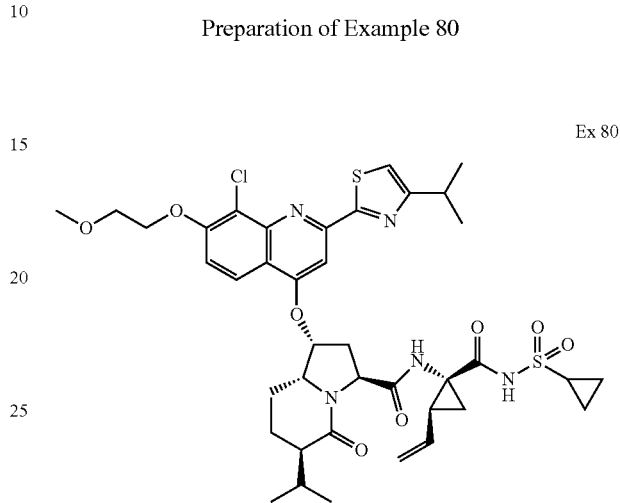

Example 80 was prepared in a similar fashion to that described in method B, except that 4,8-dichloro-2-(4-isopropyl-thiazol-2-yl)-7-(2-methoxy-ethoxy)-quinoline was used instead of 4-chloro-2-(4-isopropyl-thiazol-2-yl)-7-methoxy-8-methyl-quinoline

LC/MS=814 (M$^+$)

$^1$H NMR (400 MHz, (CD$_3$)$_2$SO): δ 10.51 (s, 1H), 8.97 (s, 1H), 7.99 (d, J=10.6 Hz, 1H), 7.64 (s, 1H), 7.55 (d, J=9.2 Hz, 1H), 7.48 (s, 1H), 5.61-5.54 (m, 2H), 5.19 (d, J=17.2 Hz, 1H), 5.05 (d, J=11.2 Hz, 1H), 4.35-4.30 (m, 3H), 4.05-3.93 (m, 2H), 3.73 (s, 2H), 3.33 (s, 3H), 3.12 (quint, J=6.8 Hz, 1H), 2.89-2.85 (m, 1H), 2.47-2.41 (m, 1H), 2.30-2.01 (m, 4H), 1.84-1.53 (m, 5H), 1.30 (d, J=6.8 Hz, 6H), 1.06-0.94 (m, 4H), 0.88 (d, J=6.8 Hz, 3H), 0.75 (d, J=6.8 Hz, 3H)

Preparation of Example 81

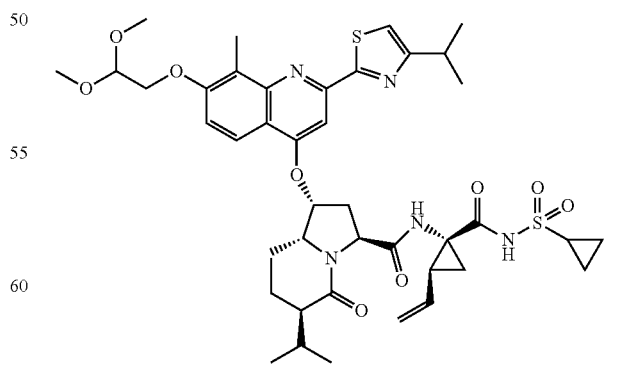

Compound 54 was prepared in a similar fashion to that described in method B, except that 4-chloro-7-(2,2-dimethoxy-ethoxy)-2-(4-isopropyl-thiazol-2-yl)-8-methylquinoline was used instead of 4-chloro-2-(4-isopropyl-thiazol-2-yl)-7-methoxy-8-methyl-quinoline.

LC/MS=824 (M⁺)

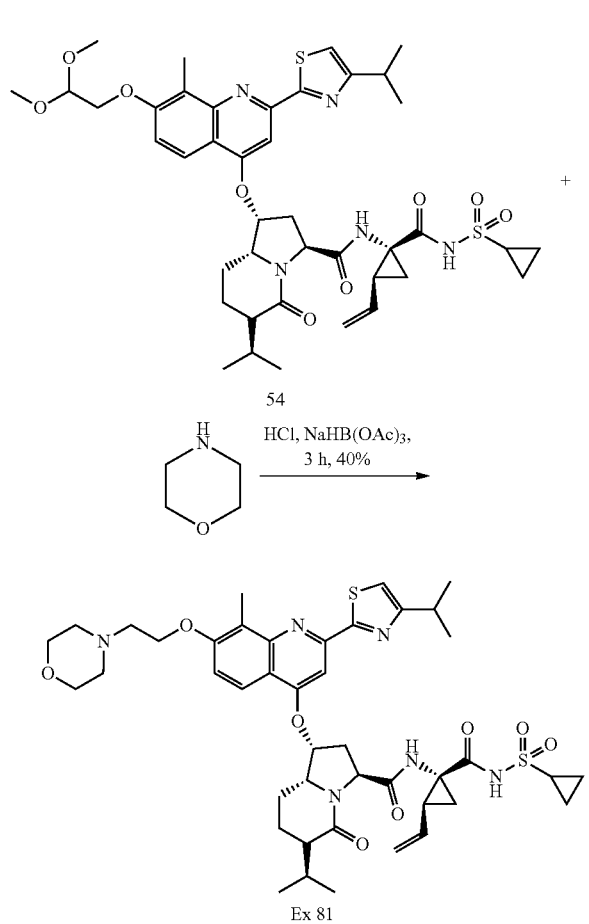

Compound 54 (40 mg, 0.05 mmol) was dissolved in THF (1 mL). 4M HCl in dioxane (125 μL, 0.5 mmol) was added. The reaction was stirred for 1 h. The reaction was neutralized with a saturated NaHCO₃ aqueous solution and extracted with ethyl acetate. The organic layer was dried with sodium sulfate, filtered and was concentrated. The reaction was taken up in DCM (1 mL). To the reaction was added morpholine (4 μL, 0.05 mmol). After 15 minutes, sodium triacetoxyborohydride (32 mg, 0.15 mmol) was added. The reaction was stirred at room temperature for 1 h. The reaction was quenched with water. The organic layer was dried with sodium sulfate, filtered and was concentrated. Example 81 (20 mg, 40%) was purified by HPLC to afford the TFA salt.

LC/MS=849 (M⁺)

¹H NMR (400 MHz, (CD₃)₂SO): δ 10.53 (s, 1H), 8.99 (s, 1H), 8.00 (d, J=10.6 Hz, 1H), 7.63 (s, 1H), 7.55 (d, J=9.2 Hz, 1H), 7.48 (s, 1H), 5.62-5.54 (m, 2H), 5.19 (d, J=17.2 Hz, 1H), 5.07 (d, J=11.2 Hz, 1H), 4.36-4.31 (m, 3H), 4.02-3.92 (m, 5H), 3.72 (s, 2H), 3.12 (quint, J=6.8 Hz, 1H), 2.89-2.85 (m, 1H), 2.47-2.41 (m, 1H), 2.30-1.3 (m, 13H), 1.30 (d, J=6.8 Hz, 6H), 1.06-0.94 (m, 4H), 0.90 (d, J=6.8 Hz, 3H), 0.76 (d, J=6.8 Hz, 3H)

Preparation of Example 82

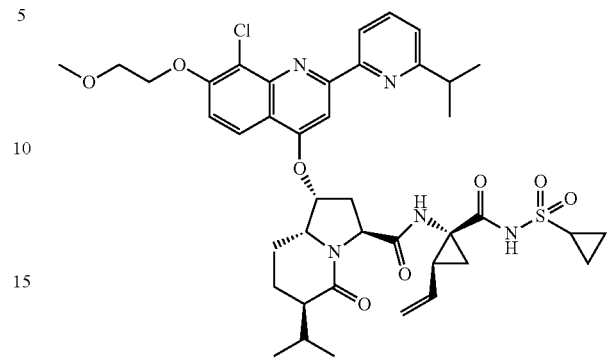

Example 82 was prepared in a similar fashion to that described in method B, except that 4,8-dichloro-2-(6-isopropyl-pyridin-2-yl)-7-(2-methoxy-ethoxy)-quinoline was used instead of 4-chloro-2-(4-isopropyl-thiazol-2-yl)-7-methoxy-8-methyl-quinoline.

LC/MS=809 (M⁺+1)

¹H NMR (400 MHz, (CD₃)₂SO): δ 10.56 (s, 1H), 9.00 (s, 1H), 8.48 (d, J=7.6 Hz, 1H), 8.07-8.04 (m, 2H), 7.96 (t, J=8.0 Hz, 1H), 7.59 (d, J=9.2 Hz, 1H), 7.45 (d, J=7.6 Hz, 1H), 5.67-5.58 (m, 1H), 5.52 (s, 1H), 5.23 (d, J=17.2 Hz, 1H), 5.09 (d, J=12.0 Hz, 1H), 4.40-4.34 (m, 2H), 4.10 (d, J=10.8 Hz, 2H), 3.77 (t, J=4.4 Hz, 2H), 3.37 (s, 3H), 3.174 (quint, J=6.8 Hz, 1H), 2.922 (quint, J=4.4 Hz, 1H), 2.50-2.45 (m, 2H), 2.37-2.32 (m, 1H), 2.24-2.19 (m, 1H), 2.13-2.07 (m, 2H), 1.90-1.89 (m, 1H), 1.80-1.70 (m, 2H), 1.64-1.57 (m, 1H), 1.36 (d, J=6.8 Hz, 6H), 1.12-1.01 (m, 4H), 0.92 (d, J=6.8 Hz, 3H), 0.78 (d, J=6.8 Hz, 3H)

Preparation of Example 83

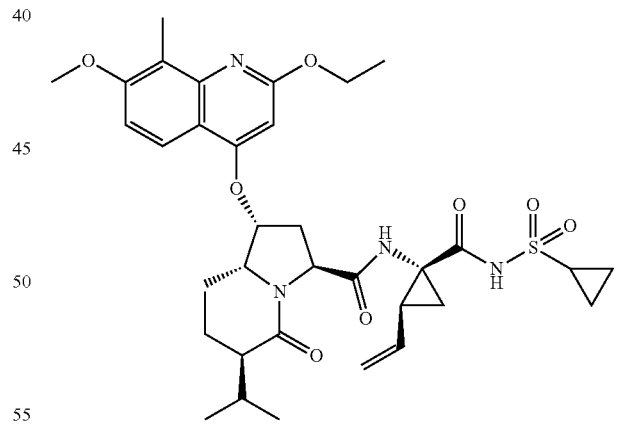

Example 83 was prepared in a similar fashion to that described in method B, except that 4-chloro-2-ethoxy-7-methoxy-8-methyl-quinoline was used instead of 4-chloro-2-(4-isopropyl-thiazol-2-yl)-7-methoxy-8-methyl-quinoline.

LC/MS=669 (M⁺+1)

¹H NMR (400 MHz, (CD₃)₂SO): δ 10.51 (s, 1H), 8.96 (s, 1H), 7.73 (d, J=9.2 Hz, 1H), 7.16 (d, J=9.6 Hz, 1H), 6.40 (s, 1H), 5.63-5.54 (m, 1H), 5.28 (s, 1H), 5.20 (d, J=17.2 Hz, 1H), 5.06 (d, J=11.2 Hz, 1H), 4.43 (quart, J=6.8 Hz, 2H), 4.30-4.26 (m, 1H), 3.94 (d, J=8.4 Hz, 1H), 3.86 (s, 3H), 2.884 (quint, J=6.0 Hz, 1H), 2.40 (s, 3H), 2.36-2.28 (m, 2H), 2.10-2.02 (m, 2H), 1.83-1.79 (m, 1H), 1.69 (t, J=7.6 Hz, 1H), 1.58 (sept, J=12.0 Hz, 1H), 1.36-1.28 (m, 5H), 1.08-1.00 (m, 4H), 0.87 (d, J=6.8 Hz, 3H), 0.73 (d, J=6.8 Hz, 3H)

Preparation of Example 84

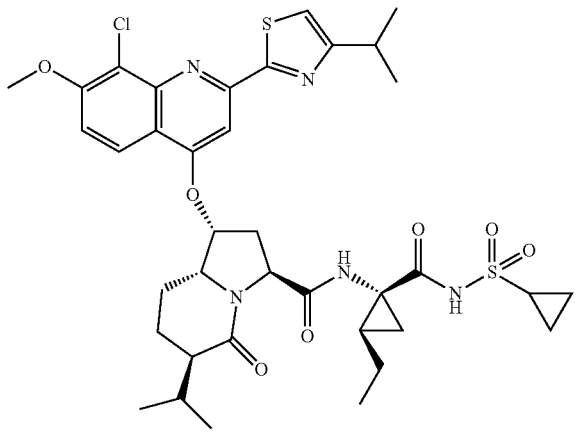

Ex 84

Example 84 was prepared in a similar manner to method B, except 4,8-dichloro-2-(4-isopropyl-thiazol-2-yl)-7-methoxy-quinoline was used in place of 4-chloro-2-(4-isopropyl-thiazol-2-yl)-7-methoxy-8-methyl-quinoline, and the HCl salt of cyclopropanesulfonic acid ((1R,2S)-1-amino-2-ethyl-cyclopropanecarbonyl)-amide was used in place of the HCl salt of cyclopropanesulfonic acid ((1R,2S)-1-amino-2-vinyl-cyclopropanecarbonyl)-amide.

LC/MS=795 (M$^+$+1)

$^1$H NMR (400 MHz, CDCl$_3$): δ (ppm) 10.029 (s, 1H); 7.929 (d, J=9.2 Hz, 1H); 7.753 (s, 1H); 7.470 (s, 1H); 7.308 (d, J=9.2 Hz, 1H); 7.161 (s, 1H); 5.390 (brs, 1H); 4.585 (t, J=8.8 Hz, 1H); 4.101-4.070 (m, 4H); 3.289-3.254 (m, 1H); 2.954-2.913 (m, 1H); 2.636-2.405 (m, 4H); 2.131-2.106 (m, 1H); 1.958-1.926 (m, 1H); 1.805-1.772 (m, 1H); 1.693-1.631 (m, 2H); 1.554-1.494 (m, 2H); 1.386-1.343 (m, 9H); 1.202-1.165 (m, 1H); 1.044-0.924 (m, 8H); 0.839 (d, J=6.66 Hz, 3H).

Preparation of Example 85

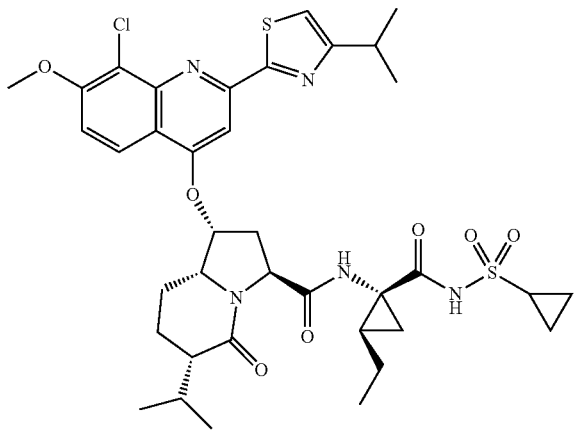

Ex 85

Example 85 was prepared in a similar manner to method B, except 4,8-dichloro-2-(4-isopropyl-thiazol-2-yl)-7-methoxy-quinoline was used in place of 4-chloro-2-(4-isopropyl-thiazol-2-yl)-7-methoxy-8-methyl-quinoline, and the HCl salt of cyclopropanesulfonic acid ((1R,2S)-1-amino-2-ethyl-cyclopropanecarbonyl)-amide was used in place of the HCl salt of cyclopropanesulfonic acid ((1R,2S)-1-amino-2-vinyl-cyclopropanecarbonyl)-amide. Examples 85 formed due to epimerization of the iPr bearing carbon during the installation of the quinoline piece during the synthesis of example 84. The resulting mixture of diastereomers was carried on until the end of the synthesis, at which point the two diastereomers were separated by reverse phase HPLC.

LC/MS=795 (M$^+$+1)

Retention time: 4.25 min

LC: Thermo Electron Surveyor HPLC

MS: Finnigan LCQ Advantage MAX Mass Spectrometer

Column: Phenomenex Polar RP 30 mm×4.6 mm

Solvents: Acetonitrile with 0.1% formic acid, Water with 0.1% formic acid

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Preparation of Example 86

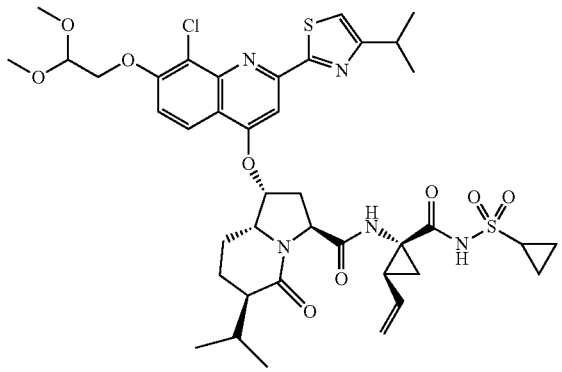

Ex 86

Example 86 was prepared in a similar manner to method B, except 4,8-dichloro-7-(2,2-dimethoxy-ethoxy)-2-(4-isopropyl-thiazol-2-yl)-quinoline was used in place of 4-chloro-2-(4-isopropyl-thiazol-2-yl)-7-methoxy-8-methyl-quinoline.

LC/MS=843 (M$^+$+1)

Retention time: 4.34 min

LC: Thermo Electron Surveyor HPLC

MS: Finnigan LCQ Advantage MAX Mass Spectrometer

Column: Phenomenex Polar RP 30 mm×4.6 mm

Solvents: Acetonitrile with 0.1% formic acid, Water with 0.1% formic acid

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Preparation of Example 87

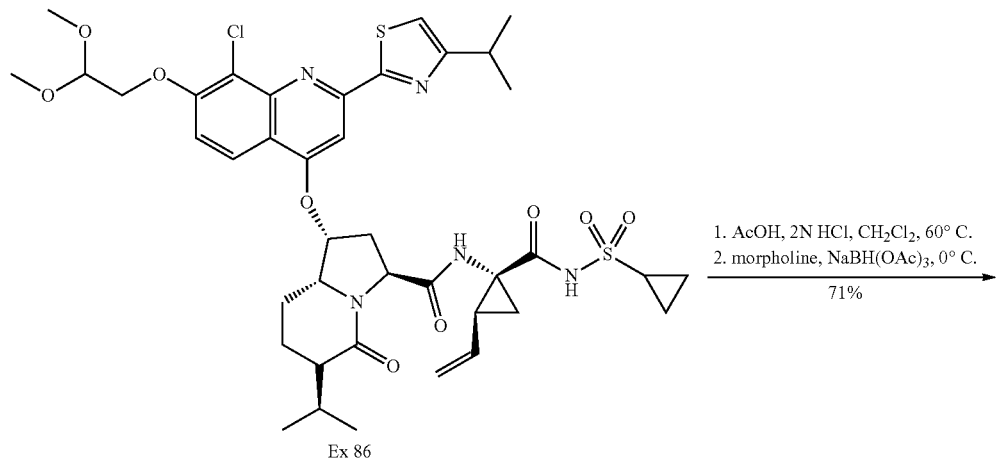

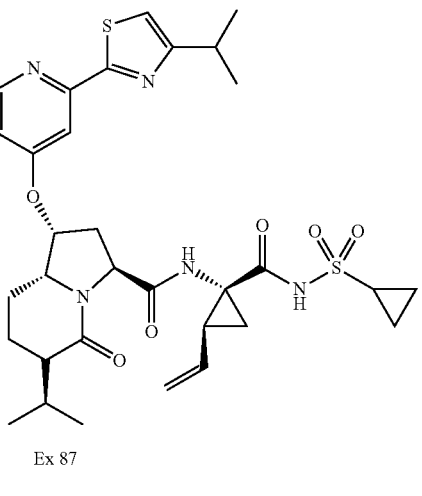

Example 86 (86 mg, 0.102 mmol) was taken up in AcOH (2.0 mL), followed by 2N HCl$_{(aq)}$. The reaction mixture was placed in a 60° C. preheated oil bath and stirred for 1 h. Solvents were removed under reduced pressure. The crude material was partitioned between EtOAc and sat NaHCO$_{3(aq)}$. The organics were dried over Na$_2$SO$_4$, filtered and concentrated under reduced pressure. The crude material was taken up in CH$_2$Cl$_2$ (5 mL), and morpholine (12 µL, 0.137 mmol) was added. The reaction mixture was stirred for 5 min, then NaBH(OAc)$_3$ was added. The reaction was determined to be complete in 10 min by LC/MS. Quench with H$_2$O, remove organics under reduced pressure, and then dilute with CH$_3$OH (3 mL). Example 87 was isolated by reverse phase HPLC as the TFA salt.

LC/MS=870 (M$^+$+1)

$^1$H NMR (400 MHz, CDCl$_3$): δ (ppm) 10.062 (s, 1H); 7.919 (brs, 1H); 7.813 (brs, 1H); 7.731 (s, 1H); 7.143 (s, 1H); 5.721 (m, 1H); 5.351 (brs, 1H); 5.260 (brs, 1H); 5.219 (brs, 1H); 5.128, brd, J=11.15 Hz, 1H); 4.651 (m, 4H); 4.104-3.662 (m, 6H); 3.235 (m, 4H); 2.912 (m, 1H); 2.618 (m, 2H); 2.443 (m, 2H); 2.075 (m, 2H); 1.963 (m, 2H); 1.841 (m, 1H); 1.662 (m, 1H); 1.384 (m, 10H); 1.026 (m, 2H); 0.978 (d, J=6.65, 3H); 0.832 (d, J=7.04 Hz, 3H).

Preparation of Example 88

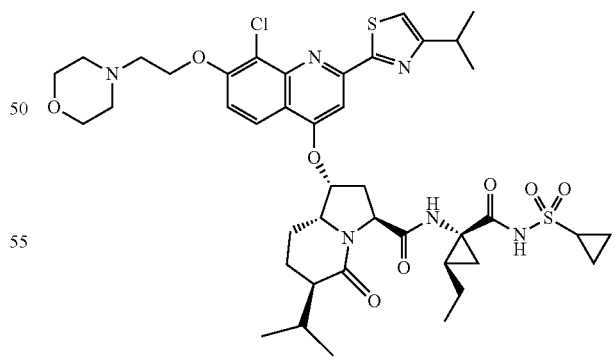

Example 88 was prepared in a similar manner to method B, except 4,8-dichloro-2-(4-isopropyl-thiazol-2-yl)-7-(2-morpholin-4-yl-ethoxy)-quinoline was used in place of 4-chloro-2-(4-isopropyl-thiazol-2-yl)-7-methoxy-8-methyl-quinoline, and the HCl salt of cyclopropanesulfonic acid ((1R,2S)-1-amino-2-ethyl-cyclopropanecarbonyl)-amide was used in place of the HCl salt of cyclopropanesulfonic acid ((1R,2S)-1-amino-2-vinyl-cyclopropanecarbonyl)-amide.

LC/MS=872 (M$^+$+1)

$^1$H NMR (400 MHz, CDCl$_3$): δ (ppm) 7.846 (d, J=9.2 Hz, 1H); 7.622 (s, 1H); 7.538 (brs, 1H); 7.193 (d, J=9.2 Hz, 1H); 7.067 (s, 1H); 5.321 (brs, 1H); 4.572 (t, J=8.02 Hz, 1H); 4.376 (m, 2H); 4.07 (m, 1H); 3.746 (t, J=4.5 Hz, 4H); 3.169 (quint, J=6.85 Hz, 1H); 2.968 (m, 3H); 2.745 (brs, 4H); 2.646 m, 1H); 2.518 (dd, J=7.82, 7.63 Hz, 1H); 2.411 (m, 1H); 2.110 (brdd, J=2.94, 9.59 Hz, 2H); 1.946 (m, 2H); 1.846 (brq, J=13.89 Hz, 1H); 1.635 (m, 1H); 1.532 (dquint, J=2.15, 7.23 Hz, 1H); 1.351 (m, 10H); 1.161 (dd, J=5.48, 3.91 Hz, 1H); 1.009 (m, 9H); 0.833 (d, J=6.65 Hz, 3H).

Preparation of Example 89

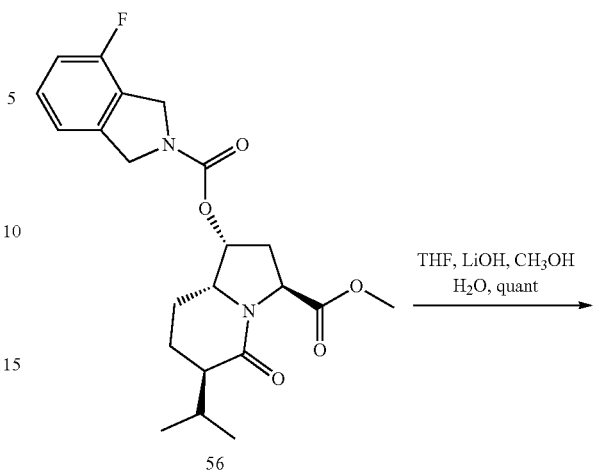

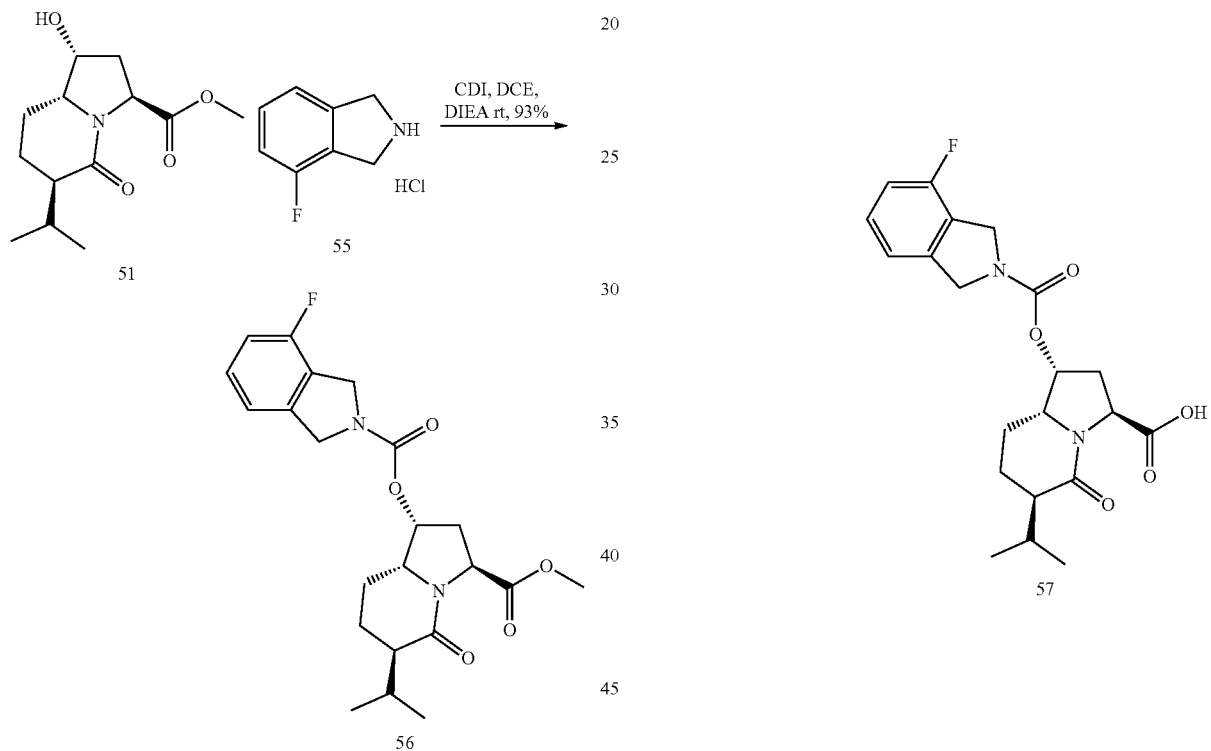

Compound 51 (208 mg, 0.816 mmol) was added to ClCH$_2$CH$_2$Cl (8 mL). Carbonyldiimidazole (172 mg, 1.06 mmol) was added in one portion and the mixture was stirred for 1 h. Compound 55 (564 mg, 3.26 mmol) was added to the reaction mixture followed by DIEA (1.84 mL, 10.56 mmol). The reaction was stirred for 5 h. The reaction was determined complete by LC/MS. The reaction was quenched with H$_2$O. The reaction mixture was partitioned between CH$_2$Cl$_2$ and H$_2$O. The layers were separated and the aqueous layer was back extracted with CH$_2$Cl$_2$. The combined organic layers were dried over Na$_2$SO$_4$. The drying agent was removed by vacuum filtration and compound 56 (318 mg, 93%) was purified by silica gel chromatography and isolated as an off-white solid.

LC/MS=419 (M$^+$+1)

Compound 56 (310 mg, 0.741 mmol) was dissolved in THF (3 mL) and CH$_3$OH (2 mL). This solution was cooled in an ice bath and then a solution of LION (94 mg, 2.22 mmol) dissolved in H$_2$O (2 mL) was added to the reaction mixture. The ice bath was removed and the reaction was stirred at rt. The reaction progress was monitored by LC/MS. After 1 h the reaction was complete. The reaction placed in an ice bath and 2N HCl (2.5 mL) was slowly added. The organics were removed under reduced pressure and the mixture was partitioned between EtOAc and H$_2$O. The aqueous was back extracted with EtOAc. The organics were combined and dried over Na$_2$SO$_4$. The drying agent was removed by vacuum filtration and solvent removed under reduced pressure. Compound 57 was used as is for the next step.

LC/MS=405 (M$^+$+1)

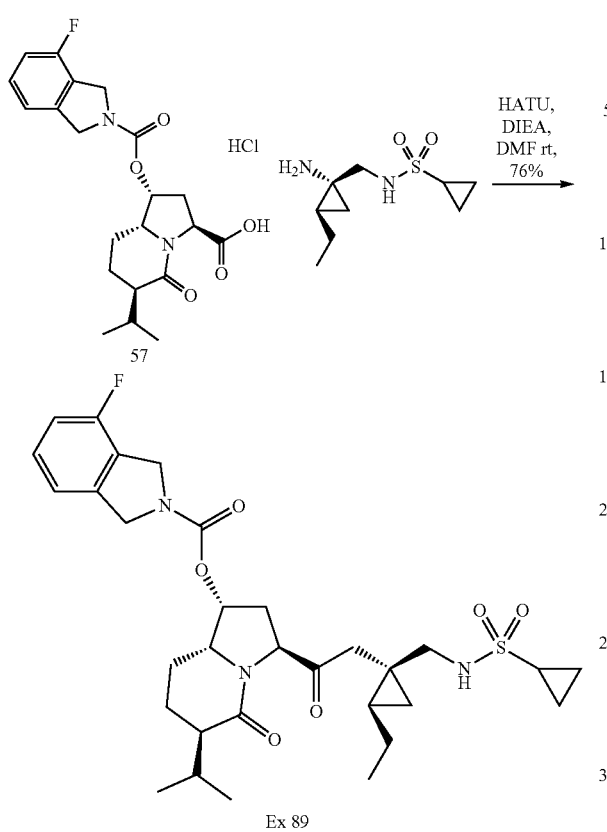

Ex 89

Compound 57 (270 mg, 0.668 mmol), the HCl salt of cyclopropanesulfonic acid ((1R,2S)-1-amino-2-ethyl-cyclopropanecarbonyl)-amide (340 mg, 1.34 mmol), HATU (634 mg, 1.67 mmol), were dissolved in DMF (4 mL). To this solution was added DIEA (840 μL, 4.67 mmol) in one portion. The reaction was stirred for 30 min. The reaction was determined to be complete by LC/MS. The reaction was quenched with H$_2$O (5 mL). Solids were removed through a PTFE filter, and diluted with CH$_3$OH (3 mL). Example 89 (374 mg, 76%) was isolated by reverse phase HPLC as the TFA salt.

LC/MS=619 (M$^+$+1)

$^1$H NMR (400 MHz, D$_6$-DMSO): δ (ppm) 10.468 (d, J=6.2 Hz, 1H); 9.008 (d, J=30.27 Hz, 1H); 7.365 (m, 1H); 7.182 (m, 3H); 5.237 (d, J=3.6 Hz, 1H); 4.685 (m, 4H); 4.308 (dd, J=9.84 Hz and J=7.27, 1H); 3.826 (m, 1H); 2.933 (m, 1H); 2.471 (m, 3H); 2.262 (m, 2H); 2.016-1.749 (m, 3H); 1.535-1.312 (m, 5H); 1.091 (m, 4H); 0.886 (m, 5H); 0.709 (m, 3H).

Preparation of Example 90

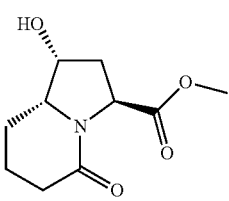

58

Compound 58 was prepared in a similar fashion to that described in method B, except that (diethoxy-phosphoryl)-acetic acid methyl ester was used instead of 2-(diethoxy-phosphoryl)-3-methyl-butyric acid methyl ester

LC/MS=214 (M$^+$+1)

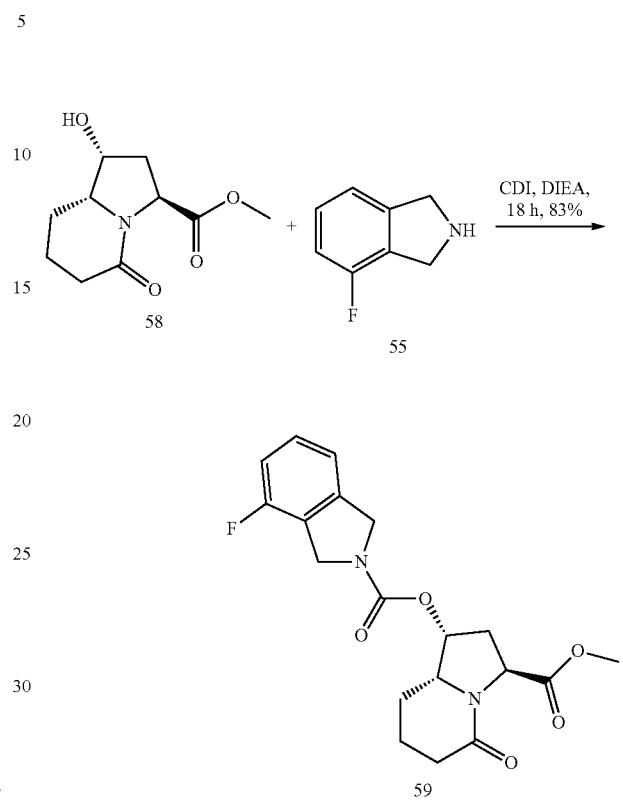

Compound xx (284 mg, 1.2 mmol) was dissolved in dichloroethane (3 ml) under an atmosphere of nitrogen. CD (280 mg, 137 mmol) was added. After 30 minutes, diisopropyl-ethyl amine (453 μL, 2.6 mmol) and compound 55 (675 mg, 3.9 mmol) were added. After 18 h the reaction was washed with a saturated solution of sodium bicarbonate in water. The solution was extracted with DCM. The combined organic layers were dried with sodium sulfate, filtered and were concentrated. Compound 59 (405 mg, 83%) was purified by silica gel chromatography.

LC/MS=377 (M$^+$+1)

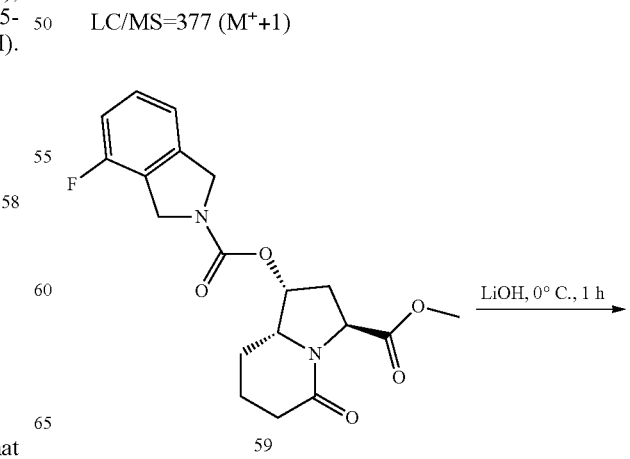

59

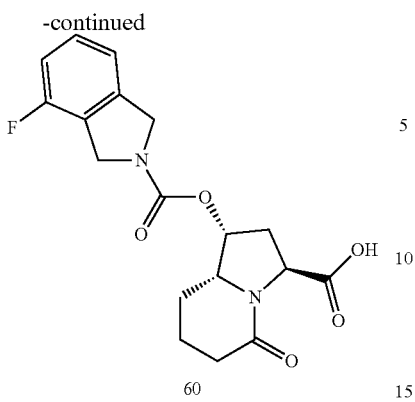

Compound 59 (405 mg, 1.1 mmol) was dissolved in THF (2.5 mL) and cooled to 0° C. A LiOH (129 mg, 5.5 mmol) solution in water (2.5 mL) was added. After 1 h, 1N HCl (5.5 mL, 5.5 mmol) in water was added. The reaction was concentrated to yield compound 60.

LC/MS=363 (M$^+$+1)

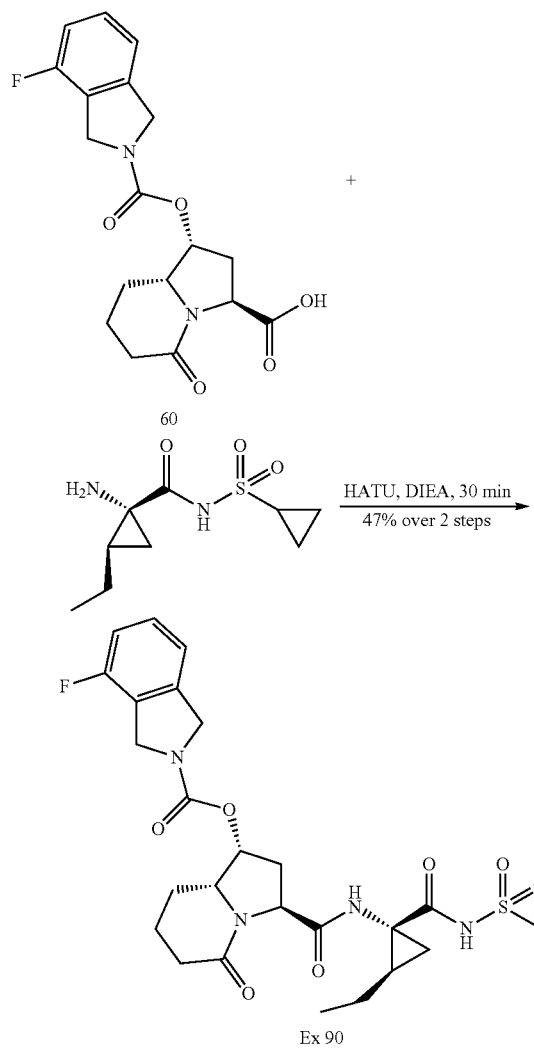

Compound 60 (1.1 mmol) was dissolved in DMF (5 mL). HATU (1.05 g, 2.75 mmol) and diisopropylethylamine (1.34 mL, 7.7 mmol) were added. After 10 minutes, the HCl salt of cyclopropanesulfonic acid ((1R,2S)-1-amino-2-ethyl-cyclopropanecarbonyl)-amide was added. After 20 minutes, the reaction was diluted with ethyl acetate and washed with water. The organic layer was concentrated. Example 90 (353 mg, 47%) was purified by HPLC.

LC/MS=577 (M$^+$+1)

$^1$H NMR (400 MHz, CDCl$_3$): δ 9.88 (s, 1H), 7.38 (s, 1H), 7.24-7.19 (m, 1H), 7.00-6.88 (m, 2H), 5.036 (s, 1H), 4.70-4.64 (m, 4.59 (d, J=8.4 Hz, 2H), 4.41 (t, J=8 Hz, 1H), 3.83 (d, J=10.8 Hz, 1H), 3.72-3.63 (m, 1H), 2.88 (sept, J=4.4 Hz, 1H), 2.55-2.45 (m, 2H), 2.30-2.20 (m, 2H), 2.02-1.92 (m, 2H), 1.75-1.64 (m, 2H), 1.52-1.12 (m, 5H), 0.97 (d, J=8.0 Hz, 2H), 0.90 (t, J=7.6 Hz, 3H), Preparation of Example 91

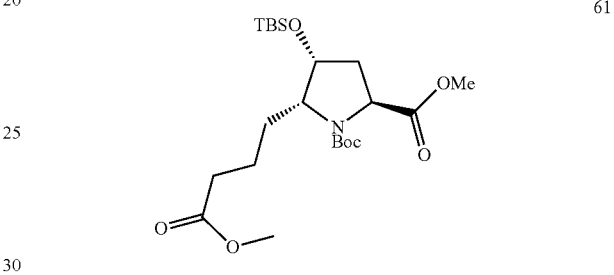

Compound 61 was prepared in a similar fashion to compound 48 in method B, except that (diethoxy-phosphoryl)-acetic acid methyl ester was used instead of 2-(diethoxy-phosphoryl)-3-methyl-butyric acid methyl ester.

LC/MS=459 (M$^+$), 360 (M$^+$−99)

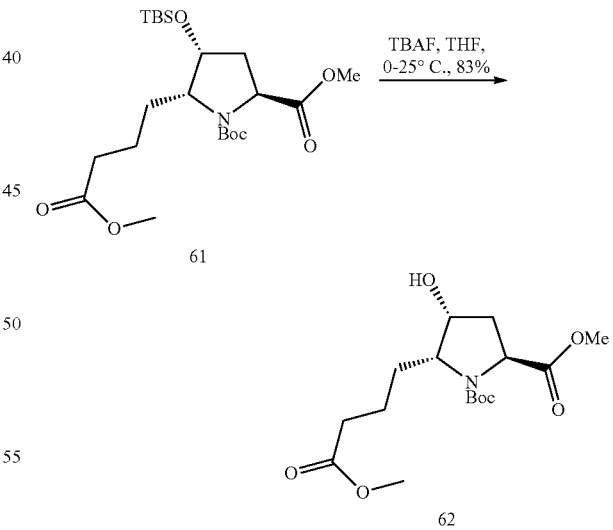

Compound 61 (3 g, 6.8 mmol) was dissolved in THF (40 mL) under a nitrogen atmosphere and was cooled to 0° C. in an ice bath. Tetrabutylammonium fluoride (20.4 mL, 20.4 mmol, 1M in THF) was added over 3 minutes and stirred for 10 minutes. The ice bath was removed and the reaction was stirred at rt for 1 h. The reaction was quenched with H$_2$O (5 mL) and was diluted with EtOAc. The layers were partitioned and the organic phase was dried over sodium sulfate, filtered and the solvent was removed under reduced pressure. Compound 62 (1.95 g, 83%) was purified by silica gel chromatography to afford a clear oil.

LC/MS=246 (M⁺−99)

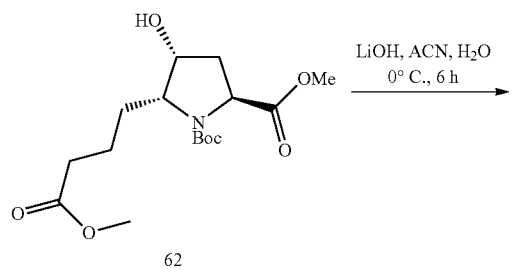

Compound 62 (1.95 g, 5.7 mmol) was dissolved in ACN (25 mL) and was cooled to 0° C. in an ice bath. Lithium hydroxide (678 mg, 28.3 mmol) was dissolved in H₂O (25 mL) and was added to the reaction mixture. The reaction was stirred for 6 h at 0° C. HCl (7 mL, 4N in H₂O) was added and stirred for 5 minutes. The solvent was removed under reduced pressure to yield compound 63.

LC/MS=318 (M⁺+1), 218 (M⁺−99)

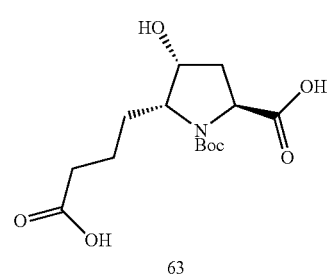

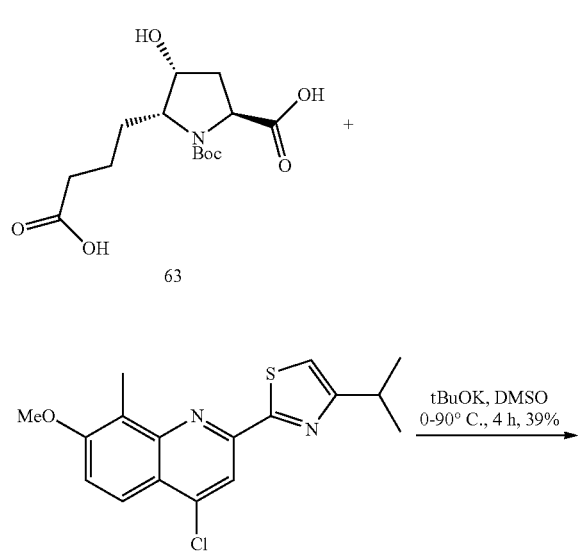

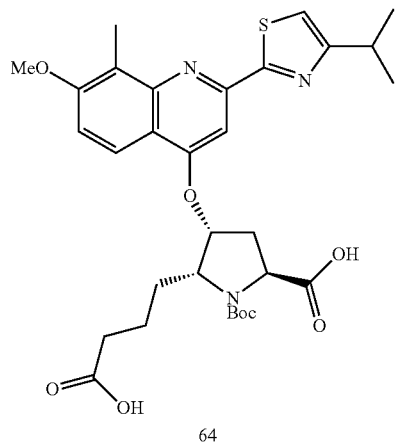

Compound 64 was prepared in a similar fashion to compound 53 in method B, except that compound 63 was used.

LC/MS=314 (M⁺+1)

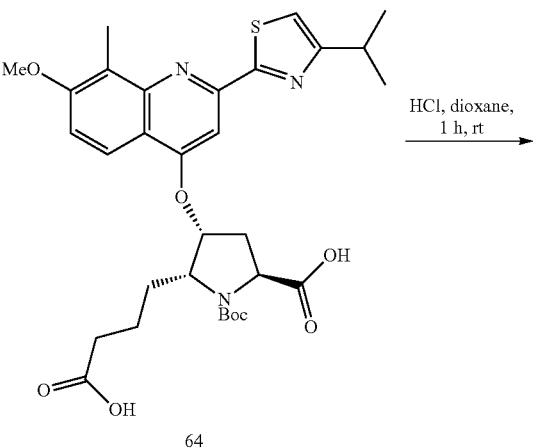

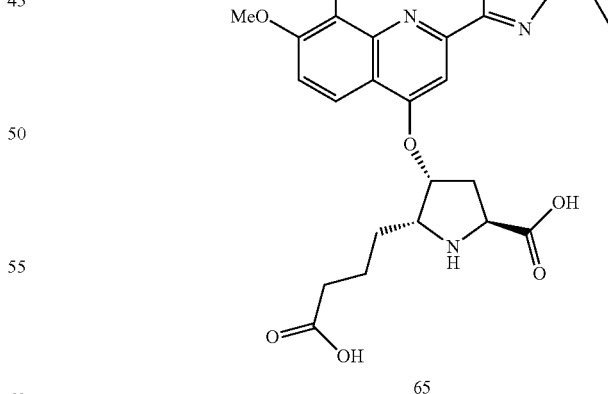

Compound 64 (342 mg, 0.56 mmol) was dissolved in HCl (0.56 mL, 2.24 mmol, 4N in dioxane) under a nitrogen atmosphere and was stirred for 1 h. The solvent was removed under reduced pressure to yield compound 65.

LC/MS=513 (M⁺+1)

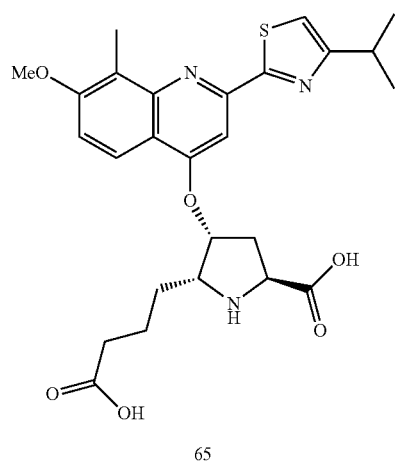

65

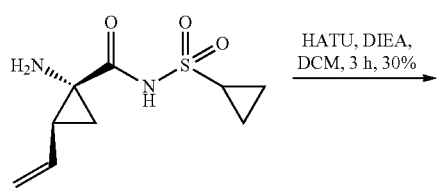

HATU, DIEA,
DCM, 3 h, 30%

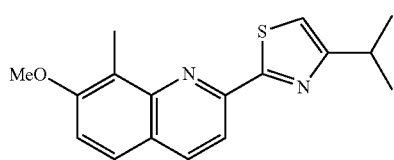

Ex 91

J=6.0 Hz, 1H), 2.47-2.43 (m, 1H), 2.40 (s, 3H), 2.28-2.14 (m, 4H), 1.97-1.88 (m, 2H), 1.74-1.69 (m, 3H), 1.30 (d, J=6.4 Hz, 6H), 1.16-0.88 (m, 4H)

Preparation of Example 92

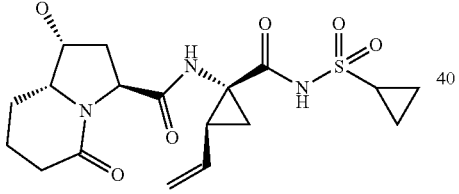

Ex 91

PTS Hydrazide, NaOAc, 93°, 80%

Ex 92

Compound 65 (0.56 mmol) was dissolved in DCM (10 mL) under a nitrogen atmosphere. Diisopropyl ethyl amine (486 μL, 2.79 mmol) was added to the reaction. After 15 minutes, HATU (426 mg, 1.12 mmol) was added. The reaction was stirred at room temperature for 2 hours. The HCl salt of cyclopropanesulfonic acid ((1R,2S)-1-amino-2-vinyl-cyclopropanecarbonyl)-amide (162 mg, 0.61 mmol) was added. After 1 hour, the reaction was washed with water and concentrated. Example 91 (118 mg, 30%) was purified by HPLC.

LC/MS=708 (M$^+$+1)

$^1$H NMR (400 MHz, (CD$_3$)$_2$SO): δ (ppm) 10.53 (s, 1H), 8.98 (s, 1H), 8.03 (d, J=9.2 Hz, 1H), 7.65 (s, 1H), 7.55 (d, J=9.6 Hz, 1H), 7.41 (s, 1H), 5.58-5.53 (m, 2H), 5.23, (d, J=17.2 Hz, 1H), 5.07 (d, J=10.4 Hz, 1H), 4.35-4.30 (m, 1H), 4.06-4.00 (m, 5H), 3.11 (quint, J=6.8 Hz, 1H), 2.88 (quint, Example 91 (15 mg, 0.02 mmol) was dissolved in dimethoxyethane (0.75 mL) and water (0.25 mL). PTS hydrazide (20 mg, 0.1 mmol) and sodiumacetate (16 mg, 0.2 mmol) were added. The reaction was heated to 93° C. for 1 hour. The reaction was concentrated. Example 92 (11 mg, 80%) was purified by HPLC.

LC/MS=710 (M$^+$+1)

$^1$H NMR (400 MHz, (CD$_3$)$_2$SO): δ (ppm) 10.53 (s, 1H), 8.98 (s, 1H), 8.03 (d, J=9.2 Hz, 1H), 7.66 (s, 1H), 7.55 (d, J=9.6 Hz, 1H), 7.41 (s, 1H), 5.56 (s, 1H), 5.23, 4.35-4.30 (m, 1H), 4.06-3.99 (m, 5H), 3.10 (quint, J=6.8 Hz, 1H), 2.89 (quint, J=6.0 Hz, 1H), 2.47-2.44 (m, 1H), 2.42 (s, 3H), 2.28-2.14 (m, 4H), 1.97-1.88 (m, 2H), 1.75-1.69 (m, 3H), 1.31 (d, J=6.4 Hz, 6H), 1.16-0.88 (m, 9H)

Preparation of Example 93

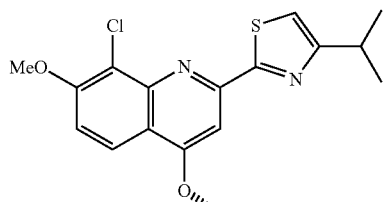

Example 93 was prepared in a similar fashion to example 91 except that 4,8-dichloro-2-(4-isopropyl-thiazol-2-yl)-7-methoxy-quinoline was used instead of 4-chloro-2-(4-isopropyl-thiazol-2-yl)-7-methoxy-8-methyl-quinoline.

LC/MS=728 (M+)

$^1$H NMR (400 MHz, (CD$_3$)$_2$SO): δ 10.51 (s, 1H), 8.97 (s, 1H), 8.03 (d, J=9.2 Hz, 1H), 7.64 (s, 1H), 7.56 (d, J=9.6 Hz, 1H), 7.49 (s, 1H), 5.57-5.53 (m, 2H), 5.23, (d, J=17.2 Hz, 1H), 5.06 (d, J=10.4 Hz, 1H), 4.35-4.29 (m, 1H), 4.06-4.00 (m, 5H), 3.12 (quint, J=6.8 Hz, 1H), 2.873 (quint, J=6.0 Hz, 1H), 2.47-2.43 (m, 1H), 2.28-2.13 (m, 4H), 1.97-1.88 (m, 2H), 1.74-1.68 (m, 3H), 1.29 (d, J=6.4 Hz, 6H), 1.16-0.98 (m, 4H)

Preparation of Example 94

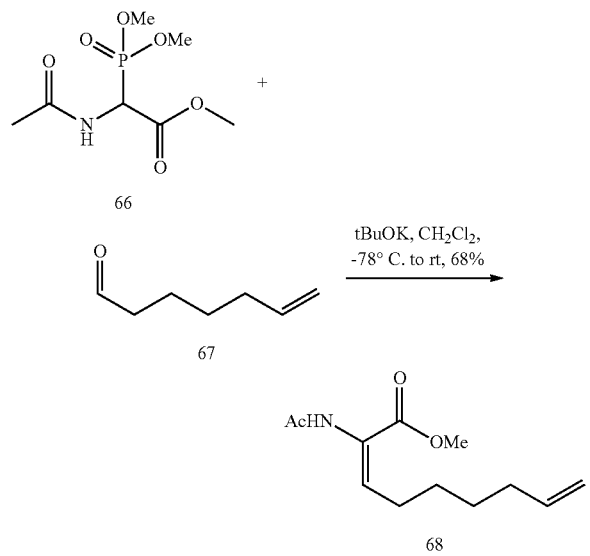

To a suspension of tBuOK (2.36 g, 21 mmol) in CH$_2$Cl$_2$ (100 mL) cooled in a −78° C. cold bath was added a solution of compound 66 (5 g, 21 mmol) in CH$_2$Cl$_2$ (50 mL). The reaction was stirred cold for 1 h and then a solution of compound 67 (2.14 g, 19.1 mmol) in CH$_2$Cl$_2$ was slowly added over 15 min. After 2.5 h in a −78° C. cold bath, the bath was removed and the reaction was stirred for 1 h. The reaction was quenched by the pipette-wise addition of sat. NH$_4$Cl$_{(aq)}$. The reaction was then portioned between CH$_2$Cl$_2$ and sat. NH$_4$Cl$_{(aq)}$. The layers were separated and the organic layer was extracted with sat. NH$_4$Cl$_{(aq)}$, water and brine. The organic layer was then dried over Na$_2$SO$_4$. The drying agent was removed by vacuum filtration and compound 68 (3.21 g, 68%) was isolated as a colorless oil from the concentrated filtrate by silica gel column chromatography LC/MS=225.90 (M$^+$+1)

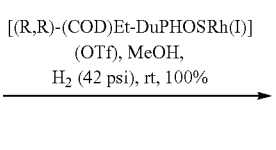

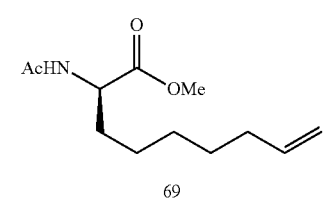

Compound 68 (500 mg, 2.22 mmol) was dissolved in MeOH (18 mL) that had been degassed by sparging with argon for 45 min. This was done in a Fisher-Porter flask. [(R,R)—(COD)Et-DuPHOSRh(I)](OTf) (2 mg, 0.0022 mmol) was then added to the solution. The reaction vessel was evacuated and then pressurized to 42 psi of H$_2$. This evacuation/re-pressurization was repeated three more times and then the reaction was left to shake for 15 min. The reaction was concentrated and compound 69 (480 mg, 95%) was isolated as a clear, colorless oil by silica gel column chromatography.

LC/MS=227.91 (M$^+$+1)

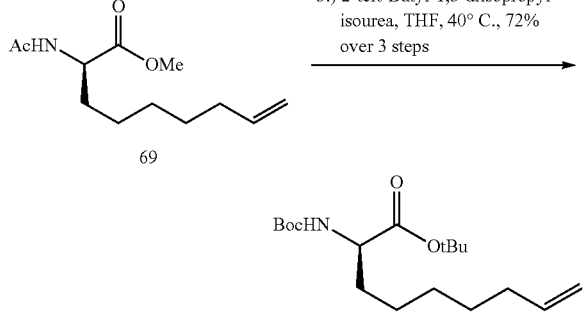

Compound 69 (2.58 g, 11.35 mmol) was dissolved in THF (35 mL). Boc$_2$O (4.95 g, 22.7 mmol) was added to this solution, followed by DMAP (277 mg, 2.27 mmol). The reaction vessel was then placed in a 55° C. oil bath, which was then raised to 75° C., in order to achieve reflux. The reaction was cooled to rt after 3 h and then concentrated. The residue was dissolved in CH$_2$Cl$_2$ and this solution was extracted with 0.5N HCl (2×100 mL), brine and sat. NaHCO$_{3(aq.)}$. The organic phase was dried over MgSO$_4$, and the drying agent was removed by vacuum filtration. The filtrate was concentrated and the residue was taken on to the next reaction.

The residue from the above reaction was dissolved in THF (23 mL) and a solution of LiOH.H$_2$O (952 mg, 22.7 mmol) in H$_2$O (15 mL) was added by pipette at rt. The reaction was stirred overnight. The reaction was still not complete so additional LiOH.H$_2$O (1.06 g) in H$_2$O (10 mL) was added. After another 1.5 h the reaction was complete. The reaction placed in an ice bath and made brought to ~pH 2 with 2N HCl. The mixture was concentrated and then partitioned between CH$_2$Cl$_2$ and H$_2$O. The layers were separated and the aqueous layer was back-extracted with CH$_2$Cl$_2$. The combined organics were dried over Na$_2$SO$_4$. The drying agent was removed by vacuum filtration and the product carboxylic acid was semi-purified by silica gel column chromatography. The semi-purified material was taken on to the next reaction.

The product from the above reaction was dissolved in THF (100 mL). 2-tert-Butyl-1,3-diisopropyl-isourea (5 g, 25 mmol) was added to this solution and the reaction was placed in a 40° C. oil bath and stirred overnight. The next day additional 2-tert-Butyl-1,3-diisopropyl-isourea (6.8 g) was added and the bath temperature was increased to 55° C. After 2.5 h the reaction was cooled to it and then cooled to 0° C. The precipitated solids were removed by vacuum filtration and were washed with ice cold Et$_2$O. The filtrate was concentrated and compound 70 (2.68 g, 72% over 3 steps) was isolated from the residue by silica gel column chromatography as a clear, colorless oil.

$^1$H NMR (400 MHz, D$_6$-DMSO): δ 7.06 (d, J=7.6 Hz, 1H), 6.73 (d, J=6 Hz, 1H), 5.78 (m, 1H), 4.99 (dd, J=16.8, 1.6 Hz, 1H), 4.93 (dt, J=10, 1 Hz, 1H), 3.74 (dd, J=13.6, 8.4 Hz, 1H), 2.00 (quart, J=7.2 Hz, 2H), 1.54 (m, 2H), 1.19-1.40 (m, 23H)

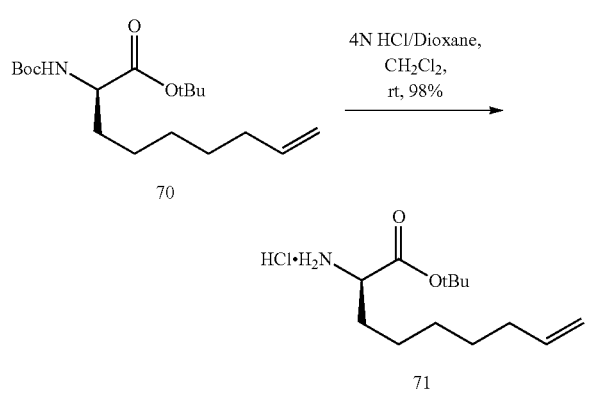

Compound 70 (2.68 g, 8.19 mmol) was dissolved in CH$_2$Cl$_2$ (20 mL). This solution was cooled in an ice bath and then a 4N solution of HCl in dioxane (20 mL., 81.9 mmol) was added. The ice bath was removed and the reaction was stirred for 2 h. The reaction was concentrated, the residue was suspended in Et$_2$O and concentrated and then re-dissolved in CH$_2$Cl$_2$ and concentrated. This yielded compound 71 (2.11 g, 98%) as a white solid that was used in the next reaction.

$^1$H NMR (400 MHz, D$_6$-DMSO): δ 8.38 (s, 3H), 5.79 (m, 1H), 5.00 (dd, J=17.2, 1.6 Hz, 1H), 4.95 (d, J=10.4 Hz, 1H), 3.85 (t, J=6 Hz, 1H), 2.02 (quart, J=6.8 Hz, 2H), 1.75 (quart, J=6.8 Hz, 2H), 1.46 (s, 9H), 1.2-1.42 (m, 6H)

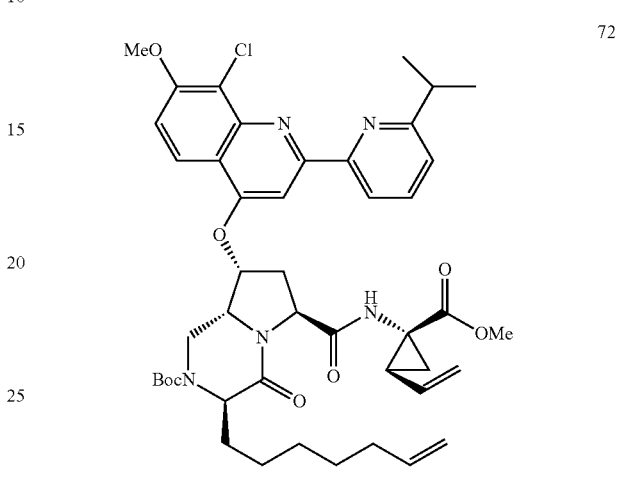

Compound 72 was prepared in a manner similar to that described in method A, except 4,8-dichloro-2-(6-isopropyl-pyridin-2-yl)-7-methoxy-quinoline was used in place of 4-chloro-2-(4-isopropyl-thiazol-2-yl)-7-methoxy-8-methyl-quinoline, the HCl salt of 2R-amino-non-8-enoic acid tert-butyl ester in place of 2R-amino-3,3-dimethyl-butyric acid tert-butyl ester and the HCl salt of (1R,2S)-1-amino-2-vinyl-cyclopropanecarboxylic acid methyl ester was used in place of the HCl salt of 1-methyl-cyclopropanesulfonic acid ((1R, 2S)-1-amino-2-vinyl-cyclopropanecarbonyl)-amide.

LC/MS=830.40 (M$^+$+1)

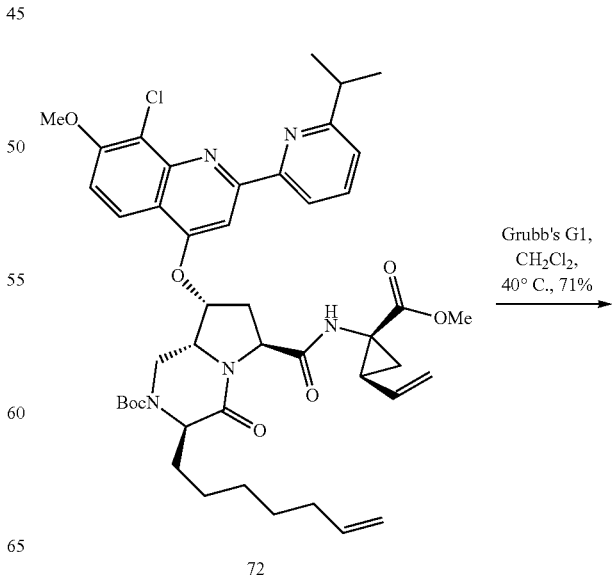

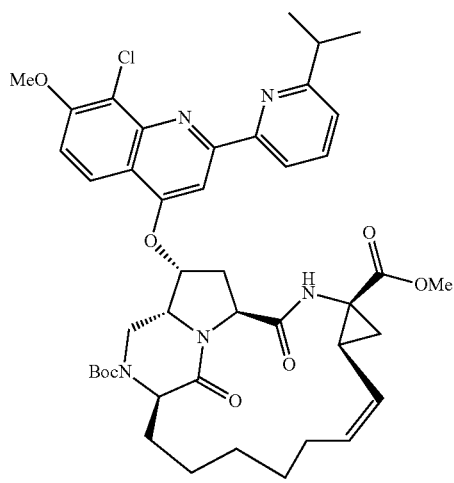

73

Compound 72 (290 mg, 0.349 mmol) was dissolved in CH₂Cl₂ (35 mL) that had been degassed by sparging with argon for 45 min. To this solution was added Grubb's first generation catalyst (29 mg, 0.039 mmol). The reaction was placed in a 50° C. oil bath. After 1.5 h the reaction was quenched by the addition of a solution comprised of P(CH₂OH)₃ (130 mg), Et₃N (438 □L) and H₂O (7 mL). The mixture was stirred vigorously while heating in the 50° C. oil bath for 1 h. The reaction was cooled to rt and the layers were separated. The organic layer was combined with the organic layer from a smaller test reaction using 83 mg of compound 72. The organic layers were then washed 0.5N HCl, sat. NaHCO₃(aq.), and brine. The organic layer was dried over a mixture of Na2SO4 and MgSO4. The drying agents were removed by vacuum filtration and compound 73 (199 mg, 71%) was isolated from the filtrate by silica gel column chromatography as a white solid.

LC/MS=802.42 (M⁺+1)

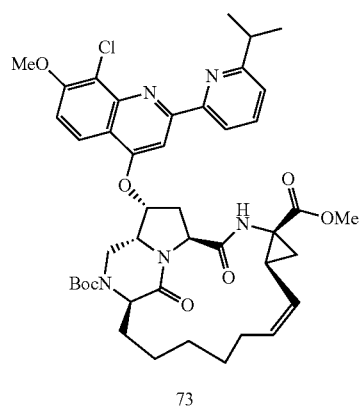

1.) LiOH—H₂O, THF, MeOH, H₂O, rt
2.) CDI, THF, 40° C., then NH₂SO₂cPr, DBU, rt, 18% over 2 steps

73

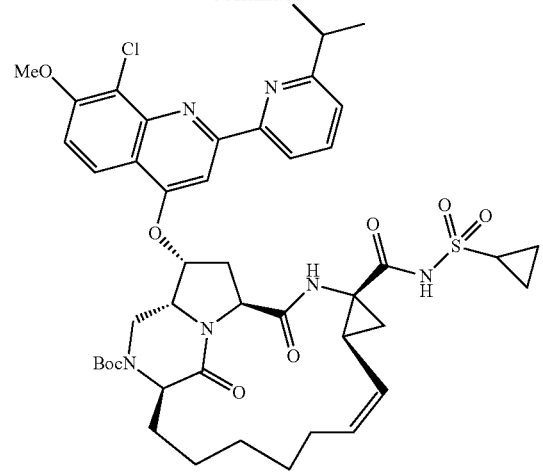

Ex 94

Compound 73 (199 mg, 0.248 mmol) was dissolved in THF (3 mL) and MeOH (2 mL). This solution was cooled in an ice bath and then a solution of LiOH.H₂O (50 mg, 0.992 mmol) in H₂O (1 mL) was added. The ice bath was removed and the reaction was stirred for 5 h. The reaction was placed in an ice bath and the base was neutralized with 2N HCl. The reaction was made acidic (~pH 2) and then partitioned between EtOAc and H₂O. The organic layer was separated and then washed with brine and dried over Na₂SO₄. The drying agent was removed by vacuum filtration and the filtrate was concentrated. The crude product was used as is in the next reaction The product from the above hydrolysis was dissolved in THF (3 mL) and CDI (58 mg, 0.360 mmol) was added to the solution. The reaction was placed in a 65° C. oil bath and stirred for 1 h 50 min. The reaction was determined to be complete by LC/MS (sample prepared with anhydrous MeOH). The reaction was removed from the oil bath and a solution of NH₂SO₂cPr (29 mg, 0.238 mmol) in THF (1 mL) was added to the reaction. The reaction was stirred for 1 h 30 min. The reaction was determined to be complete by LC/MS. The reaction was quenched by the addition of 0.5N HCl. A fine white precipitate forms. The reaction was partitioned between EtOAc and H₂O. The organic phase was white with a suspended, fine white solid. The layers were separated and the organic was concentrated and the residue was suspended in minimal EtOAc. The white solid was removed by vacuum filtration. Example 94 (38 mg, 18% over 2 steps) was isolated from the filtrate by reverse phase HPLC as a slightly yellow lyophilized powder.

LC/MS=891.76 (M⁺+1)

¹H NMR (400 MHz, D₆-DMSO): δ 11.04 (s, 1H), 8.95 (s, 1H), 8.47 (d, J=8 Hz, 1H), 8.11 (m, 2H), 7.95 (t, J=8 Hz, 1H), 7.56 (d, J=9.6 Hz, 1H), 7.45 (d, J=7.6 Hz, 1H), 5.73 (s, 1H), 5.57 (dd, J=18, 8.4 Hz, 1H), 5.23 (t, J=10.2 Hz, 1H), 4.44 (t, J=8 Hz, 1H), 4.31 (brd, J=10.8 Hz, 1H), 4.11 (dd, J=12.4, 3.6 Hz, 1H), 4.04 (s, 3H), 3.96 (d, J=7.6 Hz, 1H), 3.17 (m, 2H), 2.92 (quint, J=6.4 Hz, 1H), 2.70 (dd, J=15.2, 7.6 Hz, 1H), 2.28 (quart, J=8.8 Hz, 1H), 2.16 (m, 1H), 2.06 (m, 1H), 1.94 (m, 1H), 1.75 (m, 1H), 1.54 (m, 3H), 1.39 (s, 9H), 1.36 (d, J=7.2 Hz, 6H), 1.23 (s, 3H), 1.04 (brs, 2H), 0.85 (brs, 2H), 0.11 (brs, 3H)

Preparation of Example 95

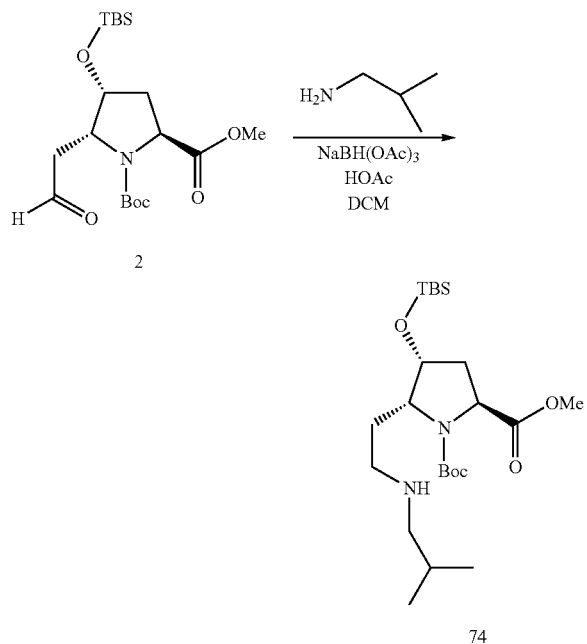

Compound 2 (0.8 g, 2.0 mmol) amine (0.4 mL, 4.0 mmol) in DCM (10 mL) was added NaBH(OAc)$_3$ (636 mg, 3.0 mmol) and AcOH (0.06 mL, 1.0 mmol). The reaction was allowed to stir for 2 h at RT. The reaction progress was monitored by LC/MS. The reaction was quenched by the addition of sat'd NaHCO$_3$ (10 mL) and this mixture was then partitioned between EtOAc and H$_2$O. The organic phase was washed with brine then dried over Na$_2$SO$_4$. The drying agent was removed by vacuum filtration and compound 74 (582 mg, 64%) was isolated from the filtrate by silica gel column chromatography.

LC/MS=459 (M$^+$+1)

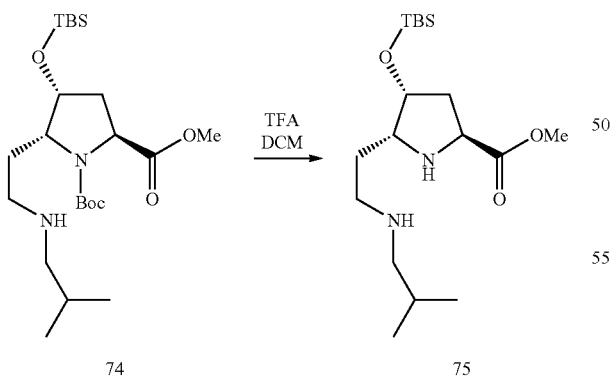

Compound 74 (66 mg, 0.114 mmol) was dissolved in CH$_2$Cl$_2$ (5 mL). TFA (0.275 mL, 3.6 mmol) was added to this solution in five portions. The reaction was then stirred for 24 h. The reaction was determined to be complete by LC/MS. The reaction was quenched with sat. NaHCO$_{3(aq.)}$ to pH 8-9 and then extracted with CH$_2$Cl$_2$. The combined organic phase was dried over Na$_2$SO$_4$ and concentrated to give compound 75 (52 mg, 100%).

LC/MS=359 (M$^+$+1)

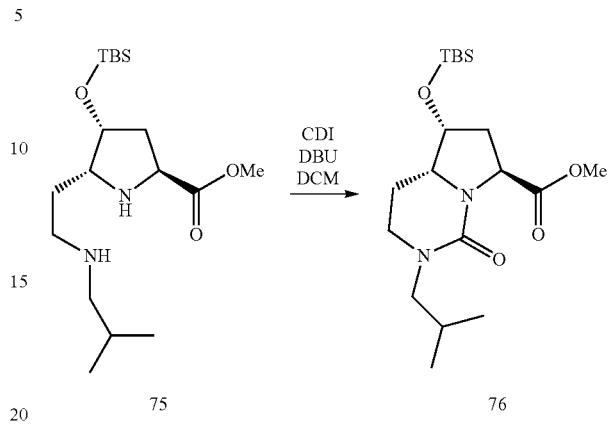

Compound 75 (134 mg, 0.37 mmol) was dissolved in CH$_2$Cl$_2$ (2 mL) at RT under N$_2$. To this solution was added CDI (72 mg, 0.444 mmol) and DBU (0.125 mL, 0.888 mmol). The reaction was stirred for 3 h. The reaction was then partitioned between 5% citric acid$_{(aq.)}$ and EtOAC. The organic phase was washed with brine and then dried over Na$_2$SO$_4$. Compound 76 (116 mg, 81%) was isolated by silica gel column chromatography with MeOH/DCM.

LC/MS=385 (M$^+$+1)

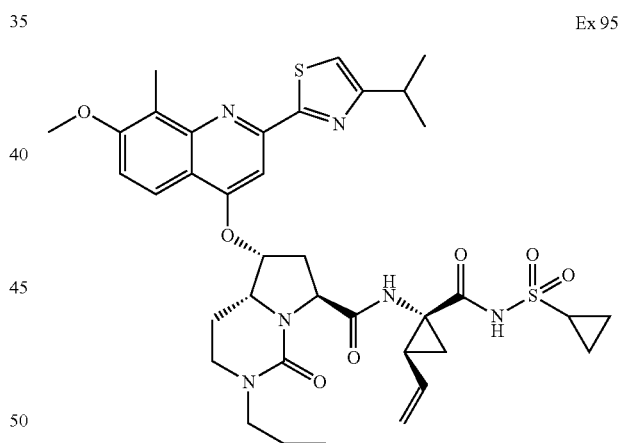

Ex 95

Example 95 was prepared in a similar manner to that described in method B, except compound 76 was used.

LC/MS=766 (M$^+$+1)

$^1$H NMR (400 MHz, CD$_3$Cl): δ (ppm) 10.50 (br, 1H), 8.05 (br, 1H), 7.96 (d J=9.2 Hz, 1H), 7.74, (s, 1H), 7.69 (s, 1H), 7.28 (d, J=9.2 Hz, 1H), 7.19 (s, 1H), 5.77 (m, 1H), 5.53 (br, 1H), 5.27-5.08 (dd, 2H), 4.47 (m, 1H), 4.27 (m, 1H), 4.00 (s, 3H), 3.49 (m, 1H), 3.40 (m, 1H), 3.28 (m, 2H), 3.03 (m, 1H), 2.91 (m, 1H), 2.64 (s, 3H), 2.55 (m, 1H), 2.12-1.87 (m, 5H), 1.46-0.90 (m, 17H).

Preparation of Example 96

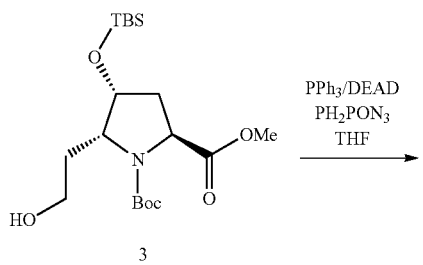

To compound 3 (0.97 g, 2.40 mmol) in THF (12 mL) was added DEAD (1.2 mL, 2.64 mmol) and Ph₃P (699 mg, 2.64 mmol) at RT under N₂. DPPA (0.57 mL, 2.64 mmol) was added slowly. The reaction was allowed to stir for 22 h at RT. The reaction progress was monitored by LC/MS. The reaction was quenched by the addition of sat'd NaHCO₃ (10 mL), this mixture was then partitioned between EtOAc and H₂O. The organic phase was washed with 10% citric acid and brine. The organic phase was then dried over Na₂SO₄. The drying agent was removed by vacuum filtration and compound 77 (1.12 g, 109%) was isolated from the filtrate by silica gel column chromatography with EtOAc/Hexane.

LC/MS=429 (M⁺+1)

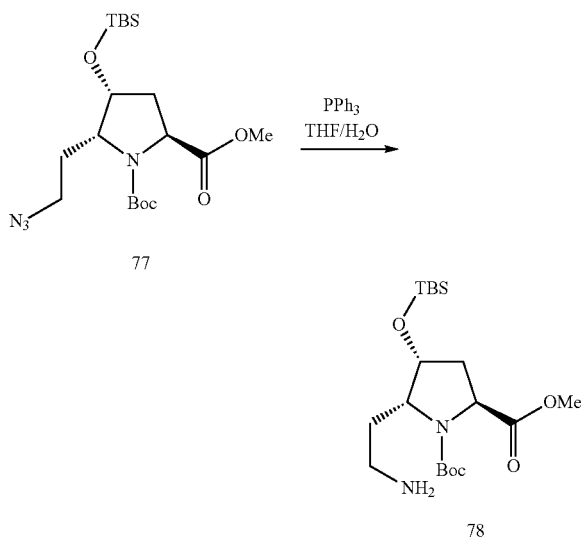

Compound 77 (1.12 g, 2.40 mmol) in THF (40 mL) was added Ph₃P (763 mg, 2.88 mmol) at RT under N₂. The reaction was heated to 50° C. for 5 h, then added H₂O (2 mL) and continued for 15 h at 50° C. The reaction progress was monitored by LC/MS. After cooled to RT, the reaction was quenched by the addition of sat'd NaHCO₃ (10 mL). This mixture was then partitioned between EtOAc and H₂O. The organic phase was washed with brine. The organic phase was then dried over Na₂SO₄. The drying agent was removed by vacuum filtration and compound 78 (0.43 g, 45% for two steps) was isolated from the filtrate by silica gel column chromatography with MeOH/DCM.

LC/MS=403 (M⁺+1)

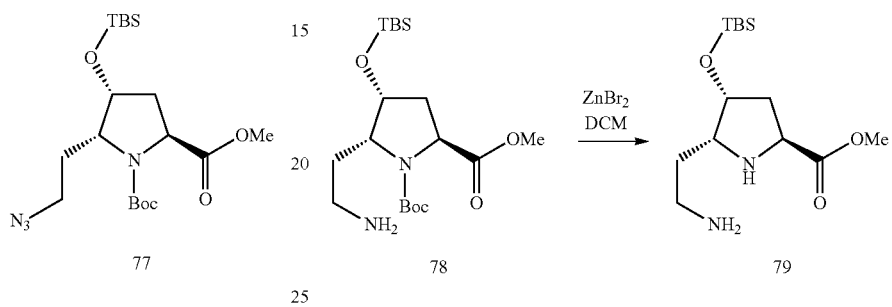

Compound 78 (0.43 g, 1.07 mmol) was dissolved in CH₂Cl₂ (28 mL). ZnBr₂ (963 mg, 4.28 mmol) was added to this solution in one portion. The reaction was then stirred for 24 h. The reaction was determined to be complete by TLC. The reaction was quenched with sat. NaHCO₃₍ₐq.₎. The reaction was then partitioned between CH₂Cl₂ and H₂O. The aqueous phase was brought to pH 8-10 with sat. NaHCO₃₍ₐq.₎ and then extracted with CH₂Cl₂. The combined organic phase was extracted with brine and then dried over Na₂SO₄. The drying agent was removed by vacuum filtration and compound 79 (314 mg, 97%) was isolated from the filtrate by silica gel column chromatography.

LC/MS=303 (M⁺+1)

Compound 79 (314 mg, 1.04 mmol) was dissolved in CH₂Cl₂ (10 mL) at RT under N₂. To this solution was added CDI (202 mg, 1.25 mmol) and DBU (0.352 mL, 2.50 mmol). The reaction was stirred for 2 h. The crude mixture was loaded on a silica gel column directly and compound 80 (155 mg, 45%) was isolated by flash chromatography.

LC/MS=329 (M⁺+1)

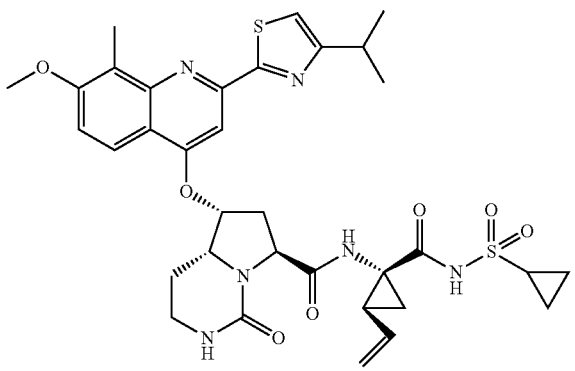

Ex 96

Example 96 was prepared in a similar manner to that described in method B, except compound 80 was used.

LC/MS=709 (M$^+$+1)

$^1$H NMR (400 MHz, CD$_3$OD): δ (ppm) 9.12 (br, 1H), 7.97 (d J=9.2 Hz, 1H), 7.67, (s, 1H), 7.35 (d, J=9.2 Hz, 1H), 7.28 (s, 1H), 5.67 (m, 1H), 5.50 (br, 1H), 5.27-5.05 (dd, 2H), 4.40 (m, 1H), 4.23 (m, 1H), 3.95 (s, 3H), 3.37 (m, 2H), 3.14 (m, 1H), 2.92 (m, 1H), 2.58 (s, 3H), 2.57 (m, 1H), 2.35-1.80 (m, 5H), 1.42-0.85 (m, 11H).

PROPHETIC EXAMPLES

In a manner similar to the synthetic procedures described above, compounds with a ketoamide functionality may be prepared as well. As a non-limiting example, a compound such as

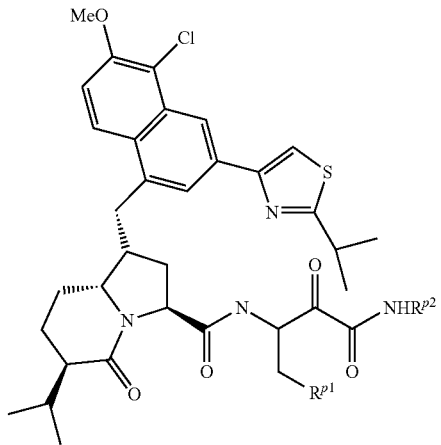

or a pharmaceutically acceptable salt thereof, may be prepared using analogous methods to those herein described. In this prophetic example, the value of each of R$^{p1}$ and R$^{p2}$ independently may be hydrogen, C$_{1-6}$alkyl (such as ethyl), or C$_{3-8}$cycloalkyl (such as cyclopropyl).

BIOLOGICAL EXAMPLES

Assay Protocol

High Throughput Replicon Assay (HTBS)

Replicon cells harboring H77 (genotype 1a) or Con1 (genotype 1b) HCV RNA and Renilla luciferase reporter were seeded in 384-well black plates at a density of 1.6×10$^3$ cells per well in 90 µl of DMEM culture medium, excluding G-418. Compounds were serially diluted in 100% DMSO and added to cells at a 1:225 dilution, achieving a final concentration of 0.44% DMSO in a total volume of 90 µL with a Biotek uFlow Workstation. Cell plates were incubated at 37° C. with 5% CO$_2$ for 3 days, after which culture media were removed and cells were assayed for luciferase activity as a marker for replication level. Luciferase expression was measured using Dual-Glo luciferase assay reagents (Promega, Madison, Wis.). Briefly, 20 µL of Dual-Glo luciferase buffer was added to lyse the cells for 10 min and subsequently 20 µL of a diluted Dual-Glo Stop & Glo substrate (1:100) was added to each well. Luminescence signal was measured on a Perkin Elmer Envision Plate Reader after incubation for 10 minute. Luciferase levels were converted into percentages relative to the untreated controls (defined as 100%) and data were fit to the logistic dose response equation $y=a/(1+(x/b)^c)$ using XLFit4 software (IDBS, Emeryville, Calif.). EC$_{50}$ values were calculated from the resulting equations.

When tested, certain compounds of this invention were found to inhibit viral replication as listed in Table 1:

TABLE 1

| Example # | INH @1 µM (Mean) |
|---|---|
| 1 | >99 |
| 2 | >99 |
| 4 | >99 |
| 6 | >99 |
| 8 | >99 |
| 9 | >99 |
| 11 | >50 |
| 13 | >99 |
| 16 | >25 |
| 18 | >35 |
| 19 | >55 |
| 20 | >90 |
| 21 | >99 |
| 22 | >99 |
| 24 | >99 |
| 26 | >99 |
| 28 | >99 |
| 30 | >35 |
| 34 | >95 |
| 35 | >35 |
| 36 | >90 |
| 38 | >95 |
| 40 | >75 |
| 42 | >95 |
| 44 | >99 |
| 46 | >99 |
| 49 | >95 |
| 51 | >99 |
| 51 | >99 |
| 54 | >45 |
| 55 | >95 |
| 58 | >85 |
| 59 | >45 |
| 62 | >99 |
| 63 | >40 |
| 70 | >10 |
| 73 | >90 |
| 74 | >90 |
| 94 | >99 |

Alternatively, antiviral activity may be analyzed by HCV NS3 Protease IC$_{50}$ Determination.

HCV NS3 protease activity was monitored using a fluorescence resonance energy transfer (FRET) depsipeptide substrate (RET S1, Anaspec, San Jose, Calif.) based on the method of Taliani, Taliani M, Bianchi E, Narjes F, Fossatelli M, Urbani A, Steinkuhler C, et al. *A continuous assay of hepatitis C virus protease based on resonance energy transfer*

*depsipeptide substrates.* Anal Biochem 1996; 240 (1):60-7, herein incorporated by reference with regard to performing such assay.

Briefly, 2-10 nM of purified NS3 protease domains were pre-incubated at 37° C. for 10 minutes with 20 μN isogenic NS4A peptide cofactors (Sigma, St. Louis, Mo.), in 40% glycerol buffer with 50 mM HEPES pH 7.5 and 10 mM DTT. Compounds were diluted serially 1:3 in DMSO, incubated with the enzyme/cofactor mixture for 10 minutes and reactions were started by the addition of 2 μM RET S1 substrate (final concentration). Fluorescence increase was measured continuously over one hour using a Victor[3] V fluorescence plate reader (Perkin Elmer, Waltham, Mass.). Initial velocities were calculated for each inhibitor concentration using Workout 1.5 software (DAZDAQ, East Sussex, UK) with the maximal slope algorithm. Velocity data were converted into percentages relative to the untreated control (defined as 100%) and non-linear regression was performed to calculate 50% inhibitory concentrations ($IC_{50}$ values).

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention. Nevertheless, certain compounds may demonstrate less than optimal activity. For example, when tested Example 90 fails to demonstrate optimal activity in either the enzymatic or cellular assay. As such, one aspect of the present invention provides for excluding such compounds from the scope of the appended claims.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound selected from the group consisting of:

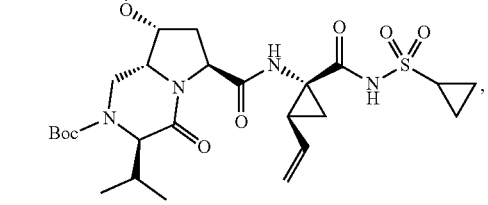

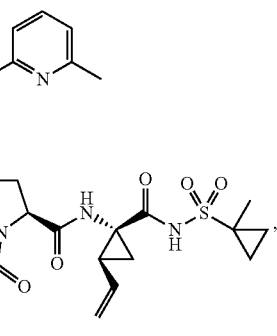

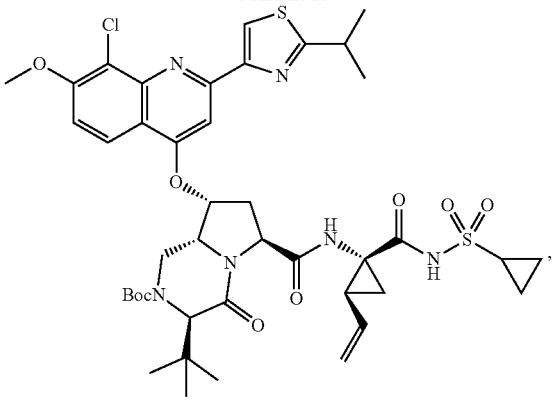

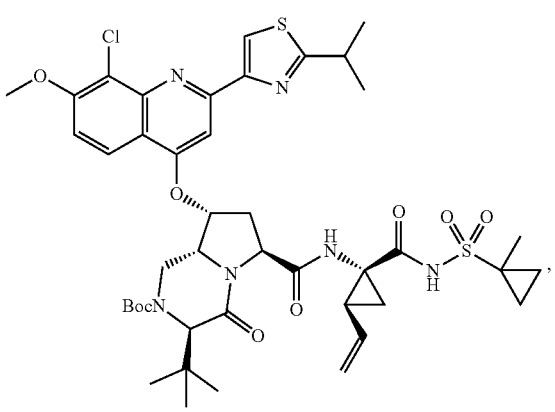

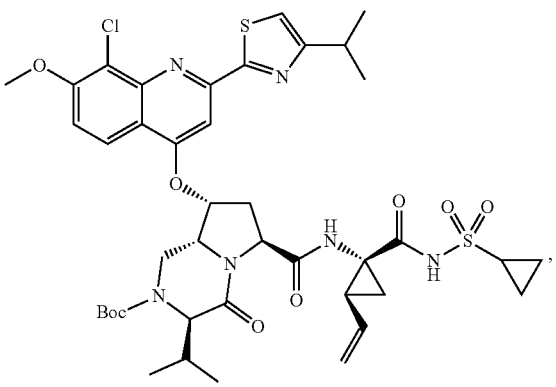

157
-continued
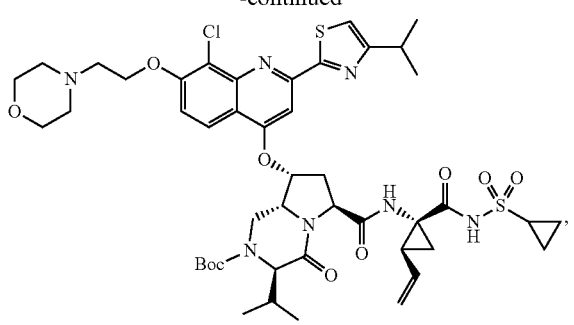
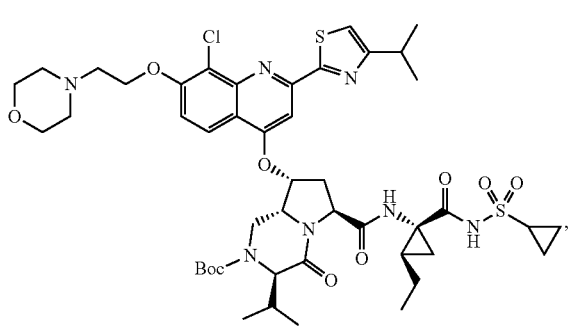
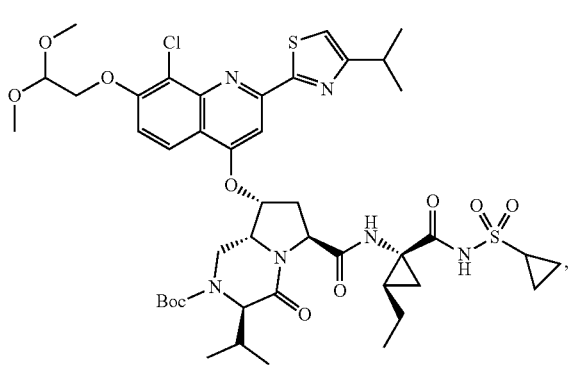
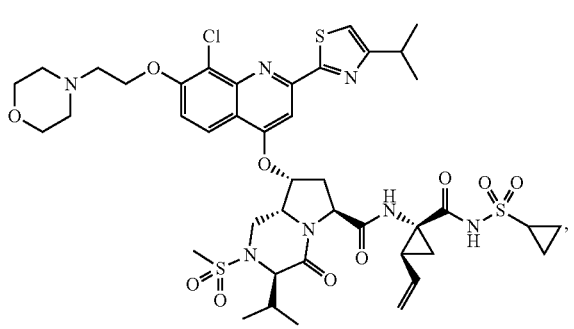
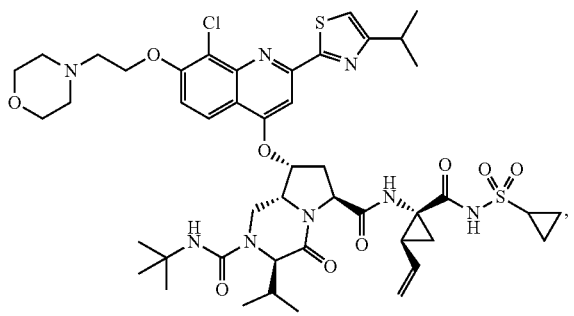
158
-continued
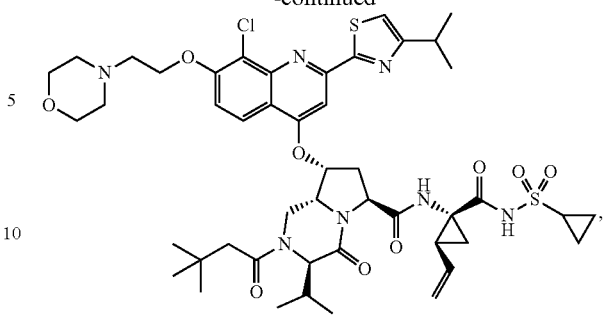
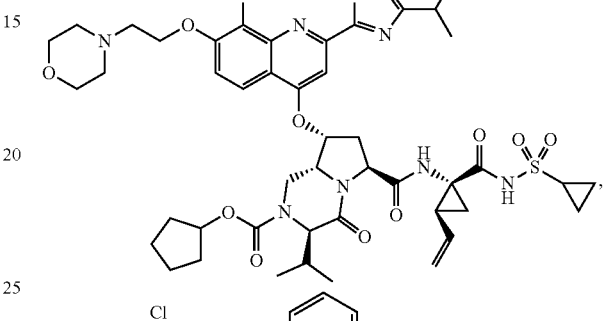
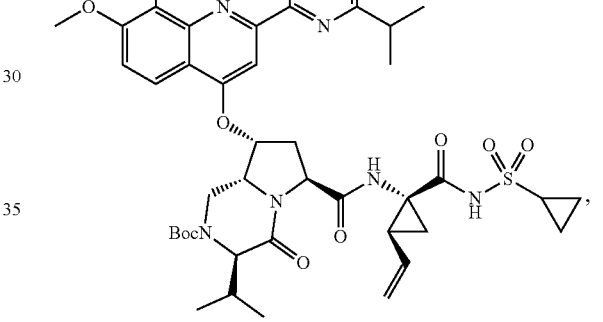
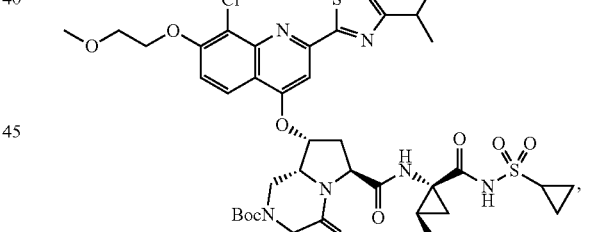
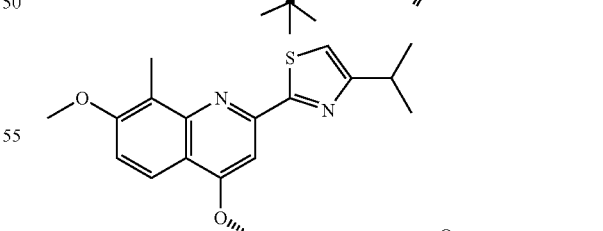
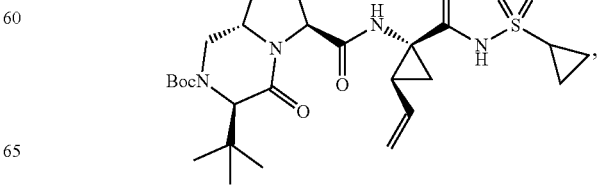

159
-continued
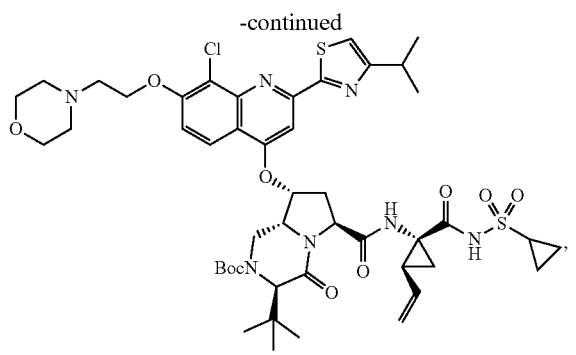
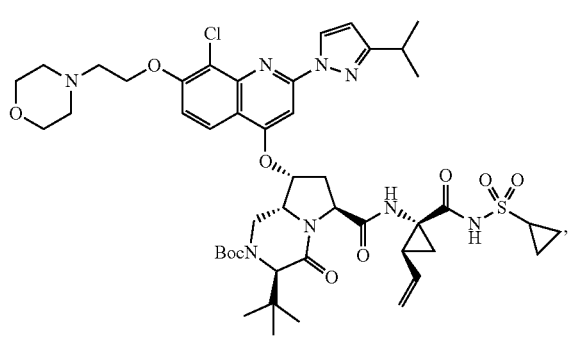
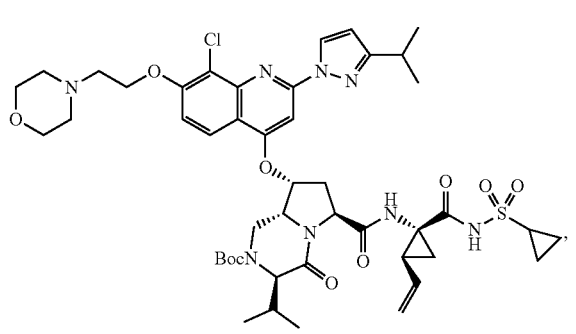
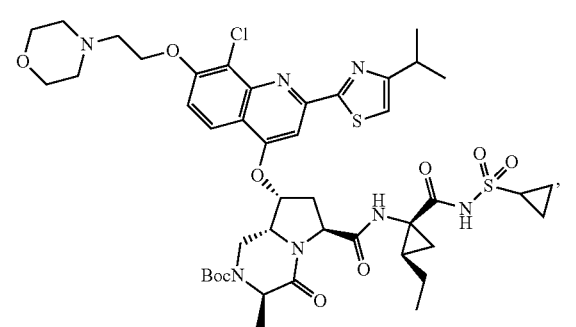
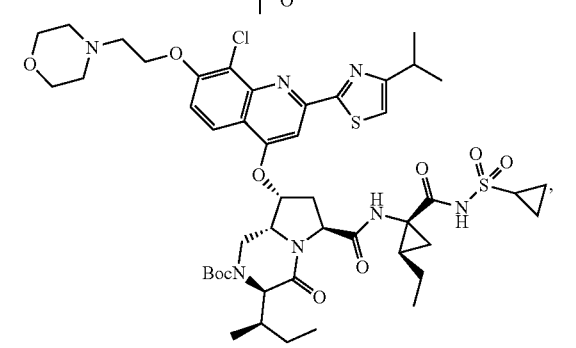
160
-continued
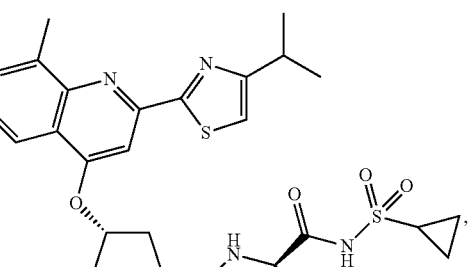
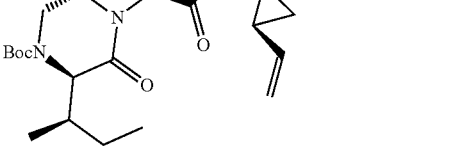
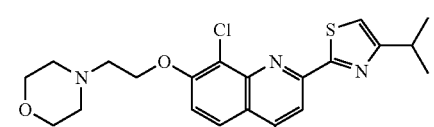
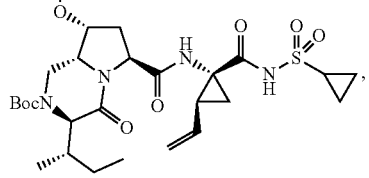
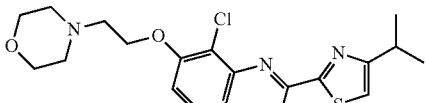
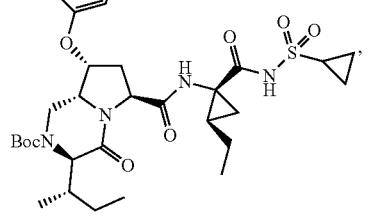
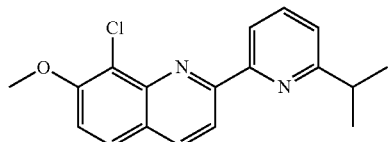
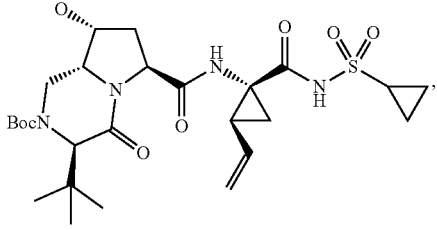

161
-continued
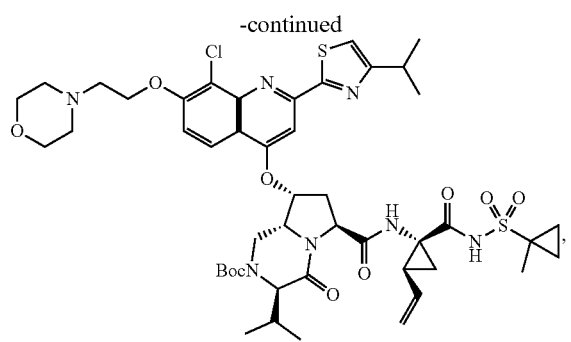
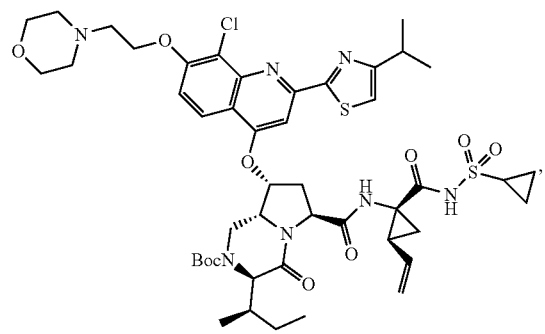
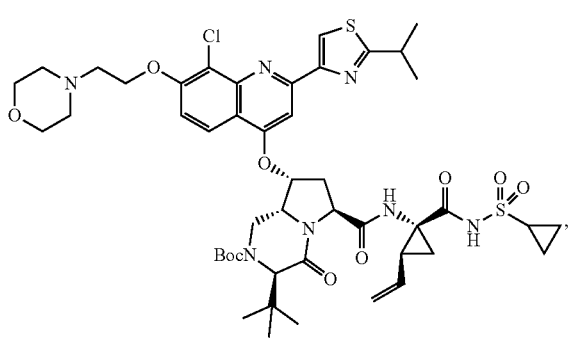
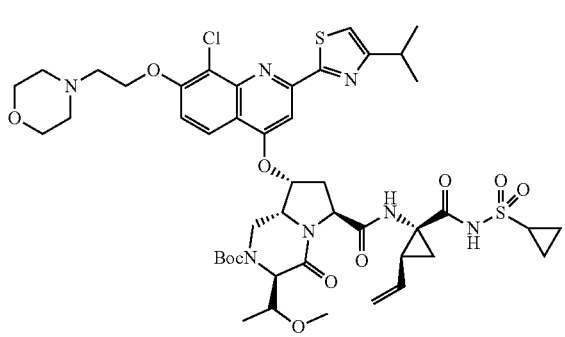
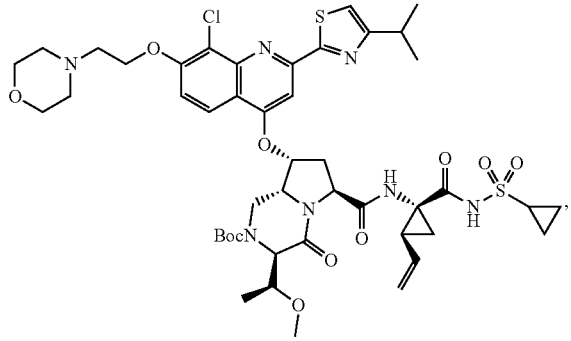
162
-continued
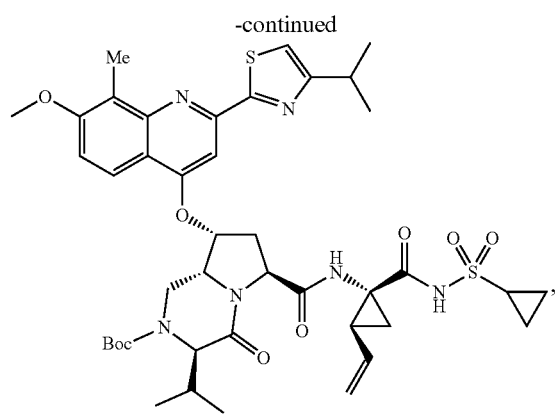
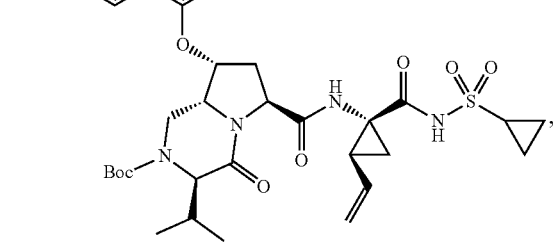
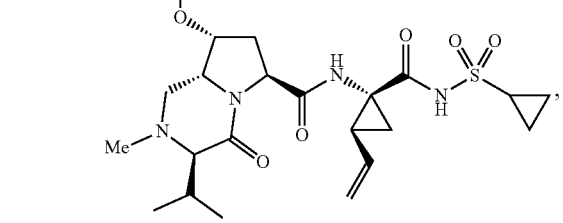

-continued
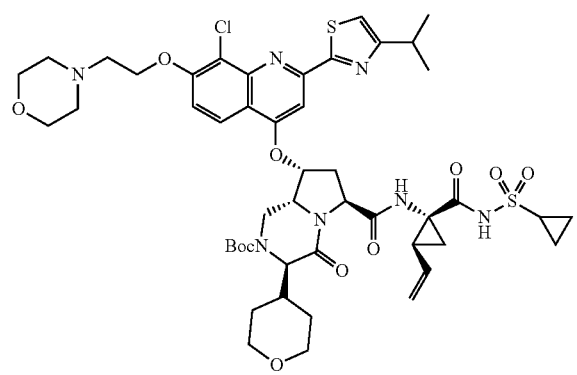
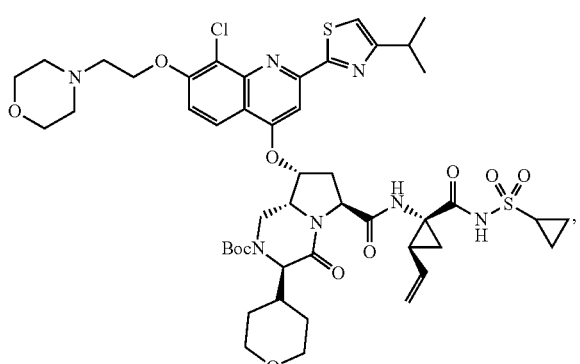
and
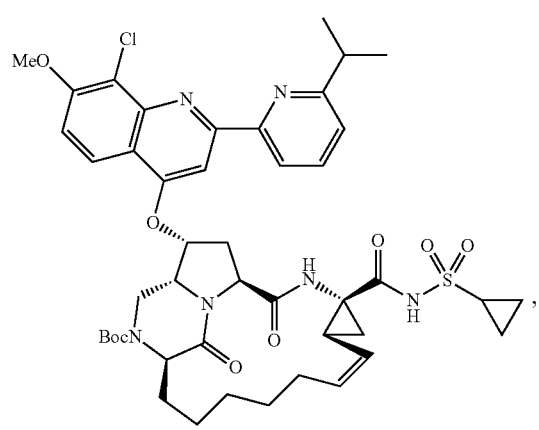
or a pharmaceutically acceptable salt thereof, wherein Boc is tert-butyloxycarbonyl.
2. A compound of claim 1 selected from the group consisting of:
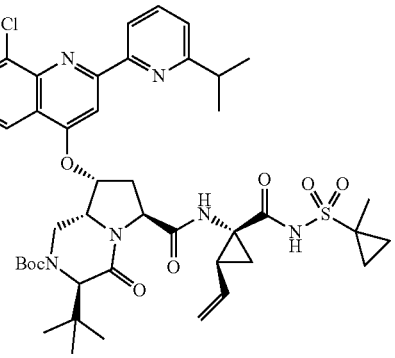
and
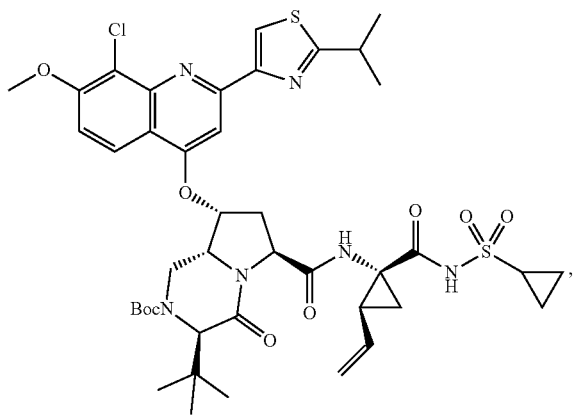
or a pharmaceutically acceptable salt thereof.
3. A compound of claim 1 selected from the group consisting of:
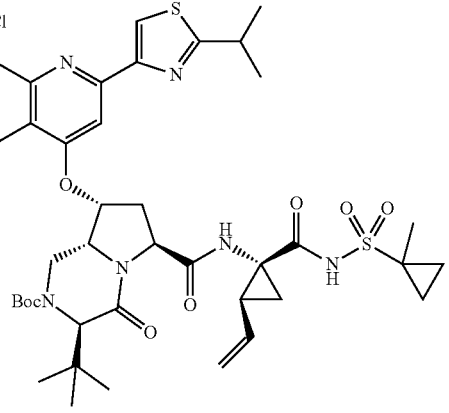
and -continued

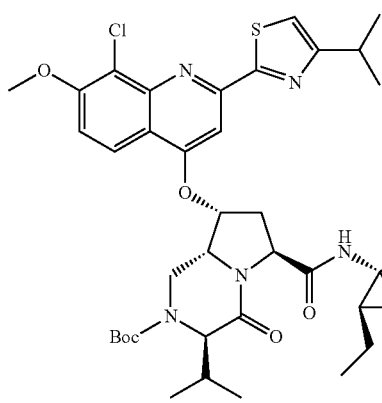

or a pharmaceutically acceptable salt thereof.

4. A compound of claim 1 selected from the group consisting of:

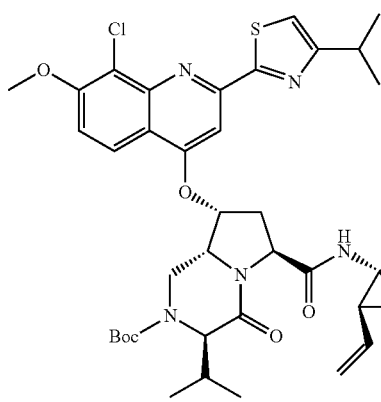

and

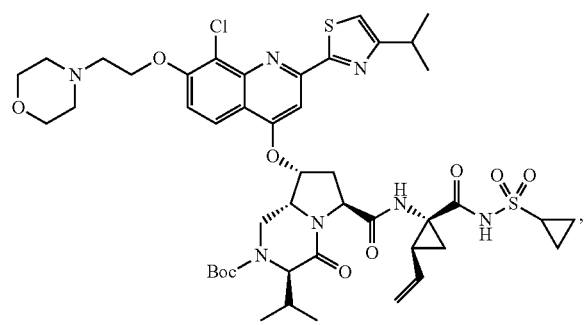

or a pharmaceutically acceptable salt thereof.

5. A compound of claim 1 selected from the group consisting of:

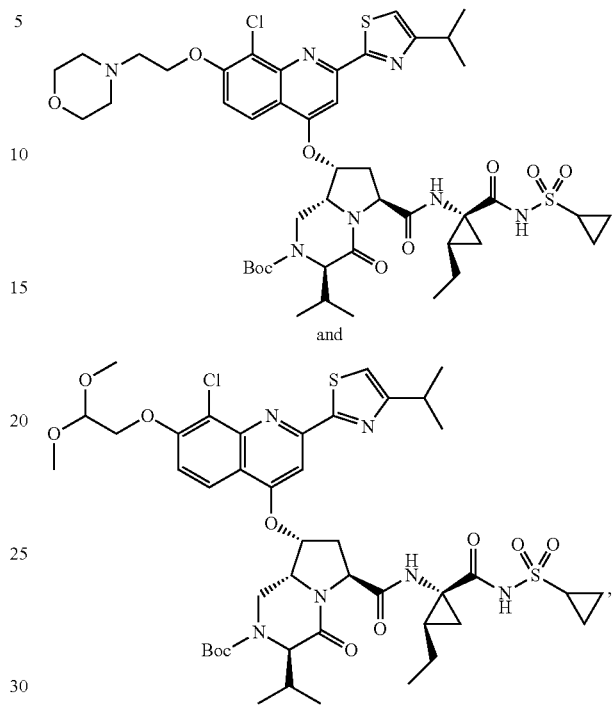

and or a pharmaceutically acceptable salt thereof.

6. A compound of claim 1 selected from the group consisting of:

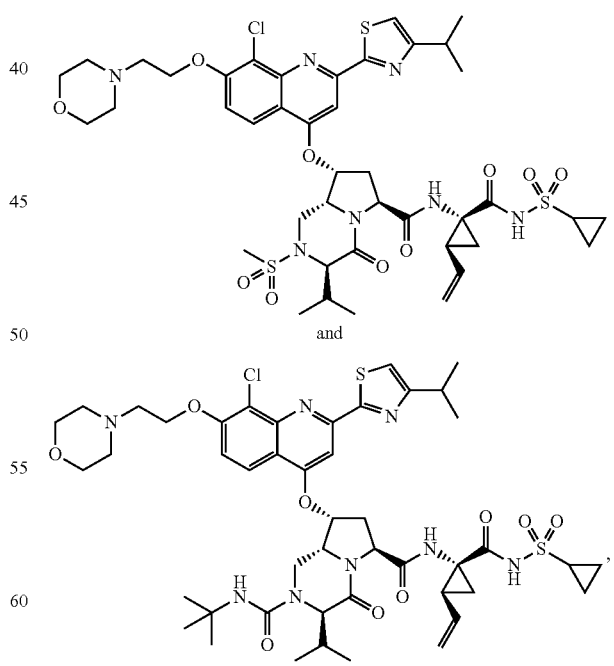

and or a pharmaceutically acceptable salt thereof.

7. A compound of claim 1 selected from the group consisting of:

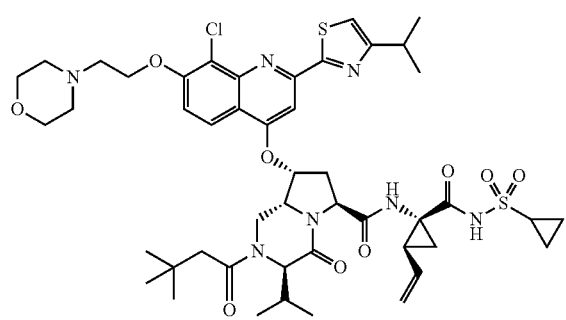
and
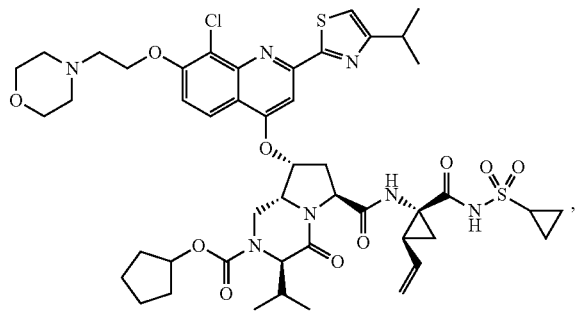
or a pharmaceutically acceptable salt thereof.
8. A compound of claim 1 selected from the group consisting of:
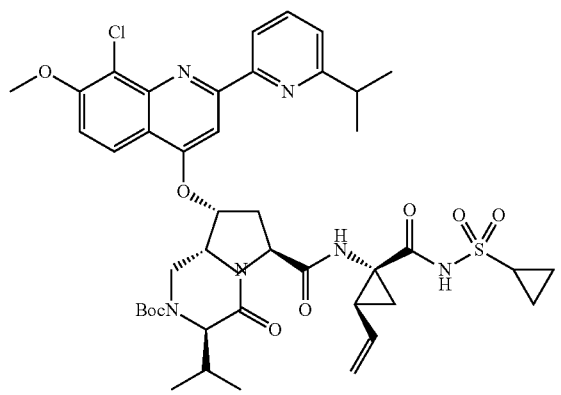
and
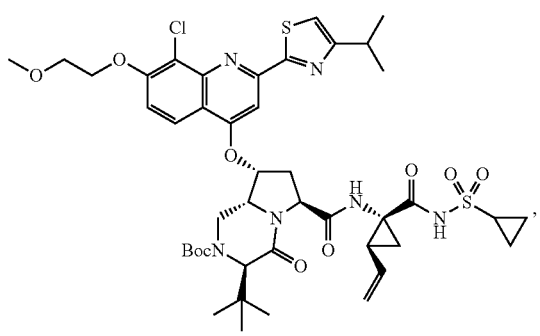
or a pharmaceutically acceptable salt thereof.
9. A compound of claim 1 selected from the group consisting of:
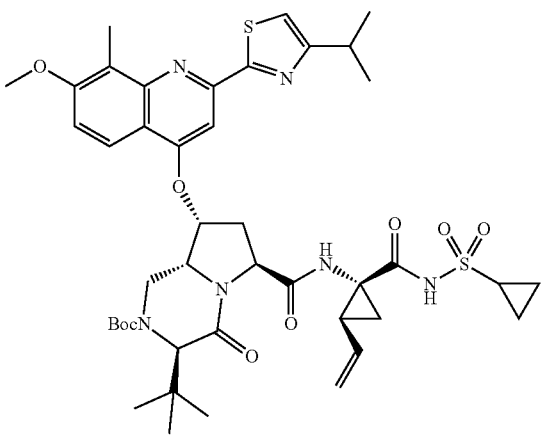
and
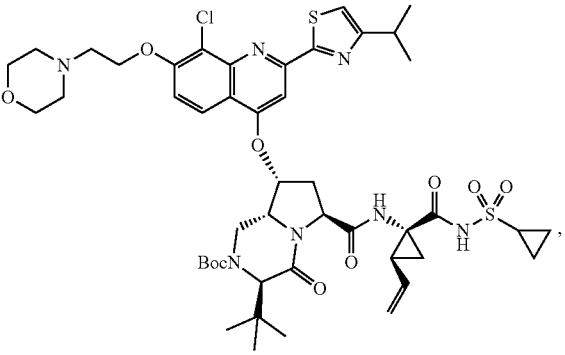
or a pharmaceutically acceptable salt thereof.

10. A compound of claim 1 selected from the group consisting of:

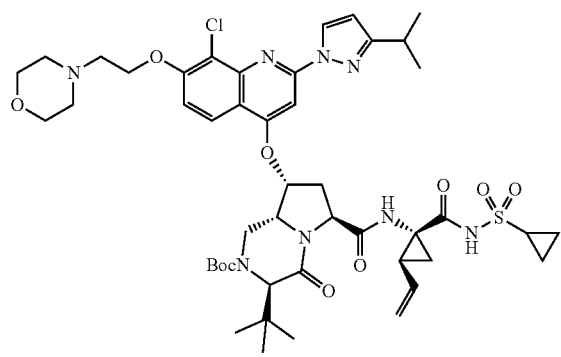

and

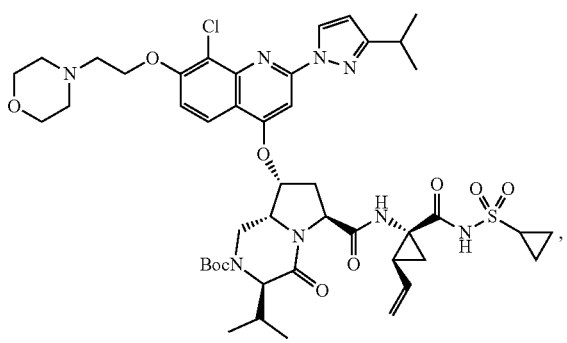

or a pharmaceutically acceptable salt thereof.

11. A compound of claim 1 selected from the group consisting of:

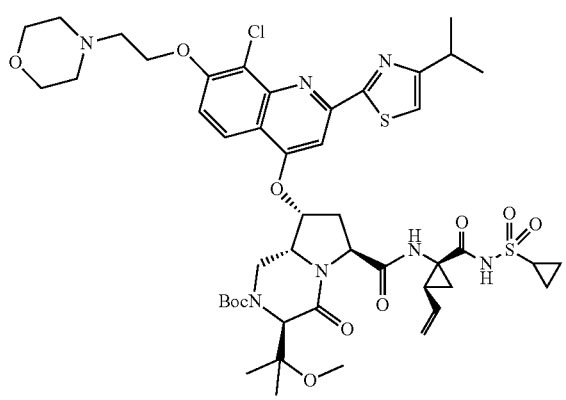

and

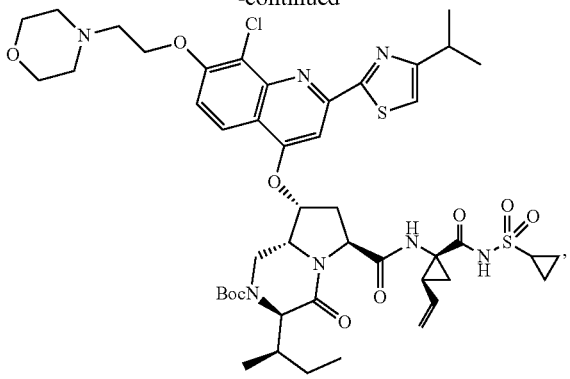

or a pharmaceutically acceptable salt thereof.

12. A compound of claim 1 selected from the group consisting of:

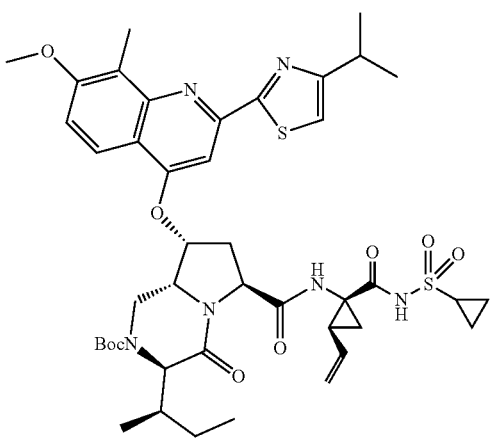

and

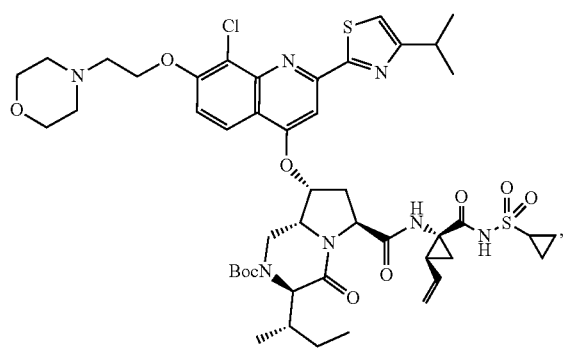

or a pharmaceutically acceptable salt thereof.

13. A compound of claim 1 selected from the group consisting of:

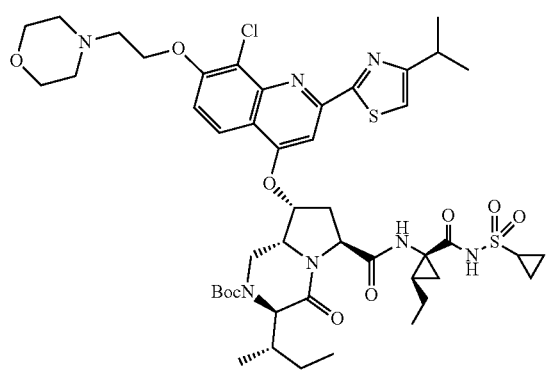
and
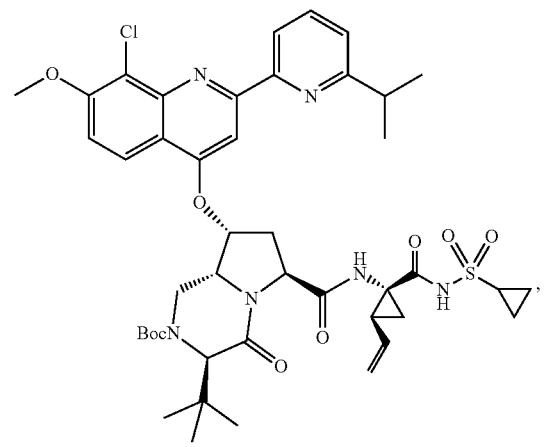
or a pharmaceutically acceptable salt thereof.
14. A compound of claim 1 selected from the group consisting of:
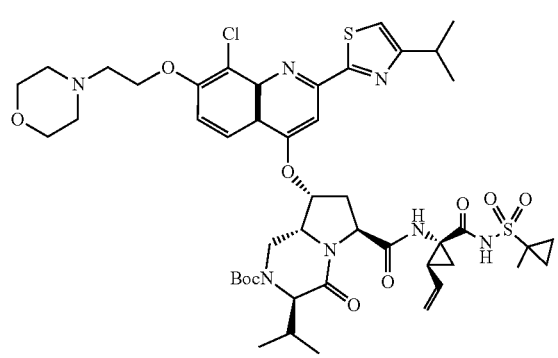
and
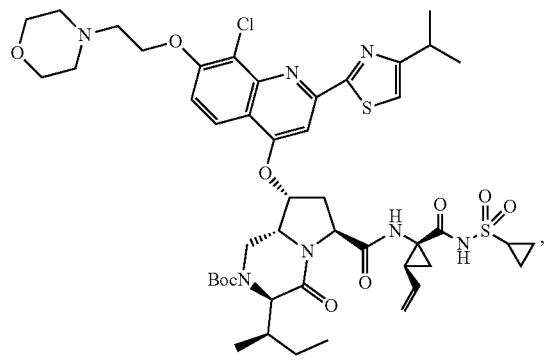
or a pharmaceutically acceptable salt thereof.
15. A compound of claim 1 selected from the group consisting of:
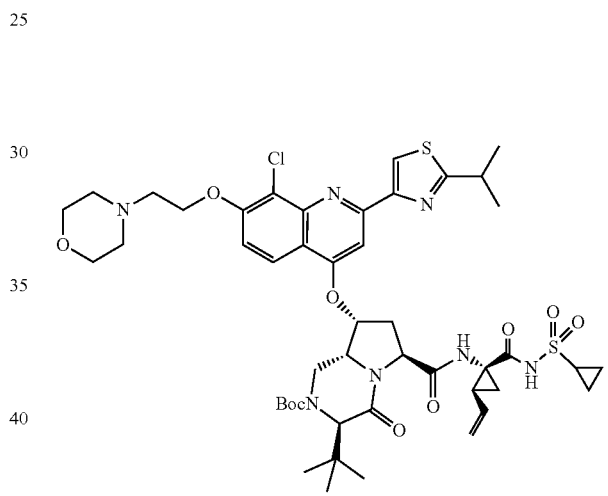
and
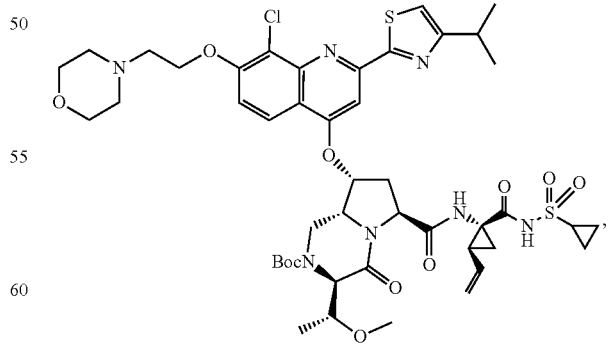
or a pharmaceutically acceptable salt thereof.
16. A compound of claim 1 selected from the group consisting of:

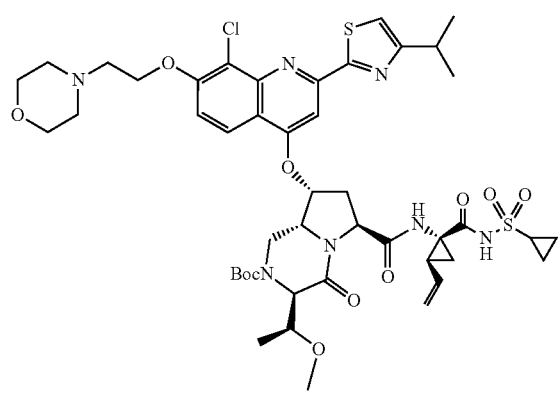
and
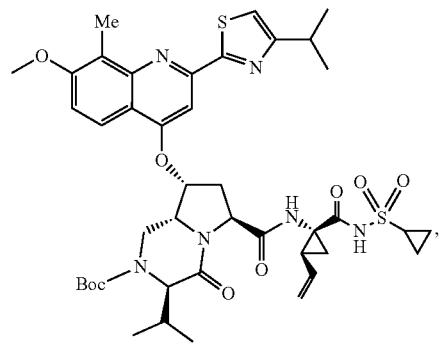
or a pharmaceutically acceptable salt thereof.
17. A compound of claim 1 selected from the group consisting of:
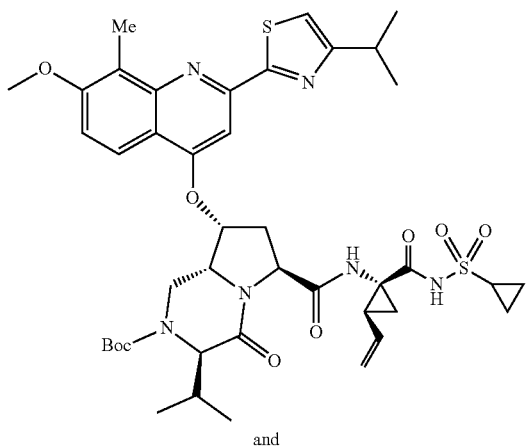
and
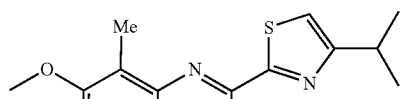
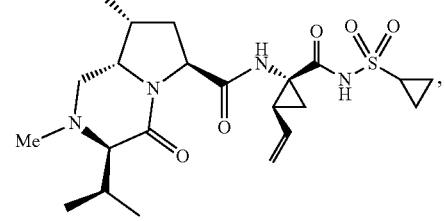
or a pharmaceutically acceptable salt thereof.
18. A compound of claim 1 selected from the group consisting of:
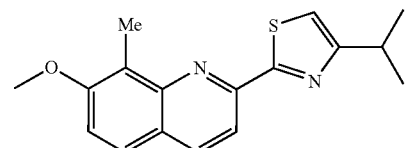
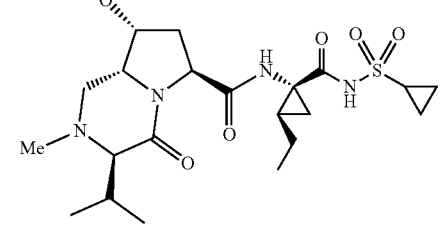
and
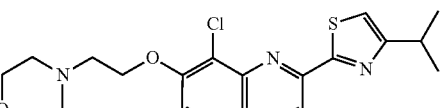
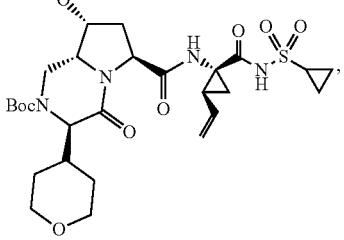
or a pharmaceutically acceptable salt thereof.

19. A compound of claim 1, wherein the compound is:
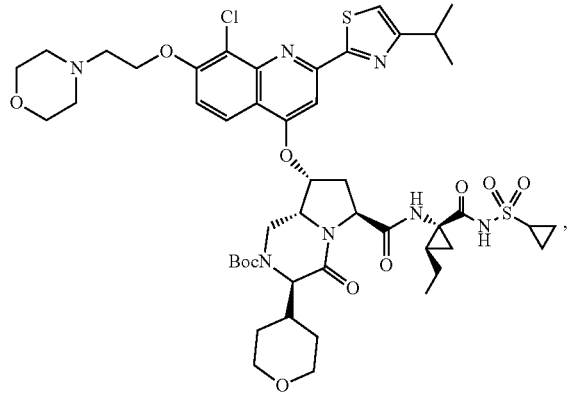 [SMILES: CC[C@@H]1C[C@]1(NC(=O)[C@@H]1C[C@@H](Oc2cc(-c3nc(C(C)C)cs3)nc3c(Cl)c(OCCN4CCOCC4)ccc23)[C@H]2CN(C(=O)OC(C)(C)C)[C@H](C3CCOCC3)C(=O)N21)C(=O)NS(=O)(=O)C1CC1]
or a pharmaceutically acceptable salt thereof.
20. A compound of claim 1, wherein the compound is:
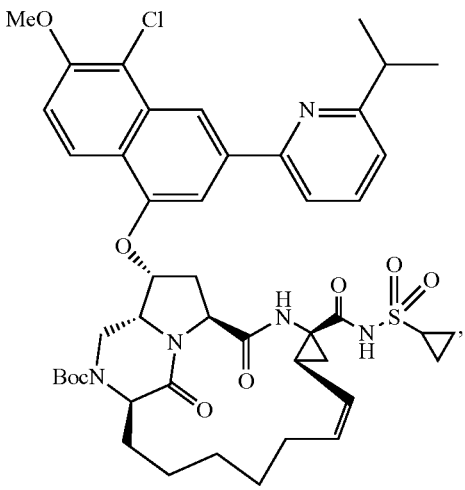 [SMILES: COc1ccc2c(O[C@@H]3C[C@H]4C(=O)N[C@]5(C(=O)NS(=O)(=O)C6CC6)C[C@H]5/C=C\CCCCC[C@@H]5C(=O)N4[C@@H]3CN5C(=O)OC(C)(C)C)cc(-c3cccc(C(C)C)n3)cc2c1Cl]
or a pharmaceutically acceptable salt thereof.
* * * * *